United States Patent
Fox et al.

(10) Patent No.: US 11,230,601 B2
(45) Date of Patent: Jan. 25, 2022

(54) METHODS OF USING ANTI-LAP ANTIBODIES

(71) Applicant: Tilos Therapeutics, Inc., Lexington, MA (US)

(72) Inventors: Barbara S. Fox, Wayland, MA (US); Randall Burton, Billerica, MA (US); Stavros Kopsiaftis, West Roxbury, MA (US); Xiufeng Song, Jamaica Plain, MA (US); Patricia Rao, Acton, MA (US); Kenneth J. Simon, Milton, MA (US); Jessie M. English, Cambridge, MA (US)

(73) Assignee: Tilos Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/156,857

(22) Filed: Oct. 10, 2018

(65) Prior Publication Data

US 2019/0144549 A1    May 16, 2019

Related U.S. Application Data

(60) Provisional application No. 62/570,338, filed on Oct. 10, 2017.

(51) Int. Cl.
| | | |
|---|---|---|
| *C07K 16/28* | (2006.01) | |
| *C07K 16/22* | (2006.01) | |
| *C07K 16/30* | (2006.01) | |
| *G01N 33/574* | (2006.01) | |
| *A61K 39/395* | (2006.01) | |
| *A61K 47/68* | (2017.01) | |
| *A61P 35/00* | (2006.01) | |
| *A61K 39/00* | (2006.01) | |
| *A61K 9/00* | (2006.01) | |
| *A61K 45/06* | (2006.01) | |

(52) U.S. Cl.
CPC ........ *C07K 16/2863* (2013.01); *A61K 9/0019* (2013.01); *A61K 39/3955* (2013.01); *A61K 39/39558* (2013.01); *A61K 45/06* (2013.01); *A61K 47/6851* (2017.08); *A61K 47/6879* (2017.08); *A61K 47/6887* (2017.08); *A61P 35/00* (2018.01); *C07K 16/22* (2013.01); *C07K 16/2827* (2013.01); *C07K 16/2839* (2013.01); *C07K 16/30* (2013.01); *G01N 33/574* (2013.01); *G01N 33/57492* (2013.01); *A61K 2039/505* (2013.01); *C07K 2317/24* (2013.01); *C07K 2317/31* (2013.01); *C07K 2317/54* (2013.01); *C07K 2317/565* (2013.01); *C07K 2317/622* (2013.01); *C07K 2317/76* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,439,196 A | 3/1984 | Higuchi |
| 4,444,887 A | 4/1984 | Hoffmann |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,716,111 A | 12/1987 | Osband et al. |
| 4,790,824 A | 12/1988 | Morrow et al. |
| 4,816,567 A | 3/1989 | Cabilly et al. |
| 4,881,175 A | 11/1989 | Ladner |
| 4,941,880 A | 7/1990 | Burns |
| 4,946,778 A | 8/1990 | Ladner et al. |
| 5,013,653 A | 5/1991 | Huston et al. |
| 5,064,413 A | 11/1991 | McKinnon et al. |
| 5,091,513 A | 2/1992 | Huston et al. |
| 5,132,405 A | 7/1992 | Huston et al. |
| 5,225,539 A | 7/1993 | Winter |
| 5,229,275 A | 7/1993 | Goroff |
| 5,258,498 A | 11/1993 | Huston et al. |
| 5,260,203 A | 11/1993 | Ladner et al. |
| 5,312,335 A | 5/1994 | McKinnon et al. |
| 5,374,548 A | 12/1994 | Caras et al. |
| 5,383,851 A | 1/1995 | McKinnon, Jr. et al. |

(Continued)

FOREIGN PATENT DOCUMENTS

| | | |
|---|---|---|
| EP | 0154316 A2 | 9/1985 |
| EP | 0401384 A1 | 12/1990 |

(Continued)

OTHER PUBLICATIONS

Lloyd et al., Protein Engineering, Design & Selection 22, 159-168, 2009. (Year: 2009).*

(Continued)

*Primary Examiner* — Elly-Gerald Stoica

(74) *Attorney, Agent, or Firm* — Su Kyung Suh; Anna L. Cocuzzo

(57) ABSTRACT

Provided herein are antibodies which bind to latency-associated peptide (LAP) of TGF-β1 and are characterized by particular functional features, such as binding specifically to LAP-TGFβ1 on cells but not to LAP-TGFβ1 in extracellular matrix, as well as compositions including the same. Also provided are uses of these antibodies in therapeutic applications, such as in the treatment of cancer, and diagnostic applications.

14 Claims, 51 Drawing Sheets

Specification includes a Sequence Listing.

(56) References Cited

U.S. PATENT DOCUMENTS

| | | |
|---|---|---|
| 5,399,163 A | 3/1995 | Peterson et al. |
| 5,399,331 A | 3/1995 | Loughrey et al. |
| 5,416,016 A | 5/1995 | Low et al. |
| 5,455,030 A | 10/1995 | Ladner et al. |
| 5,476,786 A | 12/1995 | Huston |
| 5,482,858 A | 1/1996 | Huston et al. |
| 5,530,101 A | 6/1996 | Queen et al. |
| 5,565,332 A | 10/1996 | Hoogenboom et al. |
| 5,567,610 A | 10/1996 | Borrebaeck et al. |
| 5,585,089 A | 12/1996 | Queen et al. |
| 5,624,821 A | 4/1997 | Winter et al. |
| 5,648,260 A | 7/1997 | Winter et al. |
| 5,677,425 A | 10/1997 | Bodmer et al. |
| 5,693,762 A | 12/1997 | Queen et al. |
| 5,714,350 A | 2/1998 | Co et al. |
| 5,714,352 A | 2/1998 | Jakobobits |
| 5,723,323 A | 3/1998 | Kauffman et al. |
| 5,763,192 A | 6/1998 | Kauffman et al. |
| 5,766,886 A | 6/1998 | Studnicka et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,869,046 A | 2/1999 | Presta et al. |
| 5,976,862 A | 11/1999 | Kauffman et al. |
| 6,005,079 A | 12/1999 | Casterman et al. |
| 6,121,022 A | 9/2000 | Presta et al. |
| 6,165,745 A | 12/2000 | Ward et al. |
| 6,180,370 B1 | 1/2001 | Queen et al. |
| 6,194,551 B1 | 2/2001 | Idusogie et al. |
| 6,204,023 B1 | 3/2001 | Robinson et al. |
| 6,207,156 B1 | 3/2001 | Kuchroo et al. |
| 6,277,375 B1 | 8/2001 | Ward |
| 6,350,861 B1 | 2/2002 | Co et al. |
| 6,737,056 B1 | 5/2004 | Presta |
| 6,946,292 B2 | 9/2005 | Kanda et al. |
| 6,989,452 B2 | 1/2006 | Ng et al. |
| 7,029,872 B2 | 4/2006 | Gerngross |
| 7,087,600 B2 | 8/2006 | Ng et al. |
| 7,125,689 B2 | 10/2006 | Carr et al. |
| 7,129,261 B2 | 10/2006 | Ng et al. |
| 7,132,255 B2 | 11/2006 | Blumberg |
| 7,214,775 B2 | 5/2007 | Hanai et al. |
| 7,317,091 B2 | 1/2008 | Lazar et al. |
| 7,388,088 B2 | 6/2008 | Marks et al. |
| 7,449,308 B2 | 11/2008 | Gerngross et al. |
| 7,635,757 B2 | 12/2009 | Freeman et al. |
| 7,803,553 B2 | 9/2010 | Kojima et al. |
| 8,101,720 B2 | 1/2012 | Lazar et al. |
| 8,198,412 B2 | 6/2012 | Kojima et al. |
| 8,217,149 B2 | 7/2012 | Irving et al. |
| 8,951,521 B2 | 2/2015 | Kojima et al. |
| 9,573,995 B2 | 2/2017 | Schurpf et al. |
| 9,580,500 B2 | 2/2017 | Schurpf et al. |
| 10,017,567 B2 | 7/2018 | Weiner et al. |
| 10,233,247 B2 | 3/2019 | Hanai et al. |
| 2003/0068661 A1 | 4/2003 | Hockfield et al. |
| 2005/0276802 A1 | 12/2005 | Adams et al. |
| 2005/0276812 A1 | 12/2005 | Ebens et al. |
| 2006/0004081 A1 | 1/2006 | Chen et al. |
| 2006/0024317 A1 | 2/2006 | Boyd et al. |
| 2006/0247295 A1 | 11/2006 | Gangwar et al. |
| 2008/0038748 A1 | 2/2008 | Kojima et al. |
| 2008/0206219 A1 | 8/2008 | Coussens et al. |
| 2008/0227704 A1 | 9/2008 | Kamens et al. |
| 2008/0280827 A1 | 11/2008 | Kojima et al. |
| 2009/0317368 A1 | 12/2009 | Chen |
| 2011/0064653 A1 | 3/2011 | Hansen et al. |
| 2011/0070163 A1 | 3/2011 | Gonda et al. |
| 2011/0070238 A1 | 3/2011 | Triebel et al. |
| 2011/0150892 A1 | 6/2011 | Thudium et al. |
| 2013/0028915 A1 | 1/2013 | Baylor et al. |
| 2013/0071403 A1 | 3/2013 | Rolland et al. |
| 2014/0328860 A1 | 11/2014 | Scandura et al. |
| 2015/0033703 A1 | 2/2015 | Hyde et al. |
| 2015/0273056 A1 | 10/2015 | Blumberg et al. |
| 2015/0284455 A1 | 10/2015 | Springer et al. |
| 2015/0337034 A1 | 11/2015 | Schurpf |
| 2016/0289315 A1 | 10/2016 | Mirza et al. |
| 2017/0073406 A1 | 3/2017 | Schurpf et al. |
| 2017/0190767 A1 | 7/2017 | Schurpf et al. |
| 2017/0210798 A1 | 7/2017 | Schurpf et al. |
| 2018/0009886 A1 | 1/2018 | Weiner et al. |
| 2018/0030128 A1 | 2/2018 | Weiner et al. |
| 2018/0207267 A1 | 7/2018 | Schurpf et al. |
| 2019/0071493 A1 | 3/2019 | Schurpf et al. |

FOREIGN PATENT DOCUMENTS

| | | |
|---|---|---|
| EP | 404097 B1 | 12/1990 |
| EP | 0239400 B1 | 8/1994 |
| EP | 1176195 A1 | 4/2000 |
| EP | 1229125 A1 | 8/2002 |
| EP | 0592106 B1 | 11/2004 |
| EP | 0519596 B1 | 2/2005 |
| EP | 1674480 A1 | 6/2006 |
| EP | 2 878 308 A1 | 6/2015 |
| EP | 2916867 A2 | 9/2015 |
| EP | 2981822 A2 | 2/2016 |
| EP | 3139957 A2 | 3/2017 |
| EP | 3277716 A2 | 2/2018 |
| EP | 3365368 A1 | 8/2018 |
| JP | 2006523179 A | 10/2006 |
| JP | 2008247900 A | 10/2008 |
| JP | 2008289478 A | 12/2008 |
| WO | 1990014424 A1 | 11/1990 |
| WO | 1990014430 A1 | 11/1990 |
| WO | 1990014443 A1 | 11/1990 |
| WO | 1991009967 A1 | 7/1991 |
| WO | 1991010741 A1 | 7/1991 |
| WO | 1992001047 A1 | 1/1992 |
| WO | 1992003461 A1 | 3/1992 |
| WO | 1992011272 A1 | 7/1992 |
| WO | 1993006213 A1 | 4/1993 |
| WO | WO199311161 A1 | 6/1993 |
| WO | WO1994404678 A1 | 3/1994 |
| WO | 1994011026 A2 | 5/1994 |
| WO | 1994018219 A1 | 8/1994 |
| WO | 9425591 A1 | 11/1994 |
| WO | 199429351 A2 | 12/1994 |
| WO | 1995017886 A1 | 7/1995 |
| WO | 1996032478 A1 | 10/1996 |
| WO | 1996033735 A1 | 10/1996 |
| WO | 1996034096 A1 | 10/1996 |
| WO | 1997020032 A1 | 6/1997 |
| WO | 199734631 A1 | 9/1997 |
| WO | 1998016654 A1 | 4/1998 |
| WO | 1998024893 A2 | 6/1998 |
| WO | 1998042752 A1 | 10/1998 |
| WO | 1998046645 A2 | 10/1998 |
| WO | 1998050433 A2 | 11/1998 |
| WO | 1999006834 A2 | 2/1999 |
| WO | 199954342 A1 | 10/1999 |
| WO | 2000031246 A2 | 6/2000 |
| WO | WO0037504 A2 | 6/2000 |
| WO | 200042072 A2 | 7/2000 |
| WO | 2000061739 A1 | 10/2000 |
| WO | 2001058957 A2 | 8/2001 |
| WO | 2002006919 A2 | 1/2002 |
| WO | 2002031240 A2 | 4/2002 |
| WO | 02085306 A2 | 10/2002 |
| WO | 2002096910 A1 | 12/2002 |
| WO | WO03011878 A2 | 2/2003 |
| WO | 2003035835 A2 | 5/2003 |
| WO | 2003086310 A2 | 10/2003 |
| WO | 2003099196 A2 | 12/2003 |
| WO | 2004016750 A2 | 2/2004 |
| WO | 2004029207 A2 | 4/2004 |
| WO | 2004035752 A2 | 4/2004 |
| WO | 2004063351 A2 | 7/2004 |
| WO | 2004074455 A2 | 9/2004 |
| WO | 2004099249 A2 | 11/2004 |
| WO | 2005/023870 A1 | 3/2005 |
| WO | 2005040217 A2 | 5/2005 |
| WO | 2005070963 A1 | 8/2005 |

(56) References Cited

FOREIGN PATENT DOCUMENTS

| | | | |
|---|---|---|---|
| WO | 2005092925 A2 | 10/2005 | |
| WO | 2005117973 A2 | 12/2005 | |
| WO | 2005120571 A2 | 12/2005 | |
| WO | 2006020114 A2 | 2/2006 | |
| WO | WO2006014679 A1 | 2/2006 | |
| WO | 2006057702 A2 | 6/2006 | |
| WO | 2006/086469 A2 | 8/2006 | |
| WO | 2006091209 A2 | 8/2006 | |
| WO | 2006/116002 A2 | 11/2006 | |
| WO | 2006122150 A1 | 11/2006 | |
| WO | 2007038658 A2 | 4/2007 | |
| WO | 2007051081 A1 | 5/2007 | |
| WO | 2007059404 A2 | 5/2007 | |
| WO | 2007075598 A2 | 7/2007 | |
| WO | 2008036642 A2 | 3/2008 | |
| WO | 2008036653 A2 | 3/2008 | |
| WO | 2008083312 A2 | 7/2008 | |
| WO | 2008103693 A2 | 8/2008 | |
| WO | WO2008132601 A1 | 11/2008 | |
| WO | 2009014708 A2 | 1/2009 | |
| WO | 2009044273 A2 | 4/2009 | |
| WO | 2009059278 A1 | 5/2009 | |
| WO | 2009073620 A2 | 6/2009 | |
| WO | 2009114335 A2 | 9/2009 | |
| WO | 2009119455 A1 | 10/2009 | |
| WO | 2010019570 A2 | 2/2010 | |
| WO | 2010/124276 A2 | 10/2010 | |
| WO | 2011056652 A1 | 5/2011 | |
| WO | 2011066389 A1 | 6/2011 | |
| WO | 2011070024 A1 | 6/2011 | |
| WO | 2011102483 A1 | 8/2011 | |
| WO | 2011107553 A1 | 9/2011 | |
| WO | 2011109400 A2 | 9/2011 | |
| WO | 2011131407 A1 | 10/2011 | |
| WO | 2011140249 A2 | 11/2011 | |
| WO | 2011161699 A2 | 12/2011 | |
| WO | 2012/029792 A1 | 3/2012 | |
| WO | 2012032433 A1 | 3/2012 | |
| WO | 2012142237 A1 | 10/2012 | |
| WO | 2012145493 A1 | 10/2012 | |
| WO | 2013/079174 A1 | 6/2013 | |
| WO | 2013087699 A1 | 6/2013 | |
| WO | 2013119716 A1 | 8/2013 | |
| WO | 2013/134365 A1 | 9/2013 | |
| WO | 2013132044 A1 | 9/2013 | |
| WO | 2013169264 A1 | 11/2013 | |
| WO | 2013173223 A1 | 11/2013 | |
| WO | 2014008218 A1 | 1/2014 | |
| WO | 2014036357 A1 | 3/2014 | |
| WO | 2014059251 A1 | 4/2014 | |
| WO | 2014074532 A2 | 5/2014 | |
| WO | 2014182676 A2 | 11/2014 | |
| WO | 2015/171691 A2 | 11/2015 | |
| WO | 2016/115345 A1 | 7/2016 | |
| WO | 2016/161410 A2 | 10/2016 | |
| WO | 2017/156500 A1 | 9/2017 | |
| WO | 2018/013939 A1 | 1/2018 | |
| WO | 2018/043734 A1 | 3/2018 | |
| WO | 2018/129329 A1 | 7/2018 | |
| WO | 2018/208888 A1 | 11/2018 | |
| WO | 2019/023661 A1 | 1/2019 | |
| WO | 2019075090 A1 | 4/2019 | |

OTHER PUBLICATIONS

Ali, N. et al., "Latency associated peptide has in vitro and in vivo immune effects independent of TGF-.beta 1," PLoS ONE, vol. 3(4):e1914. 9 pages. (2008).
Almagro et al., "Humanization of antibodies," Front Biosci., vol. 13:1619-1633 (2008).
Andersson, J. et al., "CD4+ FoxP3+ regulatory T cells confer infectious tolerance in a TGF-beta-dependent manner," J Exp Med. vol. 205(9):1975-1981 (2008) doi: 10.1084/jem.20080308. Epub Aug. 18, 2008.
Biolegend: "LEAFTM Purified anti-human/mouse Latent TGF-beta Antibody", 2 pages (2014).
Biolegend: "Ultra-LEAHTM Purified anti-mouse/human LAP (TGF[beta] 1) Antibody," Version 2, Revision Date Aug. 27, 2014, 2 pages.
Broderick, L. et al., "Membrane-associated TGF-beta1 inhibits human memory T cell signaling in malignant and nonmalignant inflammatory microenvironments," J Immunol., vol. 177(5):3082-3088 (2006).
Cao, X., et al., "Granzyme B and perforin are important for regulatory T cell-mediated suppression of tumor clearance," Immunity, vol. 27(4):635-646 (2007).
Carambia, A., "TGF-beta-dependent induction of CD4+CD25+ Foxp3+ Tregs by liver sinusoidal endothelial cells," J Hepatol, vol. 61(3): 594-599 (2014).
Carrillo-Galvez, A. B., et al., "Mesenchymal stromal cells express GARP/LRRC32 on their surface: effects on their biology and immunomodulatory capacity," Stem Cells, vol. 33(1): 183-195 (2015).
Chen, M-L., et al., "Latency-associated peptide identifies a novel CD4+CD25+ regulatory T cell subset with TGFbeta-mediated function and enhanced suppression of experimental autoimmune encephalomyelitis," J Immunol., vol. 180(11)7327-7337 (2008).
Cohn, A. et al., "A phase I dose-escalation study to a predefined dose of a transforming growth factor-β1 monoclonal antibody (TβM1) in patients with metastatic cancer," International Journal of Oncology, vol. 45: 2221-2231 (2014).
Cunha, A. et al., "In vivo anti-LAP mAb enhances IL-17/IFN-y responses and abrogates anti-CD3-induced oral tolerance," International Immunology, vol. 27(2)73-82 (2014) https://doi.org/10.1093/intimm/dxu083.
Curran, M. et al., "PD-1 and CTLA-4 combination blockade expands infiltrating T cells and reduces regulatory T and myeloid cells within B16 melanoma tumors," PNAS, vol. 107(9):4275-4280 (2010). doi: 10.1073/pnas.0915174107. Epub Feb. 16, 2010.
D'Ambrosio, A., et al., "Lamina Propria CD4+LAP+ Regulatory T Cells Are Increased in Active Ulcerative Colitis but Show Increased IL-17 Expression and Reduced Suppressor Activity," J Crohns Colitis, 10(3): 346-353 (2016).
Database accession No. EMB-623504224; Database Embase [Online]Elsevier Science Publishers, Amsterdam, NL, Jul. 1, 2018, Kopsiaftis S. et al. Radiation induces LAP, latency-associated peptide of TGF-beta, on the surface of lymphoid cells in the tumor microenvironment, XP002788173, abstract, 2 pages.
Duan, W., et al., "Inducible CD4+LAP+Foxp3-regulatory T cells suppress allergic inflammation," J Immunol., vol. 187(12): 6499-6507 (2011).
Edwards, J.P. et al.,"The GARP/Latent TGF-beta1 complex on Treg cells modulates the induction of peripherally derived Treg cells during oral tolerance," Eur J Immunol, vol. 46:1480-1489 (2016).
Elkord, E., et al., "Helios, and not FoxP3, is the marker of activated Tregs expressing GARP/LAP," Oncotarget, vol. 6(24): 20026-20036 (2015).
English Language Translation of International Preliminary Report on Patentability for PCT/JP2011/053559 dated Sep. 18, 2012, 6 pages.
Extended European Search Report for EP 16737879.3, dated May 29, 2018, 12 pages.
Frank, S. et al., Immunology and Evolution of Infectious Disease, Chapter 4 "Specificity and Cross-Reactivity," Princeton University Press, 33 page (2002).
Gabriely, G. et al., "Targeting latency-associated peptide promotes anti-tumor immunity," Sci Immunol., vol. 2(11) (2017) pii: eaaj1738. doi: 10.1126/sciimmunol.aaj1738.
Gandhi, R., et al., "Cutting edge: human latency-associated peptide+ T cells: a novel regulatory T cell subset," J Immunol., vol. 184(9): 4620-4624 (2010).
Gandhi, R., et al., "Cutting Edge: Immature human dendritic cells express latency-associated peptide and inhibit T cell activation in a TGF-beta-dependent manner," J Immunol., vol. 178(7): 4017-4021 (2007).

(56) References Cited

OTHER PUBLICATIONS

Gerlach et al., "Recurrence of hepatitis C virus after loss of virus-specific CD4(+) T-cell response in acute hepatitis C," Gastroenterology, vol. 117(4):933-941 (1999).
Gray, J. et al., "Optimising anti-tumour CD8 T-cell responses using combinations of immunomodulatory antibodies," Eur J Immunol. vol. 38(9):2499-2511 (2008) doi: 10.1002/eji.200838208.
International Preliminary Report on Patentability for PCT/US2013/064506, dated Apr. 14, 2015, 11 pages.
International Preliminary Report on Patentability for PCT/US2016/013408, dated Jul. 27, 2017, 20 pages.
International Search Report and Written Opinion for PCT/US2013/064506, dated Jan. 30, 2014, 18 pages.
International Search Report and Written Opinion for PCT/US2016/013408, dated May 2, 2016, 24 pages.
International Search Report and Written Opinion, PCT/US2018/055253, dated Feb. 26, 2019, 17 pages.
Jie, H. B., et al., "Intratumoral regulatory T cells upregulate immunosuppressive molecules in head and neck cancer patients," Br J Cancer, 109(10): 2629-2635 (2013).
Kopsiaftis, S. et al., "Radiation induces LAP, latency-associated peptide of TGF-beta, on the surface of lymphoid cells in the tumor microenvironment [abstract]," In: Proceedings of the American Association for Cancer Research Annual Meeting 2018; Apr. 14-18, 2018; Chicago, IL. Philadelphia (PA): AACR; Cancer Res 2018;78(13 Suppl):Abstract hro. 72.
Leger et al., Molecular Medicine and Medicinal Chemistry, Jan. 1, 2011. Chapter 1: "Humanization of Antibodies" pp. 1-23.
Lonning, S. et al. "Antibody Targeting of TGF-beta in Cancer Patients," Current Pharmaceutical Biotechnology, vol. 12:2176-2189 (2011).
Mahalingam, J. et al., "CD4+ T cells expressing latency-associated peptide and Foxp3 are an activated subgroup of regulatory T cells enriched in patients with colorectal cancer," PLoS One, vol. 9(9):e108554 (2014) doi:10.1371/journal.pone.0108554. eCollection 2014.
Mahalingam, J. et al., "LAP+CD4+ T cells are suppressors accumulated in the tumor sites and associated with the progression of colorectal cancer," Clin Cancer Res., vol. 18(19):5224-5233. (2012)doi: 10.1158/1078-0432. CCR-12-0211. Epub Aug. 9, 2012.
Maynard, J. et al., "Antibody engineering," Annu Rev Biomed Eng., vol. 2:339-376 (2000).
Melero, I. et al., "Immunostimulatory monoclonal antibodies for cancer therapy," Nature Reviews, Cancer, vol. 7:95-106 (2007).
Nakamura, K. et al., "TGF-beta 1 plays an important role in the mechanism of CD4+CD25+ regulatory T cell activity in both humans and mice," J Immunol., vol. 172(2):834-842 (2004).
Oida, T. et al., "Overexpression of TGF-Beta 1 gene induces cell surface localized glucose-regulated protein 78-associated latency-associated peptide/TGF-Beta," J Immunol., vol. 185(6):3529-3235 (2010). doi: 10.4049/jimmunol.0904121. Epub Aug. 18, 2010.
Oida, T. et al., "TGF-.beta. induces surface LAP expression on murine CD4 T cells independent of Foxp3 induction," PLoS One. vol. 5(11):e15523 (2010) doi: 10.1371/journal.pone.0015523.
Oida, T. ett al., "Depletion of TGF-beta from fetal bovine serum," J Immunol Methods, vol. 362(1-2): 195-198 (2010).
Oida, T., et al., "CD4+CD25- T cells that express latency-associated peptide on the surface suppress CD4+CD45RBhigh-induced colitis by a TGF-beta-dependent mechanism," J Immunol, vol. 170(5): 2516-2522 (2003).
Samid, M. et al., "Combining FoxP3 and Helios with GARP/LAP markers can identify expanded Treg subsets in cancer patients," Oncotarget, 7(12): 14083-14094 (2016).
Santegoeis, S. et al., "Monitoring regulatory T cells in clinical samples: consensus on an essential marker set and gating strategy for regulatory T cell analysis by flow cytometry," Cancer Immunol Immunother, vol. 64(10):1271-1286 (2015). doi: 10.1007/s00262-015-1729-x. Epub Jun. 28, 2015.
Scurr, M. et al., "Highly prevalent colorectal cancer-infiltrating LAP+ Foxp3-T cells exhibit more potent immunosuppressive activity than Foxp3+ regulatory T cells," Mucosal Immunol., vol. 7(2):428-439 (2014). doi: 10.1038/mi.2013.62. EpubSep. 25, 2013.
Shah et al., "Neutralisation of TGF-beta 1 and TGF-beta 2 or exogenous addition of TGF-beta 3 to cutaneous rat wounds reduces scarring," J Cell Sci.., vol. 108 ( Pt 3):985-1002 (1995).
Sun, J. et al., "Identification of human regulatory T cells in the setting of T-cell activation and anti-CTLA-4 immunotherapy on the basis of expression of latency-associated peptide," Cancer Discov., vol. 2(2): 122-130 (2011). doi:10.1158/2159-8290.CD-11-0236. Epub Dec. 27, 2011.
Tran, D. Q., et al., "GARP (LRRC32) is essential for the surface expression of latent TGF-beta on platelets and activated FOXP3+ regulatory T cells," PNAS, vol. 106(32): 13445-13450 (2009).
Tsumura, H. et al., "Generation of Recombinant Human Large Latent Transforming Growth Factor-β1 and Monoclonal Antibodies to It," Bioscience, Biotechnology, and Biochemistry, vol. 64 (1): 17-23 (2000).
Von Regenmortel, "From absolute to exquisite specificity. Reflections on the fuzzy nature of species, specificity and antigenic sites," J Immunol Methods., vol. 216(1-2):37-48 (1998).
Zhang, H. et al., "Critical Role of Myeloid-Derived Suppressor Cells in Tumor-Induced Liver Immune Suppression through Inhibition of NKT Cell Function," Frontiers In Immunology, vol. 8: Article 129 (2017).
Zhang, S. et al., "Tumor-associated macrophages promote tumor metastasis via the TGF-beta/SOX9 axis in non-small cell lung cancer," Oncotarget, vol. 8:99801-9985 (2017).
Zhang, Y., et al., "Mammary-tumor-educated B cells acquire LAP/TGF-beta and PD-L1 expression and suppress anti-tumor immune responses," Int Immunol, vol. 28(9):423-433 (2016).
Zhong, W., et al., "Role of LAP(+)CD4(+) T cells in the tumor microenvironment of colorectal cancer," World J Gastroenterol, vol. 23(3): 455-463 (2017).
Afonine, Pavel V. et al., Real-space refinement in PHENIX for cryo-EM and crystallography, Acta Cryst., 2018, 531-544, 74.
Alexander, Anthony J. et al., Monitoring of IgG Antibody Thermal Stability by Micellar Electrokinetic Capillary Chromatography and Matrix-Assisted Laser Desorption/Ionization Mass Spectrometry, Anal. Chem., 1995, 3626-3632, 67.
Altschul S.F. et al, Gapped BLAST and PSI-BLAST: a new generation of protein database search programs, Nucleic Acids Research, 1997, 3389-3402, 25-17, Oxford University Press.
Altschul, Stephen F. et al., Basic Local Alignment Search Tool, J. Mol. Biol., 1990, 403-410, 215.
Annes, Justin P. et al., Integrin alpha v beta6-mediated activation of latent TGF-beta requires the latent TGF-beta binding protein-1, The Journal of Cell Biology, 2004, 723-734, 165.
Arnon, Ruth et al., Monoclonal Antibodies for Immunotargeting of Drugs in Cancer Therapy, Monoclonal Antibodies and Cancer Therapy, 1985, 243-256, N/A.
Basile, J. I. et al., *Mycobacterium tuberculosis* multi-drug-resistant strain M induces IL-17+ IFNy-CD4+ T cell expansion through an IL-23 and TGF-b-dependent mechanism in patients with MDR-TB tuberculosis, Clinical and Experimental Immunology, 2016, 160-173, 187.
Berge, S.M., et al.,, "Pharmaceutical Salts", J. Pharm. Sci, 1977, pp. 1-19, vol. 66, No. 1.
Biernacka, Anna et al., TGF-β signaling in fibrosis, Growth Factors, 2011, 196-202, 29(5).
Bird, Robert E. et al., Single-Chain Antigen-Binding Proteins, Science, 1988, 423-426, 242.
Bird, Thomas G et al., TGFβ inhibition restores a regenerative response in acute liver injury by suppressing paracrine senescence, Sci Transl Med., 2018, 1-30, 10:aan1230.
Bischoff, Rainer et al., Deamidation of asparagine and glutamine residues in proteins and peptides: structural determinants and analytical methodology, Journal of Chromatography B., 1994, 261-278, 662.
Bloemen, P.G.M. et al., Adhesion molecules: a new target for immunoliposome-mediated drug delivery, FEBS Letters, 1995, 140-144, 357.
Bordusa, Frank, Protease-catalyzed Formation of C—N Bonds, Highlights in Bioorganic Chemistry, 2004, 389-403, Chapter 5.

(56) References Cited

OTHER PUBLICATIONS

Brubaker, Marcus A. et al., Building Proteins in a Day: Efficient 3D Molecular Structure Estimation with Electron Cryomicroscopy, IEEE Trans Pattern Anal Mach Intell, 2017, 706-718, 39.
Brummell, David A. et al., Probing the Combining Site of an anti-Carbohydrate Antibody by Saturation-Mutagenesis: role of the Heavy-Chain CDR3 Residues, Biochemistry, 1993, 1180-1187, 32.
Burks, Elizabeth A. et al., In vitro scanning saturation mutagenesis of an antibody binding pocket, Proc. Natl. Acad. Sci. USA, 1997, 412-417, 94.
Camacho, L. H. et al., Phase 1 clinical trial of anti-CTLA4 human monoclonal antibody CP-675,206 in patients (pts) with advanced solid malignancies, J. Clin. Oncology, 2004,1-3,22(145): Abstract 2505.
Cardone, Giovanni et al., One number does not fit all: mapping local variations in resolution in cryo-EM reconstructions, J Struct Biol, 2013, 226-236, 184.
Carter, Paul et al., Humanization of an anti-p185HER2 antibody for human cancer therapy, Proc. Natl. Acad. Sci. USA, 1992, 4285-4289, 89.
Ceska, Tom et al., Cryo-EM in drug discovery, Biochemical Society Transactions, 2019, 281-293, 47.
Champe, Mark et al., Monoclonal Antibodies That Block the Activity of Leukocyte Function-associated Antigen 1 Recognize Three Discrete Epitopes in the Inserted Domain of CD11a, J. Biol. Chem., 1995, 1388-1394, 270.
Chappel, M. Suzanne et al., Identification of a Secondary Fc-γRI Binding Site within a Genetically Engineered Human IgG Antibody, J. Biol. Chem., 1993, 25124-25131, 268.
Chen, et al., Influence of histidine on the stability and physical properties of a fully human antibody in aqueous and solid forms, 2003, 1952-1960, 20(12), Pharm Res.
Chen, Xianghong et al., Induction of myelodysplasia by myeloid-derived suppressor cells, The Journal of Clinical Investigation, 2013, 4595-4611, 123.
Cheung et al., Epitope-specific antibody response to the surface antigen of duck hepatitis B virus in infected ducks, Virology, 1990, pp. 546-552, 176.
Cheung, Ka-Wai et al., alpha4beta7+ CD4+ Effector/Effector Memory T Cells Differentiate into Productively and Latently Infected Central Memory T Cells by Transforming Growth Factor beta1 during HIV-1 Infection, Journal of Virology, 2018, 1-18, 92(8):e01510-17.
Choi et al., PNAS, PNAS, 2003, pp. 5022-5027, 100.
Chothia et al, Canonical Structures for the Hypervariable Regions of Immunoglobins, J. Mol. Biol., 1987, 901-917, 196.
Chothia, Cyrus et al., Conformations of immunoglobulin hypervariable regions, Nature, 1989, 878-883, 342.
Clackson et al., Making Antibody Fragments Using Phage Display Libraries, Nature, 1991, pp. 624-628, vol. 352.
Cunningham et al., High resolution Epitope mapping of hgH-receptor interactions by alanine-scanning mutagenesis, Science, 1985, pp. 1081-1085, 244.
Dall'Acqua, William F. et al., Properties of Human IgG1s Engineered for Enhanced Binding to the Neonatal Fc Receptor (FcRn), Journal of Biological Chemistry, 2006, 23514-23524, 281(33).
Dall'Acqua, William F. et al., Increasing the Affinity of a Human IgG1 for the Neonatal Fc Receptor: Biological Consequences, Journal of Immunology, 2002, 5171-5180, 169.
De Graaf, Albert J. et al., Nonnatural Amino Acids for Site-Specific Protein Conjugation, Bioconjug. Chem., 2009, 1281-1295, 20.
Dranoff, Glenn et al., Vaccination with irradiated tumor cells engineered to secrete murine granulocyte-macrophage colony-stimulating factor stimulates potent, specific, and long-lasting anti-tumor immunity, Proc. Natl. Acad. Sci. USA, 1993, 3539-3543, 90.
Dussiot, Michael et al., An activin receptor IIA ligand trap corrects ineffective erythropoiesis in β-thalassemia, Nature Medicine, 2014, 398-407, 20.
Emsley et al., Features and development of Coot, Biological Crystallography, 2010, pp. 486-501, D66.
Fernandez, Isis E. et al., Peripheral blood myeloid-derived suppressor cells reflect disease status in idiopathic pulmonary fibrosis, Eur Respir J, 2016, 1171-1183, 48.
Foote et al., Antibody Framework Residues Affecting the Conformation of the Hypervariable Loops, J. Mol. Biol., 1992, pp. 487-499, vol. 224.
Frese, Marc-Andre et al., Formylglycine Aldehyde Tag—Protein Engineering through a Novel Post-translational Modification, ChemBioChem, 2009, 425-427, 10.
Fridrich, Sven et al., How Soluble GARP Enhances TGFβ Activation, PLOS One, 2016, 1-16, 11(4):e0153290.
Gala, Françise A. et al., V Region Carbohydrate and Antibody Expression, The Journal of Immunology, 2004, 5489-5494, 172.
Gautier, Arnaud et al., An Engineered Protein Tag for Multiprotein Labeling in Living Cells, Chemistry & Biology, 2008, 128-136, 15.
Geyh, Stefanie et al., Transforming growth factor β1-mediated functional inhibition of mesenchymal stromal cells in myelodysplastic syndromes and acute myeloid leukemia, Haematologica, 2018, 1462-1471, 103.
Ghirlando, Rodolfo et al., Glycosylation of human IgG-Fc: influences on structure revealed by differential scanning microcalorimetry, Immunology Letters, 1999, 47-52, 68.
Greenberg, Philip D. et al., Deficient Cellular Immunity—Finding and Fixing the Defects, Science, 1999, 546-551, 285.
Hackenberger, Christian P. R. et al., Chemoselective Ligation and Modification Strategies for Peptides and Proteins, Angew. Chem. Int. Ed., 2008, 10030-10074, 47.
Hamilton, Stephen R. et al., Glycosylation engineering in yeast: the advent of fully humanized yeast, Current Opinion in Biotechnology, 2007, 387-392, 18.
Hamilton, Stephen R. et al., Humanization of Yeast to Produce Complex Terminally Sialylated Glycoproteins, Science, 2006, 1441-1443, 313.
Hamilton, Stephen R. et al., Production of Complex Human Glycoproteins in Yeast, Science, 2003, 1244-1246, 301.
Hammerling, Gunter J., Monoclonal Antibodies and T-Cell Hybridomas, Elsevier, N.Y., 1981, 563-587, N/A.
Hanada, Tetsuro et al., Suppressive regulatory T cells and latent transforming growth factor-β-expressing macrophages are altered in the peritoneal fluid of patients with endometriosis, Reproductive Biology and Endocrinology, 2018, 1-8, 16:9.
Harlow, ED, Antibodies, A Laboratory Manual, 1988, 139-243, Chapter 6.
He, Yu-Fei et al., Blocking Programmed Death-1 Ligand-PD-1 Interactions by Local Gene Therapy Results in Enhancement of Antitumor Effect of Secondary Lymphoid Tissue Chemokine, J. Immunol., 2004, 4919-4928, 173.
Hinton, Paul R. et al., An Engineered Human IgG1 Antibody with Longer Serum Half-Life, Journal of Immunology, 2006, 346-356, 176.
Hinton, Paul R. et al., Engineered Human IgG Antibodies with Longer Serum Half-lives in Primates, The Journal of Biological Chemistry, 2004, 6213-6216, 279(8).
Holliger et al., Diabodies, Proc. Natl. Acad. Sci. USA, 1993, No. 14, pp. 6444-6448, 90.
Holliger et al., Engineered antibody fragments and the rise of single domains, Nat. Biotechnol., 2005, pp. 1126-1136, 23.
Hurwitz, Arthur A. et al., CTLA-4 blockade synergizes with tumor-derived granulocyte-macrophage colony-stimulating factor for treatment of an experimental mammary carcinoma, Proc. Natl. Acad. Sci. USA, 1998, 10067-10071, 95(17).
Huston, James S. et al., Protein engineering of antibody binding sites: Recovery of specific activity in an anti-digoxin single-chain Fv analogue produced in *Escherichia coli*. Proc Natl. Acad. Sci. USA, 1988, 5879-5883, 85.
Jespers, Guiding the selection of human antibodies from phage display repertoires to a single epitope of an antigen, Bio Technology, 1994, pp. 899-903, 12.
Jones, Peter T. et al., Replacing the complementarity-determining regions in a human antibody with those from a mouse, Nature, 1986, 522-525, 321.
Kabat, The Structural Basis of Antibody Complementarity, Adv. Prot. Chem., 1978, 1-75, 32.

(56) References Cited

OTHER PUBLICATIONS

Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.
Keinanen, Kari et al., Biosynthetic lipid-tagging of antibodies, FEBS Letters, 1994, 123-126, 346.
Killion, Jerald J. et al., Systemic Targeting of Liposome-Encapsulated Immunomodulators to Macrophages for Treatment of Cancer Metastasis, Immunomethods, 1994, 273-279, 4.
Kirkland et al., Analysis of the fine specificity and cross-reactivity of monoclonal anti-lipid A antibodies, J. Immunol., 1986, pp. 3614-3619, 137.
Kobayashi, Hiroyski et al., Tryptophan H33 plays an important role in pyrimidine (6-4) pyrimidone photoproduct binding by a high-affinity antibody, Protein Eng., 1999, 879-884, 12(10).
Kohler et al., Continuous Cultures of Fused Cells Secreting Antibody of Predefined Specificity, Nature, 1975, pp. 495-497, vol. 256.
Kohrt, Holbrook E. et al., CD137 stimulation enhances the antilymphoma activity of anti-CD20 antibodies, Blood, 2011, 2423-2432, 117.
Kostelny et al., Formation of a bispecific antibody by the use of leucine zippers, J. Immunol., 1992, pp. 1547-1553, 148.
Krishnamurthy, Rajesh et al., The Stability Factor: Importance in Formulation Development, Current Pharmaceutical Biotechnology, 2002, 361-371, 3.
Krissinel, Evgeny et al., Inference of Macromolecular Assemblies from Crystalline State, J Mol Biol, 2007, 774-797, 372.
Kugler, Alexander et al., Regression of human metastatic renal cell carcinoma after vaccination with tumor cell-dendritic cell hybrids, Nature Medicine, 2000, 332-336, 6.
Lazar, Greg A. et al., Engineered antibody Fc variants with enhanced effector function, Proc Natl Acad Sci USA, 2006, 4005-4010, 103(11).
Lee, Robert J. et al., Folate-mediated tumor cell targeting of liposome-entrapped doxorubicin in vitro, Biochimica et Biophysica Acta, 1995, 134-144, 1233.
Li, Huijuan et al., Optimization of humanized IgGs in glycoengineered *Pichia pastoris*, Nature Biotechnology, 2006, 210-215, 24(2).
Liénart, Stéphanie et al., Structural basis of latent TGF-beta1 presentation and activation by GARP on human regulatory T cells, Science, 2018, 952-956, 362.
Lonberg, Nils et al., Human Antibodies from Transgenic Mice, Intern. Rev. Immunol., 1995, 65-93, 13.
Marks et al., By passing Immunization, J. Mol. Biol., 1991, pp. 581-597, 222.
Marks et al., By-Passing Immunization: Building High Affinity Human Antibodies by Chain Shuffling, Bio/Technology, 1992, Issue No. 7, pp. 779-783, 10.
Marshall, R. D., Glycoproteins, Ann. Rev. Biochem., 1972, 673-702, 41.
Mascarenhas, John et al., Anti-transforming growth factor-b therapy in patients with myelofibrosis, Leukemia & Lymphoma, 2014, 450-452, 55.
McCafferty, John et al., Phage antibodies: filamentous phage displaying antibody variable domains, Nature, 1990, 552-554, 348.
Metelli, Alessandra et al., Immunoregulatory functions and the therapeutic implications of GARP-TGF-β in inflammation and cancer, Journal of Hematology & Oncology, 2018, 1-11, 11:24.
Mies, Anna et al., Activin Receptor II Ligand Traps and Their Therapeutic Potential in Myelodysplastic Syndromes with Ring Sideroblasts, Curr Hematol Malig Rep, 2016, 416-424, 11.
Mimura, Y. et al., The influence of glycosylation on the thermal stability and effector function expression of human IgG1-Fc: properties of a series of truncated glycoforms, Molecular Immunology, 2000, 697-706, 37.
Mokyr, Margalit B. et al., Realization of the Therapeutic Potential of CTLA-4 Blockade in Low-Dose Chemotherapy-treated Tumor-bearing Mice, Cancer Research, 1998, 5301-5304, 58.
Moldenhauer et al., Identity of HML-1 Antigen on Intestinal Intra Epithelial T Cells and of B-ly7 Antigen on Hairy Dell Leukemia, Scan. J Immunol., 1990, pp. 77-82, 32.
Morel et al., Monoclonal Antibodies to Bovine Serum Albumin: Affinity and Specificity Determinations, Mol. Immunol., 1988, Issue No. 1, pp. 7-15, 25.
Morrison, Sherie L. et al., Chimeric human antibody molecules: Mouse antigen-binding domains with human constant region domains, Proc. Natl. Acad. Sci. USA, 1984, 6851-6855, 81.
Murray, A. et al., Epitope Affinity Chromatography and Biophysical Studies of Monoclonal Antibodies and Recombinant Antibody Fragments, Journal of Chromatographic Science, 2002, 343-349, 40.
Muyldermans, Recognition of antigens by single-domain antibody fragments: the superfluous luxury of paired domains. Trends Biochem. Sci., 2001, 230-235, 26.
Myers, Eugene W. et al., Optimal alignments in linear space, Comput. Appl. Biosci., 1988, 11-17, 4(1).
Needleman, Saul. B. et al., A General Method Applicable to the Search for Similarities in the Amino Acid Sequence of Two Proteins, J. Mol. Biol., 1970, 443-453, 48.
Nestle, Frank O. et al., Vaccination of melanoma patients with peptide- or tumor lysate-pulsed dendritic cells, Nature Medicine, 1998, 328-332, 4.
Nett, Juergen H. et al., A combinatorial genetic library approach to target heterologous glycosylation enzymes to the endoplasmic reticulum or the Golgi apparatus of Pichia pastoris, Yeast, 2011, 237-252, 28.
Nicolaou, K. C. et al., Calicheamicin θ1: A Rationally Designed Molecule with Extremely Potent and Selective DNA Cleaving Properties and Apoptosis Inducing Activity, Angew. Chem. Int. Ed. Engl., 1994, 183-186, 33.
Nordstrom, Jeffrey L. et al., Anti-tumor activity and toxicokinetics analysis of MGAH22, an anti-HER2 monoclonal antibody with enhanced Fcgamma receptor binding properties, Breast Cancer Research, 2011, 1-14, 13.
Owais, Mohammad et al., Chloroquine Encapsulated in Malaria-Infected Erythrocyte-Specific Antibody-Bearing Liposomes Effectively Controls Chloroquine-Resistant Plasmodium berghei Infections in Mice, Antimicrobial Agents and Chemotherapy, 1995, 180-184, 39.
Padlan, Eduardo A., A Possible Procedure for Reducing the Immunogenicity of Antibody Variable Domains While Preserving Their Ligand-Binding Properties, Molecular Immunology, 1991, 489-498, 28(4/5).
Parekh, R. B. et al., Association of rheumatoid arthritis and primary osteoarthritis with changes in the glycosylation pattern of total serum IgG, Nature, 1985, 452-457, 316.
Pluckthun, A. et al., Antibodies from *Escherichia coli*, The Pharmacology of Monoclonal Antibodies, 1994, 269-315, Chapter 11.
Presta, L G et al., Humanization of an antibody directed against IgE, The Journal of Immunology, 1993, 2623-2632, 151.
Presta, Leonard G. et al., Antibody engineering, Curr. Op. Struct. Biol., 1993, 593-596, 2.
Presta, Leonard G. et al., Selection, design, and engineering of therapeutic antibodies, J. Allergy Clin. Immunol., 2005, 731-736, 116(4).
Presta, Leonard G., Engineering of therapeutic antibodies to minimize immunogenicity and optimize function, Advanced Drug Delivery Reviews, 2006, 640-656, 58.
Punjani, Ali et al., cryoSPARC: algorithms for rapid unsupervised cryo-EM structure determination, Nature Methods, 2017, 290-296, 14.
Qin, Yan et al., A Milieu Molecule for TGF-beta Required for Microglia Function in the Nervous System, Cell, 2018, 1-16, 174.
Raghunathan, Gopalan et al., Antigen-binding site anatomy and somatic mutations in antibodies that recognize different types of antigens, J. Mol. Recognit, 2012, 103-113, 25.
Ranade, Vasant V., Drug Delivery Systems. 1. Site-Specific Drug Delivery Using Liposomes as Carriers, J. Clin. Pharmacol., 1989, 685-694, 29.

(56) References Cited

OTHER PUBLICATIONS

Reichmann, Single domain antibodies: comparison of camel VH and camelised human VH domains, J. Immunol. Methods, 1999, 25-38, 231.
Reissner, K. J. et al., Deamidation and isoaspartate formation in proteins: unwanted alterations or surreptitious signals?, Cell. Mol. Life Sci., 2003, 1281-1295, 60.
Ren, Hongjun et al., A Biocompatible Condensation Reaction for the Labeling of Terminal Cysteine Residues on Proteins, Angew. Chem. Int. Ed., 2009, 9658-9662, 48.
Renaud, Jean-Paul et al., Cryo-EM in drug discovery: achievements, limitations and prospects, Nature Reviews / Drug Discovery, 2018, 471-492, 17.
Restifo, N. et al., Cancer Vaccines, Cancer: Principles & Practice of Oncology, Fifth Edition, 1997, 3023-3043, Chapter 61.
Riechmann, Lutz et al., Reshaping human antibodies for therapy, Nature, 1988, 323-329, 332.
Rifkin, Daniel B. et al., LTBPs in Biology and Medicine; LTBP Diseases, Matrix Biol., 2018, 90-99, 71-72.
Robertson, Ian B. et al., Unchaining the beast; insights from structural and evolutionary studies on TGFbeta secretion, sequestration, and activation, Cytokine Growth Factor Rev., 2013, 355-372, 24.
Roguska, Michael A. et al., Humanization of murine monoclonal antibodies through variable domain resurfacing, Proc. Natl. Acad Sci. USA, 1994, 969-973, 91.
Sarmay, Gabriella et al., Mapping and Comparison of the Interaction Sites on the Fc Region of IgG Responsible for Triggering Antibody Dependent Cellular Cytotoxicity (ADCC) Through Different Types of Human Fcγ Receptor, Molec. Immunol., 1992, 633-639, 29(5).
Scapin, Giovanna et al., Cryo-EM for Small Molecules Discovery, Design, Understanding, and Application, Cell Chemical Biology, 2018, 1318-1325, 25.
Schreier, Hans et al., Targeting of Liposomes to Cells Expressing CD4 Using Glycosylphosphatidylinositol-anchored gp120, Journal of Biological Chemistry, 1994, 9090-9098, 269.
Senter, Peter D, Potent antibody drug conjugates for cancer therapy, Curr. Opin. Chem. Biol., 2009, 235-244, 13.
Shields et al., Lack of fucose on human IgG1 N linked oligosaccharide improves binding to human Fc gamma RIII and antibody dependent cellular toxicity, J. Biol. Chem., 2002, pp. 26733-26740, 277.
Shields, Robert L. et al., High Resolution Mapping of the Bidning Site on Human IgG1 for FcγRI, FcγRII, FcγRIII, and ReRn and Design of IgG1 Variants with Improved Binding to the FcγR*, The Journal of Biological Chemistry, 2001, 6591-6604, 276(9).
Sims, M J et al., A humanized CD18 antibody can block function without cell destruction, The Journal of Immunology, 1993, 2296-2308, 151.
Songsivilai et al., Bispecific antibody: a tool for diagnosis and treatment of disease, Clin. Exp. Immunol., 1990, pp. 315-321, 79.
Spiro et al., Protein Glycosylation, Glycobiol., 2002, pp. 43R-56R, 12.
Stahli et al., Distinction of Epitopes by monoclonal antibodies, Methods in Enzymology, 1983, pp. 242-253, 9.
Stavenhagen, Jeffrey B. et al., Fc Optimization of Therapeutic Antibodies Enhances Their Ability to Kill Tumor Cells In vitro and Controls Tumor Expansion In vivo via Low-Affinity Activating Fcgamma Receptors, Cancer Research, 2007, 8882-8890, 67.
Strohl, William R., Optimization of Fc-mediated effector functions of monoclonal antibodies, Current Opinion in Biotechnology, 2009, 685-691, 20.
Studnicka, Gary M. et al., Human-engineered monoclonal antibodies retain full specific binding activity by preserving non-CDR complementaritymodulating residues, Protein Engineering, 1994, 805-814, 7(6).
Sunbul, Murat et al., Site specific protein labeling by enzymatic posttranslational modification, Organic & Biomolecular Chemistry, 2009, 3361-3371, 7.
Taki, Masumi et al., Transglutaminase-mediated N- and C-terminal fluorescein labeling of a protein can support the native activity of the modified protein, Protein Engineering, Design & Selection, 2004, 119-126, 17(2).
Tansey, Malu G. et al., The TNF superfamily in 2009: new pathways, new indications, and new drugs, Drug Discovery Today, 2009, 1082-1088, 14.
Taylor, E. Vogel et al., Native Chemical Ligation: SemiSynthesis of Post-translationally Modified Proteins and Biological Probes, Nucleic Acids and Molecular Biology, 2009, 65-96, 22.
Umana et al., Engineered glycoforms of an antineuroblastoma IgG1 with optimized antibody dependent cellular cytotoxic activity, Nature Biotechnology, 1999, pp. 176-180, 17.
Umezawa, F. et al., Liposome Targeting to Mouse Brain: Mannose as a Recognition Marker, Biochemical and Biophysical Research Communications, 1988, 1038-1044, 153.
Verhoeyen, Martine et al., Reshaping Human Antibodies: Grafting an Antilysozyme Activity, Science, 1988, 1534-1537, 239.
Wallace, Caroline H. et al., B lymphocytes confer immune tolerance via cell surface GARP-TGF-β complex, JCI Insight, 2018, 1-18, 3:e99863.
Wallick, Susan C. et al., Glycosylation of a VH Residue of a Monoclonal Antibody Against α (I-6) Dextran Increases Its Affinity for Antigen, J. Exp. Med., 1988, 1099-1109, 168.
Ward, E. Sally et al., Binding activities of a repertoire of single immunoglobulin variable domains secreted from *Escherichia coli*, Nature, 1989, 544 546, 341.
Waterhouse, Peter et al., Combinatorial infection and in vivo recombination: a strategy for making large phage antibody repertoires, Nuc. Acids. Res., 1993, 2265-2266, 21.
Xu, Xin et al., Transforming growth factor-β in stem cells and tissue homeostasis, Bone Research, 2018, 1-31, 6(2).
Veung, Yik Andy et al., Engineering Human IgG1 Affinity to Human Neonatal Fc Receptor: Impact of Affinity Improvement on Pharmacokinetics in Primates, J. Immunol., 2009, 7663-7671, 182.
Zhang, Congcong et al., Chimeric Antigen Receptor-Engineered NK-92 Cells: An Off-the-Shelf Cellular Therapeutic for Targeted Elimination of Cancer Cells and Induction of Protective Antitumor Immunity, Frontiers in Immunology, 2017, 1-17, 8.
Zheng, Liwei et al., Aberrant activation of latent transforming growth factor-β initiates the onset of temporomandibular joint osteoarthritis, Bone Research, 2018, 1-10, 6:26.

* cited by examiner

24E3

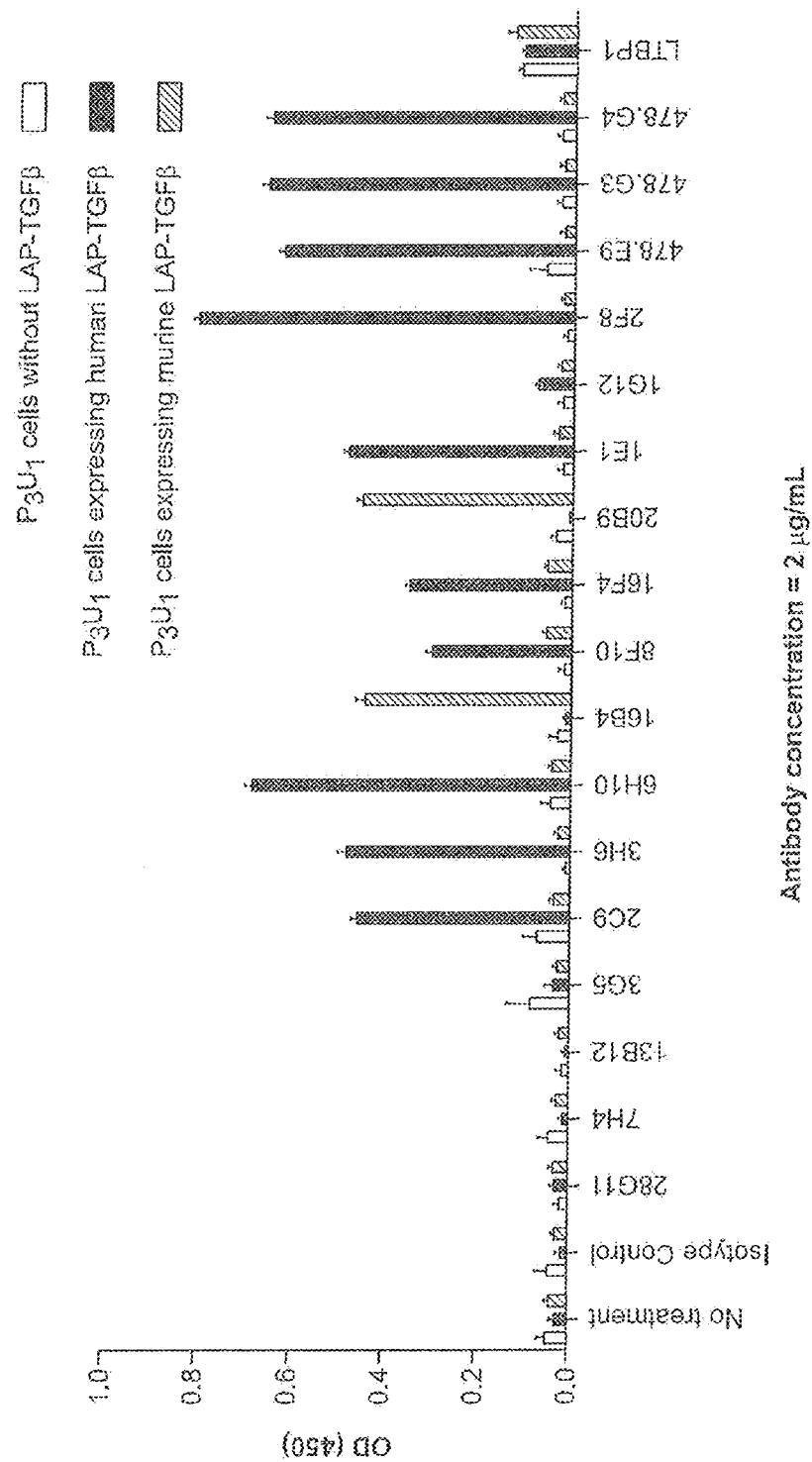

METHODS OF USING ANTI-LAP ANTIBODIES

CROSS-REFERENCE TO RELATED APPLICATIONS

This application claims priority to U.S. Provisional Patent Application No. 62/570,338, filed on Oct. 10, 2017. The contents of the aforementioned application are hereby incorporated by reference.

SEQUENCE LISTING

The instant application contains a Sequence Listing which has been submitted electronically in ASCII format and is hereby incorporated by reference in its entirety. Said ASCII copy, created on Jan. 31, 2019, is named TTJ_002_Sequence_Listing.txt and is 56,677 bytes in size.

BACKGROUND

TGFβ1 is synthesized as a pro-protein complex, in which the mature cytokine is caged within LAP, the latency associated peptide of TGFβ1. The LAP-TGFβ1 complex is disulfide bonded to one of five currently known anchor proteins: GARP, LRRC33, LTBP1, LTBP3, and LTBP4. These anchor proteins localize latent TGFβ1 in particular sites and on particular cells within the body:
 GARP is a transmembrane protein that anchors LAP-TGFβ1 to the surface of lymphocytes, most notably regulatory T cells. GARP is also expressed on platelets, B cells, NK cells, and endothelial cells and also governs LAP-TGFβ1 expression on those cell types.
 LRRC33 is a transmembrane protein that anchors LAP-TGFβ1 to the surface of myeloid cells, most notably macrophages, dendritic cells, and myeloid derived suppressor cells (MDSCs).
 LTBP1, LTBP3, and LTBP4 are secreted molecules that anchor LAP-TGFβ1 into the extracellular matrix.

Although LAP binding agents have been used in the art as tools to identify certain cell populations, little is known about LAP's relevance in disease states.

The location of the LAP-TGFβ1 complex is of critical biological and clinical importance because, once the mature TGFβ1 cytokine, which has a short half-life in solution, is released, it acts locally, either in an autocrine or near paracrine fashion. Therefore, the anchor proteins are a principal mechanism whereby latent TGFβ1 is staged in a specific location, awaiting the release of the potent mature cytokine to act on the local tissue.

LAP-TGFβ1 has different functions when expressed in different locations. For example, LAP-TGFβ1 anchored by LTBPs in the extracellular matrix is of primary importance for tissue homeostasis. In this regard, Xu et al. (Bone Research 2018; 6:2) noted that "the TGF-β complex is more like a molecular sensor that responds instantly to ECM perturbations through the release of an active ligand that exerts physiological effects at a cellular level, thus ensuring normal tissue homeostasis."

Alterations in LAP-TGFβ1 incorporation into the extracellular matrix are known to result in human disease. For example, deletion of LTBP-3 in both mice and humans results in similar defects in both bone and dental formation. LTBP-3 defects are also associated with the aortic dilation seen in Marfan syndrome (Rifkin et al., Matrix Biol 2018; 71-72:90-99). These effects are believed to be due to aberrant direct effects of TGFβ1 in the local extracellular matrix (Xu et al, Bone Research 2018; 6:2).

In contrast to anchor proteins that localize LAP-TGFβ1 to the extracellular matrix, LAP-TGFβ1 anchored by GARP is of primary importance for the immunosuppressive function of regulatory T cells (Edwards et al, Eur J Immunol 2016; 46:1480-9) and of suppressive B cell subpopulations (Wallace et al, JCI Insight 2018; 3:e99863). Some tumors have also been shown to express GARP, allowing them to locally express TGFβ and directly suppress the immune system in the tumor microenvironment and support their own growth (Metelli et al, Journal of Hematology & Oncology 2018; 11:24).

LAP-TGFβ1 anchored to myeloid cells is of primary importance for the immunosuppressive function of MDSCs (Zhang H et al, Frontiers in Immunology 2017; 8:1-15) and of M2 macrophages (Zhang et al, Oncotarget 2017; 8:99801-15). According to a recent study, myeloid cells have been shown to use the anchor protein LRRC33 to anchor latent TGFβ to the cell surface (Qin et al., Cell 2018; 174:1-16).

Recent developments in cancer therapy have focused on harnessing a patient's immune system by, e.g., activation of exhausted immune cell populations, vaccination, and removal of immunosuppressive cell populations. Given the ongoing need for improved strategies for targeting (and diagnosing) diseases such as cancer, novel agents and methods that are useful for these purposes are desired.

SUMMARY

The present invention is based on the discovery that antibodies specific for LAP exhibit diverse functional properties which can be selectively tailored to treat particular diseases (e.g., cancer), with maximal therapeutic benefit and minimal undesired effects.

Accordingly, described herein are anti-LAP antibodies that specifically bind to LAP-TGFβ1 expressed on cells (e.g., immunosuppressive cells such as suppressive T cells (e.g., regulatory T cells), M2 macrophages, and monocytic MDSCs), but not to LAP-TGFβ1 in the extracellular matrix. Notably, these antibodies are specific to the LAP-TGFβ1 complex itself, and can bind to recombinant LAP-TGFβ1 in the absence of cell- or extracellular matrix-associated anchor proteins (e.g., GARP, LRRC33, LTBP1, LTBP3, LTBP4). Thus, these antibodies differ from anti-LAP antibodies known in the art which bind to LAP-TGFβ1 both on cells and extracellular matrix, as well as anti-LAP antibodies which bind to LAP-TGFβ1 only in the presence of an anchor protein (e.g., GARP), for example, by binding an epitope that includes both a region from LAP and the anchor protein.

These anti-LAP antibodies provide the advantage of selectively inhibiting TGFβ1 activation on clinically relevant cell types (e.g., suppressive T cells (e.g., regulatory T cells), M2 macrophages, and monocytic MDSCs), without impacting the natural function/activation of LAP-TGFβ1 on extracellular matrix. For example, these anti-LAP antibodies can be used to treat diseases where immunosuppression is the primary function of TGFβ1 that leads to pathology. These antibodies will target immunosuppressive cells while sparing normal tissue homeostasis, and will not interfere with bone development. Moreover, these antibodies, unlike those that bind to anchor proteins (e.g., GARP, LRRC33), are able to inhibit TGFβ1 function across all immunosuppressive cell populations in the body, and are thus clinically beneficial. By binding specifically to LAP-TGFβ1, these antibodies also are safer to use than pan-TGFβ inhibitors. These antibodies may also be used to target LAP-TGFβ1 specifically on the surface of cells, engaging effector functions of an intact antibody (e.g., ADCC or ADCP), or localizing a bispecific or ADC to the relevant cell population, while sparing the extracellular matrix.

In one aspect, provided herein is an anti-LAP antibody which selectively inhibits TGFβ1 activation on immunosuppressive cells without inhibiting TGFβ1 activation on extracellular matrix for use in treating cancer, wherein the antibody (a) specifically binds to or has been determined to bind to LAP-TGFβ1 in the absence of an anchor protein, and (b) binds to or has been determined to bind to immunosuppressive cells but not to extracellular matrix.

Immunosuppressive cells include, for example, suppressive T cells (e.g., regulatory T cells, activated T cells), M2 macrophages, cancer cells expressing LAP-TGFβ1, and/or monocytic myeloid-derived suppressor cells.

In some embodiments, the antibody binds to human LAP-TGFβ1 (e.g., with a $K_D$ of 10 nM or less), but not to human LAP-TGFβ2 or human LAP-TGFβ3. In some embodiments, the antibody inhibits or is determined to inhibit TGFβ1 activation. In some embodiments, the antibody binds or is determined to bind to murine and/or human LAP-TGFβ1. In some embodiments, the antibody does not bind or is determined not to bind to free TGFβ1 or empty LAP. In some embodiments, the antibody binds or is determined to bind to LAP-TGFβ1 complexed with an anchor protein (e.g., GARP, LRRC33) on immunosuppressive cells, but does not bind to the anchor protein or to an epitope composed of residues of both LAP-TGFβ1 and the anchor protein. In some embodiments, the antibody does not bind or is determined to not to bind to LAP-TGFβ1 complexed with LTBP1, LTBP3 and/or LTBP4. In some embodiments, the antibody binds or is determined to bind to human LAP-TGFβ1 comprising K27C and Y75C mutations, but not human LAP-TGFβ1 comprising the Y74T mutation.

In some embodiments, the antibody binds or is determined to bind to both GARP-positive immunosuppressive cells and GARP-negative immunosuppressive cells. In some embodiments, the antibody binds or is determined to bind to platelets, but does not cause platelet aggregation or platelet degranulation.

In some embodiments, the antibody is an IgG1, IgG2, IgG3, IgG4, IgD, IgA, IgE, or IgM antibody, or variant thereof. In some embodiments, the antibody is a chimeric, humanized, or human antibody.

In another aspect, provided herein is a bispecific antibody comprising a first binding region with a specificity for LAP of an anti-LAP antibody described herein, and a second binding region which binds to another antigen, e.g., a tumor-associated antigen, CD4, CD8, CD45, CD56, CD14, CD16, CD19, CD11b, CD25, CD20, CD22, CD30, CD38, CD114, CD23, CD163, CD206, CD203, CD200R or CD39.

In another aspect, provided herein is an immunoconjugate comprising an anti-LAP antibody described herein linked to a detectable moiety, a binding moiety, a labeling moiety, or a biologically active moiety.

In another aspect, provided herein is a pharmaceutical composition comprising an anti-LAP antibody described herein and a pharmaceutically acceptable carrier. In some embodiments, the composition comprises one or more additional therapeutic agents, such as an anti-cancer agent, a chemotherapeutic agent, an immunomodulatory agent (e.g., an immunostimulatory agent or immunosuppressive agent), an anti-inflammatory agent, and an immune checkpoint blocker (e.g., an anti-PD-1 antibody, an anti-PD-L1 antibody, an anti-LAG-3 antibody, an anti-CTLA-4 antibody, an anti-TIGIT antibody, and an anti-TIM3 antibody).

In another aspect, provided herein are kits comprising an anti-LAP antibody described herein and instructions for use.

In another aspect, provided herein is a method of selectively inhibiting TGFβ1 activation on immunosuppressive cells, but not TGFβ1 activation on extracellular matrix, comprising administering to the subject an anti-LAP antibody which selectively inhibits TGFβ1 activation on immunosuppressive cells without inhibiting TGFβ activation on extracellular matrix, wherein the antibody specifically binds to LAP-TGFβ1 in the absence of an anchor protein and binds to immunosuppressive cells but not to extracellular matrix.

In another aspect, provided herein is a method of treating cancer comprising administering to a subject in need thereof a therapeutically effective amount of an anti-LAP antibody which selectively inhibits TGFβ1 activation on immunosuppressive cells without inhibiting TGFβ1 activation on extracellular matrix, wherein the antibody specifically binds to LAP-TGFβ1 in the absence of an anchor protein and binds to immunosuppressive cells but not to extracellular matrix.

In some embodiments, the cancer is characterized by abnormal TGFβ activity. In some embodiments, the cancer is associated with fibrosis. In some embodiments, the cancer is associated with infiltration of CD4+ regulatory T cells, CD8+ regulatory T cells, regulatory B cells, myeloid-derived suppressor cells, tumor-associated macrophages, cancer-associated fibroblasts, and/or innate lymphoid cells.

In some embodiments, the cancer is breast cancer, bladder cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, or myelodysplastic syndromes.

In some embodiments of the methods described above, the immunosuppressive cells are suppressive T cells (e.g., regulatory T cells, activated T cells), M2 macrophages, and/or monocytic myeloid-derived suppressor cells. In some embodiments, the antibody does not cause platelets to degranulate or aggregate.

In another aspect, provided herein is a method of treating cancer associated with an increased number of circulating platelets or an increased platelet to lymphocyte ratio comprising administering to a subject in need thereof an effective amount of an antibody which specifically binds to LAP, wherein the antibody binds to platelets but does not cause platelet aggregation or platelet degranulation.

In some embodiments of the methods described above, one or more additional therapies is administered, for example, radiation therapy, chemotherapy, an immune checkpoint inhibitor (e.g., an anti-PD-1 antibody, an anti-PD-L1 antibody, an anti-LAG-3 antibody, an anti-CTLA-4 antibody, an anti-TIGIT antibody, and an anti-TIM3 antibody), immunostimulatory therapy, immunosuppressive therapy, cell therapy, and a therapeutic agent (e.g., anti-cancer agent, a chemotherapeutic agent, an immunosuppressive agent, an immunomodulatory agent, and an anti-inflammatory agent).

In another aspect, provided herein is a method of detecting LAP comprising contacting a sample (e.g., a biological sample) with an anti-LAP antibody described herein, and detecting the complex.

In another aspect, provided herein is a method of diagnosing a cancer associated with regulatory T cell infiltration comprising contacting a biological sample from a patient afflicted with the cancer with an anti-LAP antibody described herein, wherein positive staining with the antibody indicates the cancer is associated with regulatory T cell infiltration.

In another aspect, provided herein is a method of diagnosing a cancer associated with GARP-negative suppressive cells comprising contacting a biological sample from a patient afflicted with the cancer with an anti-LAP antibody described herein which binds to GARP-negative suppressive cells, wherein positive staining with the antibody and negative staining with an anti-GARP antibody indicates the cancer is associated with GARP-negative suppressive cells.

In another aspect, provided herein is a method of selecting a patient afflicted with cancer for treatment with an anti-LAP antibody described herein comprising contacting a biological sample from the patient with the antibody, wherein positive staining with the antibody indicates the cancer is amenable to treatment with the antibody.

In another aspect, provided herein is a method of determining the response of a patient afflicted with cancer to treatment with an anti-LAP antibody described herein comprising contacting a biological sample from the patient with the antibody, wherein reduced staining with the antibody indicates the cancer is responding to treatment with the antibody.

In another aspect, provided herein is a method of selecting an anti-LAP antibody among a plurality of antibodies for the treatment of cancer or fibrosis comprising:

(a) determining whether one or more anti-LAP antibodies selectively inhibit TGFβ1 activation on immunosuppressive cells without inhibiting TGFβ1 activation on extracellular matrix;

(b) determining whether one or more anti-LAP antibodies specifically bind to LAP-TGFβ1 in the absence of an anchor protein;

(c) determining whether one or more anti-LAP antibodies specifically binds to immunosuppressive cells but not to extracellular matrix; and (d) selecting an antibody that (i) selectively inhibits TGFβ1 activation on immunosuppressive cells without inhibiting TGFβ1 activation on extracellular matrix; (ii) specifically binds to LAP-TGFβ1 in the absence of an anchor protein, and (iii) binds to immunosuppressive cells but not to extracellular matrix.

Also provided herein are uses of the anti-LAP antibodies described herein for selectively inhibiting TGFβ1 activation on immunosuppressive cells, but not TGFβ1 activation on extracellular matrix; treating cancer; diagnosing a cancer (e.g., a cancer associated with regulatory T cell infiltration or GARP-negative suppressive cells); selecting a patient afflicted with cancer; and determining the response of a patient afflicted with cancer to treatment with the anti-LAP antibodies described herein. Also provide are uses of the anti-LAP antibodies described herein for preparing a medicament to selectively inhibit TGFβ1 activation on immunosuppressive cells, but not TGFβ1 activation on extracellular matrix, and to treat cancer.

BRIEF DESCRIPTION OF THE FIGURES

FIGS. 12A and 12B are graphs showing binding of the indicated anti-LAP antibodies to extracellular matrix (ECM) deposited by P3U1 cells. Three types of cells were tested: P3U1 cells without LAP-TGFβ, P3U1 cells expressing human LAP-TGFβ1, and P3U1 cells expressing murine LAP-TGFβ1. Antibodies were used at a concentration of 2 µg/mL.

FIG. 30A (anti-PD-1 antibody alone), FIG. 30B (28G11_IgG2a+anti-PD-1 antibody), FIG. 30C (IgG2a isotype control), FIG. 30D (anti-PD-1 antibody alone), FIG. 30E (16B4_IgG2a alone), and FIG. 30F (16B4_IgG2a+anti-PD-1 antibody). The anti-PD-1 antibody was a rat anti-PD-1 RMP1-14-IgG2a antibody.

DETAILED DESCRIPTION

Figure 1:
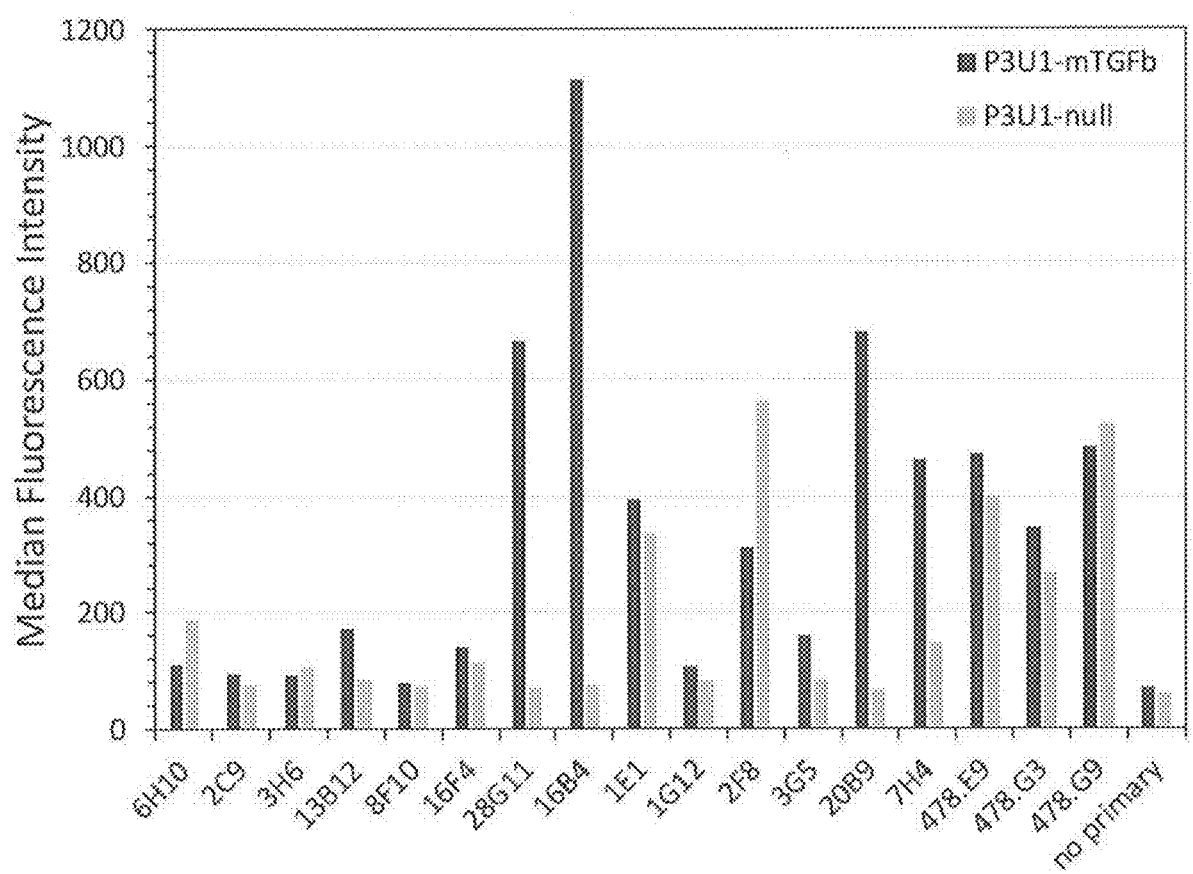
FIG. 1 is a graph depicting the binding of the indicated anti-LAP antibodies to murine LAP-TGFβ1 expressing P3U1 cells.

Provided herein are isolated antibodies that specifically bind to LAP-TGFβ1 and are characterized by combinations of therapeutically advantageous functional features (e.g., binding to LAP-TGFβ1 on immunosuppressive cells but not in the extracellular matrix). Also provided herein are methods of making such antibodies, bispecific antibodies, immunoconjugates, pharmaceutical compositions, and methods of treating various diseases/disorders using such antibodies.

Definitions

In order for the following detailed description to be readily understood, certain terms are first defined. Additional definitions are provided throughout.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising," "consisting essentially of," and "consisting of" may be optionally replaced with either of the other two terms, thus describing alternative aspects of the scope of the subject matter. The invention illustratively described herein suitably may be practiced in the absence of any element or elements, limitation or limitations which is not specifically disclosed herein.

As used herein, the singular forms "a," "an," and "the" include plural referents unless the context clearly dictates otherwise. The use of "or" or "and" means "and/or" unless stated otherwise. Furthermore, use of the term "including" as well as other forms, such as "include," "includes," and "included," is not limiting.

The term "about" as used herein when referring to a measurable value such as an amount, a temporal duration and the like, encompasses variations of up to ±10% from the specified value. Unless otherwise indicated, all numbers expressing quantities of ingredients, properties such as molecular weight, reaction conditions, etc., used herein are to be understood as being modified by the term "about".

One of ordinary skill in the art will appreciate that starting materials, biological and chemical materials, biological and chemical reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this disclosure.

As used herein, "Latency associated peptide" or "LAP" refers to the amino-terminal domain of the human TGFβ1 precursor peptide and has the amino acid sequence set forth in SEQ ID NO: 1. "LAP-TGFβ1" is used herein to refer to the human TGFβ1 precursor peptide (which includes the TGFβ1 cytokine) and has the amino acid sequence of SEQ ID NO: 2. LAP can also refer to the amino-terminal domains of the human TGFβ2 precursor peptide (LAP domain: SEQ ID NO: 3, LAP-TGFβ2: SEQ ID NO: 4) and human TGFβ3 precursor peptide (LAP domain: SEQ ID NO: 5, LAP-TGFβ2: SEQ ID NO: 6), as well as their counterparts from other species (e.g., murine TGFβ1 precursor peptide (murine LAP domain: SEQ ID NO: 7; murine LAP-TGFβ1: SEQ ID NO: 8), murine TGFβ2 precursor peptide (murine LAP domain: SEQ ID NO: 9; murine LAP-TGFβ2: SEQ ID NO: 10), and murine TGFβ3 precursor peptide (murine LAP domain: SEQ ID NO: 11; murine LAP-TGFβ3: SEQ ID NO: 12)) and other naturally occurring allelic, splice variants, and processed forms thereof. LAP is synthesized as a complex with TGFβ. LAP in the absence of mature TGFβ is referred to as "empty LAP." Unless otherwise specified, "empty LAP" as used herein refers to LAP originating from the N-terminal domain of human TGFβ1.

As used herein "free TGFβ1" refers to the mature TGFβ1 cytokine, i.e., TGFβ1 that is not complexed with LAP.

As used herein, "anchor protein" refers to a protein that anchors LAP-TGFβ to a cell surface or to the extracellular matrix. Exemplary anchor proteins include GARP, LRRC33, LTBP1, LTBP3, and LTBP4. GARP and LRRC33 are proteins that anchor LAP-TGFβ to the surface of cells, and LTBP1, LTBP3, and LTBP4 are proteins that anchor LAP-TGFβ to the extracellular matrix.

The term "antibody" as used herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens.

The phrase "antigen-binding portion" of an antibody, as used herein, refers to one or more fragments of an antibody that retain the ability to specifically bind to an antigen (e.g., human and/or murine LAP). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "multispecific antibody" is an antibody (e.g., bispecific antibodies, tri-specific antibodies) that recognizes two or more different antigens or epitopes.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Bifunctional antibodies include, for example, heterodimeric antibody conjugates (e.g., two antibodies or antibody fragments joined together with each having different specificities), antibody/cell surface-binding molecule conjugates (e.g., an antibody conjugated to a non-antibody molecule such as a receptor), and hybrid antibodies (e.g., an antibody having binding sites for two different antigens).

The term "monoclonal antibody," as used herein, refers to an antibody that displays a single binding specificity and affinity for a particular epitope or a composition of antibodies in which all antibodies display a single binding specificity and affinity for a particular epitope.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A "human" antibody refers to an antibody having variable regions in which both the framework and CDR regions are derived from human germline immunoglobulin sequences. Furthermore, if the antibody contains a constant region, the constant region also is derived from human germline immunoglobulin sequences. Also encompassed are antibodies derived from human germline immunoglobulin sequences that include normal somatic hypermutations which alter the germline immunoglobulin sequences relative to the wild-type germline immunoglobulin sequences.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one or more species and the constant regions are derived from another species, such as an antibody in which the variable regions are derived from a mouse antibody and the constant regions are derived from a human antibody.

An "isolated antibody," as used herein, is intended to refer to an antibody which is substantially free of other antibodies having different antigenic specificities.

An "effector function" refers to the interaction of an antibody Fc region with an Fc receptor or ligand, or a biochemical event that results therefrom. Exemplary "effector functions" include Clq binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) using a predetermined antigen as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The term "cross-reacts," as used herein, refers to the ability of an antibody described herein to bind to LAP-TGFβ1 from a different species. For example, an antibody described herein that binds human LAP-TGFβ1 may also bind another species of LAP-TGFβ1 (e.g., murine LAP-TGFβ1). Cross-reactivity may be measured by detecting a specific reactivity with purified antigen in binding assays (e.g., SPR, ELISA, bio-layer interferometry) or binding to, or otherwise functionally interacting with, cells physiologically expressing LAP-TGFβ1 (e.g., HT1080 cells overexpressing LAP-TGFβ1). Methods for determining cross-reactivity include standard binding assays as described herein, for example, by bio-layer interferometry or flow cytometric techniques.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

The term "$k_{assoc}$" or "$k_a$", as used herein, refers to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system, flow cytometry, bio-layer interferometry, and Scatchard analysis.

The term "EC50" in the context of an in vitro or in vivo assay using an antibody refers to the concentration of an antibody that induces a response that is 50% of the maximal response, i.e., halfway between the maximal response and the baseline.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody fragments (e.g., $V_H$, $V_L$, CDR3), is intended to refer to a nucleic acid molecule in which the nucleotide sequences are essentially free of other genomic nucleotide sequences, e.g., those encoding antibodies that bind antigens other than LAP, which other sequences may naturally flank the nucleic acid in human genomic DNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and may be a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "inhibition" as used herein, refers to any statistically significant decrease in biological activity, including partial and full blocking of the activity. For example, "inhibition" can refer to a statistically significant decrease of about 10%, 20%, 30%, 40%, 50%, 60%, 70%, 80%, 90%, 95%, 96%, 97%, 98%, 99%, or 100% in biological activity.

As used herein, "TGFβ1 activation" refers to the release of the mature cytokine TGFβ1 from the latent complex made up of LAP and TGFβ1. There are many mechanisms known to induce TGFβ1 activation (see Robertson I B, Rifkin D B. Unchaining the beast; insights from structural and evolutionary studies on TGFβ1 secretion, sequestration, and activation. Cytokine Growth Factor Rev. 2013 August; 24(4): 355-72). The mature cytokine can be detected using a specific ELISA or similar detection methodology or through the use of a reporter cell line that expresses a TGFβ receptor.

For example, as used herein, the term "inhibits TGFβ1 activation" includes any measurable decrease in TGFβ1 activation, e.g., an inhibition of TGFβ1 activation by at least about 10%, for example, at least about 20%, at least about 30%, at least about 40%, at least about 50%, at least about 60%, at least about 70%, at least about 80%, at least about 90%, at least about 99%, or about 100%, relative to a control (e.g., a control antibody). The inhibition may be specific to a single mechanism of TGFβ1 activation or may be generalizable to all mechanisms of TGFβ1 activation. As used herein, the term "inhibits TGFβ1 activation" includes inhibition of at least one activation mechanism.

As used herein, the term "enhances TGFβ1 activation" includes any measurable increase in TGFβ1 activation, e.g., an increase of TGFβ1 activation by at least about 10%, for example, at least about 20%, at least about 30%, at least about 40%, at least about 50%, at least about 60%, at least about 70%, at least about 80%, at least about 90%, at least about 100%, or at least about 200% or more, relative to a control (e.g., a control antibody). The enhancement may be specific to a single mechanism of TGFβ1 activation or may be generalizable to all mechanisms of TGFβ1 activation. As used herein, the term "enhances TGFβ1 activation" includes enhancement of at least one activation mechanism. The term "enhances TGFβ1 activation" also includes activation by the antibody itself in the absence of any additional activating mechanism.

The terms "treat," "treating," and "treatment," as used herein, refer to therapeutic or preventative measures described herein. The methods of "treatment" employ administration to a subject with a tumor or cancer or a subject who is predisposed to having such a disease or disorder, an anti-LAP antibody (e.g., anti-human LAP antibody) described herein, in order to prevent, cure, delay, reduce the severity of, or ameliorate one or more symptoms of the disease or disorder or recurring disease or disorder, or in order to prolong the survival of a subject beyond that expected in the absence of such treatment.

"Immunotherapy" refers to the treatment of a subject afflicted with, or at risk of contracting or suffering a recurrence of, a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

As used herein, "immune cell" refers to the subset of blood cells known as white blood cells, which include mononuclear cells such as lymphocytes, monocytes, macrophages, and granulocytes.

As used herein, "immunosuppressive cell" refers to a cell that contributes to or promotes an immunosuppressive tumor microenvironment. The presence of a population of immunosuppressive cells in a tumor microenvironment increases the tumor's resistance to an immune response, resulting in tumor protection, tumor escape, and/or tumor metastasis. Unless countered in some manner, these immunosuppressive cells can decrease the efficacy of immune-mediated anti-cancer treatments. Exemplary immunosuppressive cells include cancer-associated fibroblasts, myeloid-derived suppressor cells, regulatory T cells (Tregs), tumor cells expressing LAP, and immunosuppressive macrophages. These cell types can be identified by one skilled in the art using, e.g., flow cytometry to identify markers of Tregs (e.g, CD4, FoxP3, CD127, and CD25), macrophages (e.g., CSF-IR, CD203, CD206, CD163, IL-10, and TGFβ), cancer associated fibroblasts (e.g., alpha smooth muscle actin, fibroblast activation protein, tenascin-C, periostin, NG2, vimentin, desmin, PDGFR alpha and beta, FSP-1, ASPN, and STC1), and myeloid-derived suppressor cells (e.g., CD11b, CD33, CD14, or CD15, and low levels of HLA DR). It is understood that immunosuppressive cells may also be important in suppressing the immune system in other disease states.

As used herein, "suppressive T cells" refer to T cells that contribute to or promote an immunosuppressive microenvironment. Exemplary suppressive T cells include CD4+ regulatory T cells and CD8+ regulatory T cells. Such cells can be identified by one skilled in the art using, e.g., flow cytometry to identify markers such as FoxP3, LAP or Helios.

As used herein, "regulatory T cells" or "Tregs" refer to immunosuppressive cells that generally suppress or down-regulate induction and proliferation of effector T cells. Tregs generally express the biomarkers CD4, FOXP3, and CD25 and are thought to be derived from the same lineage as naïve CD4 cells.

"T effector" ("$T_{eff}$") cells refers to T cells (e.g., CD4+ and CD8+ T cells) with cytolytic activities as well as T helper (Th) cells, which secrete inflammatory cytokines and activate and direct other immune cells, but does not include regulatory T cells (Treg cells).

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "cancer" refers to a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

As used herein, "autoimmune disease" describes a disease state or syndrome whereby a subject's body produces a dysfunctional immune response against the subject's own body components, with adverse effects.

As used herein, "fibrosis" refers to disorders or disease states that are caused by or accompanied by the abnormal deposition of extracellular matrix (i.e., not formation of fibrous tissue in normal organ in tissue). Fibrosis is characterized by excessive accumulation of extracellular matrix in the affected tissue that often results in destruction of its normal architecture and causes significant organ dysfunction. Although fibrotic conditions in various organs have diverse etiologies, fibrosis typically results from chronic persistent inflammation induced by a variety of stimuli, such as chronic infections, ischemia, allergic and autoimmune reactions, chemical insults or radiation injury (from Biernacka, 2011). Fibrosis notably affects the heart, liver, kidney, lung and skin and is also a central feature in many cancers.

As used herein, "cell therapy" refers to a method of treatment involving the administration of live cells (e.g., CAR T cells, NK cells).

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, "adjunctive" or "combined" administration (coadministration) includes simultaneous administration of the compounds in the same or different dosage form, or separate administration of the compounds (e.g., sequential administration). Thus, a first antibody, e.g., an anti-LAP antibody, and a second, third, or more antibodies or agents can be simultaneously administered in a single formulation. Alternatively, the first and second (or more) antibodies and/or agents can be formulated for separate administration and are administered concurrently or sequentially. "Combination" therapy, as used herein, means administration of two or more therapeutic agents in a coordinated fashion, and includes, but is not limited to, concurrent dosing. Specifically, combination therapy encompasses both co-administration (e.g. administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. (See, e.g., Kohrt et al. (2011) *Blood* 117:2423). For example, the anti-LAP antibody can be administered first followed by (e.g., immediately followed by) the administration of a second antibody (e.g., an anti-PD-1 antibody), or vice versa. In one embodiment, the anti-LAP antibody is administered prior to administration of the second antibody. In another embodiment, the anti-LAP antibody is administered, for example, within about 30 minutes of the second antibody. Such concurrent or sequential administration preferably results in both antibodies being simultaneously present in treated patients The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The administration of effective amounts of the anti-LAP antibody alone, or anti-LAP antibody combined with an immune checkpoint blocker (e.g., an anti-PD-1 antibody), according to any of the methods provided herein, can result in at least one therapeutic effect, including, for example, reduced tumor growth or size, reduced number of metastatic lesions appearing over time, complete remission, partial remission, or stable disease. For example, the methods of treatment produce a comparable clinical benefit rate (CBR=complete remission (CR)+partial remission (PR)+ stable disease (SD) lasting ≥6 months) better than that achieved without administration of the anti-LAP antibody, or than that achieved with administration of any one of the combined antibodies, e.g., the improvement of clinical benefit rate is about 20% 20%, 30%, 40%, 50%, 60%, 70%, 80% or more.

By way of example, for the treatment of tumors, a therapeutically effective amount or dosage of the drug inhibits tumor cell growth by at least about 20%, by at least about 30% by at least about 40%, by at least about 50%, by at least about 60%, by at least above 70%, by at least about 80%, or by at least about 90% relative to untreated subjects. In some embodiments, a therapeutically effective amount or dosage of the drug completely inhibits cell growth or tumor growth, i.e., inhibits cell growth or tumor growth by 100%. The ability of a compound, including an antibody, to inhibit tumor growth can be evaluated using the assays described herein. Alternatively, this property of a composition can be evaluated by examining the ability of the compound to inhibit cell growth; such inhibition can be measured in vitro by assays known to the skilled practitioner.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

The term "sample" refers to tissue, body fluid, or a cell (or a fraction of any of the foregoing) taken from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained (e.g., leukemic cells from blood) and appropriately prepared. Other samples, including urine, tears, serum, plasma, cerebrospinal fluid, feces, sputum, cell extracts etc. can also be useful for particular cancers.

As used herein, "and/or" is to be taken as specific disclosure of each of the two specified features or components with or without the other. Thus, the term "and/or" as used in a phrase such as "A and/or B" includes "A and B," "A or B," "A" alone, and "B" alone. Likewise, the term "and/or" as used in a phrase such as "A, B, and/or C" encompasses each of the following: A, B, and C; A, B, or C; A or C; A or B; B or C; A and C; A and B; B and C; A alone; B alone; and C alone.

As used herein, the terms "ug" and "uM" are used interchangeably with "µg" and "µM," respectively.

Various aspects described herein are described in further detail in the following subsections.

I. Anti-LAP Antibodies

Provided herein are anti-LAP antibodies which are characterized by particular therapeutically advantageous functional features or properties, and thus can be used to treat various diseases/disorders.

In one aspect, provided herein are monoclonal antibodies which specifically bind to LAP-TGFβ1 on cells (e.g., immune cells, such as immunosuppressive cells) without binding to LAP-TGFβ1 in the extracellular matrix. These antibodies are useful in the treatment of, e.g., cancer.

In another aspect, provided herein are monoclonal antibodies which have been determined to specifically bind to LAP-TGFβ1 on cells (e.g., immune cells, such as immunosuppressive cells) without binding to LAP-TGFβ1 in the extracellular matrix.

In another aspect, provided herein are anti-LAP antibodies which selectively inhibit TGFβ1 activation on immunosuppressive cells without inhibiting TGFβ1 activation on extracellular matrix for use in treating cancer, wherein the antibody (a) specifically binds to LAP-TGFβ1 in the absence of an anchor protein, and (b) binds to immunosuppressive cells but not to extracellular matrix.

In another aspect, provided herein are anti-LAP antibodies which selectively inhibit TGFβ1 activation on immunosuppressive cells without inhibiting TGFβ1 activation on extracellular matrix for use in treating cancer, wherein the antibody has been determined to (a) specifically bind to LAP-TGFβ1 in the absence of an anchor protein, and (b) bind to immunosuppressive cells but not to extracellular matrix.

In some embodiments, the anti-LAP antibodies bind to (or are determined to bind to) LAP-TGFβ1 (e.g., recombinant LAP-TGFβ1), for example, with a $K_D$ of 10 nM or less, such as 1 nM or less, as assessed by, e.g., bio-layer interferometry.

In some embodiments, the anti-LAP antibodies do not bind to LAP-TGFβ2 and LAP-TGFβ3, as assessed by, e.g., flow cytometry using cells that overexpress LAP-TGFβ2 or LAP-TGFβ3, or bio-layer interferometry with recombinant LAP-TGFβ2 or LAP-TGFβ3. For example, in some embodiments, the anti-LAP antibodies bind to LAP-TGFβ2 or LAP-TGFβ3 with a signal or affinity that is not significantly above the signal seen with a control antibody (e.g., isotype control) or the signal seen in the absence of anti-LAP antibody (e.g., as described in Example 2).

In some embodiments, the anti-LAP antibodies inhibit (or are determined to inhibit) TGFβ1 activation, as assessed by, e.g., ELISA detection of free TGFβ1 in a culture of P3U1 cells overexpressing LAP-TGFβ1. In some embodiments, the anti-LAP antibodies inhibit (or are determined to inhibit) TGFβ1 activation by about 50% or more, e.g., by about 60% or more, by about 70% or more, by about 80% or more, or by about 90% or more, as assessed by, e.g., ELISA detection of free TGFβ1 in a culture of P3U1 cells overexpressing LAP-TGFβ1 (e.g., as described in Example 3).

In some embodiments, the anti-LAP antibodies do not inhibit (or are determined to not inhibit) TGFβ activation in the ECM, as assessed by, e.g., ELISA detection of free TGFβ1 in an assay combining a source of LAP-TGFβ1 in the ECM (e.g., as described in Example 4) with MMP-2, MMP-9, thrombospondin or cells expressing αVβ6 or αVβ8 integrins.

In some embodiments, the anti-LAP antibodies bind to (or are determined to bind to) murine and human LAP-TGFβ1, as assessed by, e.g., flow cytometry of activated immune cell populations.

In some embodiments, the anti-LAP antibodies do not bind to (or are determined not to bind to) free TGFβ1 (i.e., TGFβ1 without LAP), as assessed by, e.g., ELISA. In some embodiments, the anti-LAP antibodies do not bind to (or are determined not to bind to) empty LAP (i.e., LAP that is not complexed with TGFβ1), as assessed by, e.g., bio-layer interferometry. For example, in these embodiments, the anti-LAP antibodies bind to free TGFβ1 or empty with a signal or affinity that is not significantly above the signal seen with a control antibody (e.g., isotype control) or the signal seen in the absence of anti-LAP antibody (e.g., as described in Example 2).

In some embodiments, the anti-LAP antibodies bind to (or are determined to bind to) LAP-TGFβ1 complexed with an anchor protein on immunosuppressive cells, but does not bind to the anchor protein (e.g., GARP, LRRC33) or to an epitope composed of residues of both LAP-TGFβ1 and the anchor protein (e.g., GARP, LRRC33). Accordingly, in some embodiments, the anti-LAP antibodies do not bind to GARP. In some embodiments, the anti-LAP antibodies do not bind to LRRC33. In some embodiments, the anti-LAP antibodies do not bind to an epitope composed of residues of both LAP-TGFβ1 and GARP. In some embodiments, the anti-LAP antibodies do not bind to an epitope composed of residues of both LAP-TGFβ1 and LRRC33. In some embodiments, the anti-LAP antibodies do not bind to LTBP1. In some embodiments, the anti-LAP antibodies do not bind to LTBP3. In some embodiments, the anti-LAP antibodies do not bind to LTBP4. In some embodiments, the anti-LAP antibodies do not recognize a protease cleavage site in human TGFβ1 (e.g., the protease cleavage site between the arginine residue at position 58 and the leucine residue at position 59, between the lysine residue at position 56 and the leucine residue at position 57, between the alanine residue at position 79 and the leucine residue at position 80, between the arginine residue at position 85 and the aspartic acid residue at position 86, between the lysine residue at position 106 and the glutamic acid residue at position 107, and/or between the alanine residue at position 76 and the valine residue at position 77). In some embodiments, the anti-LAP antibodies do not recognize the edge of a protease cleavage site in human TGFβ1 (e.g., the cutting edge at the leucine residue at position 59, the arginine residue at position 58, the leucine residue at position 57, the lysine residue at position 56, the leucine residue at position 80, the alanine residue at position 79, the aspartic acid residue at position 85, the glutamic acid residue at position 107, the lysine residue at position 106, the valine residue at position 77, and/or the alanine residue at position 76).

In some embodiments, the anti-LAP antibodies bind to (or are determined to bind to) human LAP-TGFβ1 comprising K27C and Y75C mutations. In another embodiment, the anti-LAP antibodies do not bind to (or are determined not to bind to) human LAP-TGFβ1 comprising a Y74T mutation. In another embodiment, the anti-LAP antibodies bind to (or are determined to bind to) human LAP-TGFβ1 comprising K27C and Y75C mutations, but not to LAP-TGFβ1 comprising a Y74T mutation.

As discussed above, the anti-LAP antibodies bind to (or are determined to bind to) LAP-TGFβ1 on cells, such as immune cells, e.g., immunosuppressive cells. Immunosuppressive cells include, but are not limited to, suppressive T cells (e.g., regulatory T cells, activated T cells, suppressive CD8+ T cells), M1 macrophages, M2 macrophages, dendritic cells, regulatory B cells, granulocytic MDSCs, and/or monocytic MDSCs, as assessed, e.g., by flow cytometry. In some embodiments, the anti-LAP antibodies bind to cells other than immune cells, such as tumor cells, fibroblasts (including cancer associated fibroblasts), mesenchymal stromal cells, mesenchymal stem cells, hemopoietic stem cells, non-myelinating schwann cells, myofibroblasts, endothelial cells, platelets, megakaryocytes, pericytes, and/or hepatic stellate cells. In some embodiments, the anti-LAP antibodies bind to LAP-TGFβ1 on both immune cells (e.g., immunosuppressive cells) and non-immune cells.

In some embodiments, the anti-LAP antibodies bind to (or are determined to bind to) LAP-TGFβ1 on GARP-positive cells (e.g., GARP-positive immunosuppressive cells). In some embodiments, the anti-LAP antibodies bind to (or are determined to bind to) LAP-TGFβ1 on GARP-negative cells (e.g., GARP-negative immunosuppressive cells). In some embodiments, the anti-LAP antibodies bind to (or are determined to bind to) LAP-TGFβ1 on both GARP-positive and GARP-negative cells (e.g., immunosuppressive cells), as assessed, e.g., by flow cytometry.

In some embodiments, the anti-LAP antibodies reduce the endogenous expression of CD73. In some embodiments, the anti-LAP antibodies inhibit the increase of CD73 expression caused by a treatment, e.g., radiation.

In some embodiments, the anti-LAP antibodies bind to LAP-TGFβ1 expressed on cells (e.g., human or murine LAP-TGFβ1 expressed on, e.g., P3U1 cells) with an $EC_{50}$ of 1000 ng/ml or less, 500 ng/ml or less, 200 ng/ml or less, 150 ng/ml or less, 100 ng/ml or less, 50 ng/ml or less, 25 ng/ml or less, 10 ng/ml or less, 5 ng/ml or less, 2 ng/ml or less, 1 ng/ml to 200 ng/ml, 1 ng/ml to 150 ng/ml, 1 ng/ml to 100 ng/ml, 1 ng/ml to 50 ng/ml, 1 ng/ml to 25 ng/ml, 1 ng/ml to 10 ng/ml, or 1 ng/ml to 5 ng/ml, as measured by flow cytometry (e.g., as described in Example 1).

Preferably, the anti-LAP antibodies bind to soluble LAP-TGFβ1 with high affinity, for example, with a $K_D$ of $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-7}$ M to $10^{-7}$ M, $10^{-10}$ M to $10^{-7}$ M, or $10^{-9}$ M to $10^{-7}$ M, as measured by bio-layer interferometry.

The binding of anti-LAP antibodies to LAP-TGFβ1 may also be defined using quantitative immunofluorescence by flow cytometry, which allows the number of antibody molecules bound per cell to be quantified. Accordingly, in some embodiments, the number of anti-LAP antibodies bound to a cell that also expresses GARP may be equal to the number of anti-GARP antibodies bound to that cell, or may be at least 80%, at least 50%, at least 20%, at least 10%, at least 5%, at least 1%, or at least 0.1% of the number of anti-GARP antibodies bound to that cell. In some embodiments, the number of LAP-TGFβ1 molecules expressed per cell may be quantified using quantitative immunofluorescence using an anti-LAP antibody of a group that detects the majority of LAP molecules; examples of such antibodies include 2F8, 2C9, 16B4 and the anti-LAP monoclonal antibody #27232 (R&D Systems). In some embodiments, the number of anti-LAP antibodies bound to the cell may be equal to the number of LAP molecules on the cell, or may be at least 80%, at least 50%, at least 20%, at least 10%, at least 5%, at least 1% or at least 0.1% of the number of LAP molecules expressed on that cell.

In some embodiments, the anti-LAP antibodies inhibit TGFβ1 activation by, for example, 10% or more, for example, 20% or more, 30% or more, 40% or more, 50% or more, 60% or more, 70% or more, 80% or more, 90% or more, or 95% or more, relative to a control (e.g., a control antibody), as measured by ELISA (e.g., as described in Example 3).

In some embodiments, the anti-LAP antibodies do not bind to LAP-TGFβ1 in the extracellular matrix, for example, as assessed by ELISA, wherein the O.D. signal for antibody binding is not significantly above the signal seen in the absence of the anti-LAP antibody or the signal seen with a control antibody (e.g., isotype control) (e.g., as described in Example 4).

In some embodiments, the anti-LAP antibodies bind to LAP-TGFβ1 on platelets. For example, in some embodiments, at least 5%, at least 10%, at least 20% or at least 50% of platelets can be detected by binding of the anti-LAP antibody (e.g. display a signal above that seen with an isotype control antibody) by flow cytometry (e.g., as described in Example 5).

In some embodiments, the anti-LAP antibodies bind to platelets but do not cause platelet aggregation or platelet degranulation.

In some embodiments, the anti-LAP antibodies bind to immune cells, e.g., suppressive T cells (e.g., regulatory T cells), M2 macrophages, monocytic MDSCs, CD11b-positive cells, and/or dendritic cells. For example, in some embodiments, at least 0.5%, at least 1%, at least 2%, at least 5%, at least 7%, at least 10%, at least 20%, or at least 50% of these cell types can be detected by binding of the anti-LAP antibody (e.g. display a signal above that seen with an isotype control antibody) by flow cytometry (e.g., as described in Examples 6-8). In some embodiments, the anti-LAP antibodies are considered to bind to these cell types if they bind ≥2 standard deviations above isotype control.

In some embodiments, the anti-LAP antibodies bind to GARP-negative leukocytes. For example, in some embodiments, at least 0.5%, at least 1%, at least 2%, at least 5%, at least 7%, at least 10%, at least 20% or at least 50% of GARP-negative leukocytes can be detected by binding of the anti-LAP antibody (e.g. display a signal above that seen with an isotype control antibody) by flow cytometry (e.g., as described in Example 8).

In some embodiments, the anti-LAP antibodies described herein bind to murine LAP-TGFβ1. In some embodiments, the anti-LAP antibodies described herein bind to human LAP-TGFβ1. In some embodiments, the anti-LAP antibodies described herein bind to both murine and human LAP-TGFβ1. Binding of anti-LAP antibodies to murine and/or human LAP-TGFβ1 can be assessed by flow cytometry using cells that overexpress murine or human LAP-TGFβ1 (e.g., as described in Example 2).

An antibody that exhibits one or more of the functional properties described above (e.g., biochemical, immunochemical, cellular, physiological or other biological activities), as determined using methods known to the art and described herein, will be understood to relate to a statistically significant difference in the particular activity relative to that seen in the absence of the antibody (e.g., or when a control antibody of irrelevant specificity is present). Preferably, the anti-LAP antibody-induced increases in a measured parameter effects a statistically significant increase by at least 10% of the measured parameter, more preferably by at least 20%, 30%, 40%, 50%, 60%, 70%, 80%, 90%, 95%, or 100% (i.e., 2 fold), 3 fold, 5 fold or 10 fold. Conversely, anti-LAP antibody-induced decreases in a measured parameter (e.g., TGFβ1 activation) effects a statistically significant decrease by at least 10%, 20%, 30%, 40%, 50%, 60%, 70%, 80%, 90%, 95%, 97%, 98%, 99%, or 100%.

In some embodiments, a VH domain of the anti-LAP antibodies described herein is linked to a constant domain to form a heavy chain, e.g., a full-length heavy chain. In some embodiments, the VH domain is linked to the constant domain of a human IgG (e.g., IgG1, IgG2, IgG3, or IgG4), IgD, IgA, IgE, or IgM, or variants thereof (e.g., variants comprising Fc regions with altered effector function). Similarly, a VL domain of the anti-LAP antibodies described herein described herein is linked to a constant domain to form a light chain, e.g., a full-length light chain.

Antibodies disclosed herein include all known forms of antibodies and other protein scaffolds with antibody-like properties. For example, the antibody can be a human antibody, a humanized antibody, a bispecific antibody, an immunoconjugate, a chimeric antibody, or a protein scaffold with antibody-like properties, such as fibronectin or ankyrin repeats.

In some embodiments, the antibody is a bispecific antibody comprising a first and second binding region, wherein the first binding region comprises the binding specificity (e.g., antigen-binding region) of an anti-LAP antibody described herein, and a second binding region that does not bind to LAP. In some embodiments, the second binding region binds to a protein that is not expressed on platelets.

The antibody also can be a Fab, Fab'$_2$, scFv, AFFIBODY, avimer, nanobody, single chain antibody, or a domain antibody. The antibody also can have any isotype, including any of the following isotypes: IgG1, IgG2, IgG3, IgG4, IgM, IgA1, IgA2, IgAsec, IgD, and IgE. Full-length antibodies can be prepared from $V_H$ and $V_L$ sequences using standard recombinant DNA techniques and nucleic acid encoding the desired constant region sequences to be operatively linked to the variable region sequences.

In certain embodiments, the antibodies described herein may have effector function or may have reduced or no effector function. In certain embodiments, anti-LAP antibodies comprise an effectorless or mostly effectorless Fc, e.g., IgG2 or IgG4. Generally, variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

In some embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, modifications can be made in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc substitutions therein, e.g. of the specific Fc region positions identified herein.

A variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other embodiments, the Fc region may be modified to make it more compatible with a selected host cell. For example, one may remove the PA sequence near the N-terminus of a typical native Fc region, which may be recognized by a digestive enzyme in *E. coli* such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the C1q binding site, may be removed from the Fc region. For example, one may delete or substitute the EKK sequence of human IgG1. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region may be modified to increase antibody dependent cellular cytotoxicity (ADCC) and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in Kabat (WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317, 091; 8,101,720; PCT Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

Fc variants that enhance affinity for an inhibitory receptor FcγRllb may also be used. Such variants may provide an Fc fusion protein with immunomodulatory activities related to FcγRllb$^+$ cells, including for example B cells and monocytes. In one embodiment, the Fc variants provide selectively enhanced affinity to FcγRllb relative to one or more activating receptors. Modifications for altering binding to FcγRllb include one or more modifications at a position selected from the group consisting of 234, 235, 236, 237, 239, 266, 267, 268, 325, 326, 327, 328, and 332, according to the EU index. Exemplary substitutions for enhancing FcγRllb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRllb include 235Y/267E, 236D/267E, 239D/ 268D, 239D/267E, 267E/268D, 267E/268E, and 267E/328F.

In certain embodiments, the antibody is modified to increase its biological half-life. Various approaches are possible. For example, this may be done by increasing the binding affinity of the Fc region for FcRn. For example, one or more of more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276 (9):6591-6604), 252F, 252T, 252Y, 252W, 254T, 256S, 256R, 256Q, 256E, 256D, 256T, 309P, 311 1 S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671. In certain embodiments, hybrid IgG isotypes with particular biological characteristics may be used. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 4221, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A.

Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, 5239D/I332E, S239D/I332E/A330L, L235V/F243L/R292P/Y3001J P396L, and M428L/N434S.

When using an IgG4 constant domain, it is usually preferable to include the substitution S228P, which mimics the hinge sequence in IgG1 and thereby stabilizes IgG4 molecules.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Another modification of the antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0 154 316 by Nishimura et al. and EP 0 401 384 by Ishikawa et al.

The affinities and binding properties of an Fc region for its ligand may be determined by a variety of in vitro assay methods (biochemical or immunological based assays) known in the art including, but not limited to, equilibrium methods (e.g., enzyme-linked immunosorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis, and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

Additional Therapeutic Anti-LAP Antibodies

Also disclosed herein are anti-LAP antibodies which bind to LAP-TGFβ1 and exhibit two or more of the following features:
(a) inhibits TGFβ1 activation;
(b) binds to extracellular matrix;
(c) binds to regulatory T cells; and
(d) binds to GARP-negative leukocytes.

Examples of such anti-LAP antibodies include antibodies which inhibit TGFβ activation and bind to extracellular matrix. These antibodies are useful for treating, e.g., cancer and fibrosis.

Also disclosed herein are anti-LAP antibodies which exhibit two or more of the following features:
(a) inhibits TGFβ activation;
(b) does not bind to extracellular matrix; and
(c) binds to GARP-negative leukocytes.

Examples of such anti-LAP antibodies include antibodies which inhibit TGFβ1 activation, do not bind to extracellular matrix, bind to platelets, bind to regulatory T cells, and bind to GARP-negative leukocytes. These antibodies are useful for treating, e.g., cancer.

Also disclosed herein are anti-LAP antibodies which exhibit two or more of the following features:
(a) does not inhibit or enhance TGFβ1 activation;
(b) binds to extracellular matrix;
(c) binds to regulatory T cells; and
(d) does not bind to GARP-negative leukocytes.

Examples of such anti-LAP antibodies include antibodies which do not inhibit or enhance TGFβ1 activation. These anti-LAP antibodies serve to selectively target the antibody to LAP on the surface of cells or in the extracellular matrix, and are useful for e.g., engaging T cell activation, for delivering a toxin or similar agent via ADC or for targeting a bi-specific antibody. As such, these antibodies are useful for treating, e.g., cancer or other diseases where it is desirable to reduce the number of immunosuppressive cells or to deliver an antibody to diseased tissues. These antibodies may exhibit similar effects on TGFβ1 activation as a control antibody (e.g., an isotype control antibody), e.g., within ±10% of the effect of the control antibody, bind to extracellular matrix, bind to platelets, and not bind to regulatory T cells. An anti-LAP antibody is considered to bind to LAP-TGFβ1 in the extracellular matrix when the signal for binding has an O.D. significantly above the signal seen in the absence of the anti-LAP antibody in an ELISA.

Also disclosed herein are anti-LAP antibodies which enhance TGFβ activation. These anti-LAP antibodies are useful for treating, e.g., autoimmune diseases. Such antibodies may also be useful for administering to patients undergoing transplantation by enhancing Tregs and development of tolerance to the graft, which may also help speed healing. These anti-LAP antibodies may increase TGFβ activation, e.g., by at least about 20%, for example, at least about 30%, at least about 40%, at least about 50%, at least about 60%, at least about 70%, at least about 80%, at least about 90%, at least about 100%, or at least about 200%, relative to a control (e.g., a control antibody), as measured by ELISA.

II. Nucleic Acid Molecules

Also provided herein are nucleic acid molecules that encode the anti-LAP antibodies described herein. The nucleic acids may be present in whole cells, in a cell lysate, or in a partially purified or substantially pure form. A nucleic acid described herein can be, for example, DNA or RNA and may or may not contain intronic sequences. In certain embodiments, the nucleic acid is a cDNA molecule. The nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, provided herein are nucleic acid molecules that encode the VH and/or VL sequences, or heavy and/or light chain sequences, of any of the anti-LAP antibodies described herein. Host cells comprising the nucleotide sequences (e.g., nucleic acid molecules) described herein are encompassed herein. Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

Also provided herein are nucleic acid molecules with conservative substitutions that do not alter the resulting amino acid sequence upon translation of the nucleic acid molecule.

III. Methods of Production

Anti-LAP antibodies with particular functional features, for example, the anti-LAP antibodies described herein, can be generated using art-recognized methods.

Polyclonal antibodies to LAP-TGFβ1 (e.g., human LAP-TGFβ1) can be produced by various procedures well known in the art. For example, LAP-TGFβ1 or fragments thereof comprising one or more of the LAP-TGFβ1 ligand interaction sites, can be administered to various host animals including, but not limited to, rabbits, mice, rats, etc. to induce the production of sera containing polyclonal antibodies specific for the protein. Polyclonal antibodies are preferably raised in animals by multiple subcutaneous (sc) or intraperitoneal (ip) injections of the relevant antigen and an adjuvant. It can be useful to conjugate the antigen to a protein that is immunogenic in the species to be immunized, e.g., keyhole limpet hemocyanin, serum albumin, bovine thyroglobulin, or soy-bean trypsin inhibitor using a bifunctional or derivatizing agent, for example, maleimidobenzoyl sulfosuccinimide ester (conjugation through cysteine residues), N-hydroxy-succinimide (through lysine residues), glutaraldehyde, succinic anhydride, $SOCl_2$, or $R_1N=C=NR$, where R and R1 are different alkyl groups. Various other adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Suitable adjuvants are also well known to one of skill in the art.

Monoclonal antibodies can be prepared using a wide variety of techniques known in the art including the use of hybridoma, recombinant, and phage display technologies, or a combination thereof. Various methods for making monoclonal antibodies described herein are available in the art. For example, the monoclonal antibodies can be made using the hybridoma method first described by Kohler et al, Nature, 256:495 (1975), or any later developments thereof, or by recombinant DNA methods (U.S. Pat. No. 4,816,567). For example, monoclonal antibodies can be produced using hybridoma techniques including those known in the art and taught, for example, in Harlow et al, Antibodies: A Laboratory Manual, (Cold Spring Harbor Laboratory Press, 2nd ed., 1988); Hammer-ling, et al, in: Monoclonal Antibodies and T-Cell Hybridomas 563-681 (Elsevier, N.Y., 1981) (said references incorporated by reference in their entireties). Methods for producing and screening for specific antibodies using hybridoma technology are routine and well known in the art. In another example, antibodies useful in the methods and compositions described herein can also be generated using various phage display methods known in the art, such as isolation from antibody phage libraries generated using the techniques described in McCafferty et al, Nature, 348: 552-554 (1990). Clackson et al., Nature, 352:624-628 (1991) and Marks et al, J. Mol. Biol, 222:581-597 (1991) describe the isolation of murine and human antibodies, respectively, using phage libraries. Subsequent publications describe the production of high affinity (nM range) human antibodies by chain shuffling (Marks et al, Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Human antibodies can be made by a variety of methods known in the art, including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, the contents of which are herein incorporated by reference in their entireties. Human antibodies can also be produced using transgenic mice which express human immunoglobulin genes, and upon immunization are capable of producing a full repertoire of human antibodies in the absence of endogenous immunoglobulin production. For an overview of this technology for producing human antibodies, see, Lonberg and Huszar, 1995, Int. Rev. Immunol. 13:65-93. Phage display technology (McCafferty et al, Nature 348:552-553 (1990)) also can be used to produce human antibodies and antibody fragments in vitro, from immunoglobulin variable (V) domain gene repertoires from unimmunized donors. Human antibodies can also be generated by in vitro activated B cells (see U.S. Pat. Nos. 5,567,610 and 5,229,275, the contents of which are herein incorporated by reference in their entireties). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al, 1994, Bio/technology 12:899-903).

Chimeric antibodies can be prepared based on the sequence of a murine monoclonal antibody. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.).

Humanized forms of anti-LAP antibodies (e.g., humanized forms of mouse anti-LAP antibodies) are chimeric antibodies which contain minimal sequence derived from non-human immunoglobulin. Humanized antibodies are typically human immunoglobulins (recipient antibody) in which residues from a CDR or hypervariable region of the recipient are replaced by residues from a CDR or hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin consensus sequence. The humanized antibody optionally also will comprise at least a portion of an immunoglobulin constant region (Fc), typically that of a human immunoglobulin. For further details, see Jones et al, Nature 321:522-525 (1986); Riechmann et al, Nature 332:323-329 (1988); and Presta, Curr. Op. Struct. Biol. 2:593-596 (1992).

The framework and CDR regions of a humanized antibody need not correspond precisely to the parental sequences, e.g., the donor antibody CDR or the consensus framework can be mutagenized by substitution, insertion and/or deletion of at least one amino acid residue so that the CDR or framework residue at that site does not correspond exactly to either the donor antibody or the consensus framework. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see e.g., Winnaker, From Genes to Clones (Veriagsgesellschaft, Weinheim, Germany 1987). In a family of immunoglobulins, each position in the consensus sequence is occupied by the amino acid occurring most frequently at that position in the family. Where two amino acids occur equally frequently, either can be included in the consensus sequence. As used herein, "Vernier zone" refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and can impact on the structure of CDRs and the affinity of the antibody. Human immunoglobulin (Ig) sequences that can be used as a recipient are well known in the art.

Framework residues in the human framework regions can be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, including, but not limited to, those described in Jones et al., Nature 321:522 (1986); Verhoeyen et al., Science 239: 1534 (1988), Sims et al., J. Immunol. 151: 2296 (1993); Chothia and Lesk, J. Mol. Biol. 196:901 (1987), Carter et al, Proc. Natl. Acad. Sci. U.S.A. 89:4285 (1992); Presta et al, J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530, 101, 5,585,089, 5,225,539; 4,816,567, each entirely incorporated herein by reference.

The anti-LAP antibodies generated using the methods described above can be tested for desired functions, such as particular binding specificities, binding affinities, targeted cell populations, using methods known in the art and described in the Examples, for example, art-recognized protein-protein binding assays, biochemical screening assays, immunoassays, and cell-based assays. Exemplary assays include, but are not limited to, immunoprecipitation or by an in vitro binding assay, such as radioimmunoassay (RIA), FACS, enzyme-linked immunoabsorbent assay (ELISA), bio-layer interferometry (e.g., ForteBio assay), and Scatchard analysis.

IV. Multispecific Antibodies

Multispecific antibodies (e.g., bispecific antibodies) provided herein include at least one binding region for a particular epitope on LAP-TGFβ1 (e.g., human LAP-TGFβ1) as described herein, and at least one other binding region (e.g., a cancer antigen). Multispecific antibodies can be prepared as full length antibodies or antibody fragments (e.g. F(ab')$_2$ antibodies).

Methods for making multispecific antibodies are well known in the art (see, e.g., WO 05117973 and WO 06091209). For example, production of full length multispecific antibodies can be based on the coexpression of two paired immunoglobulin heavy chain-light chains, where the two chains have different specificities. Various techniques for making and isolating multispecific antibody fragments directly from recombinant cell culture have also been described. For example, multispecific antibodies can be produced using leucine zippers. Another strategy for making multispecific antibody fragments by the use of single-chain Fv (sFv) dimers has also been reported.

Examples of suitable multispecific molecule platforms include, but are not limited to, Dual Targeting (DT)-Ig (GSK/Domantis), Two-in-one Antibody (Genentech), Cross-linked Mabs (Karmanos Cancer Center), Fcab and mAb$^2$ (F-Star), CovX-body (CovX/Pfizer), Dual Variable Domain (DVD)-Ig (Abbott), IgG-like Bispecific (ImClone/Eli Lilly), Ts2Ab (Medlmmune/AZ) and BsAb (Zymogenetics), HERCULES (Biogen Idee), TvAb (Roche), ScFv/Fc Fusions, SCORPION (Emergent BioSolutions/Trubion, Zymogenetics/BMS), Dual Affinity Retargeting Technology (Fc-DART) (MacroGenics), Dual(ScFv)2-Fab (National Research Center for Antibody Medicine—China), F(ab)2 (Medarex/AMGEN), Dual-Action or Bis-Fab (Genentech), Dock-and-Lock (DNL) (ImmunoMedics), Bivalent Bispecific (Biotecnol), SEED (EMD Serono), mAb$^2$ (F-star), Fab-Fv (UCB-Celltech), Bispecific T Cell Engager (BiTE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), COMBODY (Epigen Biotech), dual targeting nanobodies (Ablynx), and Fc-engineered IgG1 (Xencor).

In a particular embodiment, the multispecific antibody comprises a first antibody (or binding portion thereof) which binds to LAP-TGFβ1 derivatized or linked to another functional molecule, e.g., another peptide or protein (e.g., another antibody or ligand for a receptor) to generate a multispecific molecule that binds to LAP-TGFβ1 and a non-LAP target molecule. An antibody may be derivatized or linked to more than one other functional molecule to generate multispecific molecules that bind to more than two different binding sites and/or target molecules. To create a multispecific molecule, an antibody disclosed herein can be functionally linked (e.g., by chemical coupling, genetic fusion, noncovalent association or otherwise) to one or more other binding molecules, such as another antibody, antibody fragment, peptide, receptor, or binding mimetic, such that a multispecific molecule results.

Accordingly, multispecific molecules, for example, bispecific antibodies and bifunctional antibodies, comprising at least one first binding specificity for a particular epitope on LAP-TGFβ1 (e.g., human LAP-TGFβ1) and a second binding specificity for a second target are contemplated. In some embodiments, the second target is the second binding region specifically binds to a tumor-associated antigen. Tumor-associated antigens are well known in the art. Exemplary tumor-associated antigens include, but are not limited to, AFP, ALK, BAGE proteins, β-catenin, brc-abl, BRCA1, BORIS, CA9, carbonic anhydrase IX, caspase-8, CCR5, CD19, CD20, CD30, CDK4, CEA, cyclin-B1, CYPB 1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, STn, survivin, TAG-72, TGF-β, TMPRSS2, Tn, TRP-1, TRP-2, tyrosinase, and uroplakin-3.

In some embodiments, the second binding region of the bispecific antibody specifically binds to CD4, CD8, CD45, CD56, CD14, CD16, CD19, CD20, CD25, CD38, CD11b, CD22, CD30, CD39, CD114, CD23, CD163, CD206, CD203, CD200R, PD-1, PD-L1, PD-L2, CTLA-4, IDO, TIM-3, LAG-3, TIGIT, PVR, PVRL2, B7H3, B7H4, CSF-1R, VISTA, KIR, OX-40, GITR, 4-1BB, CD40, CD40L, CD27/CD70, CD28, ICOS, CD3, CD56, NKG2DA, NKG2DB, NKG2DC, NKG2DD, NKG2DF, NKG2DH, CD94, NKP46, NKP30, CD33, CD73, CD47, LILRB 1, CD91, calreticulin, CD122, GARP, LRRC33, LAP2, LAP3, TGFβ1, TGFβ2, TGFβ3, FAP, and stanniocalcin 1. In some embodiments, the second binding region has agonistic properties when binding to a target, e.g., a TNF family member agonist, OX40 ligand, CD137 ligand, CD137 agonist, STING agonist, GITR agonist, ICOS agonist, and CD28 agonist.

In some embodiments, the antibody is a trispecific antibody comprising a first, second, and third binding region, wherein the first binding region comprises the binding specificity (e.g., antigen-binding region) of an anti-LAP antibody described herein, and the second and third binding regions bind to two different targets (or different epitopes on the same target), for example, the targets described above.

In some embodiments, the antibody is a bifunctional antibody comprising an anti-LAP antibody described herein and a receptor molecule (i.e., a receptor trap construct such as a TGFβ superfamily ligand receptor (e.g., ActRIIB and variants thereof) or VEGFR).

In one embodiment, the multispecific molecules comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

The multispecific molecules can be prepared by conjugating the constituent binding specificities, e.g., the anti-FcR and anti-LAP binding specificities, using methods known in the art. For example, each binding specificity of the multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the multispecific molecule is a mAb×mAb, mAb×Fab, Fab×F (ab')$_2$ or ligand x Fab fusion protein. A multispecific molecule can be a single chain molecule comprising one single chain antibody and a binding determinant, or a single chain bispecific molecule comprising two binding determinants. Multispecific molecules may comprise at least two single chain molecules. Methods for preparing multispecific molecules are described for example in U.S. Pat. Nos. 5,260, 203; 5,455,030; 4,881,175; 5,132,405; 5,091,513; 5,476, 786; 5,013,653; 5,258,498; and 5,482,858.

Binding of the multispecific molecules to their specific targets can be confirmed by, for example, enzyme-linked immunosorbent assay (ELISA), radioimmunoassay (RIA), FACS analysis, bioassay (e.g., growth inhibition), or western blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA). The radioactive isotope can be detected by such means as the use of a α γ-β counter or a scintillation counter or by autoradiography.

V. Immunoconjugates

Immunoconjugates comprising the anti-LAP antibodies described herein can be formed by conjugating the antibodies to another therapeutic agent to form, e.g., an antibody-drug conjugate (ADC). Suitable agents include, for example, a cytotoxic agent (e.g., a chemotherapeutic agent), a toxin (e.g. an enzymatically active toxin of bacterial, fungal, plant or animal origin, or fragments thereof), and/or a radioactive isotope (i.e., a radioconjugate). Additional suitable agents include, e.g., antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In some embodiments, ADCs with the anti-LAP antibodies described herein (e.g., conjugated to a cytotoxic agent) that bind to immunosuppressive cells (e.g., regulatory T cells) can be used to deplete the immunosuppressive cells from, e.g., the tumor microenvironment.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, neomycin, and the tricothecenes. Additional examples of cytotoxins or cytotoxic agents include, e.g., taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In the ADC, the antibody and therapeutic agent preferably are conjugated via a cleavable linker such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO: 48), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference. A variety of radionuclides are available for the production of radioconjugated anti-LAP antibodies. Examples include $^{212}$Bi, $^{131}$I, $^{131}$In, $^{90}$Y and $^{186}$Re.

Immunoconjugates can also be used to modify a given biological response, and the drug moiety is not to be construed as limited to classical chemical therapeutic agents. For example, the drug moiety may be a protein or polypeptide possessing a desired biological activity (e.g., lymphokines, tumor necrosis factor, IFNγ, growth factors).

Immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

The anti-LAP antibodies described herein also are used for diagnostic purposes. Such antibodies can be conjugated to an appropriate detectable agent to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels, isotopes, chromophores, fluorescent markers, luminescent markers, metal labels (e.g., for CyTOF, imaging mass cytometry), phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro {1,2-dioxetane-3, 2'-(5'-chloro)tricyclo {3.3.1.1 3,7}decan}-4-yl) phenyl phosphate (CSPD), as well as CDP and CDP-Star® or other luminescent substrates well-known to those in the art, for example the chelates of suitable lanthanides such as Terbium (III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Preferably, conjugation methods result in linkages which are substantially (or nearly) non-immunogenic, e.g., peptide- (i.e. amide-), sulfide-, (sterically hindered), disulfide-, hydrazone-, and ether linkages. These linkages are nearly non-immunogenic and show reasonable stability within serum (see e.g. Senter, P. D., Curr. Opin. Chem. Biol. 13 (2009) 235-244; WO 2009/059278; WO 95/17886).

Depending on the biochemical nature of the moiety and the antibody, different conjugation strategies can be employed. In case the moiety is naturally occurring or recombinant of between 50 to 500 amino acids, there are standard procedures in text books describing the chemistry for synthesis of protein conjugates, which can be easily followed by the skilled artisan (see e.g. Hackenberger, C. P. R., and Schwarzer, D., Angew. Chem. Int. Ed. Engl. 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, J., Org. Biomol. Chem. 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., ChemBioChem. 10 (2009) 425-427). It is also possible to obtain a desired amino acid modification by utilizing the specific enzymatic reactivity of certain enzymes with a natural amino acid in a given sequence context (see, e.g., Taki, M. et al., Prot. Eng. Des. Sel. 17 (2004) 119-126; Gautier, A. et al. Chem. Biol. 15 (2008) 128-136; and Protease-catalyzed formation of C—N bonds is used by Bordusa, F., Highlights in Bioorganic Chemistry (2004) 389-403). Site specific reaction and covalent coupling can also be achieved by the selective reaction of terminal amino acids with appropriate modifying reagents. The reactivity of an N-terminal cysteine with benzonitrils (see Ren, H. et al., Angew. Chem. Int. Ed. Engl. 48 (2009) 9658-9662) can be used to achieve a site-specific covalent coupling. Native chemical ligation can also rely on C-terminal cysteine residues (Taylor, E. Vogel; Imperiali, B, Nucleic Acids and Molecular Biology (2009), 22 (Protein Engineering), 65-96).

The moiety may also be a synthetic peptide or peptide mimic. In case a polypeptide is chemically synthesized, amino acids with orthogonal chemical reactivity can be incorporated during such synthesis (see e.g. de Graaf, A. J. et al., Bioconjug. Chem. 20 (2009) 1281-1295). Since a great variety of orthogonal functional groups is at stake and can be introduced into a synthetic peptide, conjugation of such peptide to a linker is standard chemistry.

In some embodiments, the moiety attached to an anti-LAP antibody is selected from the group consisting of a detectable moiety, binding moiety, a labeling moiety, and a biologically active moiety.

VI. Assays

Following the production and isolation of antibodies, they can be tested for desired properties, e.g., those described herein, using a variety of assays known in the art.

In one embodiment, the antibodies are tested for specific binding to LAP-TGFβ1 (e.g., human LAP-TGFβ1). Methods for analyzing binding affinity, cross-reactivity, and binding kinetics of various anti-LAP antibodies include standard assays known in the art, for example, Biacore™ surface plasmon resonance (SPR) analysis using a Biacore™ 2000 SPR instrument (Biacore AB, Uppsala, Sweden) or bio-layer interferometry (e.g., ForteBio assay), as described in the Examples. In some embodiments, the LAP used in the binding assay is complexed with TGFβ1. In some embodiments, the LAP used in the binding assay is not complexed with TGFβ1. In some embodiments, the LAP used in the binding assay is complexed with TGFβ1 and GARP or a fragment of GARP or LRRC33 or a fragment of LRRC33. In some embodiments the LAP used in the binding assay is complexed with TGFβ1 and LTBP (e.g., LTBP1, LTBP3, or LTBP4) or a fragment of LTBP.

In one embodiment, the antibodies are tested for the ability to bind to cells that have been transfected with LAP-TGFβ1. In some embodiments the cells have also been transfected with GARP or LRRC33.

In one embodiment, the antibodies are screened for the ability to bind to the surface of beads that have been coated with LAP.

In one embodiment, the antibodies are screened for the ability to bind to LAP on cells expressing a heparin sulfate glycoprotein such as syndecan-4. For example, heparin sulfate glycoprotein-expressing cells are incubated with LAP or with LAP complexed to LTBP (e.g., LTBP1, LTBP3, or LTBP4) and the antibodies are screened for binding by flow cytometry.

In one embodiment, the antibodies are tested for the ability to bind or affect TGFβ1. In one embodiment, the antibodies are screened for the ability to bind or affect TGFβ2. In one embodiment, the antibodies are tested for the ability to bind or affect TGFβ3.

In another embodiment, the antibodies are tested for their effects on TGFβ activation (e.g., inhibition, stimulation, or no effect). In some embodiments, TGFβ1 activation is mediated by the binding of integrins including, but not limited, to αvβ6, αvβ8, αvβ3, or αvβ1. In some embodiments, TGFβ1 activation is mediated by matrix metalloproteases including, but not limited to, MMP2 and MMP9. In some embodiments, TGFβ1 activation is mediated by thrombospondin. In some embodiments, TGFβ1 activation is mediated by serum proteases. In some embodiments, TGFβ1 activation is mediated by heat, by shear forces, by a shift in pH or by ionizing radiation. In some embodiments, TGFβ1 activation is mediated by reactive oxygen species (ROS). The source of LAP in the activation assays can be LAP on the surface of a transfected cell line, LAP on the surface of a cell population that expresses LAP endogenously or in response to specific stimuli, LAP bound to extracellular matrix, LAP in solution (e.g., recombinant LAP), either complexed with TGFβ1 or without TGFβ1 or complexed with TGFβ1 and an anchor protein, such as GARP, LRRC33, LTBP1, LTBP3, or LTBP4. LAP-TGFβ1 can be purchased from R&D Systems or can be isolated from cell supernatants. The effect an antibody has on TGFβ1 activation can be determined, for example, using an ELISA (e.g., as described in Example 3) which measures levels of active TGFβ1 under different conditions (e.g., with or without antibody). The effect an antibody has on LAP-TGFβ1 activation can also be determined using a reporter cell line that expresses TGFβ receptor and responds to mature TGFβ.

In another embodiment, the antibodies are tested for the ability to bind LAP in the extracellular matrix. Suitable methods for determining whether antibodies bind to LAP in the extracellular matrix include in vitro assays, wherein cells (e.g., P3U1 cells transfected with LAP-TGFβ) are cultured to lay down ECM on culture plates and subsequently removed, and labeled antibodies are tested for their ability to bind to the LAP and ECM left on the culture plate surface (e.g., as described in Example 4). Similar assays can be run using fibroblast cell lines or other cells that are known to secrete LAP-TGFβ and extracellular matrix components. In some embodiments, whether or not the anti-LAP antibodies bind to or do not bind to ECM can be determined by an ELISA, where the ECM has been shown to express latent TGFβ using commercially available antibodies.

In another embodiment, the antibodies are tested for their ability to bind to particular cell types, e.g., immune cells (e.g., immunosuppressive cells, leukocytes) or platelets. The binding of antibodies to certain leukocyte populations (e.g., Tregs, macrophages, MDSCs, GARP-negative cells) can be determined using flow cytometry, for example, as described in Examples 6-8.

Antibodies can also be tested for their ability to inhibit the proliferation or viability of cells (either in vivo or in vitro), such as tumor cells, using art-recognized methods (e.g., 3H-thymidine incorporation, immunohistochemistry with proliferation markers, animal cancer models).

Antibodies can also be tested for their anti-tumor activity in vivo (e.g., as monotherapy or combination therapy), using syngeneic tumor models well known in the art, such as the CT26 colorectal tumor model, EMT6 breast cancer model, and 4T1 breast cancer tumor metastasis model. Anti-LAP antibodies can also be tested in tumor xenogragft models which are known to be inhibited by anti-TGFβ antibodies (e.g., Detroit 562 tumor xenograft model). Exemplary methods for treating these models with anti-LAP antibodies are described, e.g., in Examples 10-14.

Exemplary criteria for determining whether an anti-LAP antibody exhibits certain binding properties (e.g., binding, inhibition of LAP-TGFβ1 activation, activation of LAP-TGFβ1) are shown in Table 1.

or bispecific antibodies comprising the same, and a carrier (e.g., pharmaceutically acceptable carrier). Such compositions are useful for various therapeutic applications.

In some embodiments, pharmaceutical compositions disclosed herein can include other compounds, drugs, and/or agents used for the treatment of various diseases (e.g., cancer, fibrosis, autoimmune diseases). Such compounds, drugs, and/or agents can include, for example, an anti-cancer agent, a chemotherapeutic agent, an immunosuppressive agent, an immunostimulatory agent, an immune checkpoint inhibitor, and/or an anti-inflammatory agent. Exemplary compounds, drugs, and agents that can be formulated together or separately with the anti-LAP antibodies described herein are described in the next section (i.e., Section VIII; Uses and Methods).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

TABLE 1

| Antibody Property | Positive |
|---|---|
| Binding to cells or ECM, as assessed by ELISA | 2 SD above the mean of a negative control |
| Binding to cell types, as assessed by flow cytometry | 2 SD above the mean (MFI on a homogeneous cell line or cell population) of a negative control |
| Binding to TGFβ by a binding assay (e.g., bio-layer interferometry | ≥100-fold difference in affinity relative to a negative control |
| Inhibition of TGFβ1 activation | ≥50% reduction in mature TGFβ1 levels in an in vitro culture relative to negative control when tested at antibody concentrations of 8 ug/mL |
| Activation of TGFβ1 | ≥2-fold increase in mature TGFβ1 levels in an in vitro culture relative to negative control when tested at antibody concentrations of 8 ug/mL |

VII. Compositions

Also provided herein are compositions (e.g., pharmaceutical compositions) comprising the anti-LAP antibodies described herein, immunoconjugates comprising the same, A pharmaceutical composition described herein may also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 or 10 mg/kg, of the host body weight. An exemplary treatment regime entails administration once per week, once every two weeks, once every three weeks, once every four weeks, once a month, once every 3 months or once every three to 6 months.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-LAP antibody described herein preferably results in a decrease in severity of disease symptoms, an increase in frequency and duration of disease symptom-free periods, or a prevention of impairment or disability due to the disease affliction. In the context of cancer, a therapeutically effective dose preferably results in increased survival, and/or prevention of further deterioration of physical symptoms associated with cancer. A therapeutically effective dose may prevent or delay onset of cancer, such as may be desired when early or preliminary signs of the disease are present.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-LAP antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-LAP antibodies described herein can be formulated to ensure proper distribution in vivo. For example, the blood-brain barrier (BBB) excludes many highly hydrophilic compounds. To ensure that the therapeutic compounds described herein cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

VIII. Uses and Methods

The antibodies, antibody compositions, and methods described herein have numerous in vitro and in vivo utilities.

For example, provided herein is a method of treating cancer comprising administering to a subject in need thereof an anti-LAP antibody described herein, such that the subject is treated, e.g., such that growth of cancerous tumors is inhibited or reduced and/or that the tumors regress and/or that prolonged survival is achieved.

In one embodiment, provided herein is a method of treating cancer comprising administering to a subject in need thereof an effective amount of an anti-LAP antibody (or a bispecific antibody or immunoconjugate comprising the antibody) which specifically binds to LAP-TGFβ1 in the absence of an anchor protein, and binds to cells (e.g., immune cells such as immunosuppressive cells) but not to extracellular matrix. In some embodiments, the anti-LAP antibody selectively inhibits TGFβ1 activation on cells (e.g., immune cells such as immunosuppressive cells) without inhibiting TGFβ1 activation in extracellular matrix.

In some embodiments, the cancer is characterized by abnormal TGFβ activity. In some embodiments, the cancer is associated with fibrosis. In some embodiments, the cancer is associated with infiltration of CD4+ regulatory T cells. In some embodiments, the cancer is associated with infiltration of CD8+ regulatory T cells. In some embodiments, the cancer is associate with infiltration of regulatory B cells. In some embodiments, the cancer is associated with infiltration of myeloid-derived suppressor cells. In some embodiments, the cancer is associated with infiltration of tumor-associated macrophages. In some embodiments, the cancer is associated with infiltration of innate lymphoid cells. In some embodiments, the cancer is associated with infiltration of cancer-associated fibroblasts. In some embodiments, the cancer is associated with a radiation-related increase in the above cell types.

In some embodiments, the cancer is associated with an increased TGFβ1 activation signature. In some embodiments the cancer is associated with an EMT signature. In some embodiments the cancer is associated with a tumor exhibiting an EMT signature and immune infiltration. In some embodiments the cancer is associated with a tumor profile of immune exclusion. In some embodiments, the cancer is associated with increased LAP expression. In some embodiments, the cancer is associated with increased GARP expression. In some embodiments, the cancer is associated with increased LRRC33 expression. Cancers whose growth may be inhibited using the anti-LAP antibodies described herein include, but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer (e.g. estrogen-receptor positive breast cancer HER2-positive breast cancer; triple negative breast cancer); cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; liver cancer (e.g. hepatocellular carcinoma; hepatoma); intra-epithelial neoplasm; kidney or renal cancer; larynx cancer; leukemia; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; and post-transplant lymphoproliferative disorder (PTLD), as well as abnormal vascular proliferation associated with phakomatoses, edema (such as that associated with brain tumors), tumors of primitive origins and Meigs' syndrome.

Additional cancers which can be treated using the anti-LAP antibodies described herein include metastatic pancreatic cancer, metastatic adenocarcinoma of the pancreas, stomach cancer, fibrotic cancer, glioma, malignant glioma, diffuse intrinsic pontine glioma, recurrent childhood brain neoplasm renal cell carcinoma, clear-cell metastatic renal cell carcinoma, metastatic castration resistant prostate cancer, stage IV prostate cancer, metastatic melanoma, malignant melanoma, recurrent melanoma of the skin, melanoma brain metastases, malignant melanoma of head and neck, squamous cell non-small cell lung cancer, metastatic breast cancer, follicular lymphoma, advanced B-cell NHL, HL including diffuse large B-cell lymphoma (DLBCL), multiple myeloma, chronic myeloid leukemia, adult acute myeloid leukemia in remission, adult acute myeloid leukemia with Inv(16)(p13.1q22), CBFB-MYH11, adult acute myeloid leukemia with t(16:16) (p13.1:q22), CBFB-MYH11, adult acute myeloid leukemia with t(8:21)(d22:q22), RUNX1-RUNX1T1, adult acute myeloid leukemia with t(9:11)(p22:q23), MLLT3-MLL, adult acute promyelocytic leukemia with tO15:17)(q22:q12), PML-RARA, alkylating agent-related acute myeloid leukemia, Richter's syndrome, adult glioblastoma, adult gliosarcoma, recurrent glioblastoma, recurrent childhood rhabdomyosarcoma, recurrent ewing sarcoma/peripheral primitive neuroectodermal tumor, recurrent neuroblastoma, recurrent osteosarcoma, colorectal cancer, MSI positive colorectal cancer, MSI negative colorectal cancer, nasopharyngeal nonkeratinizing carcinoma, recurrent nasopharyngeal undifferentiated carcinoma, cervical adenocarcinoma, cervical adenosquamous carcinoma; cervical squamous cell carcinoma, recurrent cervical carcinoma, anal canal squamous cell carcinoma, metastatic anal canal carcinoma, recurrent anal canal carcinoma, recurrent head and neck cancer, squamous cell of head and neck, head and neck squamous cell carcinoma (HNSCC), ovarian carcinoma, colon cancer, advanced GI cancer, gastric adenocarcinoma, gastroesophageal junction adenocarcinoma, bone neoplasms, soft tissue sarcoma, bone sarcoma, thymic carcinoma, urothelial carcinoma, merkel cell carcinoma, recurrent merkel cell carcinoma, mycosis fungoides, Sezary syndrome, neuroendocrine cancer, nasopharyngeal cancer, basal cell skin cancer, squamous cell skin cancer, dermatofibrosarcoma trotuberans, glioma, mesothelioma, myelodysplastic syndromes (MDS), myelofibrosis (MF), myeloproliferative neoplasms, and acute myeloid leukemia (AML).

Cancers may be metastatic or may be primary cancers. Cancers may be desmoplastic or non-desmoplastic. Cancers may be recurrent cancers.

In some embodiments, the anti-LAP antibodies described herein are used to treat myelodysplastic syndromes (MDS). MDS are a diverse group of malignant disorders marked by bone marrow failure due to defective hematopoiesis and production of dysplastic cells. TGFβ is a primary driver in MDS (Geyh et al., Haematologica 2018; 103:1462-71) and agents that inhibit the function of TGFβ have been proposed as therapeutics (Mies et al., Curr Hematol Malig Rep 2016; 11:416-24). Furthermore, MDSCs are known to be dysregulated in MDS (Chen et al., JCI 2013; 123:4595-611) and agents that reduce MDSC levels in the bone marrow are potential therapeutics.

In some embodiments, the anti-LAP antibodies described herein are used to treat myelofibrosis, which is another myeloid malignancy in which TGFβ1 plays a central role (Mascarenhas et al., Leukemia & Lymphoma 2014; 55:450-2).

In some embodiments, the cancer is resistant to checkpoint inhibitor(s). In some embodiments, the cancer is intrinsically refractory or resistant (e.g., resistant to a PD-1 pathway inhibitor, PD-1 pathway inhibitor, or CTLA-4 pathway inhibitor). In some embodiments, the resistance or refractory state of the cancer is acquired. In some embodiments, the anti-LAP antibodies described herein can be used in combination with checkpoint inhibitors to overcome resistance of the cancer to the checkpoint inhibitors. In some embodiments, the anti-LAP antibodies described herein can be used to treat tumors with a mesenchymal and/or EMT signature together with checkpoint inhibitors in combination or sequentially with agents that induce a mesenchymal phenotype, such as MAPK pathway inhibitors.

In some embodiments, the anti-LAP antibodies described herein are used to enhance the viability of immune cells ex vivo, e.g., in adoptive NK cell transfer. Accordingly, in some embodiments, anti-LAP antibodies are used in combination with adoptively transferred NK cells to treat cancer.

In some embodiments, the anti-LAP antibodies described herein are used to treat tumors with MHC loss or MHC down-regulation, as monotherapy or in combination with NK activating or enhancing treatment. In some embodiments, the anti-LAP antibodies described herein are used to treat checkpoint inhibitor resistant tumors in combination with NK activating or enhancing treatment.

Also provided herein is a method of treating cancer associated with an increased number of circulating platelets or an increased platelet to lymphocyte ratio comprising administering to a subject in need thereof an effective amount of an antibody which specifically binds to LAP, wherein the antibody binds to platelets but does not cause platelet aggregation or platelet degranulation.

The ability of a compound to inhibit cancer can be evaluated in an animal model system predictive of efficacy in human tumors. Alternatively, this property of a composition can be evaluated by examining the ability of the compound to inhibit using in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

Also encompassed are methods for detecting the presence of LAP-TGFβ1 in a sample (e.g., a tumor biopsy sample), or measuring the amount of LAP-TGFβ1 in sample, comprising contacting the sample (e.g., tumor tissue) and a control sample (e.g., corresponding healthy tissue) with a monoclonal antibody which specifically binds to LAP-TGFβ1 under conditions that allow for formation of a complex between the antibody or portion thereof and LAP-TGFβ1. The formation of a complex is then detected, wherein a difference complex formation between the sample compared to the control sample is indicative the presence of LAP-TGFβ1 in the sample. The anti-LAP antibodies described herein can also be used to purify LAP-TGFβ1 via immunoaffinity purification.

Diagnostic applications of the anti-LAP antibodies described herein are also contemplated.

In one embodiment, provided herein is a method of diagnosing a cancer associated with regulatory T cell infiltration comprising contacting a biological sample from a patient afflicted with the cancer with an anti-LAP antibody described herein which binds to regulatory T cells, wherein positive staining with the antibody indicates the cancer is associated with regulatory T cell infiltration.

In another embodiment, provided herein is a method of diagnosing a cancer associated with GARP-negative suppressive cells comprising contacting a biological sample from a patient afflicted with the cancer with an anti-LAP antibody described herein which binds to GARP-negative suppressive cells, wherein positive staining with the antibody and negative staining with an anti-GARP antibody indicates the cancer is associated with GARP-negative suppressive cells.

In another embodiment, provided herein is a method of selecting a patient afflicted with cancer for treatment with an anti-LAP antibody described herein, comprising contacting a biological sample from the patient with the antibody, wherein positive staining with the antibody indicates the cancer is amenable to treatment with the antibody.

In another embodiment, provided herein is a method of determining the response of a patient afflicted with cancer to treatment with an anti-LAP antibody described herein comprising contacting a biological sample from the patient with the antibody, wherein reduced staining with the antibody indicates the cancer is responding to treatment with the antibody.

In another embodiment, provided herein is a method of determining whether a cancer in a patient has metastasized comprising (a) identifying a patient having a cancer, (b) administering a labeled (e.g., radiolabeled) anti-LAP antibody described herein to the patient and determining the biodistribution of the labeled anti-LAP antibody, and (c) periodically repeating step (b) to determine whether the biodistribution of the labeled anti-LAP antibody has changed, wherein a change in the biodistribution of the labeled anti-LAP antibody is indicative that the cancer has metastasized.

Also provided are methods of treating fibrosis with the anti-LAP antibodies described herein.

Exemplary fibrotic disorders include, but are not limited to, heart fibrosis, muscle fibrosis, skin fibrosis, liver fibrosis, soft tissue (e.g. mediastinum or retroperitoneum) fibrosis, renal fibrosis, bone marrow fibrosis, intestinal fibrosis, joint (e.g., knee, shoulder or other joints) fibrosis, pulmonary fibrosis, idiopathic pulmonary fibrosis, cystic fibrosis, endomyocardial fibrosis, mediastinal fibrosis, myelofibrosis, retroperitoneal fibrosis, progressive massive fibrosis, pipestem fibrosis, nephrogenic systemic fibrosis, Crohn's disease, keloid, old myocardial infarction, scleroderma/systemic sclerosis, subepithelial fibrosis, arthrofibrosis, some forms of adhesive capsulitis, proliferative fibrosis, viral hepatitis induced fibrosis, drug-induced fibrosis, radiation-induced fibrosis, and fibrosis associated with cancer.

Also provided are methods of treating autoimmune disease with the anti-LAP antibodies described herein.

Exemplary autoimmune diseases include, but are not limited to, systemic lupus erythematosus (SLE), rheumatoid arthritis, type I diabetes, acute glomerulonephritis, Addison's disease, adult onset idiopathic hypoparathyroidism (AOIH), alopecia totalis, amyotrophic lateral sclerosis, ankylosing spondylitis, antiphospholipid syndrome, autoimmune aplastic anemia, autoimmune hemolytic anemia, Behcet's disease, Celiac disease, chronic active hepatitis, CREST syndrome, Crohn's disease, dermatomyositis, dilated cardiomyopathy, eosinophilia-myalgia syndrome, epidermolisis bullosa acquisita (EBA), giant cell arteritis, Goodpasture's syndrome, Graves' disease, Guillain-Barre syndrome, hemochromatosis, Henoch-Schonlein purpura, idiopathic IgA nephropathy, insulin-dependent diabetes mellitus (IDDM), juvenile rheumatoid arthritis, Lambert-Eaton syndrome, linear IgA dermatosis, lupus erythematosus, mixed connective tissue disease, multiple sclerosis, myasthenia gravis, myocarditis, narcolepsy, necrotizing vasculitis, neonatal lupus syndrome (NLE), nephrotic syndrome, pemphigoid, phemphigus, polymyositis, primary sclerosing cholangitis, psoriasis, rapidly progressive glomerulonephritis (RPGN), Reiter's syndrome, rheumatoid arthritis, scleroderma, Sjogren's syndrome, stiff-man syndrome, systemic sclerosis, thyroiditis, and ulcerative colitis. Additional autoimmune diseases are provided at www.aarda.org/diseaselist.

Also provided herein is a method of reducing the number of immunosuppressive cells in a patient before, during, and/or after transplantation comprising administering an effective amount of the anti-LAP antibodies described herein to a patient before undergoing transplantation, during transplantation and/or after transplantation (e.g., anti-LAP antibodies which bind to immunosuppressive cells). In some embodiments, the anti-LAP antibodies improve graft survival.

Inhibition of TGFβ has been shown to restore regenerative failure by reducing senescence and enhancing liver regeneration, in a model of acute liver disease (acetaminophen injury mouse model) (Bird et al., Sci Transl Med 2018; 10:eaan1230). Accordingly, also provided herein is a method of increasing the regenerative response in acute organ injury (e.g., acute liver injury) comprising administering to a subject with acute organ injury an effective amount of the anti-LAP antibodies described herein (i.e., anti-LAP antibodies which inhibit LAP-TGFβ1 activation) to treat the acute organ injury.

Aberrant activation of TGFβ has been shown to initiate the onset of temporomandibular joint osteoarthritis (Zheng et al., Bone Res 2018; 6:26). Accordingly, also provided herein is a method of treating a patient with temporomandibular joint osteoarthritis comprising administering to the patient an effective amount of the anti-LAP antibodies described herein (i.e., anti-LAP antibodies which inhibit LAP-TGFβ1 activation) to treat the temporomandibular joint osteoarthritis.

LAP-TGFβ1 has also been shown to mediate the differentiation of CD4+ effector cells into productively and latently infected central memory T cells during HIV-1 infection (Cheung et al., J Viol 2018; 92:e01510-17). Accordingly, also provided herein is a method of treating a patient with HIV-1 infection (or a patient at risk of developing HIV-1 infection) comprising administering to the patient an effective amount of the anti-LAP antibodies described herein (i.e., anti-LAP antibodies which inhibit LAP-TGFβ1 activation) to treat the HIV-1 infection.

TGFβ-expressing macrophages and suppressive regulatory T cells have been shown to be altered in the peritoneal fluid of patients with endometriosis (Hanada et al., Reprod Biol Endocrinol 2018; 16:9), suggesting that targeting LAP-TGFb1 expressed on these cells may be beneficial for treating the disorder. Accordingly, also provided herein is a method of treating a patient with endometriosis comprising administering to the patient an effective amount of the anti-LAP antibodies described herein (i.e., anti-LAP antibodies which inhibit LAP-TGFβ1 activation) to treat the endometriosis.

LAP-TGFβ1-expressing CD4+ T cells and CD14+ monocytes and macrophages have been shown to be increased in patients carrying multidrug resistant *Mycobacterium tuberculosis* (Basile et al., Clin Exp Immunol 2016; 187:160), suggesting that targeting LAP-TGFβ1 expressed on these cells may be beneficial for treating the infection. Accordingly, also provided herein is a method of treating a patient with multidrug resistant *Mycobacterium tuberculosis* comprising administering to the patient an effective amount of the anti-LAP antibodies described herein (i.e., anti-LAP antibodies which inhibit LAP-TGFβ1 activation) to treat the infection.

In certain embodiments, the anti-LAP antibody can be used alone to treat a disease or disorder (e.g., cancer). Alternatively, an anti-LAP antibody can be used in conjunction with another agent or therapy, e.g., an anti-cancer agent, a chemotherapeutic agent, an immunosuppressive agent, an immunostimulatory agent, an immune checkpoint inhibitor, an anti-inflammatory agent, and cell therapy, as described in more detail below.

Combination Therapy

The anti-LAP antibodies described herein can be used in combination with various treatments or agents (or in the context of a multispecific antibody or bifunctional partner) for the treatment of cancer, as described below.

Suitable anti-cancer agents for use in combination therapy with the anti-LAP antibodies described herein include, but are not limited to, surgery, chemotherapeutic agents, growth inhibitory agents, cytotoxic agents, radiotherapy and agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC (Imatinib Mesylate)), a COX-2 inhibitor (e.g., celecoxib), interferons, cytokines, antagonists (e.g., neutralizing antibodies) that bind to one or more of the following targets PD 1, PDL1, PDL2 (e.g., pembrolizumab; nivolumab; MK-3475; AMP-224; MPDL3280A; MEDI0680; MSB0010718C; and/or MEDI4736); CTLA4 (e.g., tremelimumab (PFIZER) and ipilimumab); LAG3 (e.g., BMS-986016); CD103; TIM-3 and/or other TIM family members; CEACAM-1 and/or other CEACAM family members, ErbB2, ErbB3, ErbB4, PDGFR-beta, BlyS, APRIL, BCMA or VEGF receptor(s), TRAIIJApo2, PARP inhibitors (e.g., AZD-2281, Lynparza Olaparib, Rubraca Rucaparib; (Zejula) niraparib), DNA damage repair inhibitors (e.g., ATMi, ATRi, DNAPKi), and other bioactive and organic chemical agents. Combinations thereof are also specifically contemplated for the methods described herein.

Suitable chemotherapeutic agents for use in combination therapy with the anti-LAP antibodies described herein include, but are not limited to, alkylating agents such as thiotepa and CYTOXAN® cyclosphosphamide; temozolomide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegal 1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, 111), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin, vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Also suitable for use in combination with the anti-LAP antibodies described herein are drugs targeting epigenetic regulators, such as HDAC inhibitors, bromodomain inhibitors, and E3 ligase (e.g., cereblon) inhibitors (e.g., lenalidomide, pomalidomide, and thalidomide).

Suitable anti-inflammatory agents for use in combination therapy with the anti-LAP antibodies described herein include, but are not limited to, aspirin and other salicylates, Cox-2 inhibitors (e.g., rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g., natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (e.g., leflunomide), IL-1 receptor blocking agents (e.g., anakinra), TNF-α blocking agents (e.g., etanercept, infliximab, and adalimumab), and the like.

Suitable immunomodulatory agents (e.g., immunostimulatory and immunosuppressive agents) include, but are not limited to, cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α, antibodies that bind to p75 of the IL-2 receptor, antibodies that bind to MHC, CD2, CD3, CD4, CD7, CD28, B7, CD40, CD45, IFN-γ, TNF-α, IL-4, IL-5, IL-6R, IL-6, IGF, IGFR1, IL-7, IL-8, IL-10, CD11a, or CD58, or antibodies binding to their ligands, soluble IL-15R, IL-10, B7 molecules (B7-1, B7-2, variants thereof, and fragments thereof), ICOS, OX40, an inhibitor of a negative T cell regulator (such as an antibody against CTLA4), and the like.

Additional immunosuppressive agents include, for example, anti-TNF agents such as etanercept, adalimumab and infliximab, and steroids. Examples of specific natural and synthetic steroids include, for example: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, paramethasone, prednisolone, prednisone, tixocortol, and triamcinolone.

Suitable immunostimulatory agents for use in combination therapy with the anti-LAP antibodies described herein include, for example, compounds capable of stimulating antigen presenting cells (APCs), such as dendritic cells (DCs) and macrophages. For example, suitable immunostimulatory agents are capable of stimulating APCs, so that the maturation process of the APCs is accelerated, the proliferation of APCs is increased, and/or the recruitment or release of co-stimulatory molecules (e.g., CD80, CD86, ICAM-1, MHC molecules and CCR7) and pro-inflammatory cytokines (e.g., IL-1β, IL-6, IL-12, IL-15, and IFN-γ) is upregulated. Suitable immunostimulatory agents are also capable of increasing T cell proliferation. Such immunostimulatory agents include, but are not be limited to, CD40 ligand; FLT 3 ligand; cytokines, such as IFN-α, IFN-0, IFN-γ and IL-2; colony-stimulating factors, such as G-CSF (granulocyte colony-stimulating factor) and GM-CSF (granulocyte-macrophage colony-stimulating factor); an anti-CTLA-4 antibody, anti-PD1 antibody, anti-41BB antibody, or anti-OX-40 antibody; LPS (endotoxin); ssRNA; dsRNA; Bacille Calmette-Guerin (BCG); Levamisole hydrochloride; and intravenous immune globulins. In one embodiment an immunostimulatory agent may be a Toll-like Receptor (TLR) agonist. For example the immunostimulatory agent may be a TLR3 agonist such as double-stranded inosine:cytosine polynucleotide (Poly I:C, for example available as Ampligen™ from Hemispherx Bipharma, PA, US or Poly IC:LC from Oncovir) or Poly A:U; a TLR4 agonist such as monophosphoryl lipid A (MPL) or RC-529 (for example as available from GSK, UK); a TLR5 agonist such as flagellin; a TLR7 or TLR8 agonist such as an imidazoquinoline TLR7 or TLR 8 agonist, for example imiquimod (e.g., Aldara™) or resiquimod and related imidazoquinoline agents (e.g., as available from 3M Corporation); or a TLR 9 agonist such as a deoxynucleotide with unmethylated CpG motifs ("CpGs", e.g., as available from Coley Pharmaceutical). In another embodiment, the immunostimulatory molecule is a STING agonist. Such immunostimulatory agents may be administered simultaneously, separately or sequentially with the anti-LAP antibodies described herein.

Suitable immune checkpoint blockers include, but are not limited to, agents (e.g., antibodies) that bind to PD-1, PD-L1, PD-L2, LAG-3, CTLA4, TIGIT, GITR, ICOS, OX40, GITR, PVR, PVRIG, VISTA, and TIM3. Also encompassed are STING agonists. Non-limiting examples of antibodies that bind to PD-1, PD-L1, and PD-L2 include pembrolizumab; nivolumab; MK-3475; MPDL32; MEDI0680; MEDI4736; AMP-224; and MSB0010718C.

In some embodiments, the anti-LAP antibody is administered with an agent that targets a stimulatory or inhibitory molecule that is a member of the immunoglobulin super family (IgSF). For example, the anti-LAP antibodies described herein, may be administered to a subject with an agent that targets a member of the IgSF family to increase an immune response. For example, an anti-LAP antibody may be administered with an agent that targets a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6 or a co-stimulatory or co-inhibitory receptor binding specifically to a B7 family member.

An anti-LAP antibody may also be administered with an agent that targets a member of the TNF and TNFR family of molecules (ligands or receptors), such as CD40 and CD40L, OX-40, OX-40L, CD70, CD27L, CD30, CD30L, 4-1BBL, CD137, TRAIlJApo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDA1, EDA2, TNFR1, Lymphotoxin α/TNFβ, TNFR2, TNFα, LTβR, Lymphotoxin α 1β2, FAS, FASL, RELT, DR6, TROY, and NGFR (see, e.g., Tansey (2009) Drug Discovery Today 00:1).

T cell responses can be stimulated by a combination of anti-LAP antibodies described herein and one or more of the following agents:

(1) An antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, CD155, GPR56, VISTA, B7-H3, B7-H4, 2B4, CD48, GARP, PD1H, LAIR1, TIM-1, and TIM-4; and/or (2) An agonist of a protein that stimulates T cell activation, such as B7-1, B7-2, CD28, 4-1BB (CD137), 4-1BBL, GITR, ICOS, ICOS-L, OX40, OX40L, CD70, CD27, CD40, DR3 and CD28H.

Exemplary agents that modulate the above proteins and may be combined with the anti-LAP antibodies described herein for treating cancer, include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4).

Other molecules that can be combined with anti-LAP antibodies for the treatment of cancer include antagonists of inhibitory receptors on NK cells or agonists of activating receptors on NK cells. For example, anti-LAP antibodies can be combined with antagonists of KIR (e.g., lirilumab).

T cell activation is also regulated by soluble cytokines, and anti-LAP antibodies may be administered to a subject, e.g., having cancer, with antagonists of cytokines that inhibit T cell activation or agonists of cytokines that stimulate T cell activation.

In certain embodiments, anti-LAP antibodies can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-ß, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

Additional agents that may be combined with anti-LAP antibodies include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Another therapy that may be combined with anti-LAP antibodies is a therapy that inhibits a metabolic enzyme such as indoleamine dioxygenase (IDO), tryptophan-2,3-dioxigenase, dioxygenase, arginase, or nitric oxide synthetase.

Another class of agents that may be used with anti-LAP antibodies includes agents that inhibit the formation of adenosine or inhibit the adenosine A2A receptor, for example, anti-CD73 antibodies, anti-CD39 antibodies, and adenosine A2A/A2b inhibitors.

Other therapies that may be combined with anti-LAP antibodies for treating cancer include therapies that reverse/prevent T cell anergy or exhaustion and therapies that trigger an innate immune activation and/or inflammation at a tumor site.

The anti-LAP antibodies may be combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking regulatory T cells or other immune suppressing cells; a therapy that stimulates positive immune regulation, e.g., with agonists that stimulate the CD-137 and/or GITR pathway and/or stimulate T cell effector function; a therapy that increases systemically the frequency of anti-tumor T cells; a therapy that depletes or inhibits regulatory T cells using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); cell therapy with adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immunorepressive cytokines.

The anti-LAP antibodies described herein can be combined with proinflammatory cytokines, for example, IL-12 and IL-2. These cytokines can be modified to enhance half-life and tumor targeting.

The anti-LAP antibodies described herein can be combined with immune cell engagers such as NK cell engagers or T cell engagers.

The anti-LAP antibodies described herein can be combined with indoleamine dioxigenase (IDO) inhibitors, tryptophan-2,3-dioxygenase (TDO) inhibitors, and dual IDO/TDO inhibitors.

The anti-LAP antibodies described herein can be combined with kynurine inhibitors.

The anti-LAP antibodies described herein can be combined with CD47 and/or SIRPa blocking therapies.

The anti-LAP antibodies described herein can be combined with JAK inhibitors and JAK pathway inhibitors (e.g., STAT3 inhibitors), e.g., for the treatment of myelofibrosis and myeloproliferative neoplasms.

The anti-LAP antibodies described herein can be combined with DNA damage repair inhibitors.

The anti-LAP antibodies described herein can be combined with angiogenesis inhibitors.

The anti-LAP antibodies described herein can be combined with erythropoietin and drugs that stimulate hematopoiesis.

Bispecific antibodies which have a first binding region with the specificity of the anti-LAP antibodies described herein and a second binding region which binds to an immune checkpoint blocker (e.g., PD-1, PD-L1) can be used in combination with at least one additional anti-cancer agent (e.g., radiation, chemotherapeutic agents, biologics, vaccines) to inhibit tumor growth.

The anti-LAP antibodies described herein can be combined with one or more immunostimulatory antibodies, such as an anti-PD-1 antagonist antibody, an anti-PD-L1 antagonist antibody, an antagonist anti-CTLA-4 antibody, an antagonist anti-TIM3 antibody, and/or an anti-LAG3 antagonist antibody, such that an immune response is stimulated in the subject, for example to inhibit tumor growth.

Exemplary anti-PD-1 antibodies include nivolumab, MK-3475 (Lambrolizumab) described in WO2012/145493; AMP-514 described in WO 2012/145493, as well as PD-1 antibodies and other PD-1 inhibitors described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368.

Exemplary anti-PD-L1 antibodies include MEDI4736 (also known as Anti-B7-H1), MPDL3280A (also known as RG7446), MSB0010718C (WO2013/79174), rHigM12B7, as well as any of the anti-PD-L1 antibodies disclosed in WO2013/173223, WO2011/066389, WO2012/145493, U.S. Pat. Nos. 7,635,757 and 8,217,149 and U.S. Publication No. 2009/145493.

Exemplary anti-CTLA-4 antibodies include Yervoy™ (ipilimumab), tremelimumab (formerly ticilimumab, CP-675,206), or an anti-CTLA-4 antibody described in any of the following publications: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304.

Exemplary anti-LAG3 antibodies include IMP731 and IMP-321, described in US 2011/007023, WO08/132601, and WO09/44273, as well as antibodies described in U.S. Patent Publication No. US2011/0150892, WO10/19570 and WO2014/008218.

Anti-LAP antibodies can also be combined with immune-oncology agents such as CD137 (4-1BB) agonists (e.g., an agonistic CD137 antibody such as urelumab or PF-05082566 (WO12/32433)); GITR agonists (e.g., an agonistic anti-GITR antibody), CD40 agonists (e.g., an agonistic CD40 antibody); CD40 antagonists (e.g., an antagonistic CD40 antibody such as lucatumumab (HCD122), dacetuzumab (SGN-40), CP-870,893 or Chi Lob 7/4); CD27 agonists (e.g., an agonistic CD27 antibody such as varlilumab (CDX-1127)), MGA271 (to B7H3) (WO11/109400)); KIR antagonists (e.g., lirilumab); IDO antagonists (e.g., INCB-024360 (WO2006/122150, WO07/75598, WO08/36653, WO08/36642), indoximod, NLG-919 (WO09/73620, WO09/1156652, WO11/56652, WO12/142237) or F001287); Toll-like receptor agonists (e.g., TLR2/4 agonists (e.g., Bacillus Calmette-Guerin); TLR7 agonists (e.g., Hiltonol or Imiquimod); TLR7/8 agonists (e.g., Resiquimod); or TLR9 agonists (e.g., CpG7909)); and TGF-β inhibitors (e.g., GC 1008, LY2157299, TEW7197, or IMC-TR1).

The anti-LAP antibodies described herein can also be combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

The anti-LAP antibodies described herein can also be combined with an anti-neoplastic antibody, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like.

Several experimental treatment protocols involve ex vivo activation and expansion of antigen specific T cells and adoptive transfer of these cells into recipients in order to antigen-specific T cells against tumor (Greenberg & Riddell, supra). Ex vivo activation in the presence of the anti-LAP antibodies described herein with or without an additional immunostimulating therapy (e.g., an immune checkpoint blocker) can be expected to increase the frequency and activity of the adoptively transferred T cells.

The anti-LAP antibody may also be administered with a standard of care treatment, or another treatment, such as radiation, surgery, or chemotherapy. The anti-LAP antibody may be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738;

see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with the anti-LAP antibodies described herein to activate more potent anti-tumor responses.

In some embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially.

IX. Kits

Also provided are kits comprising the anti-LAP antibodies, multispecific molecules, or immunoconjugates disclosed herein, optionally contained in a single vial or container, and include, e.g., instructions for use in treating or diagnosing a disease (e.g., cancer). The kits may include a label indicating the intended use of the contents of the kit. The term label includes any writing, marketing materials or recorded material supplied on or with the kit, or which otherwise accompanies the kit. Such kits may comprise the antibody, multispecific molecule, or immunoconjugate in unit dosage form, such as in a single dose vial or a single dose pre-loaded syringe.

The present disclosure is further illustrated by the following examples, which should not be construed as further limiting. The contents of all figures and all references, Genbank sequences, patents, and published patent applications cited throughout this application are expressly incorporated herein by reference.

EXAMPLES

Commercially available reagents referred to in the Examples below were used according to manufacturer's instructions unless otherwise indicated. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture,* 1987; Coligan et al., *Current Protocols in Immunology,* 1991.

Described in the Examples that follow are anti-LAP antibodies with broad therapeutic applications given their selective binding pattern and functional properties. For example, described are anti-LAP antibodies which bind specifically to LAP-TGFβ1 on cells, in particular, immunosuppressive cells, without binding to LAP-TGFβ1 on extracellular matrix. These antibodies provide the advantage of selectively inhibiting TGFβ1 activation on clinically relevant cell types (e.g., regulatory T cells, M2 macrophages, myeloid-derived suppressor cells), without impacting the natural function/activation of LAP-TGFβ1 on extracellular matrix. Another distinguishing feature of these anti-LAP antibodies is their ability to bind to recombinant LAP-TGFβ1 in the absence of cell- or ECM-associated anchor proteins (e.g., GARP, LRRC33, LTBP1, LTBP3, LTBP4). This allows for targeting cells (e.g., immunosuppressive cells) regardless of the anchor protein(s) expressed by the cells. Accordingly, these anti-LAP antibodies are distinct from antibodies which bind to LAP-TGFβ1 on both cells and extracellular matrix, as well as antibodies which bind to LAP-TGFβ1 only in the presence of an anchor protein (e.g., GARP), for example, by binding an epitope that includes both a region from LAP and the anchor protein.

Example 1: Binding of Anti-LAP Antibodies to Human and Murine LAP-TGFβ1

This Example describes the binding of a series of anti-LAP antibodies to human and murine LAP-TGFβ1. Briefly, P3U1 (mouse myeloma) cells were transfected with human LAP-TGFβ1 and GARP genes (for testing binding to human LAP-TGFβ1) or murine LAP-TGFβ1. Cells were contacted with APC-Streptavidin and a titration series of biotinylated anti-LAP monoclonal antibodies. Bound antibody/streptavidin complexes were detected by flow cytometry. Table 2 summarizes the EC50 values of the tested antibodies for human LAP-TGFβ1 in the presence or absence of GARP.

TABLE 2

| Anti-LAP mAb | Binding to P3U1 cells - $EC_{50}$ (ng/well) | |
|---|---|---|
| | Human TGFβ1 | Human TGFβ1 + GARP |
| 28G11 | 3.9 | 1.8 |
| 2C9 | 7.0 | 12.5 |
| 7H4 | 8.3 | 5.0 |
| 16F4 | 10.3 | 15.7 |
| 3H6 | 30.3 | 25.9 |
| 478.E9 | 37.0 | 51.7 |
| 8F10 | 37.1 | 27.6 |
| 6H10 | 62.5 | 143.7 |
| 478.G3 | 62.8 | 71.6 |
| 1E1 | 64.1 | 73.0 |
| 478.G4 | 114.6 | 83.9 |
| 2F8 | 122.6 | 139.9 |
| 1G12 | 288.2 | 133.7 |
| 13B12 | 6,400.0 | 33,000.0 |
| 3G5 | 14,000.0 | 11,000.0 |

As shown in Table 2, 28G11 had the lowest $EC_{50}$ (highest apparent affinity) of any of the tested antibodies. Moreover, $EC_{50}$ values shifted minimally in cells co-expressing LAP-TGFβ1 and GARP for most antibodies, indicating that the antibodies do not bind GARP.

The antibodies were also tested for binding to murine LAP-TGFβ1 expressing P3U1 cells at a single concentration (0.1 mg/mL). As shown in FIG. 1, 28G11, 7H4, 16B4, and 20B9 bind to murine LAP-TGFβ1.

Figure 2:
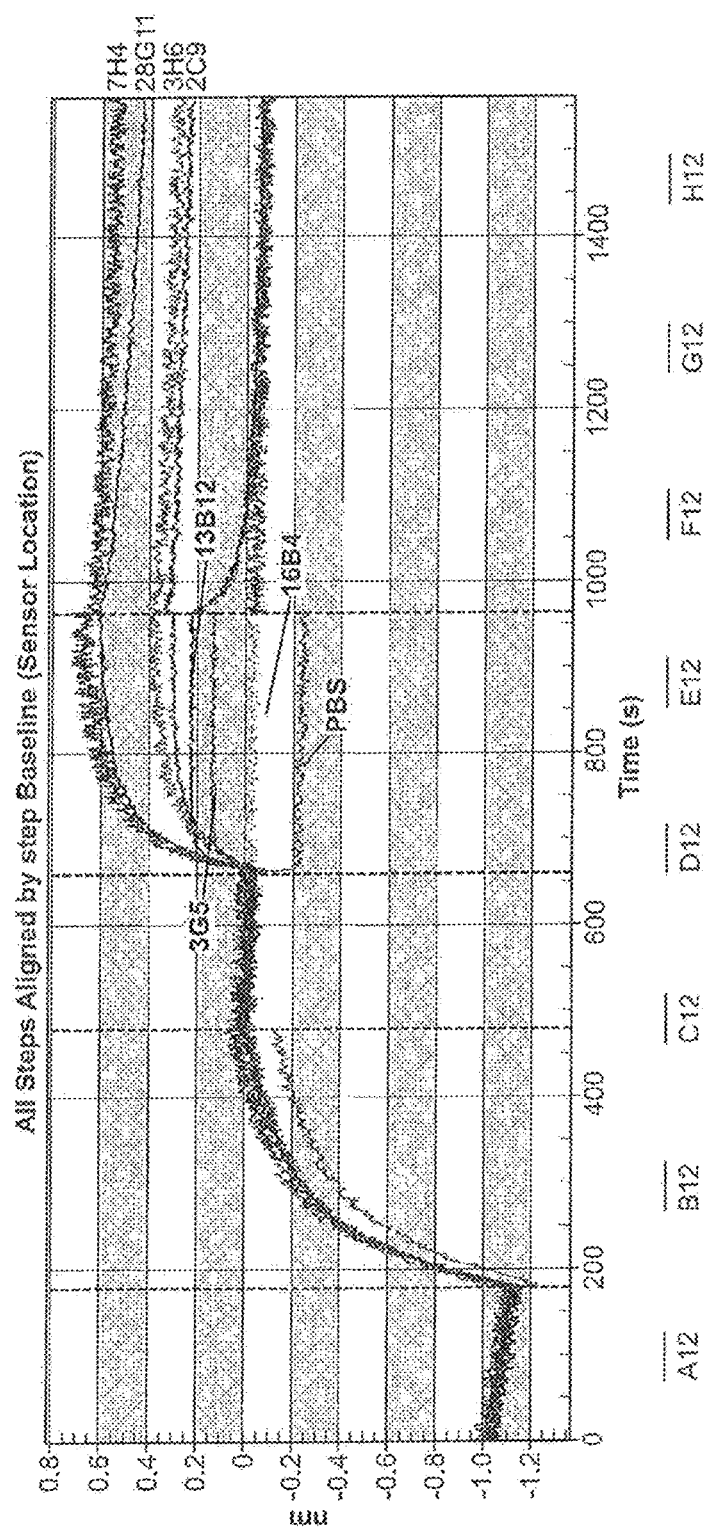
FIG. 2 is a sensorgram (Octet) of binding of the indicated anti-LAP antibodies to a recombinant human LAP-TGFβ1-Fc fusion protein.
Figure 3:
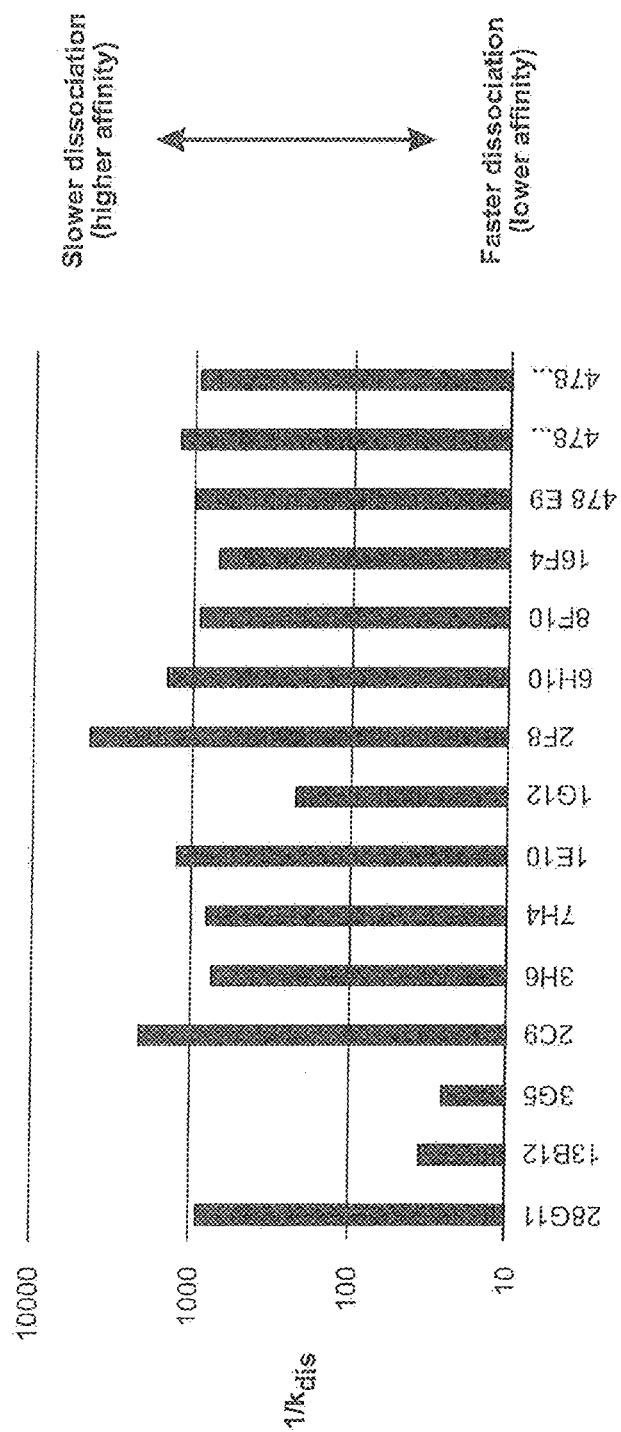
FIG. 3 is a graph comparing the dissociation constants ($k_{dis}$) for each of the indicated anti-LAP antibodies (data presented as $1/k_{dis}$).
Figure 4A:
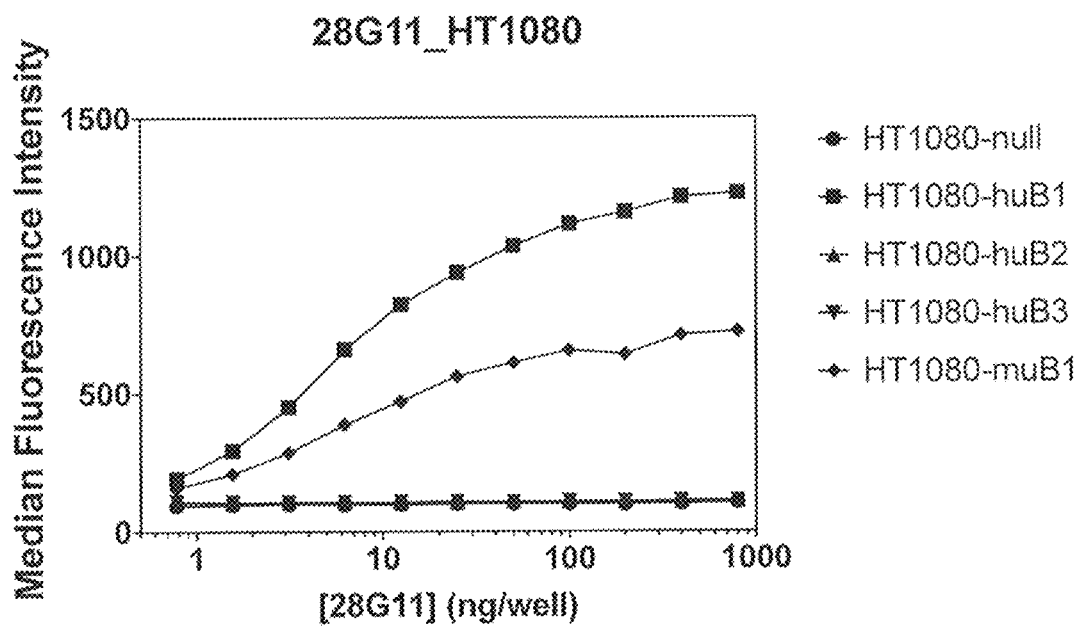
FIGS. 4A-4F are graphs showing the binding of antibodies 28G11_hIgG1, 22F9_hIgG1, 20E6_hIgG1, 17G8_hIgG1, 24E3_hIgG1, and 2C9 on non-transfected HT1080 cells and HT1080 cells overexpressing human LAP-TGFβ1, human LAP-TGFβ2, human LAP-TGFβ3, and murine LAP-TGFβ1.
Figure 4B:
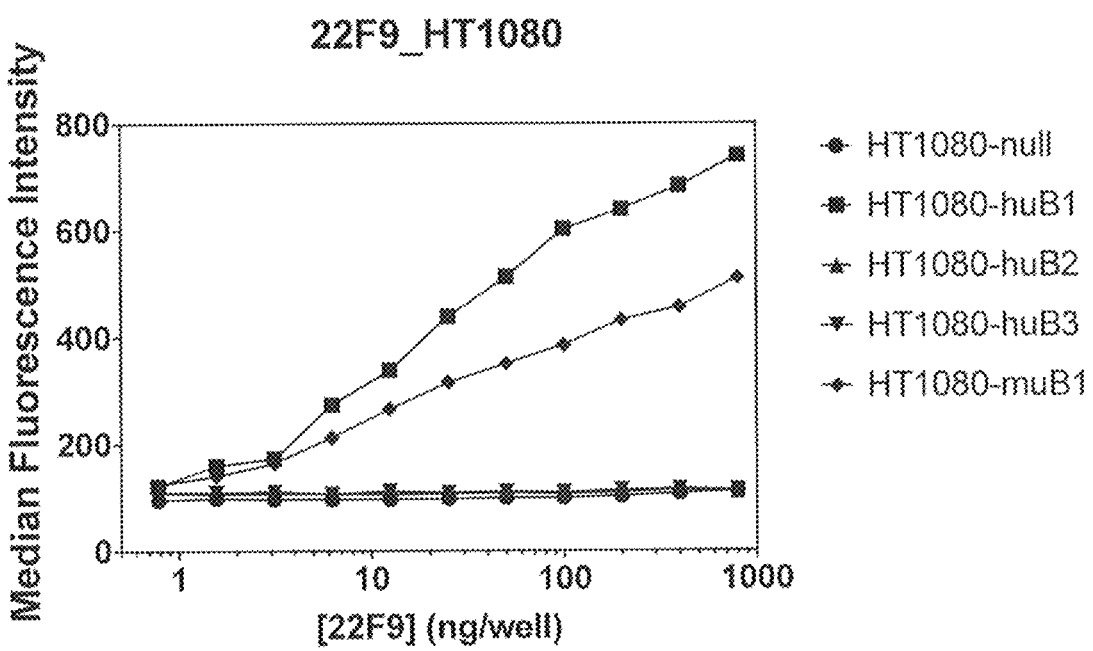
Figure 4C:
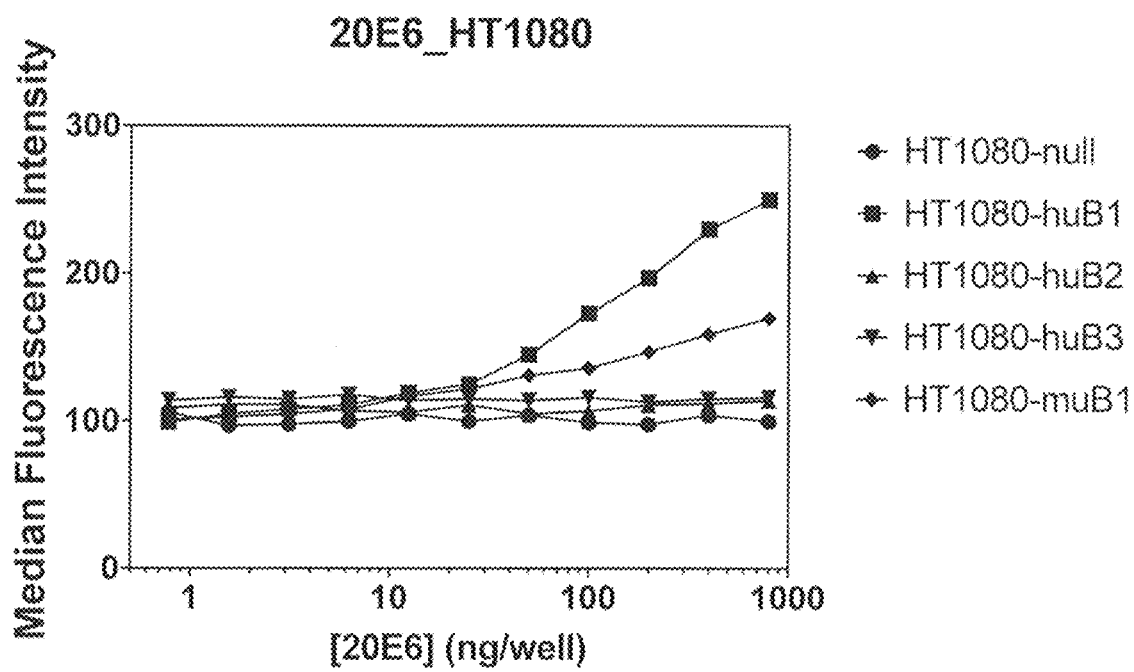
Figure 4D:
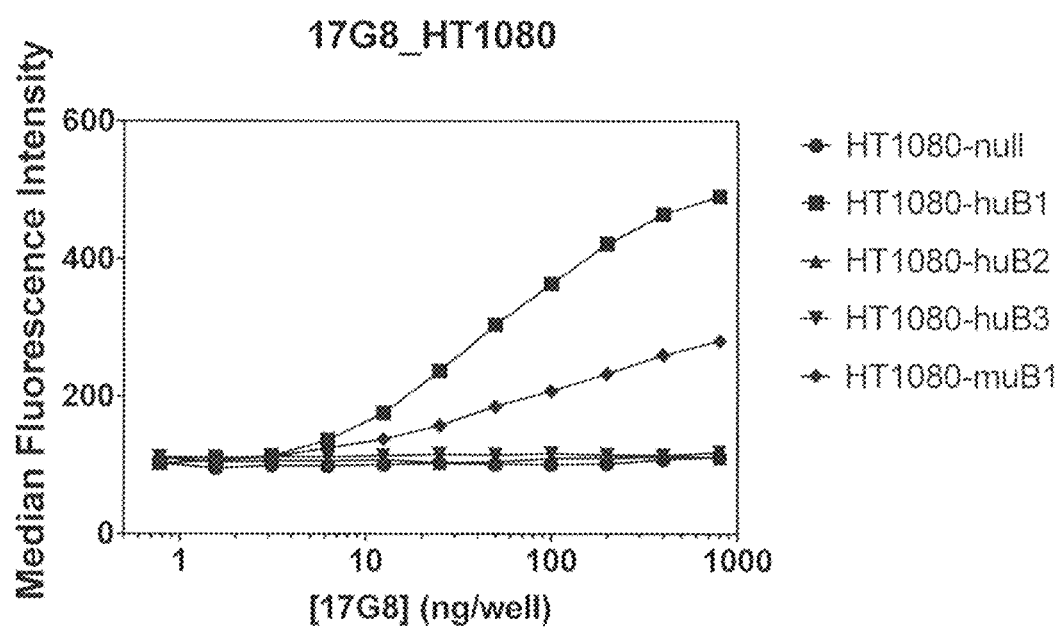
Figure 4E:
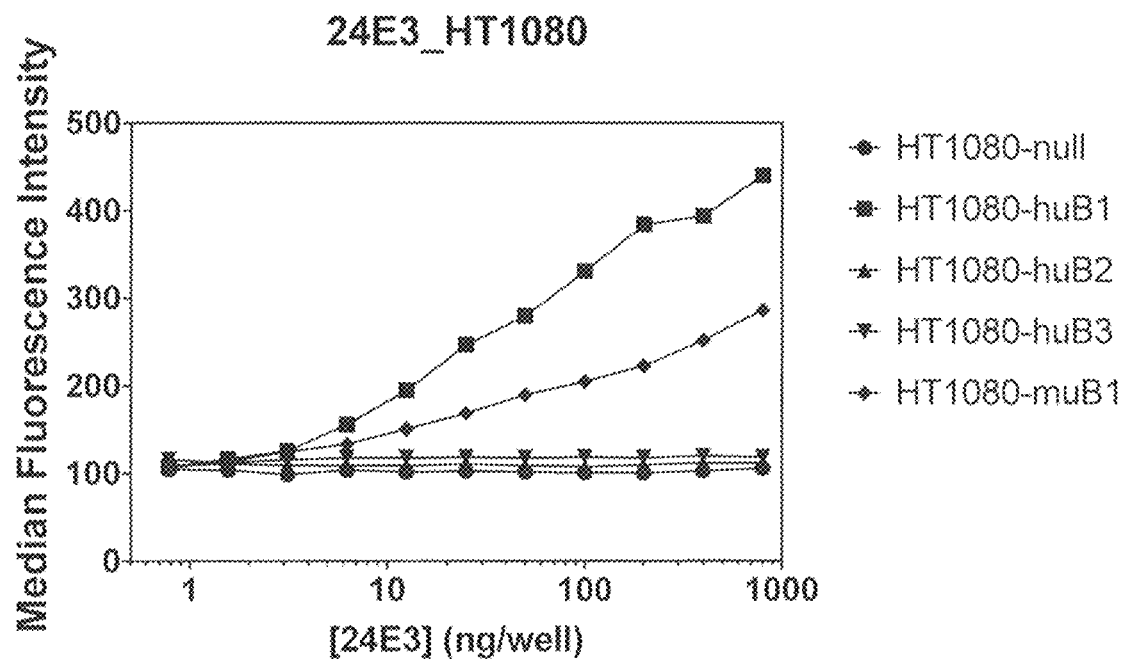
Figure 4F:
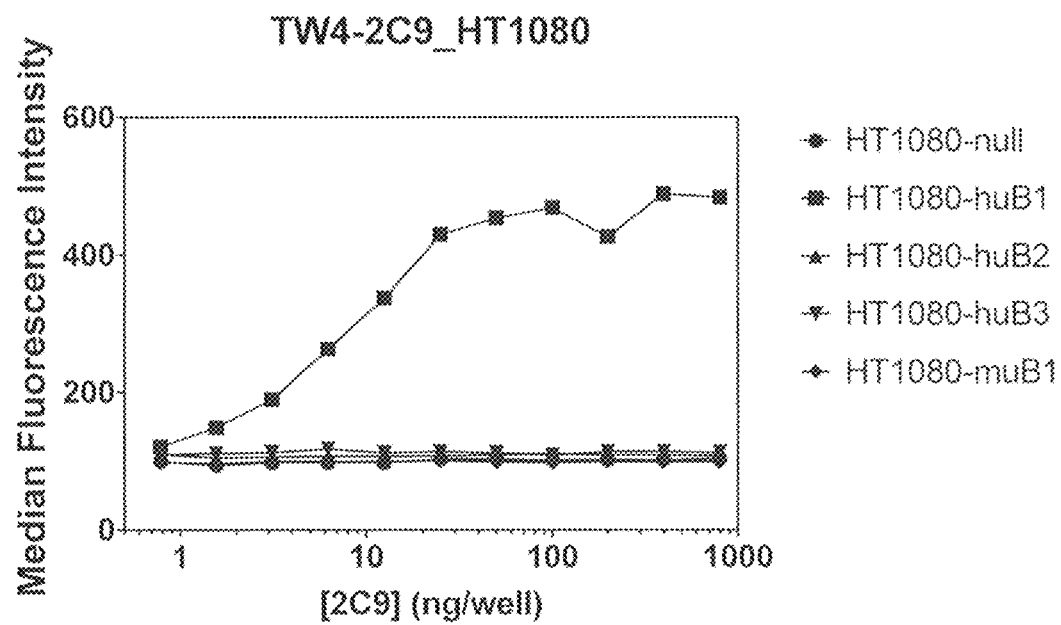
Figure 5A:
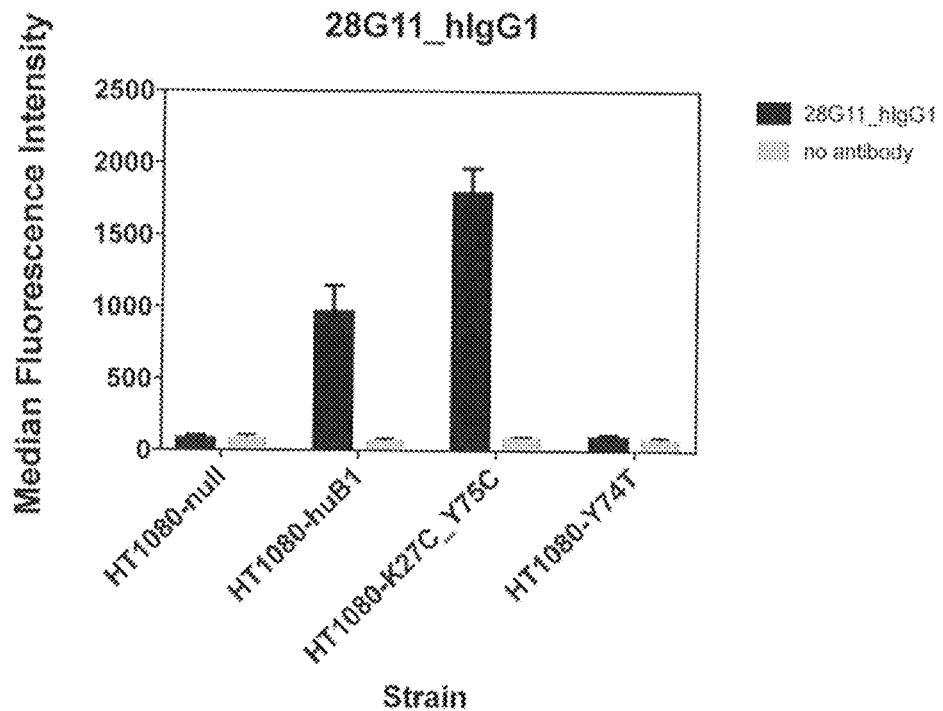
FIGS. 5A-5F are graphs showing the binding of antibodies 28G11_hIgG1, 22F9_hIgG1, 20E6_hIgG1, 17G8_hIgG1, 24E3_hIgG1, and 2C9_(hybridoma) to the indicated LAP-TGFβ variants. Black bars correspond to the indicated antibody binding to HT1080 cells over-expressing human LAP-TGFβ1. Gray bars correspond to negative controls samples where no anti-LAP antibody was added. HT1080-huB 1: HT1080 cells overexpressing LAP-TGFβ1, HT1080-K27C_Y75C: HT1080 cells overexpressing LAP-TGFβ1 with K27C and Y75C mutations (mutations that prevent TGFβ1 activation by integrins; "closed" conformation"), HT1080-Y74T: HT1080 cells overexpressing LAP-TGFβ1 with a Y74T mutation (mutation that favors spontaneous release of TGFβ1 "open conformation").
Figure 5B:
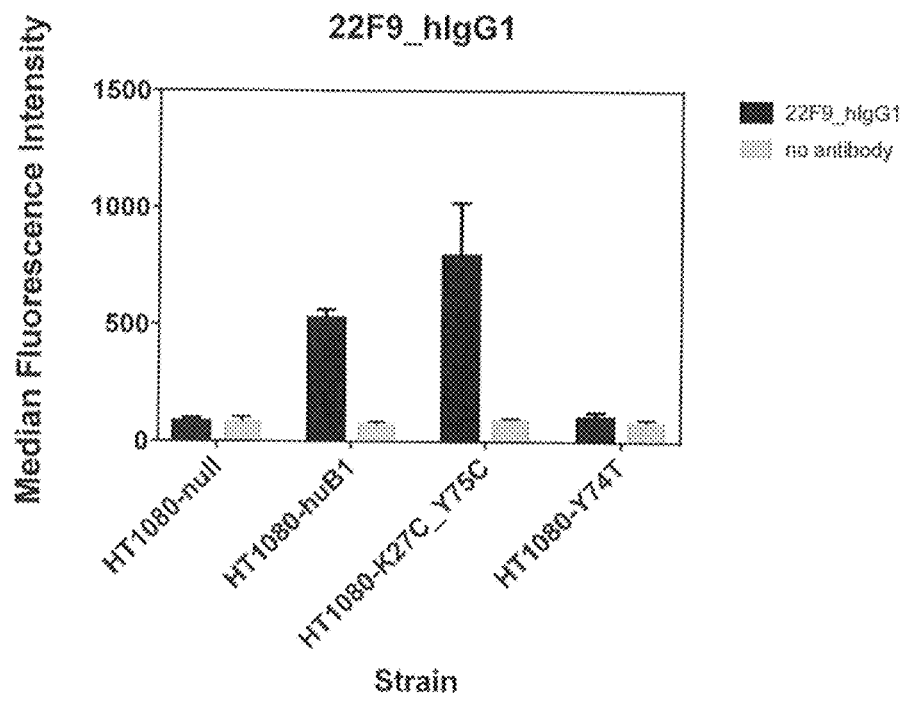
Figure 5C:
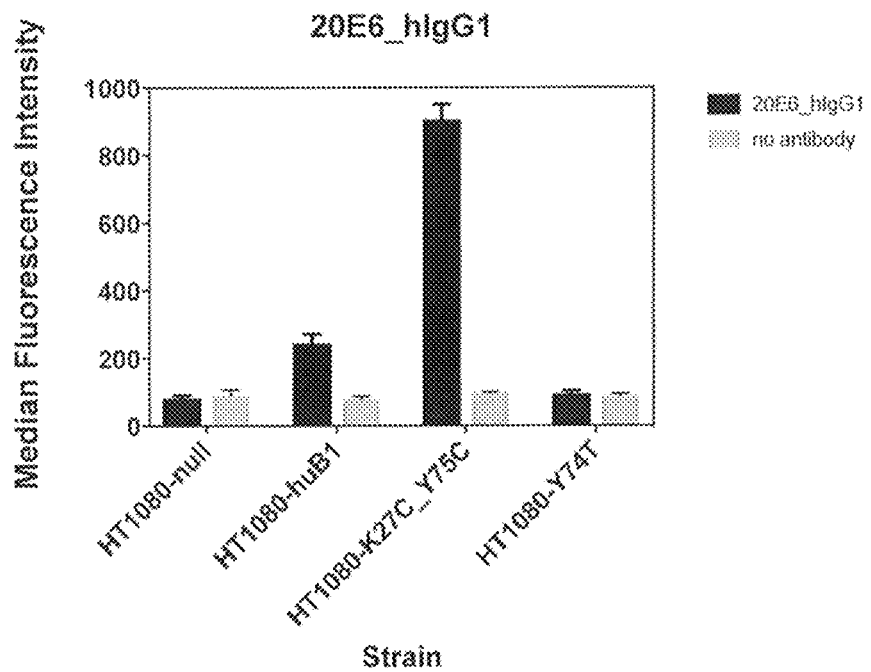
Figure 5D:
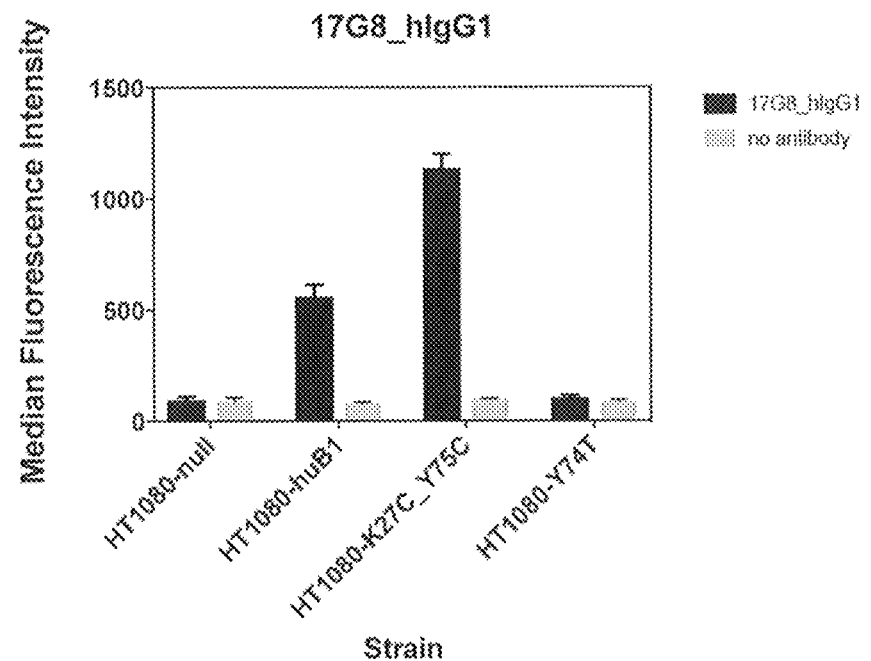
Figure 5E:
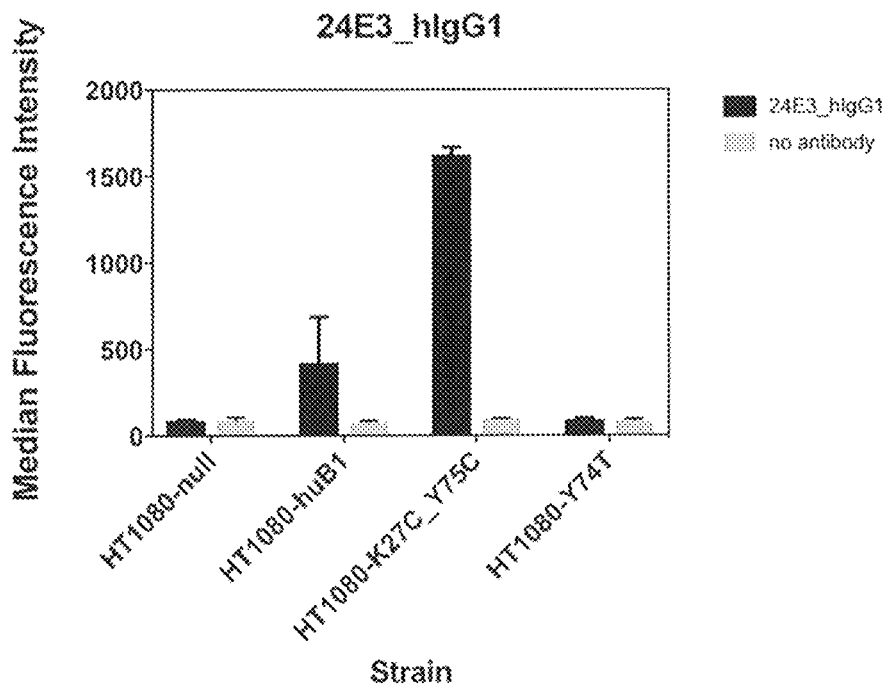
Figure 5F:
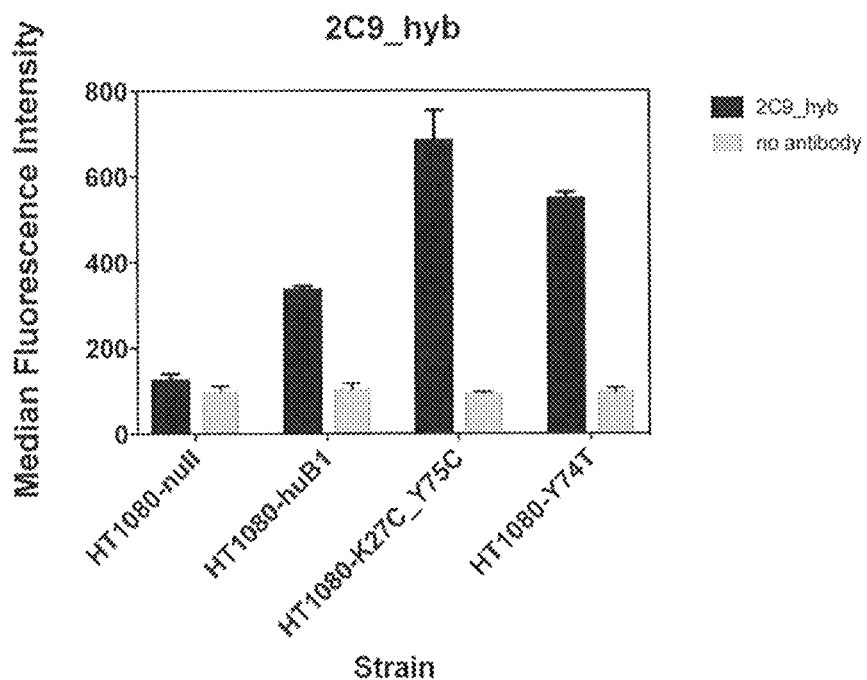
Figure 6A:
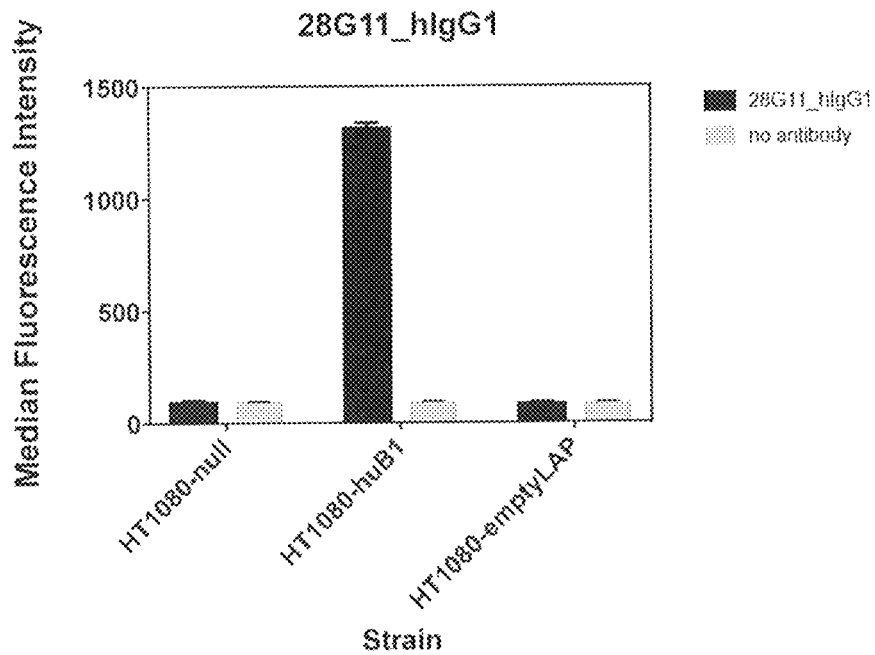
FIGS. 6A-6F are graphs showing the binding of antibodies 28G11_hIgG1, 22F9_hIgG1, 20E6_hIgG1, 17G8_hIgG1, 24E3_hIgG1, and 2C9_(hybridoma) to the indicated LAP-TGFβ variants. Black bars correspond to the indicated antibody binding to HT1080 cells over-expressing human LAP-TGFβ1. Gray bars correspond to negative controls samples where no anti-LAP antibody was added. HT1080-huB 1: HT1080 cells overexpressing LAP-TGFβ1, HT1080-emptyLAP: HT1080 cells overexpressing LAP which does not include the mature TGFβ1 cytokine.
Figure 6B:
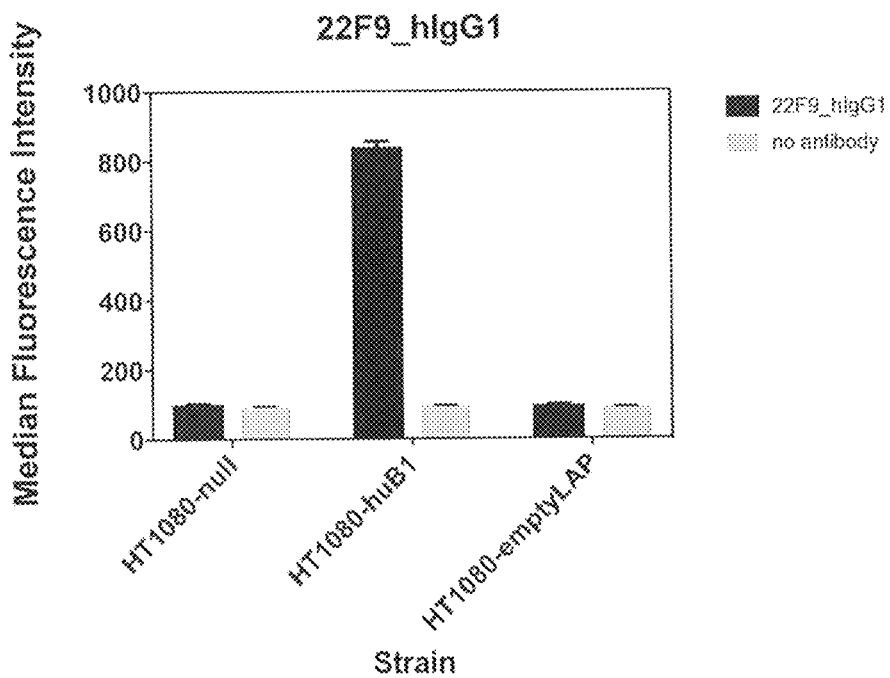
Figure 6C:
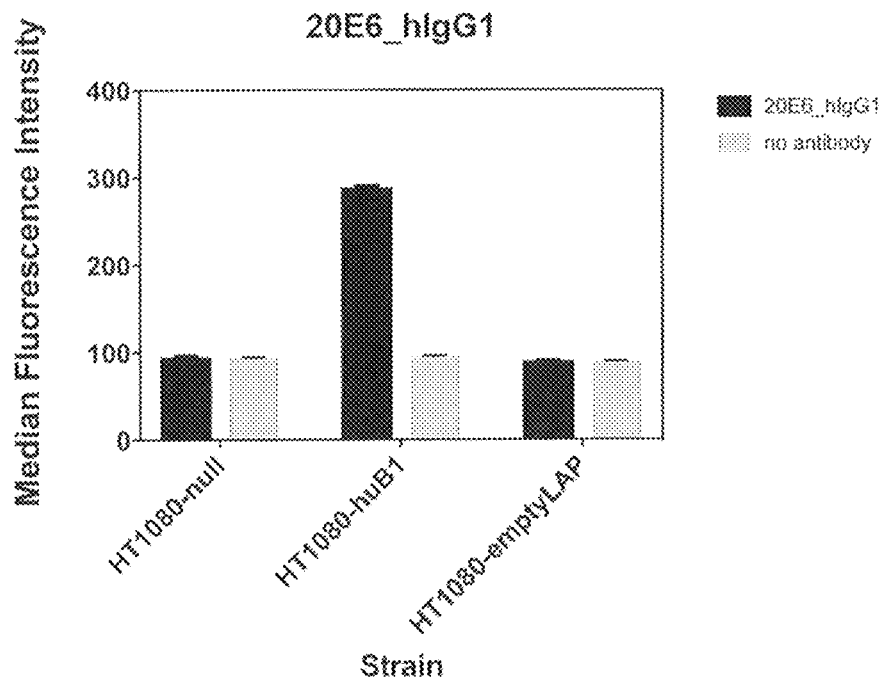
Figure 6D:
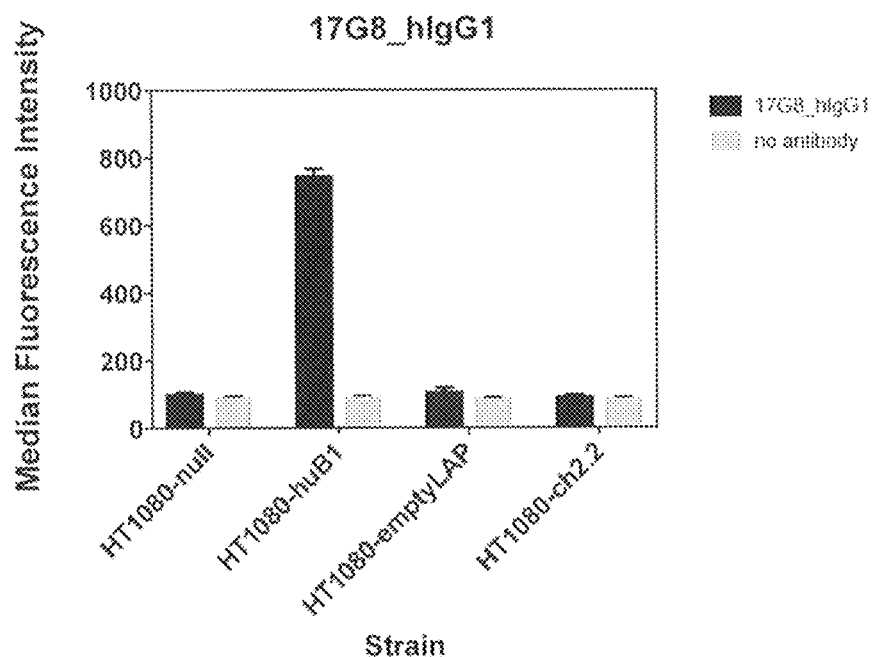
Figure 6E:
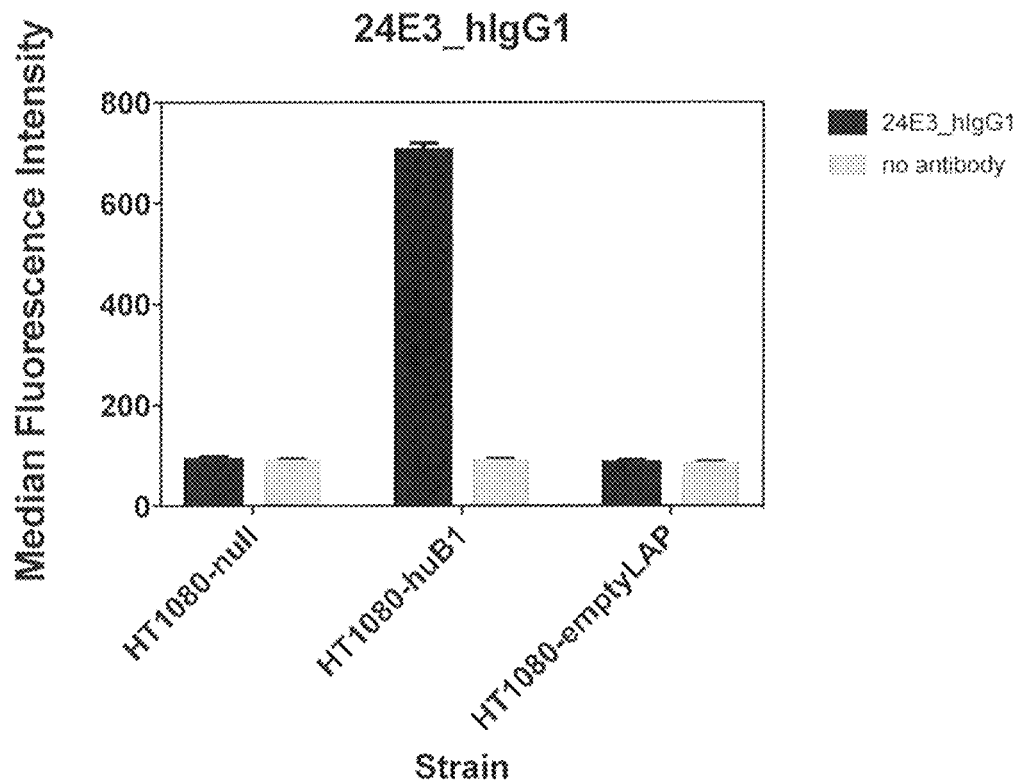
Figure 6F:
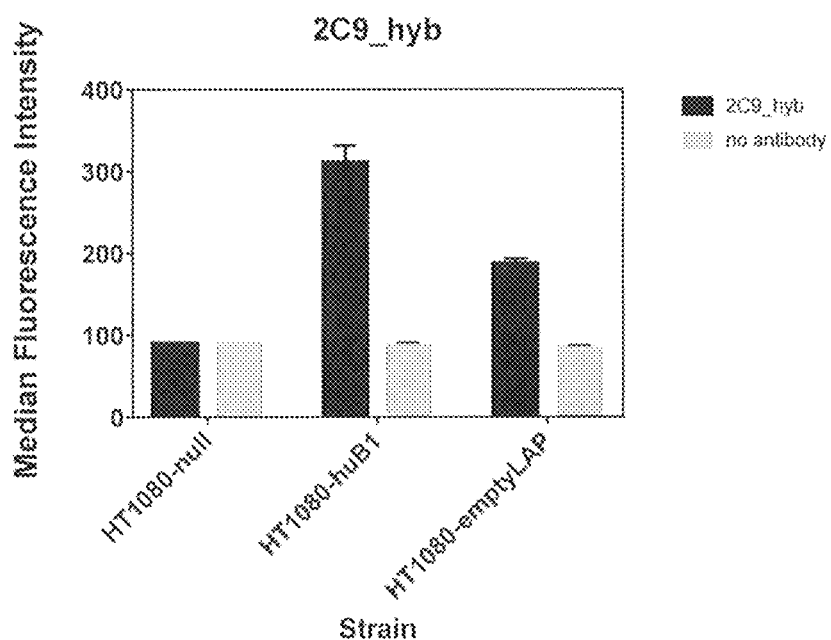

FIG. 2 shows the results of a set of anti-LAP antibodies binding to a recombinant human LAP-TGFβ1-Fc fusion protein at a single concentration using bio-layer interferometry (ForteBio assay). The ability of the antibodies to bind in this assay provides definitive evidence that the antibodies bind to LAP-TGFβ1 in the absence of an anchor protein. 16B4 failed to bind in this assay, reflecting its specificity for murine LAP-TGFβ1. FIG. 3 shows a comparison of the dissociation constant ($k_{dis}$), a concentration-independent measure of apparent affinity, for a larger panel of anti-LAP antibodies. Notably, the three antibodies with the fastest off rates, 3G5, 13B12 and 1G12, also had the highest $EC_{50}$ values in the data shown in Table 2.

The anti-LAP antibodies described above were tested for various functional properties, as described in the Examples that follow. Also included in the Examples below are data from additional exemplary anti-LAP antibodies (i.e., 22F9, 20E6 (26E10), 17G8, and 24E3) derived from different hybridomas produced from TGFβ1 knockout mice immunized with murine TGFβ1, which have VH and VL CDR sequences that are structurally distinct from those of 28G11 (Oida et al., PLoS One 2010; 5:e15523).

Example 2: Binding of Anti-LAP Antibodies to TGFβ Isoforms and TGFβ Variants This Example describes the binding of anti-LAP antibodies to TGFβ isoforms and TGFβ variants.

Briefly, $4 \times 10^5$ each of (a) HT1080 cells, (b) HT1080 cells overexpressing human LAP-TGFβ1, (c) HT1080 cells overexpressing human LAP-TGFβ2, (d) HT1080 cells overexpressing human LAP-TGFβ3, (e) HT1080 cells overexpressing murine LAP-TGFβ1, (f) P3U1 cells, (g) P3U1 cells overexpressing LAP-TGFβ1 and GARP, and (h) P3U1 cells overexpressing LAP-TGFβ1 and LRRC33 were cultured in 96-well plates. The plates were centrifuged for 5 min at 1,500 rpm, liquid was removed, and cells were resuspended with 200 μL FACS buffer. The plates were centrifuged again, diluted primary antibody was added to each well, and the plates were incubated on ice for 20 minutes, followed by centrifugation. The cells were resuspended in 200 μL FACS buffer, centrifuged again, and resuspended in 50 μL diluted secondary antibody (Alexa647-anti-Human IgG or APC-anti-Mouse IgG). The plates were incubated on ice for 20 minutes in the dark, washed twice with 200 μL FACS buffer, and cells from each well (in 200 μL FACS buffer) were read on the Attune NXT instrument.

As shown in FIGS. 4A-4F, all tested antibodies bind to HT1080 cell lines overexpressing human LAP-TGFβ1, but not to control HT1080 cells or cells overexpressing human LAP-TGFβ2 or LAP-TGFβ3. All tested antibodies bind to P3U1-hTGFβ1 cells, and the binding was enhanced when either human GARP or LRRC33 was co-expressed. Antibodies 28G11_hIgG1, 22F9_hIgG1, 20E6_hIgG1, 17G8_hIgG1, and 24E3_hIgG1, but not 2C9_(hyb), bind to HT1080 cells overexpressing murine LAP-TGFβ1. These results suggest that antibodies 28G11_hIgG1, 22F9_hIgG1, 20E6_hIgG1, 17G8_hIgG1, and 24E3_hIgG1 bind specifically to the LAP-TGFβ1 isoform of LAP-TGFβ.

The ability of the anti-LAP antibodies to bind variants of LAP-TGFβ1 that either prevent TGFβ1 activation by integrins ("closed" conformation) or favor spontaneous release ("open" conformation), and to the LAP-only variant (i.e., human LAP which does not contain mature TGFβ1), was tested.

Briefly, $4 \times 10^5$ each of (a) HT1080 cells, (b) HT1080 cells overexpressing human LAP-TGFβ1, (c) HT1080 cells overexpressing LAP-TGFβ1 with K27C and Y75C mutations, (d) HT1080 cells overexpressing LAP-TGFβ1 with a Y74T mutation, and (e) HT1080 cells overexpressing the LAP-only variant were cultured in 96-well plates. Cells were processed for flow cytometry in the same manner described above for the isoform-specific binding experiments.

As shown in FIGS. 5A-5F, while none of the tested anti-LAP antibodies bind to untransduced HT1080 cells, all tested antibodies bind to HT1080 cells overexpressing wild-type human LAP-TGFβ1. Antibodies 28G11_hIgG1, 22F9_hIgG1, 20E6_hIgG1, 17G8_hIgG1, and 24E3_hIgG1 bind to the K27C/Y75C ("closed") LAP-TGFβ1 variant, but not to the Y74T ("open") LAP-TGFβ1 variant. In contrast, antibody 2C9 binds to both the K27C/Y75C and Y74T LAP-TGFβ1 variants. Furthermore, as shown in FIGS. 6A-6F, while all tested antibodies bind to HT1080 cells overexpressing wild-type human LAP-TGFβ1, antibodies 28G11_hIgG1, 22F9_hIgG1, 20E6_hIgG1, 17G8_hIgG1, and 24E3_hIgG1 did not bind to the LAP-only variant.

Figure 7:
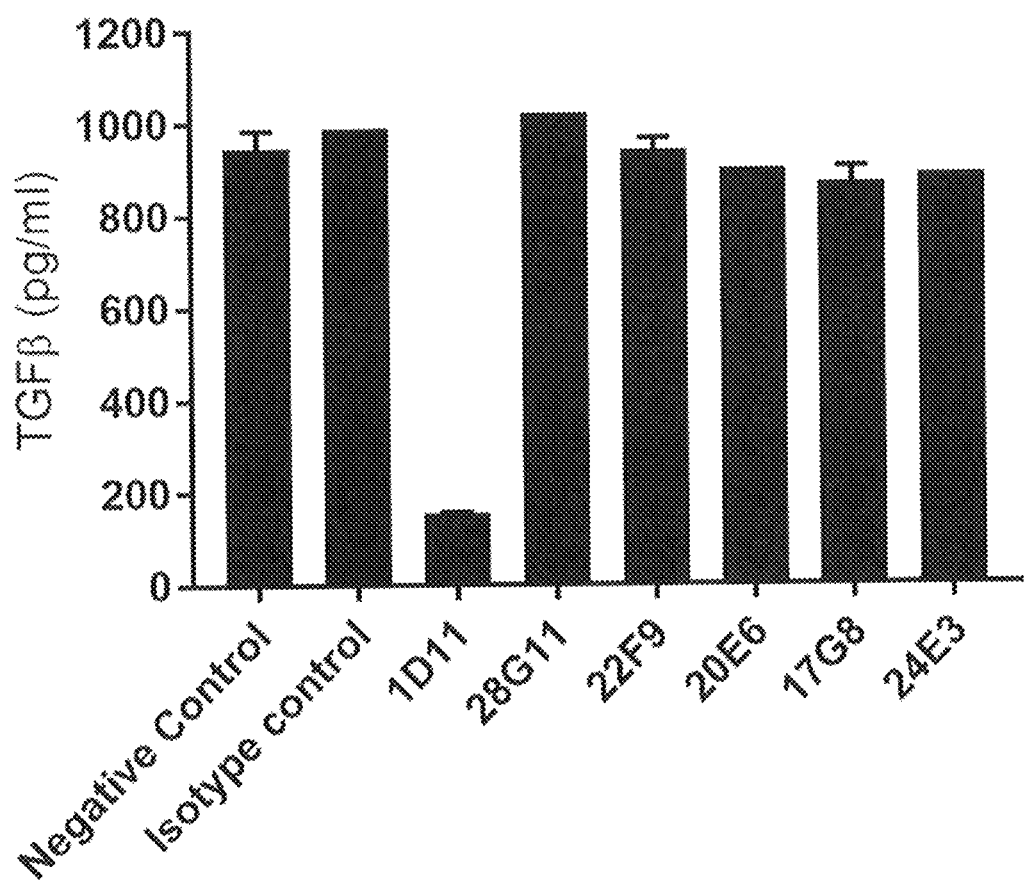
FIG. 7 is a graph showing the binding of antibodies 28G11_hIgG1, 22F9_hIgG1, 20E6_hIgG1, 17G8_hIgG1, 24E3_hIgG1, and 1D11 to mature TGFβ (i.e., TGFβ without LAP), as measured by an ELISA assay in which inhibition of signal reflects binding to mature TGFβ.

To determine whether anti-LAP antibodies 28G11_hIgG1, 22F9_hIgG1, 20E6_hIgG1, 17G8_hIgG1, and 24E3_hIgG1, bind to free human TGFβ1 (i.e., mature TGFβ1 that lacks LAP), the ability of the antibodies to inhibit an anti-TGFβ ELISA was evaluated. Briefly, mature TGFβ1 (1000 μg) was incubated with the indicated anti-LAP antibodies at 10 μg/mL, an isotype control antibody as a negative control or the anti-TGFβ antibody 1D11 as a positive control for 10 minutes on ice. Supernatants were assayed in a TGFβ1 ELISA (R&D Systems) according to the manufacturer instructions to measure free TGFβ1. As shown in FIG. 7, the anti-TGFβ antibody 1D11 bound to the mature TGFβ and inhibited the ELISA, while no inhibition was seen with 28G11_hIgG1, 22F9_hIgG1, 20E6_hIgG1, 17G8_hIgG1, and 24E3_hIgG1. These data demonstrate that 28G11_hIgG1, 22F9_hIgG1, 20E6_hIgG1, 17G8_hIgG1, and 24E3_hIgG1 do not bind to mature TGFβ1.

These results suggest that antibodies 28G11_hIgG1, 22F9_hIgG1, 20E6_hIgG1, 17G8_hIgG1, and 24E3_hIgG1 share a related epitope. These antibodies do not bind the mature cytokine directly, as described above (FIG. 7), but may be sensitive to conformational changes in the LAP region induced by the presence or absence of the mature cytokine. In contrast, antibody 2C9 binds to all variants of LAP, including the "open" and "closed" conformation variants, as well as to LAP in the presence or absence of the mature cytokine.

Example 3: Effects of Anti-LAP Antibodies on TGFβ1 Activation

The effects of the anti-LAP antibodies on TGFβ1 activation were assessed in this Example.

Briefly, human LAP-TGFβ1-P3U1 cells were cultured overnight and treated the following day with or without anti-LAP antibody (8 μg/mL) for 24 hours. Active TGFβ1 was detected in the supernatant of cell cultures by utilizing a commercially available human TGFβ1 ELISA kit (R&D systems).

As shown in Table 3, anti-LAP antibodies had varying effects on TGFβ1 activation, including inhibition of TGFβ1 activation, no effect, and stimulation of TGFβ1 activation. Activity of the antibodies was largely unaffected by the presence of GARP (with the exception of 3H6 and 6H10). No correlation was found between apparent affinity and the ability to inhibit TGFβ1 activation (antibodies in Table 3 are listed in rank order based on $EC_{50}$s in the P3U1 binding assay from Table 2), indicating that simple binding to LAP-TGFβ1 and inhibition of TGFβ1 activation are separable and distinct activities of the anti-LAP antibodies. 13B12 and 3G5 were active in the inhibition assay despite a lack of activity in any of the binding assays. These are the two antibodies with the fastest off-rates in the Octet assay.

TABLE 3

| | Effect on TGFβ1 activation | |
|---|---|---|
| mAb* | P3U1-human LAP-TGFβ1 | P3U1-human LAP-TGFβ1 + GARP |
| 28G11 | Inhibition | Inhibition |
| 2C9 | No effect | No effect |
| 7H4 | Inhibition | Inhibition |
| 16F4 | No effect | No effect |
| 3H6 | No effect | Inhibition |
| 478.E9 | Stimulate | Stimulate |
| 8F10 | Inhibition | Inhibition |
| 6H10 | Inhibition | No effect |
| 478.G3 | Stimulate | Stimulate |
| 1E1 | Inhibition | Inhibition |
| 478.G4 | Stimulate | Stimulate |
| 2F8 | No effect | No effect |
| 1G12 | No effect | No effect |
| 13B12 | Inhibition | Inhibition |
| 3G5 | Inhibition | Inhibition |

*antibodies tested at 8 μg/mL

Figure 8A:
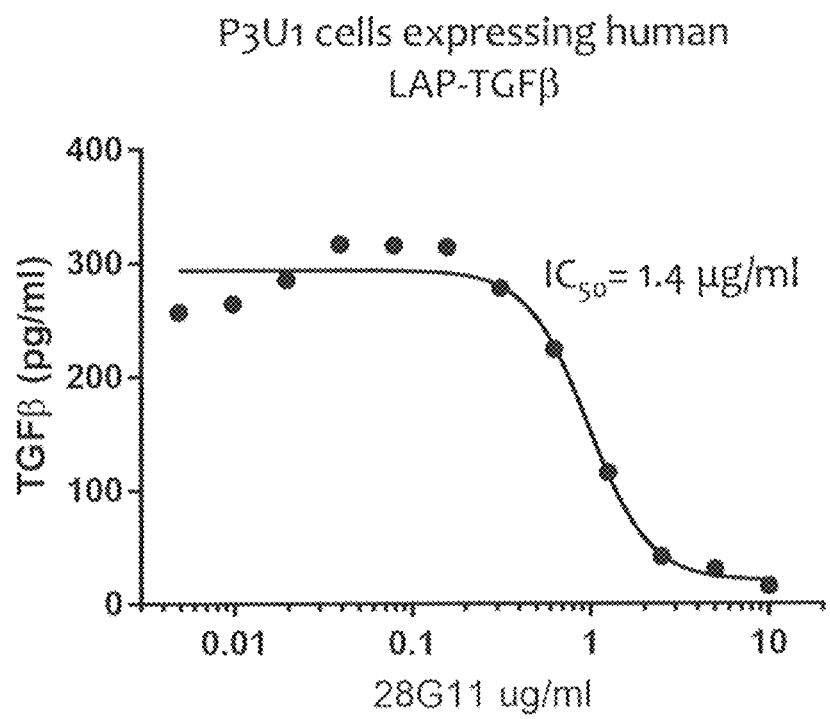
FIGS. 8A and 8B are graphs showing the effects of 28G11 on TGFβ1 activation in P3U1 cells expressing human LAP-TGFβ1 (FIG. 8A) and murine LAP-TGFβ1 (FIG. 8B).
Figure 8B:
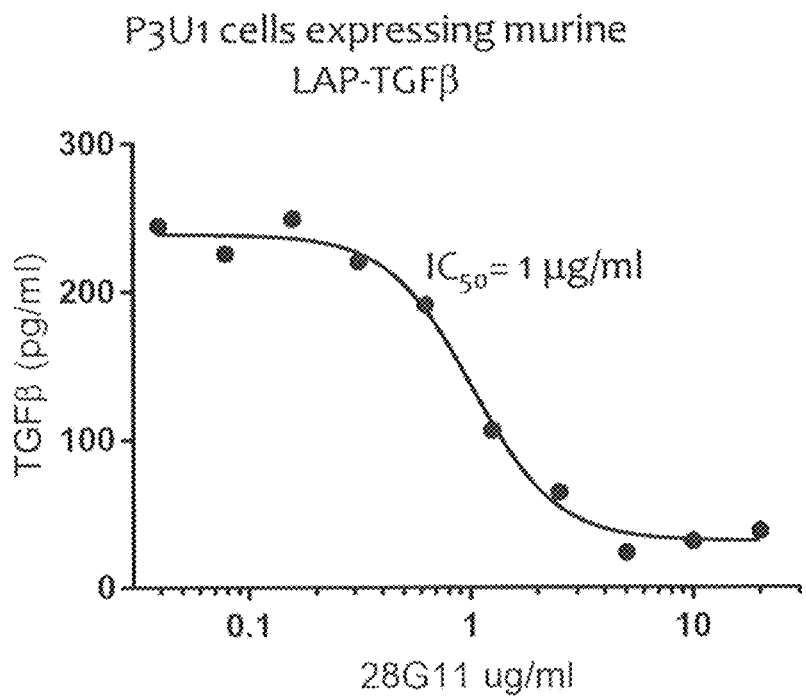
Figure 9A:
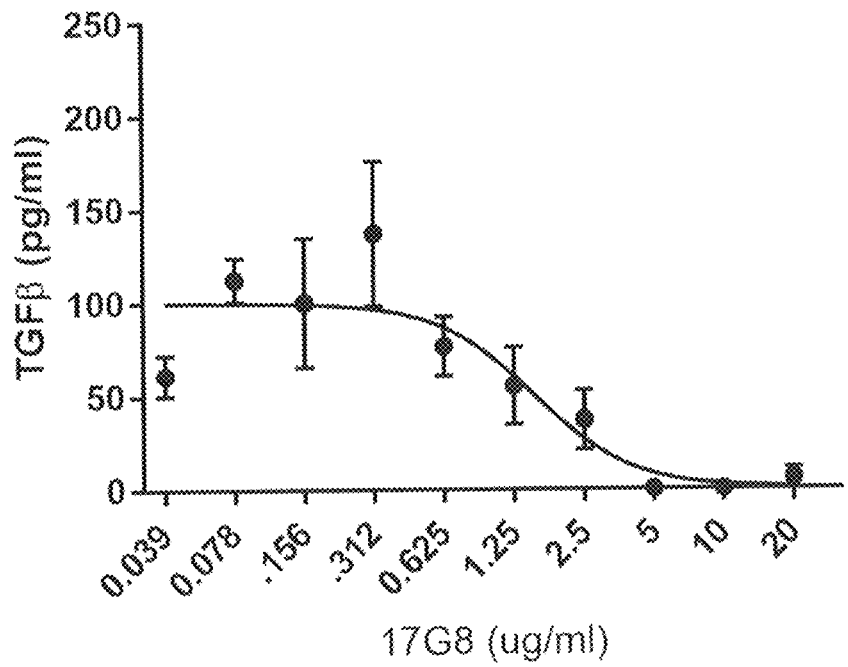
FIGS. 9A-9F are graphs showing the effects of 17G8 (FIG. 9A for human LAP-TGFβ1 and FIG. 9B for murine LAP-TGFβ1), 24E3 (FIG. 9C for human LAP-TGFβ1 and FIG. 9D for 24E3), 22F9 (FIG. 9E for human LAP-TGFβ1), and 20E6 (FIG. 9F for human LAP-TGFβ1 on TGFβ1 activation in P3U1 cells expressing murine or human LAP-TGFβ1.
Figure 9B:
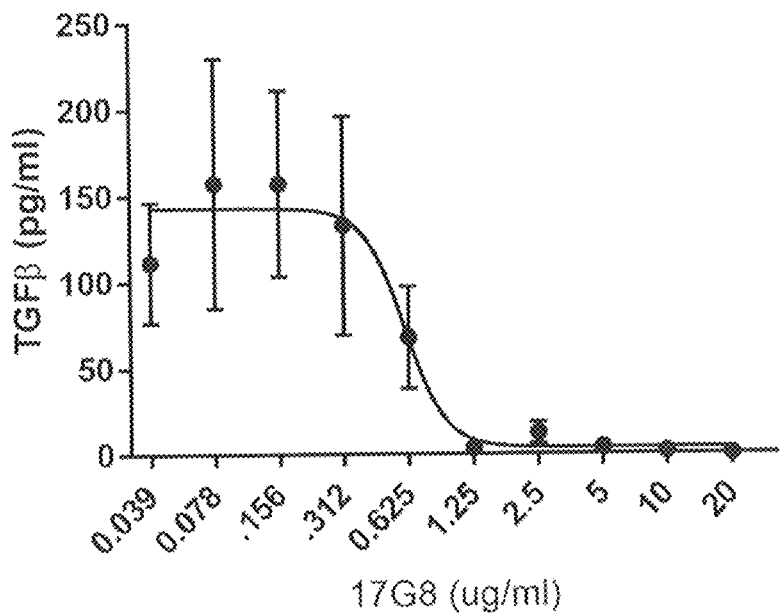
Figure 9C:
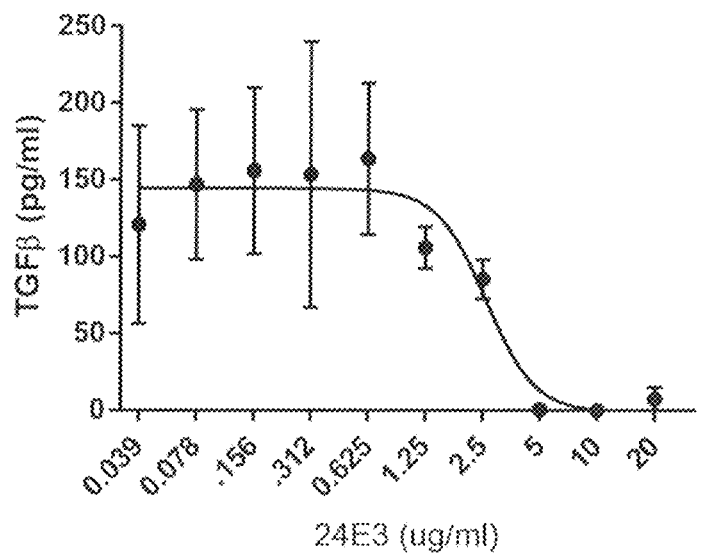
Figure 9D:
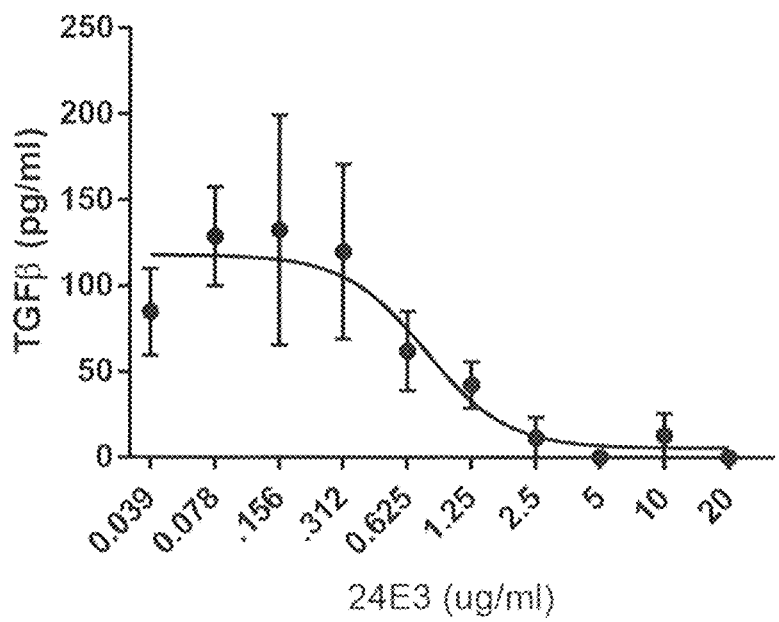
Figure 9E:
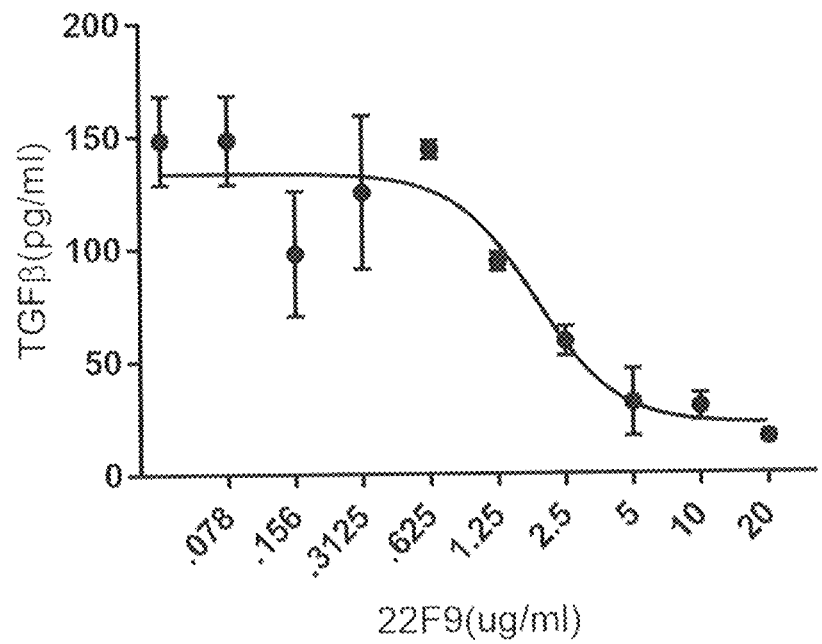
Figure 9F:
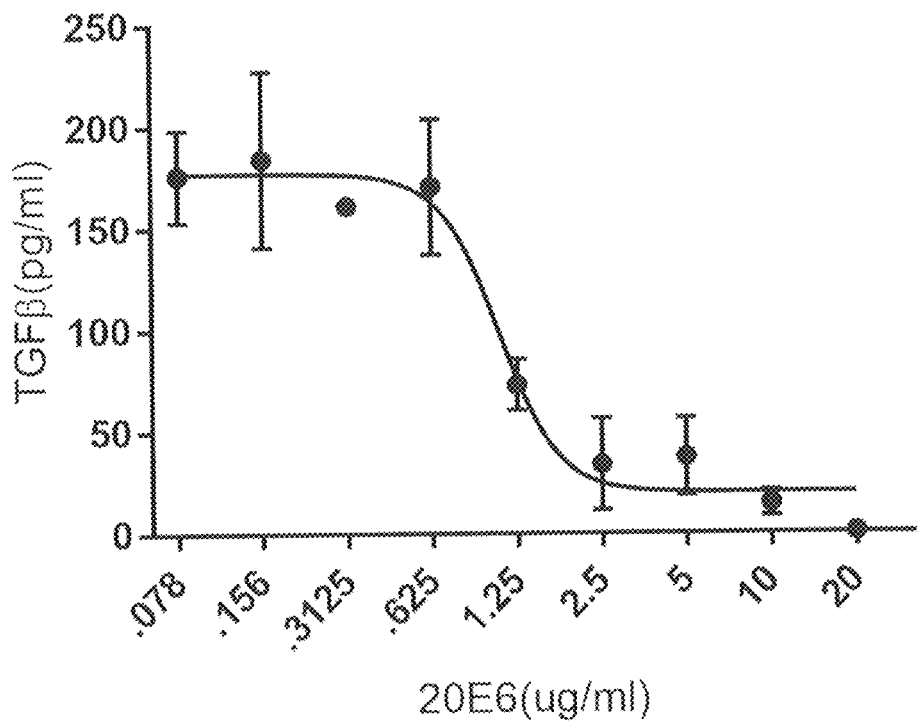

FIGS. 8A and 8B show the activity of 28G11 on TGFβ1 activation using the P3U1 cell assay. As shown in these Figures and in Table 3, 28G11 inhibited TGFβ1 activation in both P3U1 cells expressing human LAP-TGFβ1 (IC50=1.4 ug/ml) and murine LAP-TGFβ (IC50=1 ug/ml).

FIGS. 9A-9F shows the activity of antibodies 17G8, 24E3, 22F9, and 20E6 on TGFβ1 activation using the P3U1 cell assay. Briefly, P3U1 cells that overexpress human or murine TGFβ1 were incubated in advanced serum free DMEM in round bottom wells. P3U1 cells were treated with the indicated concentrations of antibodies 17G8, 24E3, 22F9, and 20E6 for 24 hours and the supernatants were assayed for active TGFβ1 using a TGFβ1 ELISA from R & D Systems. As with 28G11, the tested antibodies inhibited TGFβ1 activation in P3U1 cells expressing human LAP-TGFβ1. Data are shown in the following Figures; IC50 values are as shown: antibody 17G8 (FIGS. 9A for human TGFβ1 (IC50=1.5 ug/ml) and 9B for murine TGFβ1 (IC50=0.59 ug/ml)), antibody 24E3 (FIG. 9C for human TGFβ1 (IC50=2.6 ug/ml) and 9D for murine TGFβ1 (IC50=0.76 ug/ml)), antibody 22F9 (FIG. 9E for human TGFβ1 (IC50=1.8 ug/ml)), and antibody 20E6 (FIG. 9F for human TGFβ1 (IC50=1.08 ug/ml)).

Figure 10:
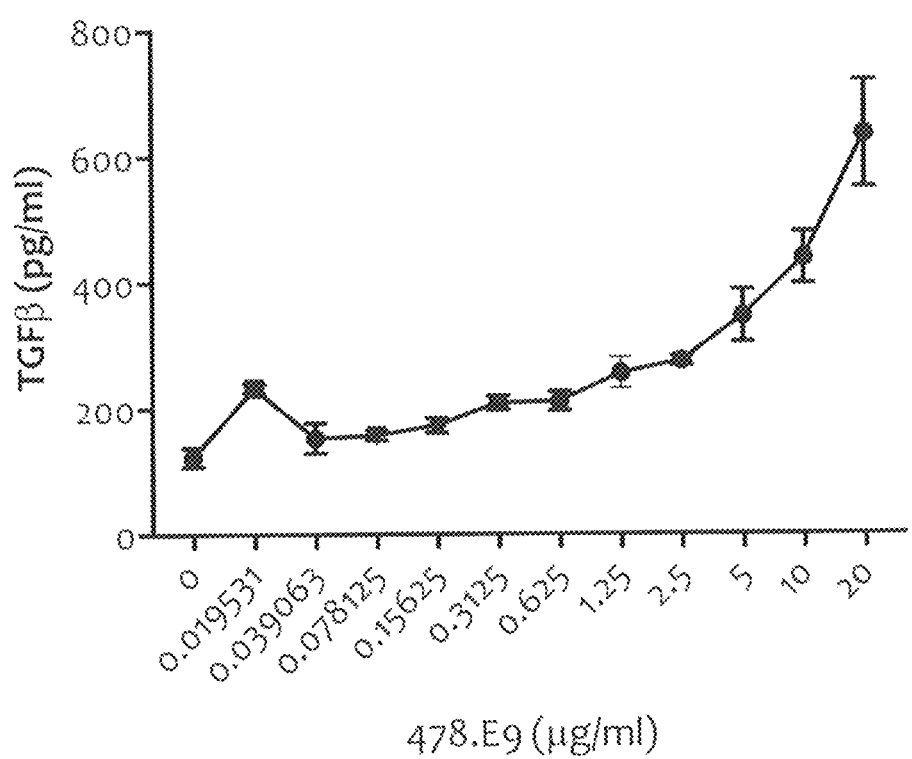
FIG. 10 is a graph showing the effects of 478.E9 on TGFβ activation in P3U1 cells expressing human LAP-TGFβ1.

FIG. 10 shows the activity of 478.E9 on TGFβ1 activation. In contrast to the inhibitory effect of 28G11 on TGFβ activation, 478.E9 stimulated TGFβ1 release.

The anti-LAP antibodies also had differing effects on P3U1 cells expressing murine LAP-TGFβ1, as shown in Table 4.

TABLE 4

| mAb* | Inhibition P3U1-murine LAP-TGFβ1 |
|---|---|
| 28G11 | + |
| 16B4** | − |
| 20B9 | − |
| 7H4 | + |

Figure 11A:
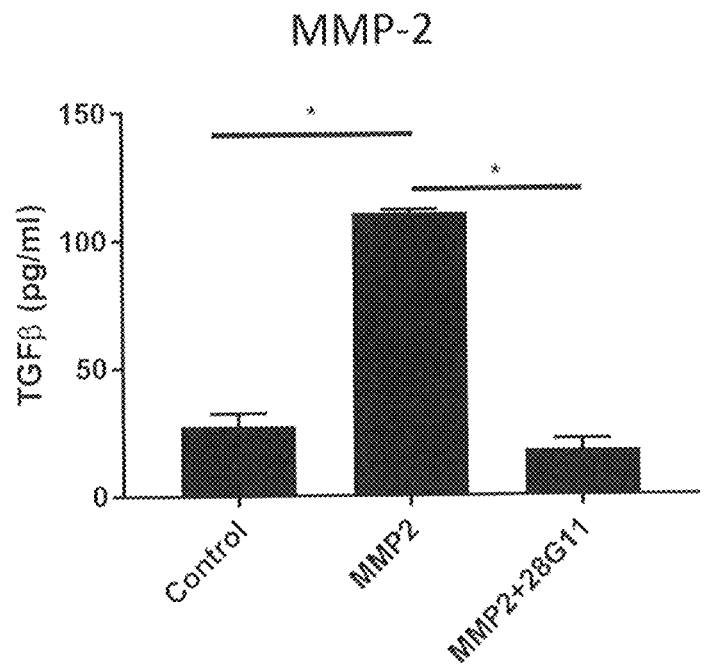
FIGS. 11A and 11B are graphs showing the effects of 28G11 on MMP-2 (FIG. 11A) and MMP-9 (FIG. 11B) mediated TGFβ activation. The control groups have no added MMP.

*antibodies tested at 8 μg/mL;
**16B4 inhibits TGFβ activation when tested at 250 μg/mL Given that TGFβ1 activation can be induced by MMPs, the effects of the antibodies on MMP-induced LAP-TGFβ1 activation was tested. Briefly, recombinant human LAP-TGFβ1 (R&D Systems) was pre-incubated with anti-LAP antibodies (8 μg/ml) for 10 minutes and then treated with 100 ng/ml active MMP2 or MMP9 (EMD Millipore). All reactions were performed in MMP assay buffer (50 mM Tris, 150 mM NaCl, 10 mM CaCl2, 10 uM ZnCl2, 0.05% Brij 35) and incubated at 37C for 2 hours. Reactions were terminated through the addition of 10 μM EDTA. Supernatants were collected and analyzed using a commercially available human TGFβ1 ELISA (R&D Systems). The results for all antibodies tested are summarized in Table 5, and the results for 28G11 are shown in FIG. 11A (MMP-2) and 11B (MMP-9).

TABLE 5

| | Effect on TGFβ1 activation by MMP | |
|---|---|---|
| mAb | MMP2 | MMP9 |
| 28G11 | Inhibition | Inhibition |
| 2C9 | Inhibition | No effect |
| 7H4 | Inhibition | Inhibition |
| 3H6 | Inhibition | No effect |
| 478.E9 | Stimulate | Stimulate |
| 6H10 | Inhibition | No effect |
| 478.G3 | Stimulate | Stimulate |
| 1E1 | Inhibition | Inhibition |
| 478.G4 | Stimulate | Stimulate |
| 2F8 | +/− | No effect |
| 13B12 | Inhibition | Inhibition |
| 3G5 | Inhibition | Inhibition |

Example 4: Binding of Anti-LAP Antibodies to Extracellular Matrix

Since the extracellular matrix is a primary source of latent TGFβ1, the ability of the anti-LAP antibodies to bind to the ECM was examined.

P3U1 cells lay down ECM via constitutive expression of LTBP, a component of the LAP-TGF I-LTBP complex which binds to ECM. To evaluate antibody binding to ECM, P3U1 cells were incubated in tissue culture plates for 48 hours. Cells were then removed, leaving behind ECM on the surface of the plates. Three different groups were compared: (a) P3U1 cells expressing human LAP-TGFβ1, (b) P3U1 cells expressing murine LAP-TGFβ1, and (c) P3U1 cells without LAP-TGFβ1 (null cells). Binding of antibody to LAP-TGFβ1/ECM was then determined using biotinylated anti-LAP antibodies.

Figure 12B:
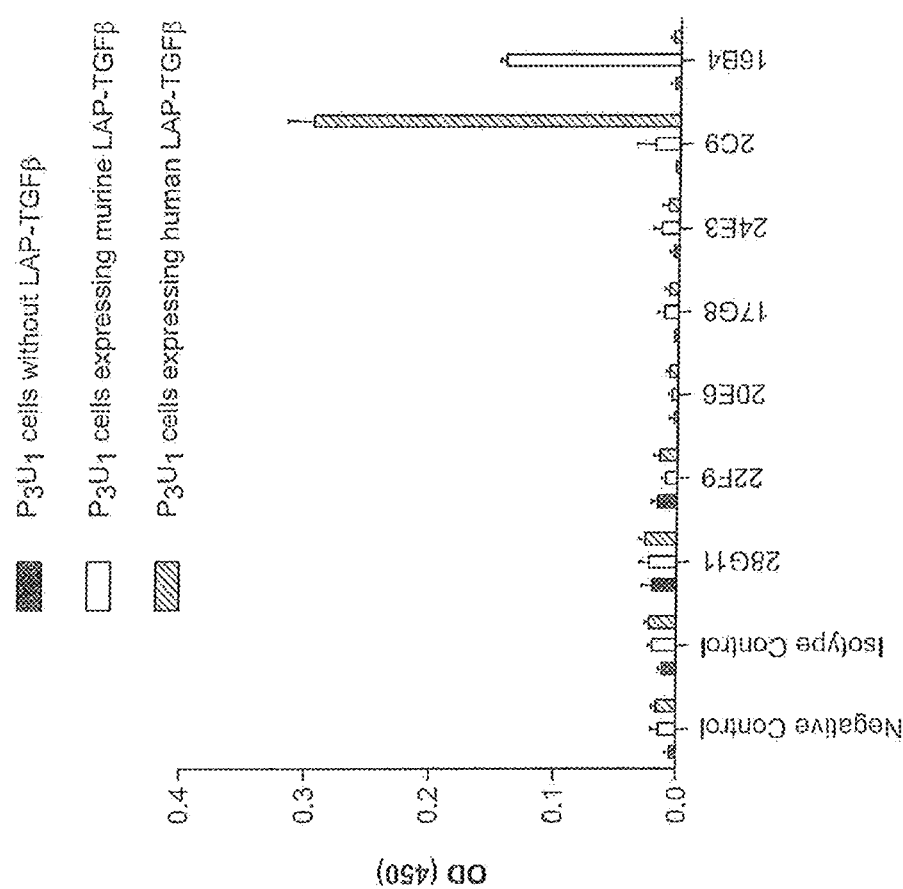

As shown in FIG. 12A, 2C9, 3H6, 6H10, 16B4, 8F10, 16F4, 20B9, 1E1, 2F8, 478.E9, 478.G3, 478.G4 bind to LAP-TGFβ1/ECM, whereas 28G11, 7H4, 13B12, 3G5 showed minimal, if any, binding to LAP-TGFβ1/ECM. In addition, as shown in FIG. 12B, antibodies 22F9, 26E10, 17G8, and 24E3 did not bind to LAP-TGFβ1/ECM, whereas antibodies 2C9 and 16B4 do bind.

Example 5: Binding of Anti-LAP Antibodies to Platelets

This Example describes the binding of anti-LAP antibodies to platelets.

Briefly, platelets and peripheral blood mononuclear cells were isolated from the blood of a single healthy donor. Cells were activated for 48 hr with plate-bound anti-CD3 monoclonal antibody (10 μg/mL), soluble anti-CD28 monoclonal antibody (2 μg/mL), and recombinant human IL-2 (3 ng/mL). The activated cells were stained with anti-CD61 and anti-LAP monoclonal antibodies. A gate was set around CD61+ platelets and LAP expression was measured using antibodies 478.E9, 28G11, 7H4, 3G5, 2F8 and 2C9, as shown. The anti-LAP antibodies were directly biotinylated and binding was measured using APC-labeled streptavidin.

Figure 13:
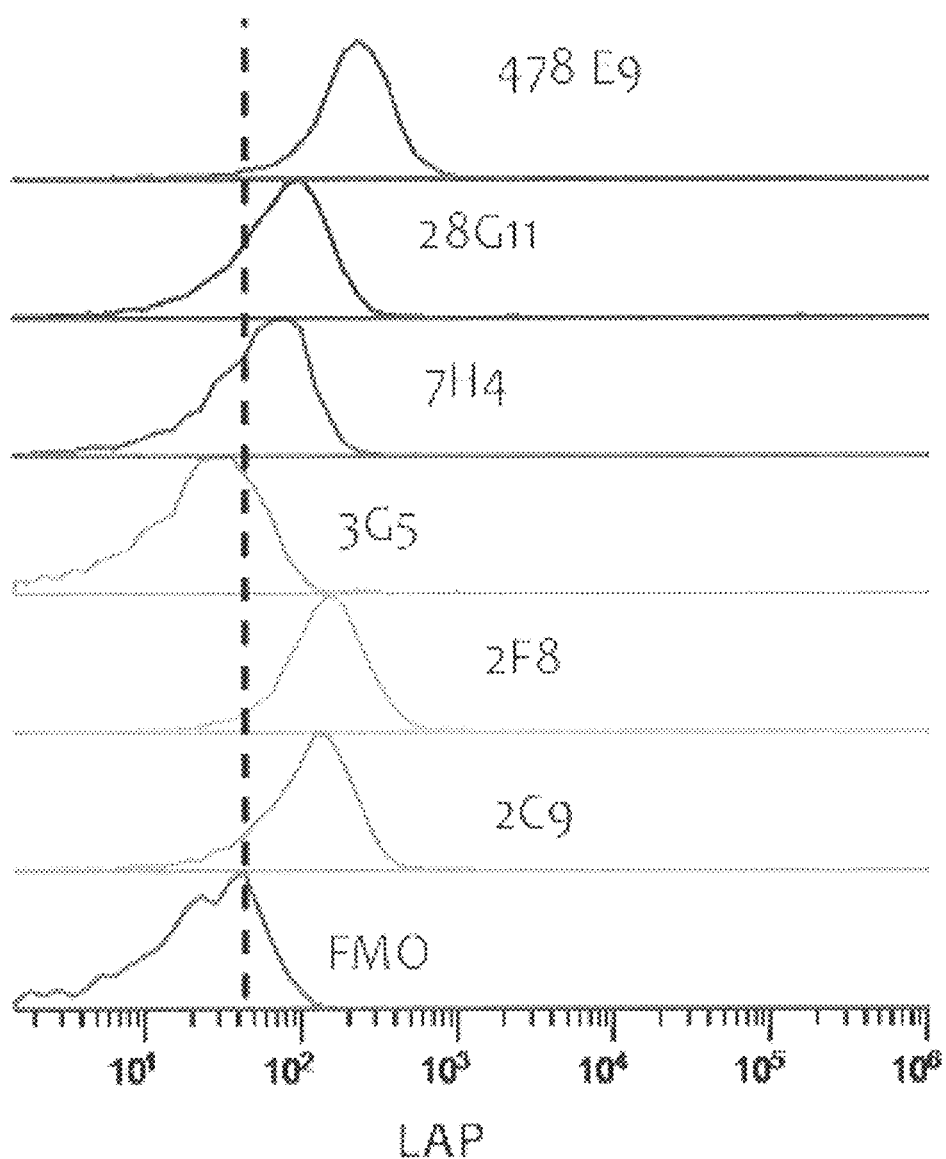
FIG. 13 is a plot depicting the binding of the indicated anti-LAP antibodies to human platelets.
Figure 14A:
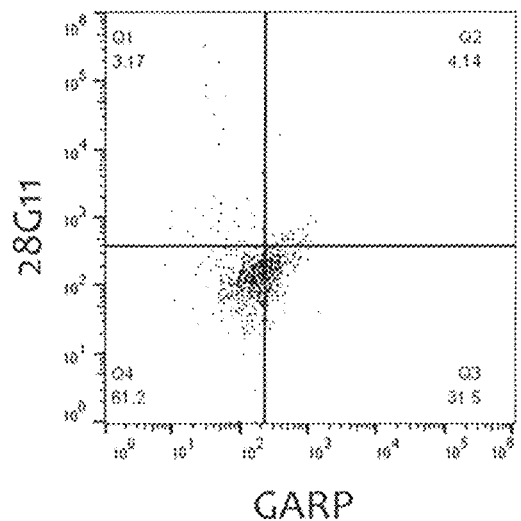
FIGS. 14A-14D are scatter plots depicting the binding of 28G11 (FIG. 14A), 7H4 (FIG. 14B), 20B9 (FIG. 14C), and 16B4 (FIG. 14D) to murine platelets.
Figure 14B:
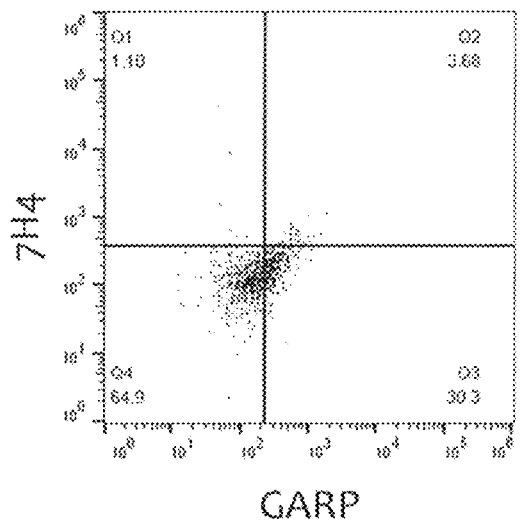
Figure 14C:
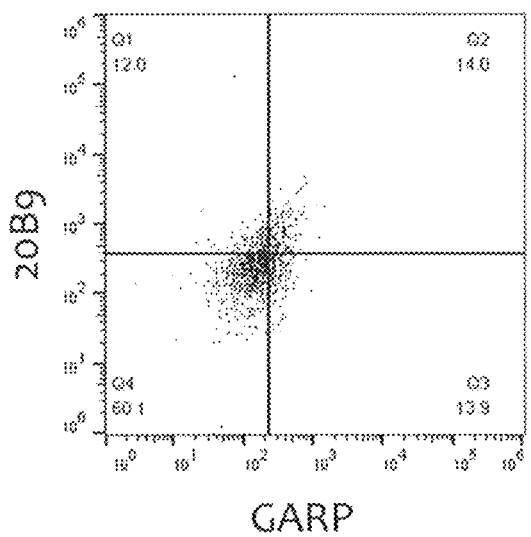
Figure 14D:
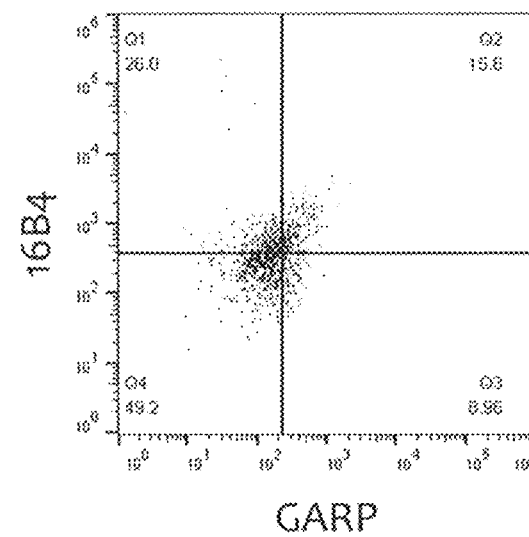

As shown in FIG. 13, anti-LAP antibodies showed varied binding to human platelets. The ability of anti-LAP antibodies to bind murine platelets also was assessed. As shown in FIGS. 14A-14D, 20B9 and 16B4 bind more strongly to platelets than do 28G11 and 7H4.

Figure 15:
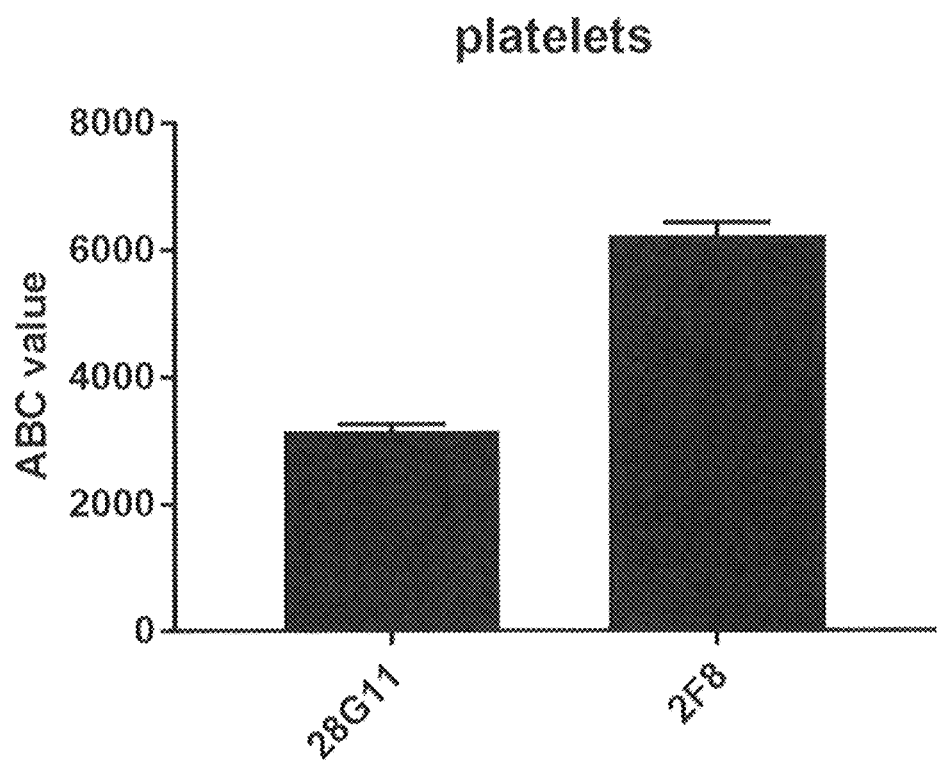
FIG. 15 is a graph showing the stoichiometry of the number of binding sites per platelet for 28G11 and 2F8.

Anti-LAP antibodies were also tested for platelet binding stoichiometry. Briefly, the number of binding sites/platelet was determined using flow cytometry. Platelet rich plasma was prepared from the blood of a healthy patient. The fluorescence level of each labeled antibody was determined using Quantum Simply Cellular beads (Bang Labs) and their respective fluorescent standard beads according to the manufacturer recommendations. Based on these determinations, the ABC (antibody binding capacity) of platelet staining by each antibody could be equated to the ratio of binding sites/platelet. As shown in FIG. 15, differences were observed in the number of binding sites on platelets between 28G11 and 2F8, with 2F8 having a roughly 2-fold higher number of binding sites. These data are consistent with one molecule of 28G11 binding to the homodimeric LAP-TGFβ1 complex, while 2 molecules of 2F8 bind to the homodimeric complex.

Figure 16:
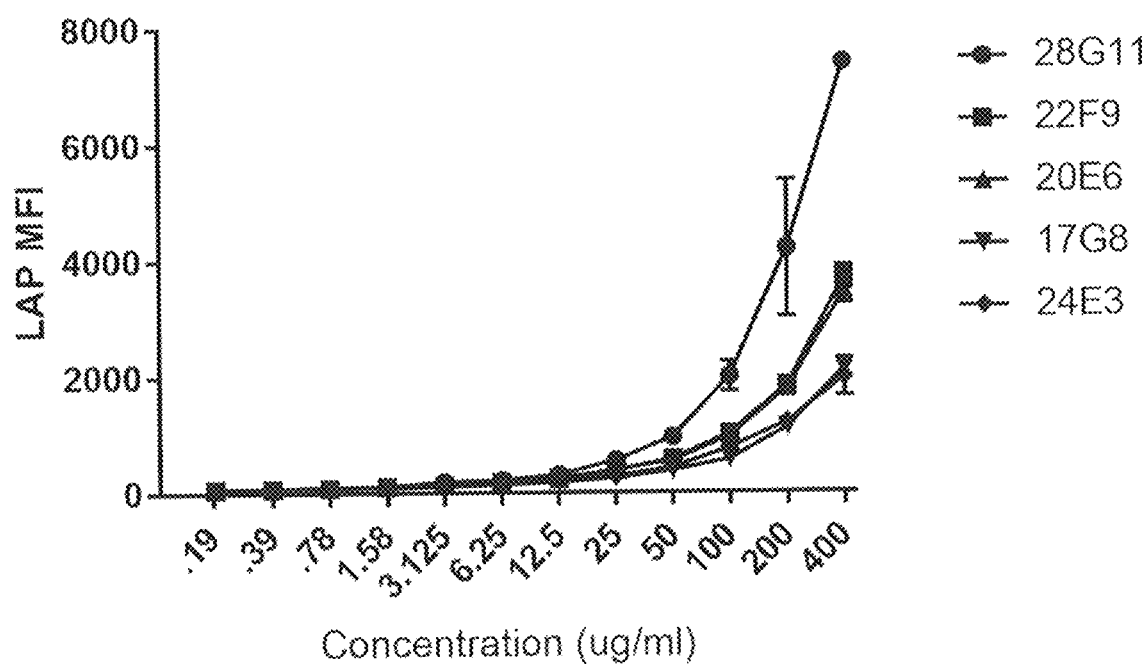
FIG. 16 is a graph showing the dose-response relationship in binding of the indicated anti-LAP antibodies to platelets.
Figure 17A:
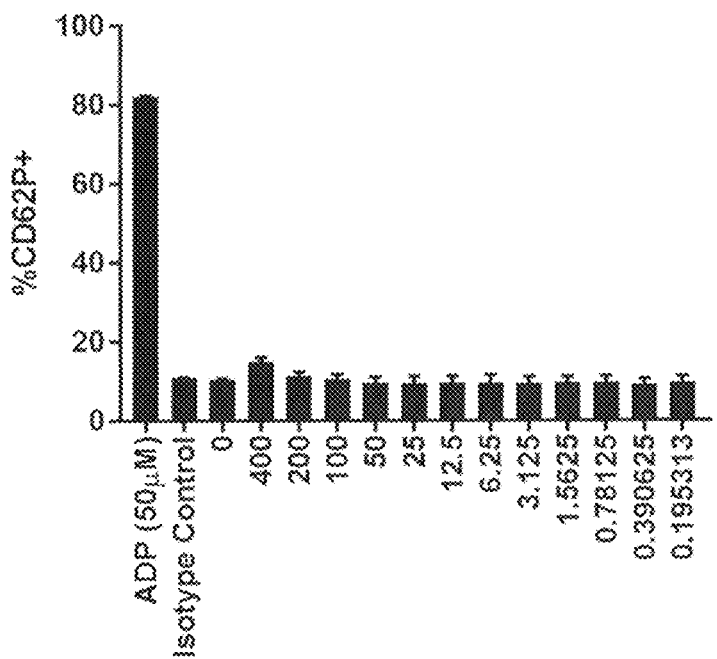
FIGS. 17A-17E are graphs showing the effects of 28G11_IgG2b (FIG. 17A), 20E6_IgG2a (FIG. 17B), 22F9_IgG2a (FIG. 17C), 17G8_hIgG1 (FIG. 17D), and 24E3_hIgG1 (FIG. 17E) on platelet degranulation.
Figure 17B:
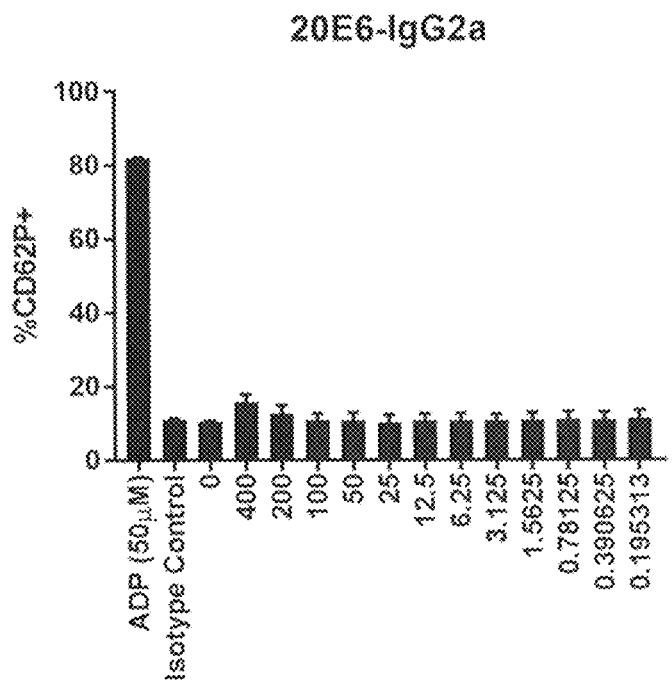
Figure 17C:
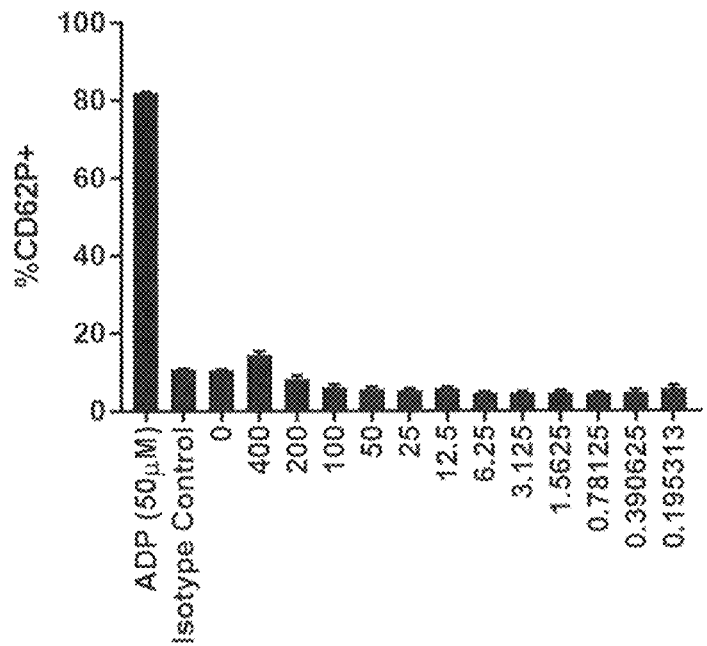
Figure 17D:
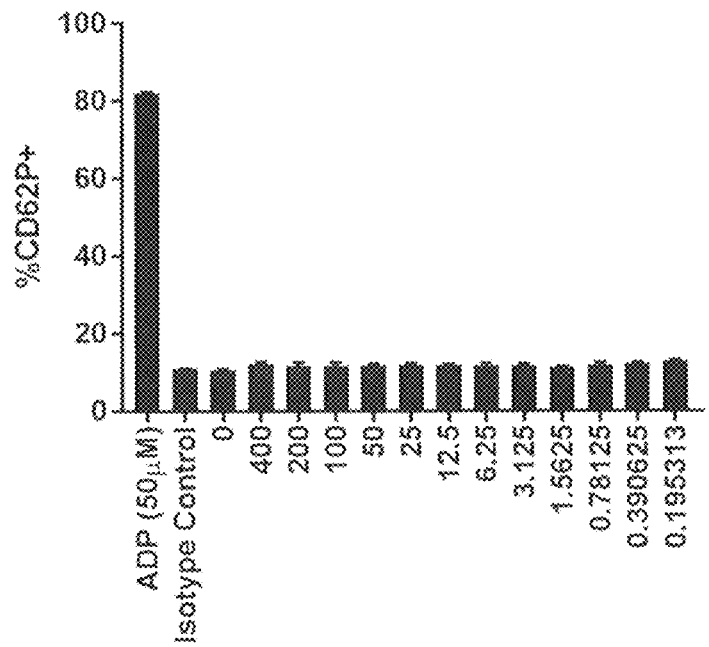
Figure 17E:
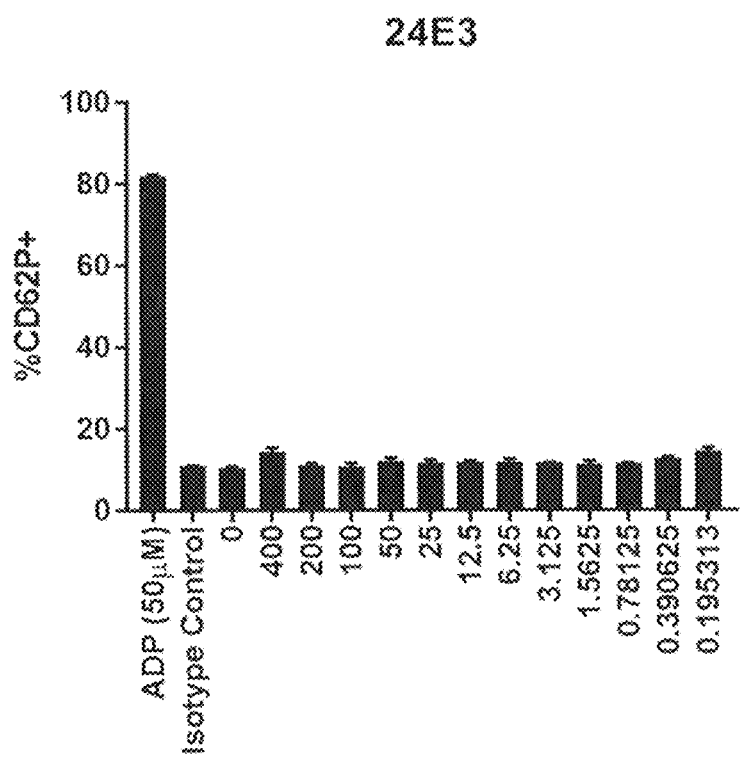

In a further experiment, additional anti-LAP antibodies were tested for binding to platelets by flow cytometry. Briefly, diluted whole human blood was incubated with the indicated concentrations of directly conjugated anti-LAP antibodies (28G11_(hyb), 20E6_mIgG2a, 22F9_mIgG2a, 17G8_hIgG1, and 24E3_hIgG1) for 15 minutes. The reactions were then incubated for an additional 15 minutes with a directly conjugated antibody against CD61, and analyzed by flow cytometry. The data represents the anti-LAP mean fluorescence intensity of CD61 positive platelets. As shown in FIG. 16, antibodies 22F9, 20E6, 17G8, and 24E3, in addition to 28G11, showed binding to platelets in a dose-responsive manner.

These additional anti-LAP antibodies were further tested for platelet degranulation. Briefly, diluted whole human blood was incubated with the indicated concentrations of anti-LAP antibodies or adenosine diphosphate (ADP) as a positive control for 15 minutes. The reactions were then incubated for an additional 15 minutes with directly conjugated antibodies against CD61, to detect whole blood platelets, and CD62P to detect degranulated platelets. The samples were analyzed by flow cytometry to determine the percentage of CD62P+ platelets.

As shown in FIGS. 17A-17E, none of the tested antibodies, i.e., 28G11, 20E6, 22F9, 17G8, and 24E3, induced significant platelet degranulation, even at the highest dose tested.

Example 6: Binding of Anti-LAP Antibodies to Resting and Activated CD4+ T Cells This Example describes the binding of anti-LAP antibodies to resting and activated CD4+ T cells from both human PBMC and murine splenocytes.

Figure 18:
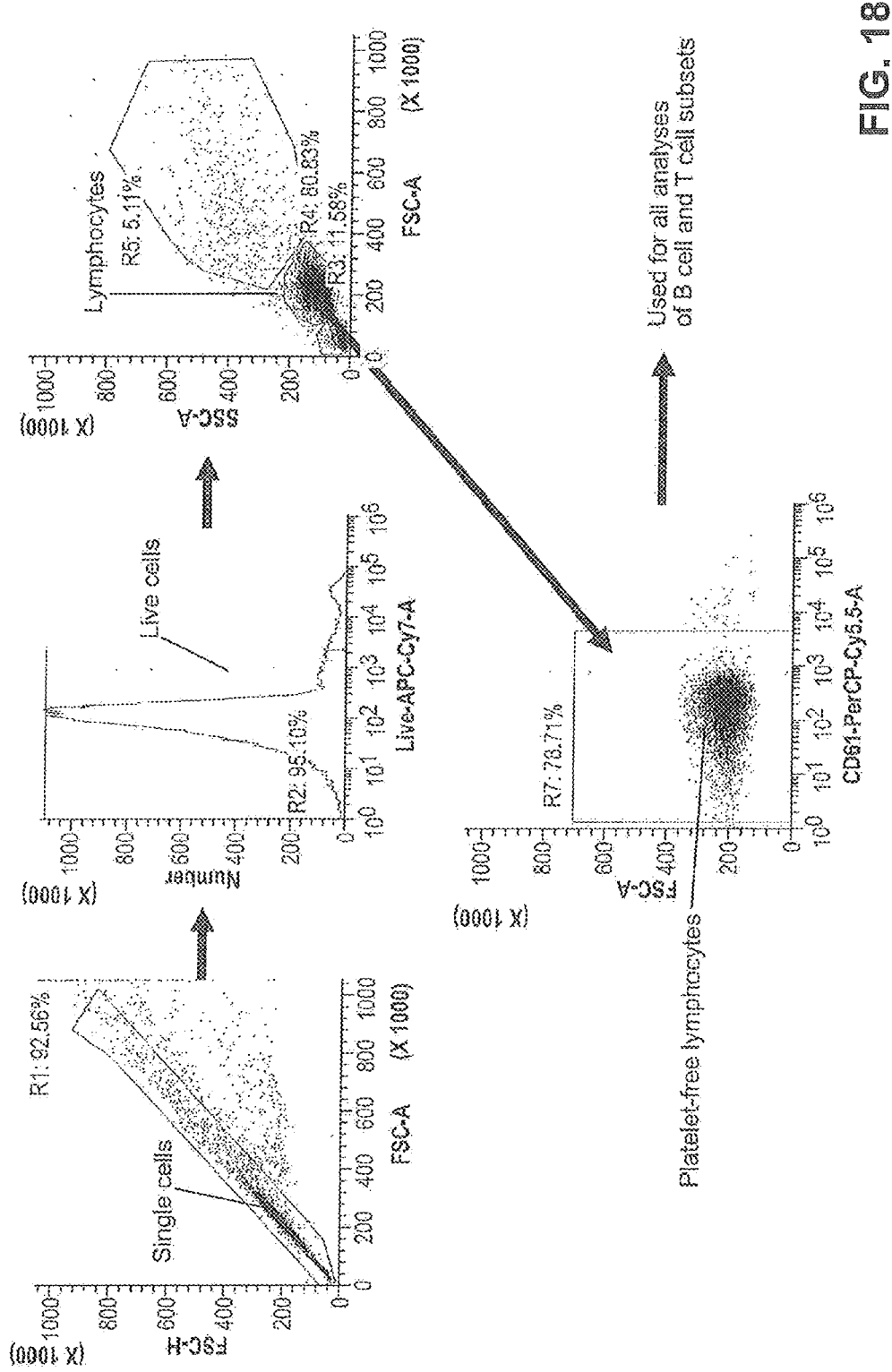
FIG. 18 is a schematic of the gating strategy for human PBMCs.

Briefly, peripheral blood mononuclear cells were isolated from the blood of a single healthy donor. Cells were rested in culture for 48 hr or were activated for 48 hr with plate-bound anti-CD3 monoclonal antibody (10 μg/mL), soluble anti-CD28 monoclonal antibody (2 μg/mL), and recombinant human IL-2 (3 ng/mL). The gating strategy used for this Example is shown in FIG. 18. Briefly, gates were first set on single cells based on forward and side scatter, then on live cells using a LIVE/DEAD fixable stain kit, then on lymphocytes based on forward and side scatter and then on CD61 negative cells to exclude lymphocytes with adhered platelets.

Figure 19:
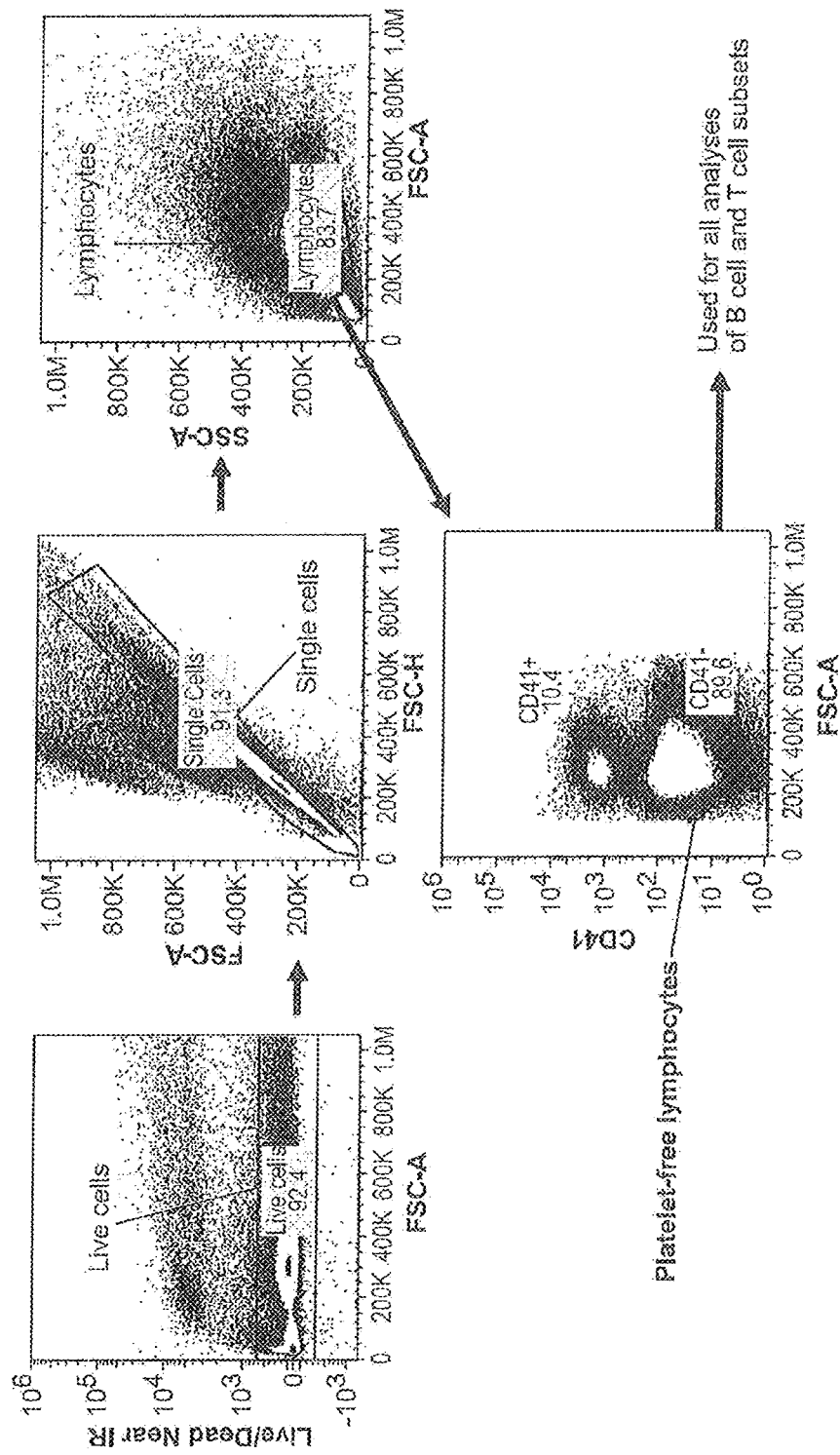
FIG. 19 is a schematic of the gating strategy for mouse splenic cells.

Murine splenocytes were isolated from a BALB/c mouse. Cells were either analyzed immediately after preparation or after activation for 48 hr with anti-CD3 antibody+ anti-CD28 antibody+IL-2. The gating strategy is shown in FIG. 19. Gates were first set on live cells, then on single cells, then on lymphocytes and finally on platelet-free lymphocytes using the platelet marker CD41.

Figures 20A, 20B:
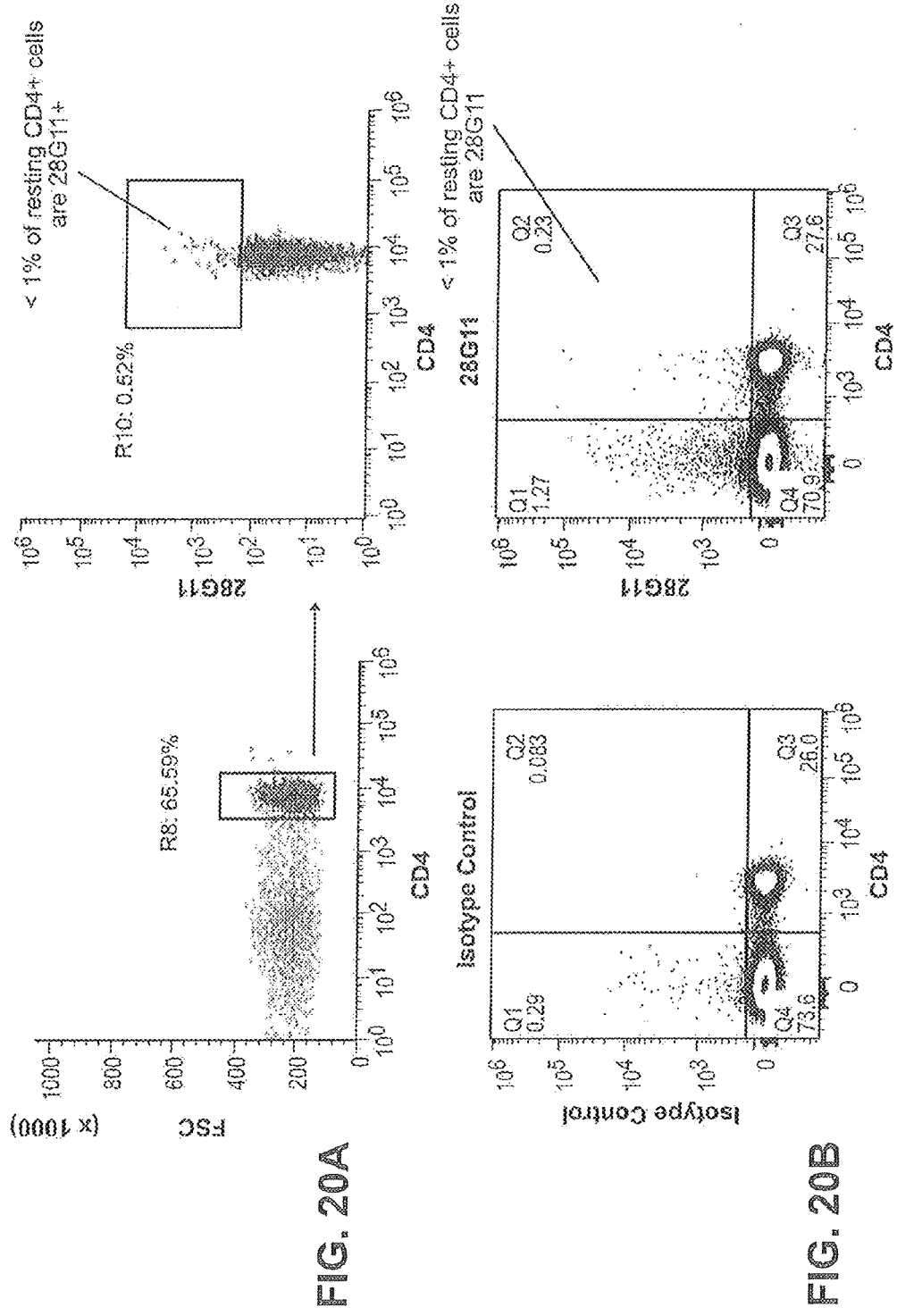
FIGS. 20A and 20B are scatter plots showing the detection of CD4+ T cells from resting human PBMCs (FIG. 20A) and resting mouse splenic cells (FIG. 20B) by 28G11.
Figure 21A:
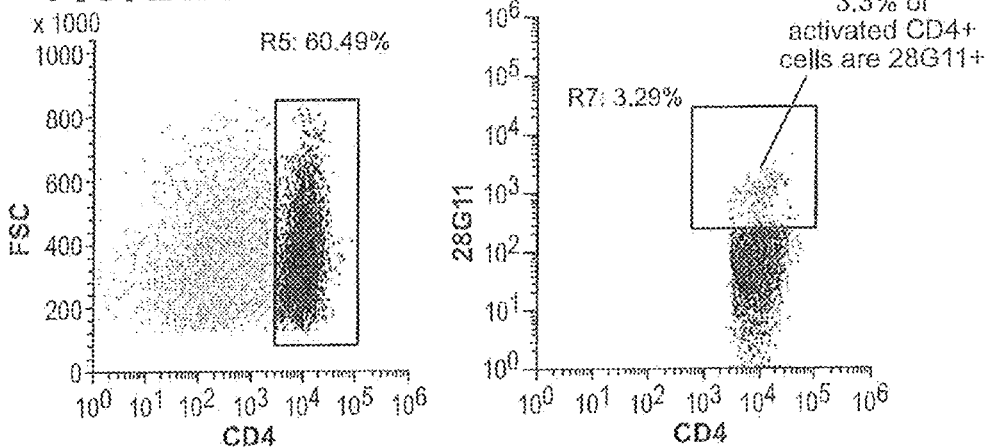
FIGS. 21A and 21B are scatter plots showing the detection of CD4+ T cells from activated human PBMCs (FIG. 21A) and activated mouse splenic cells (FIG. 21B) by 28G11.
Figure 21B:
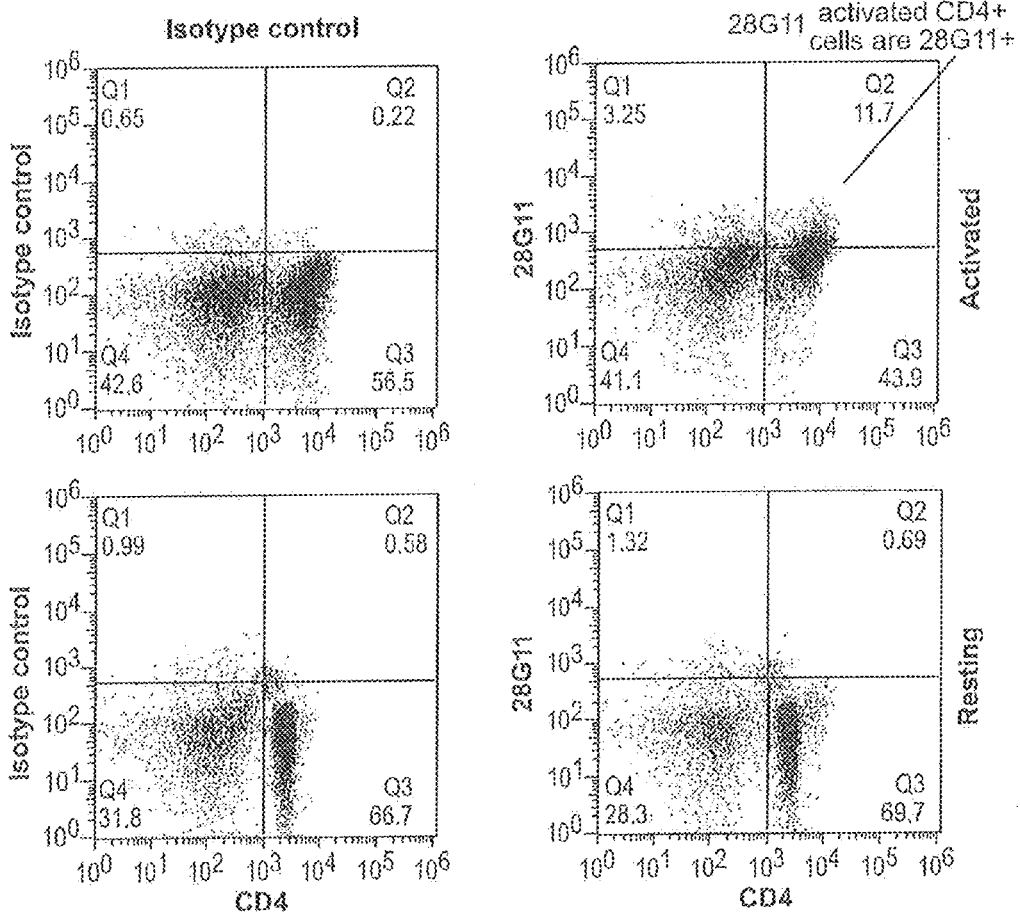

As shown in FIGS. 20A and 20B, 28G11 binds to very few CD4+ T cells from resting human PBMCs (FIG. 20A) or to CD4+ T cells from the naïve mouse spleen (FIG. 20B). Following activation, 28G11 detected LAP upregulation on CD4+ T cells (FIG. 21A (human) and 21B (mouse)). These results demonstrate that the detection of LAP on CD4+ cells using the antibody 28G11 was similar between activated mouse and human CD4+ cells.

Example 7: Binding of Anti-LAP Antibodies to Regulatory T Cells

In this example, the binding of multiple anti-LAP antibodies to regulatory T cells was analyzed.

Briefly, peripheral blood mononuclear cells were isolated from the blood of a single healthy donor. Cells were activated for 48 hr with plate-bound anti-CD3 monoclonal antibody (10 μg/mL), soluble anti-CD28 monoclonal antibody (2 μg/mL), and recombinant human IL-2 (3 ng/mL). The activated cells were stained with antibodies specific for CD4, CD25, and FoxP3 to define regulatory T cells (CD4+ CD25+ FoxP3+). Cells were analyzed by gating first on single cells and then on lymphocytes by forward and side scatter. Binding of biotinylated anti-LAP antibodies 478.E9, 28G11, 7H4, 3G5, 2F8 and 2C9 was assessed using APC-strepavidin.

Figure 22A:
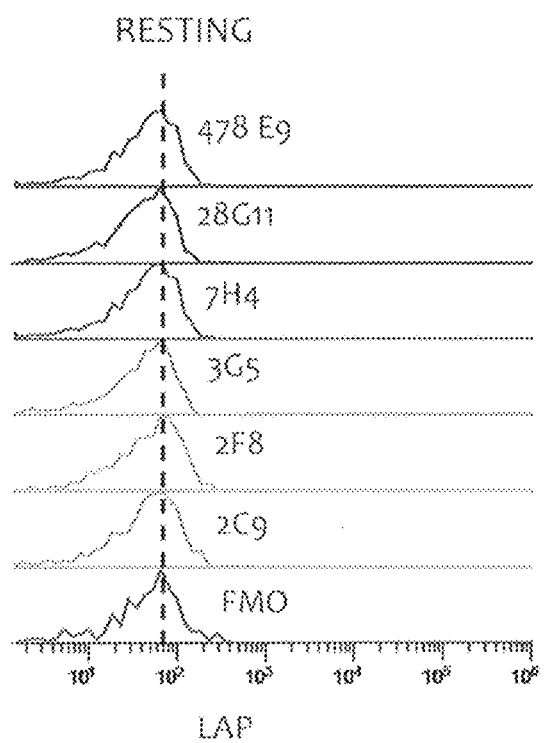
FIGS. 22A and 22B are plots depicting the binding of the indicated antibodies to LAP on Treg cells in resting and activated PBMCs.
Figure 22B:
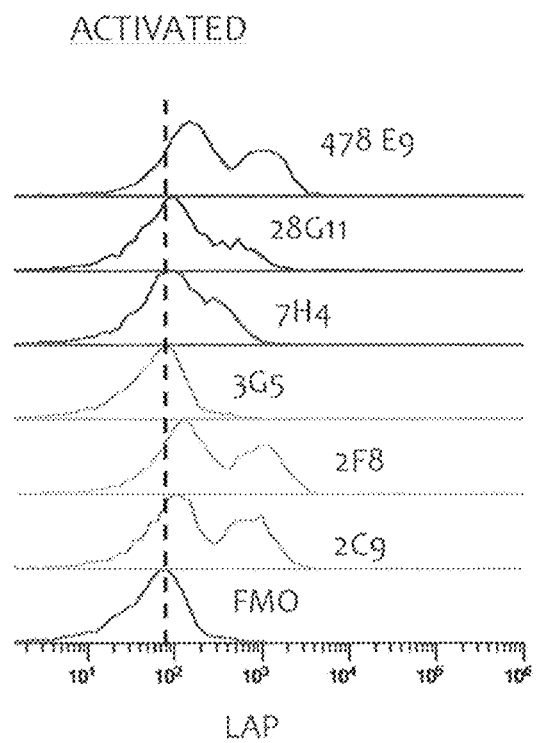
Figure 23A:
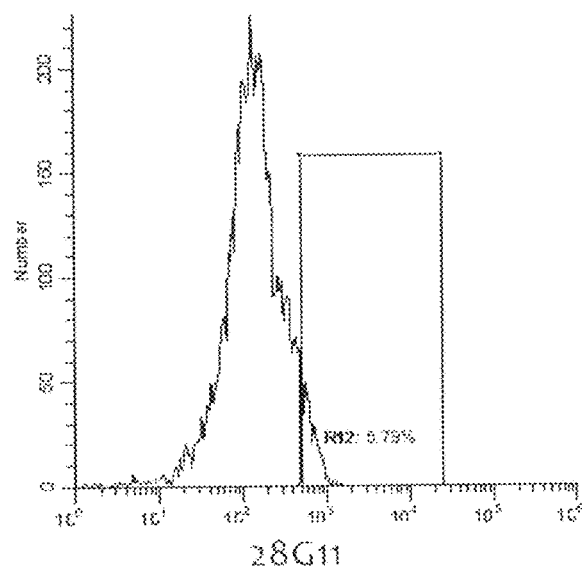
FIGS. 23A and 23B show a comparison of the binding of 28G11 (FIG. 23A) and 2F8 (FIG. 23B) to activated human Tregs.
Figure 23B:
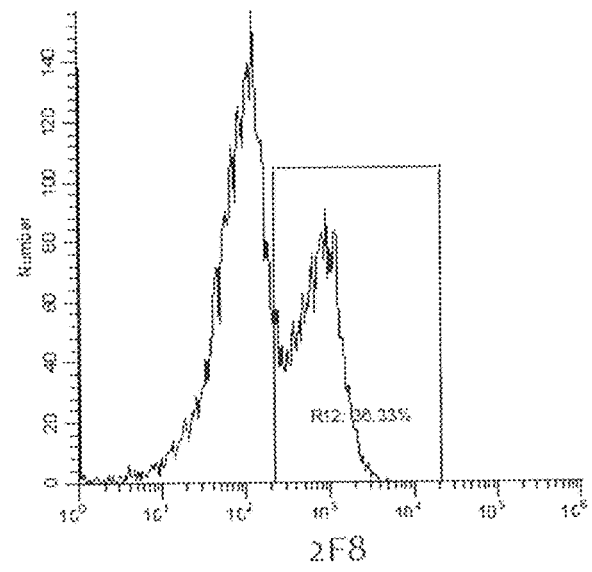

As shown in FIG. 22A, resting Treg cells express little if any LAP, as measured by any of the anti-LAP antibodies. LAP is upregulated on activated Tregs and the anti-LAP antibodies have differing Treg binding ability (FIG. 22B). Notably, two cell populations can be identified in each of the graphs. It is likely that the lower intensity peak reflects Tregs that have platelets bound to them and the antibodies are detecting platelet-associated LAP (platelet-binding lymphocytes were not gated out in this study). The higher intensity peak likely represents LAP expression on the lymphocytes themselves. The strongest binding, as measured both by the highest fluorescence intensity and the largest peak size, was seen with the anti-LAP antibodies 2C9, 2F8, and 478.E9. Fewer cells with lower level staining were seen with 28G11 and 7H4 while no binding was seen with 3G5. The binding ability of these antibodies to Tregs and platelets showed very similar patterns. To confirm the differential binding of the anti-LAP antibodies to Treg, the experiment was repeated and the cells were gated on platelet-negative lymphocytes as described in Example 6. FIGS. 23A and 23B show that anti-LAP antibody 2F8 binds to a larger percentage of the Treg cells than does anti-LAP antibody 28G11. In addition, the staining is brighter with 2F8 than with 28G11.

Figures 24A, 24B:
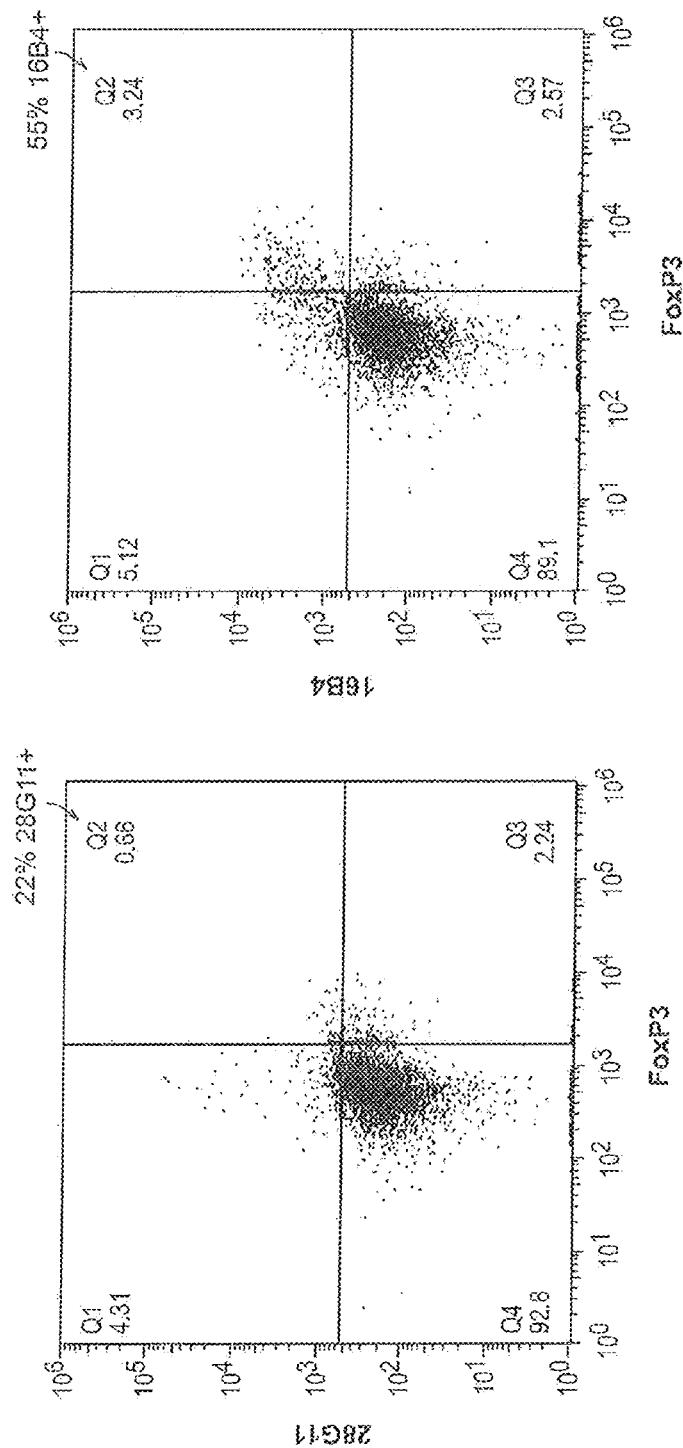
FIGS. 24A and 24B are scatter plots showing the binding of 28G11 (FIG. 24A) and 16B4 (FIG. 24B) to activated murine Tregs (FoxP3+ cells).

Antibody binding to murine Tregs was also assessed in this example. Briefly, splenocytes were isolated from a BALB/c mouse and stimulated for 24 hr with anti-CD3 antibody, anti-CD-28 antibody, and IL-2. Cells were gated on live cells, single cells, lymphocytes, and CD4+CD25+ cells. FIGS. 24A and 24B show that anti-LAP antibody 16B4 binds a higher percentage of FoxP3+ Tregs than does anti-LAP antibody 28G11. Specifically, 22% of the FoxP3+ cells were stained by 28G11, while 55% of the FoxP3+ cells were stained by 16B4. In addition, the staining is brighter with 16B4 than with 28G11. These data are consistent with the data shown in Example 6, where 16B4 binds 2-fold more sites on GARP+ platelets than does 28G11.

These results suggest that anti-LAP antibodies have differing Treg binding ability. Anti-LAP antibodies that bind a high percentage of human Tregs (e.g., 2C9, 2F8) can be used to treat cancers dominated by Treg infiltration. Anti-LAP antibodies that bind a higher percentage of murine Tregs (e.g. 16B4) can be used as surrogate antibodies to evaluate the activity of this type of antibody in mouse tumor models.

Example 8: Differential Binding of Anti-LAP Antibodies to Mononuclear Cell Populations LAP is expressed on the surface of multiple cell populations. This Example describes the ability of anti-LAP antibodies to bind LAP on various populations of cells. In addition, some of these cells do not express GARP and this example describes the binding of anti-LAP antibodies to both GARP+ and GARP$^{neg}$ cells.

Figure 11B:
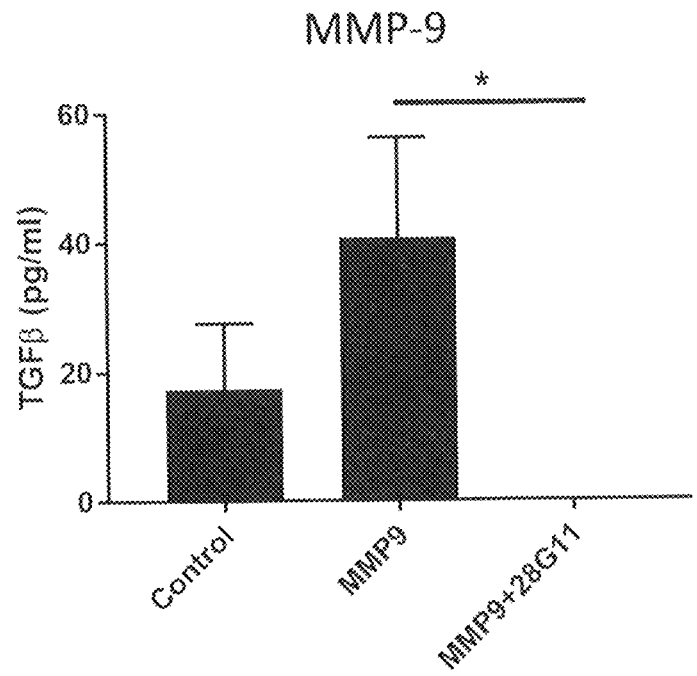
Figures 25A, 25B:
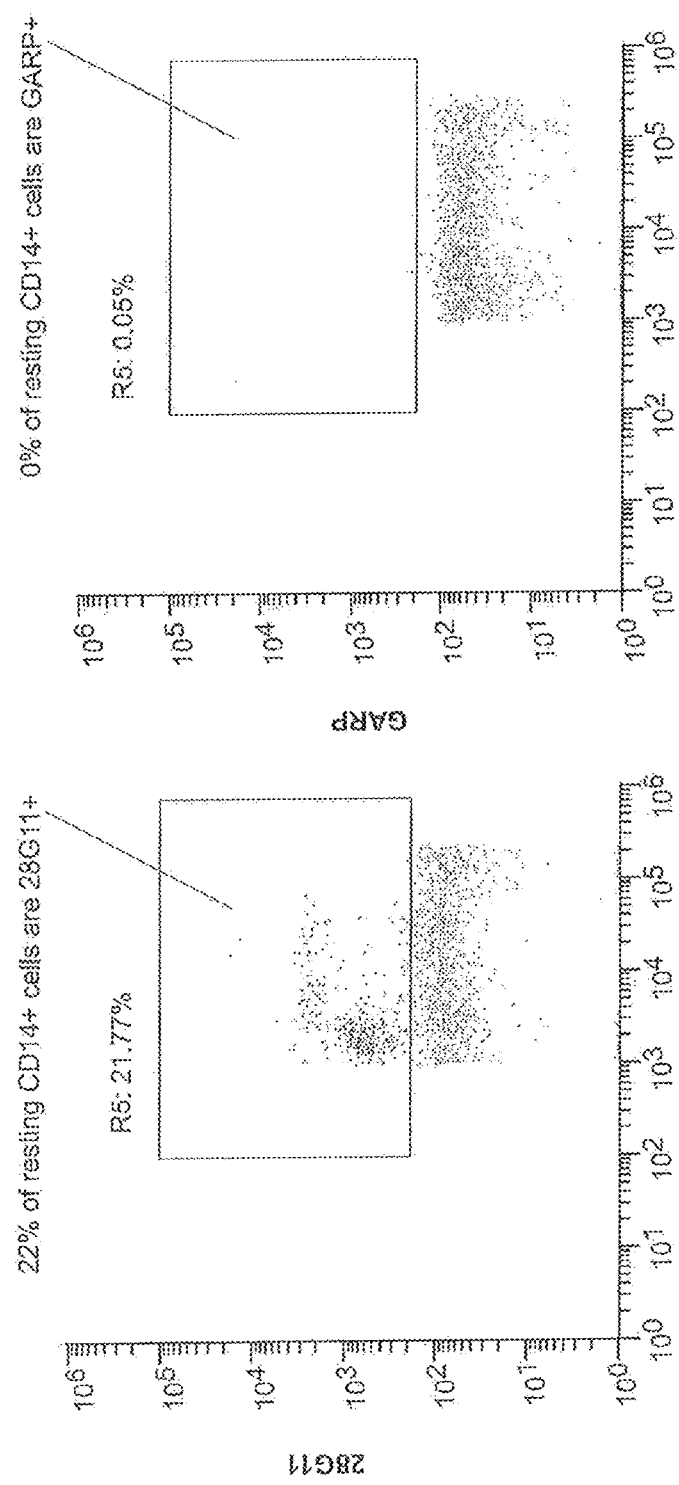
FIG. 25A is a scatter plot showing the binding of 28G11 to CD14+ monocytes.
FIG. 25B is a scatter plot showing that 0% of resting CD14+ cells are GARP+.

Briefly, to evaluate binding to human peripheral blood mononuclear cells, these cells were isolated from the blood of a single healthy donor. Cells were activated for 48 hr with plate-bound anti-CD3 monoclonal antibody (10 g/mL), soluble anti-CD28 monoclonal antibody (2 µg/mL), and recombinant human IL-2 (3 ng/mL). The activated PBMCs were first stained with LIVE/DEAD™ Fixable Dead Cell Stain Kits, then incubated with human FcR block, and then stained with anti-CD4, anti-CD25, anti-CD8, anti-CD16/56, anti-CD19, anti-FoxP3, anti-GARP, anti-CD61 and the anti-LAP antibodies 28G11 and 2F8. Live cells were gated first and then single cells. Cells were gated into lymphocyte or monocyte population was gated, and then the CD61 negative gate was set to exclude platelet-associated cells. As shown in FIG. 25A, 28G11 binds to 21.77% of CD14+ monocytes. As shown in FIG. 25B, GARP is not detected on CD14+ monocytes. Together, these data indicate that 28G11 can detect LAP on the surface of cells in the absence of GARP.

Figure 26:
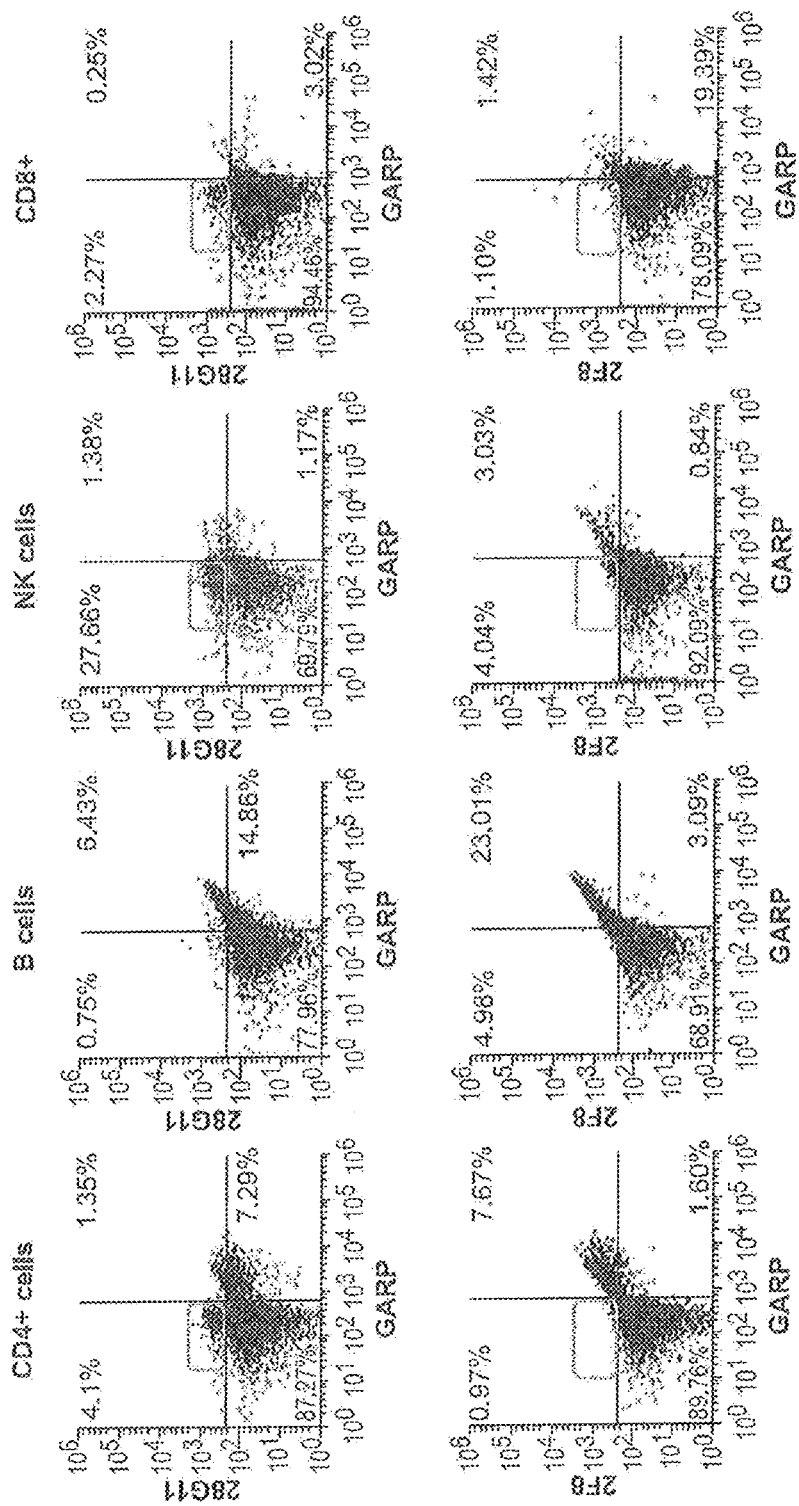
FIG. 26 shows scatter plots of the binding of 28G11 and 2F8 to GARP+ and GARP$^{neg}$ leukocyte cell populations in activated human PBMC.

As shown in FIG. 26 and in Table 6, distinct binding patterns are seen with anti-LAP antibodies 28G11 and 2F8. Binding of 2F8 correlates strongly with binding of the anti-GARP antibody, while 28G11 binds to LAP on GARP-$^{neg}$ CD4+ cells, NK cells and CD8+ cells. 2F8 binds a higher percentage of Tregs and B cells while 28G11 binds a higher percentage of NK cells.

TABLE 6

|  | 28G11 | 2F8 |
| --- | --- | --- |
| CD4+ T cells | 5-7% | 9-16% |
| CD4+ CD25+ FoxP3+ T cells | 4-7% | 24-38% |
| CD8+ T cells | 2-3% | 2-3% |
| B cells | 6-10% | 28-52% |
| NK cells | 25-30% | 7% |

Figure 27A:
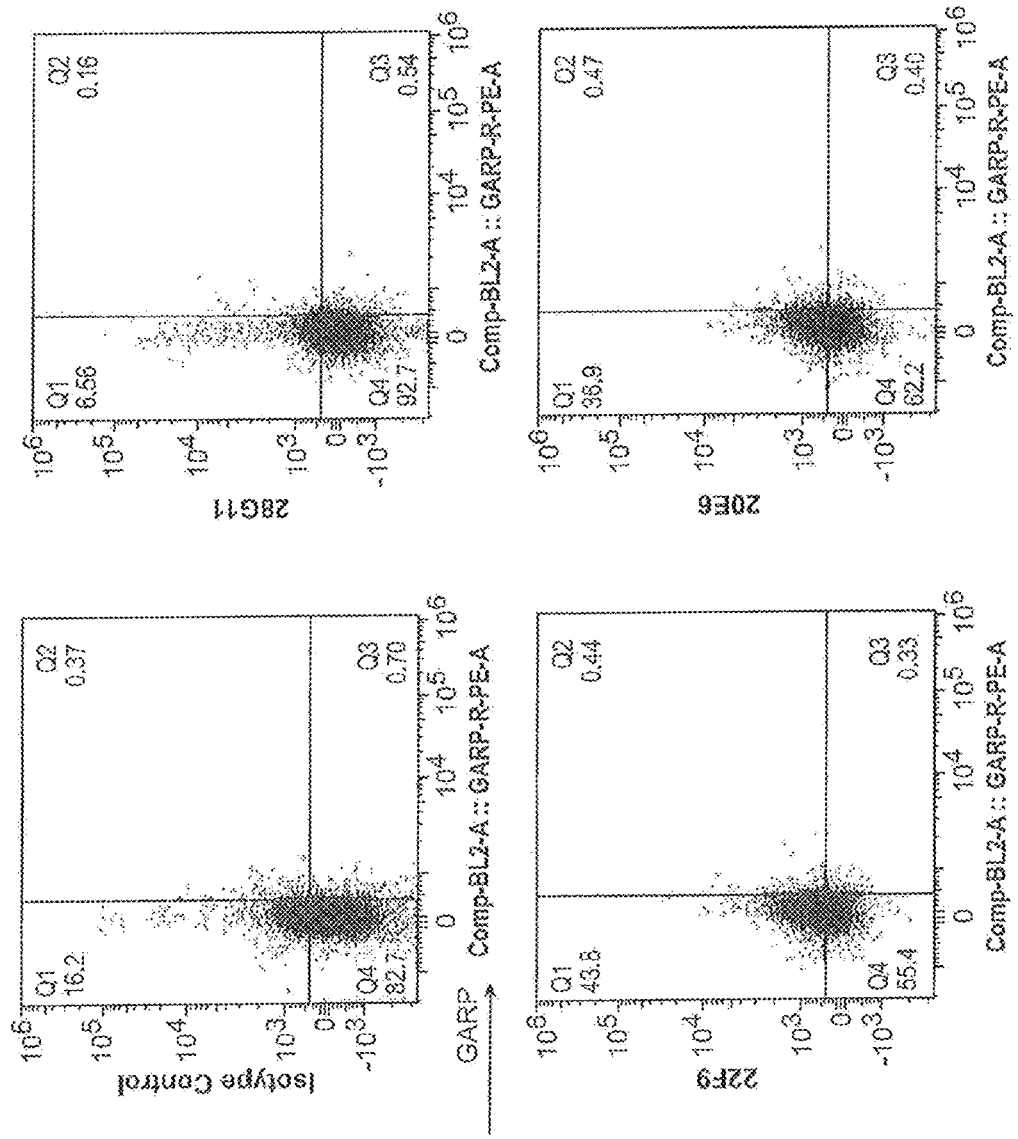
FIG. 27A is a dot plot for the binding of the indicated anti-LAP antibodies to U937 cells.
Figure 27B:
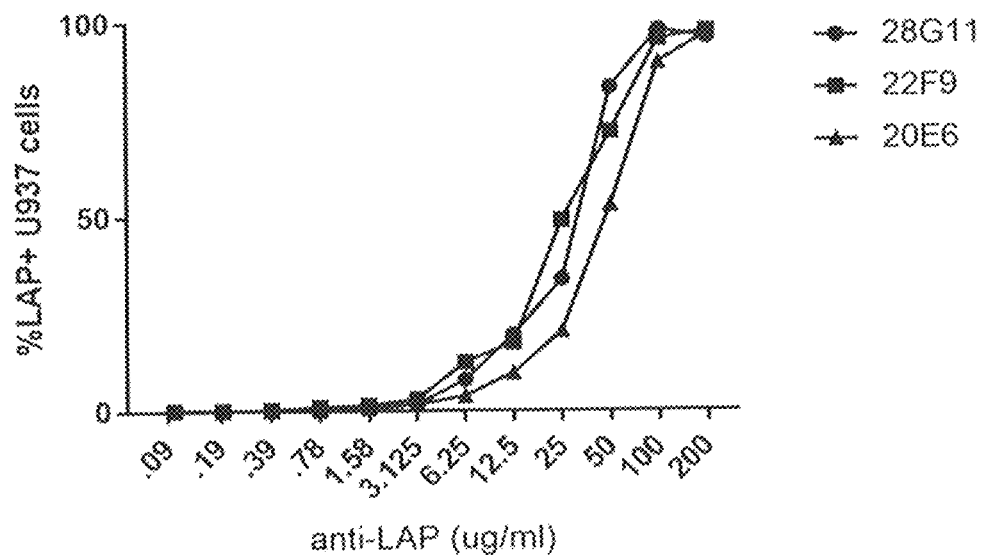
FIGS. 27B and 27C are graphs showing the binding of the indicated LAP antibodies to U937 cells. U937 binding is expressed as % of LAP+ cells in FIG. 27B and as MFI in FIG. 27C.
Figure 27C:
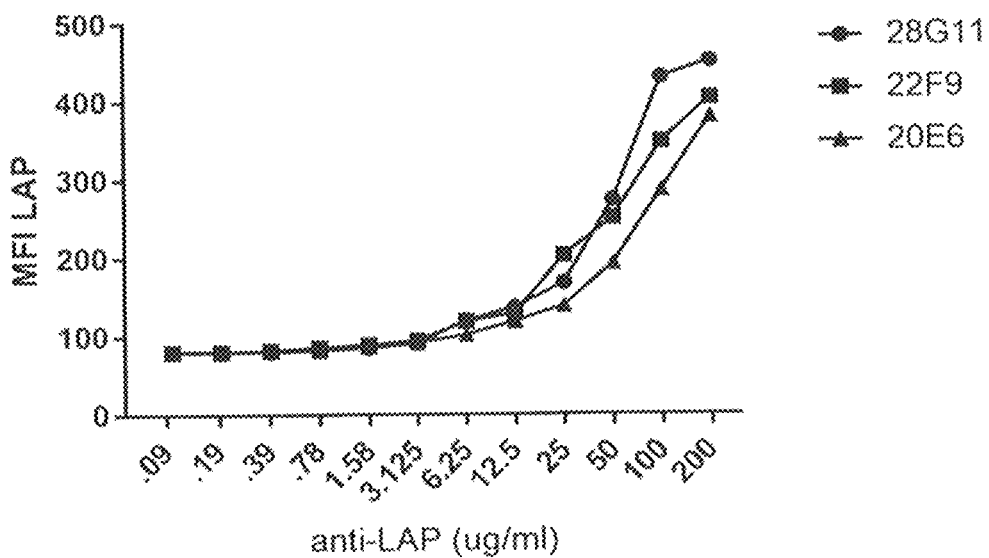
Figure 28A:
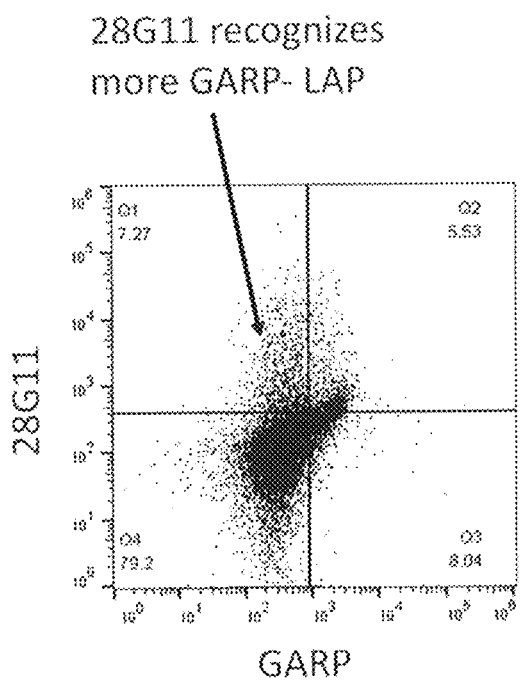
FIGS. 28A and 28B are scatter plots showing the binding of isotype control (FIG. 28A) or 28G11 (FIG. 28B) to GARP+ and GARP$^{neg}$ CD19+ murine B cells.
Figure 28B:
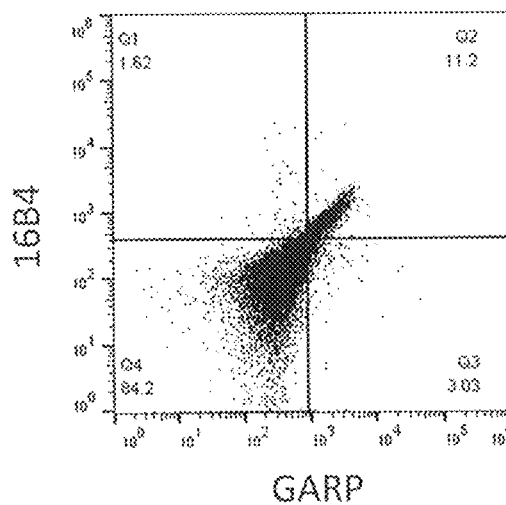

Anti-LAP antibodies were also tested for their ability to bind to U937 cells, a myeloid cell line derived from a patient with histiocytic lymphoma. U937 cells were incubated with FACS buffer and human Fc block followed by incubation with varying concentrations of Alexa 647 conjugated 28G11_hyb, 22F9_mIgG2a, or 20E6_mIgG2a. In a separate experiment U937 cells were incubated with FACS buffer and human Fc block followed by incubation with 10 ug/ml of Alexa 647 conjugated 28G11_hyb, 22F9_mIgG2a, 20E6_mIgG2a, or mIgG2a isotype control. Representative dot plots are shown in FIG. 27A; in these plots, antibodies were at 10 µg/mL. The anti-LAP antibodies 28G11, 22F9, and 20E6 were shown to bind similarly to the U937 cells, both by MFI and the dose response of binding (FIGS. 27B and 27C).

These data demonstrate that the anti-LAP antibodies 28G11, 22F9, and 20E6 display comparable binding to a LAP+ myeloid cell line.

Anti-LAP antibody binding was also evaluated using murine B cells. Murine splenocytes were isolated from naïve Balb/c mice and were activated for 48 hr with 5 µg/ml LPS. Cells were stained with a live/dead near infra-red dye followed by Fc block. Cells were then stained with anti-CD41, anti-CD19, anti-GARP and anti-LAP antibodies 28G11 and 16B4. Cells were gated by dead cell exclusion, doublet exclusion, FSC vs. SSC inclusion of lymphocytes, exclusion of platelet positive cells and inclusion of CD19+ cells. As shown in FIGS. 28A and 28B, 28G11 and 16B4 both recognize LAP on the surface of activated B cells. Notably, 16B4 only recognizes LAP on GARP positive cells, and the staining pattern, with a strong diagonal pattern, indicates that the antibodies are likely recognizing the same complex. In contrast, 28G11 recognizes LAP on both GARP+ and GARP$^{neg}$ B cells.

Finally, the binding of anti-LAP antibodies to various immune cells in tumors of CT26 tumor bearing mice were examined. Briefly, 1×10$^6$ CT26 cells were injected into the flank region of 6 male Balb/C mice. When mean tumor volumes reached about 80 mm$^3$, 3 mice were treated with IgG2a isotype control or IgG1 isotype control (10 mg/kg). Mice were treated again 3 days later and harvested 7 days post first injection. Tumors tissue was disassociated in a GentlMACS dissociator and digested with Collagenase IV/DNase1, strained through a 70-µm cell strainer and counted, and spleen tissue was dissociated by passing through a 70-µm cell strainer and counted. Cells were then analyzed by flow cytometry using the following scheme: Gate on live cells→Gate on single cells→Gate on CD45+ cells→Gate on CD41- population→Gate on appropriate immune cell subsets as follows:

Regulatory T cells—CD45+, CD3+, CD4+, Foxp3+
   CD11b—CD45+, CD11b+
   M2 macrophages—CD45+, CD11b+, F4/80+, CD206+
   Dendritic cells—CD45+, F4/80−, CD11c+
   M-MDSC—CD45+, CD11b+, F4/80−, Ly6G−, Ly6C high All three antibodies tested, i.e., 28G11, 22F9 and 20E6, were found to bind to subsets of all major immunosuppressive cell populations (i.e., regulatory T cells, CD11b-positive cells, M2 macrophages, dendritic cells, and M-MDSCs) in the tumor.

Anti-LAP antibodies which bind to LAP on cells can be used to effectively deplete or inhibit a broad range of immunosuppressive cells that are important in cancer.

Example 9: Differential Binding of Anti-LAP Antibodies to Human Tumor Samples

In this example, anti-LAP antibodies were used to examine LAP expression in human tumor sections.

Briefly, frozen human hepatocellular carcinoma tissues sections were obtained from Biochain and analyzed by immunohistochemistry. Sections were rehydrated in TBS and endogenous peroxidase activity was blocked by using Bloxall (Vector Labs). Sections were blocked with 5% horse serum for 1 hour and incubated with 28G11 (10 µg/ml) or 2C9 (10 µg/ml) overnight at 4° C. The following day mouse specific secondary antibody (Vector Labs) was incubated at 1:500 with the sections for 1 hour followed by a 30-minute incubation with ABC reagent (Vector Labs) according to the manufacturer recommendations. Anti-LAP binding was visualized using DAB (3'-Diaminobenzidine) substrate (Thermo Fisher) followed by methyl green nuclear counterstain. Images were recorded at 40× magnification.

Figure 29A:
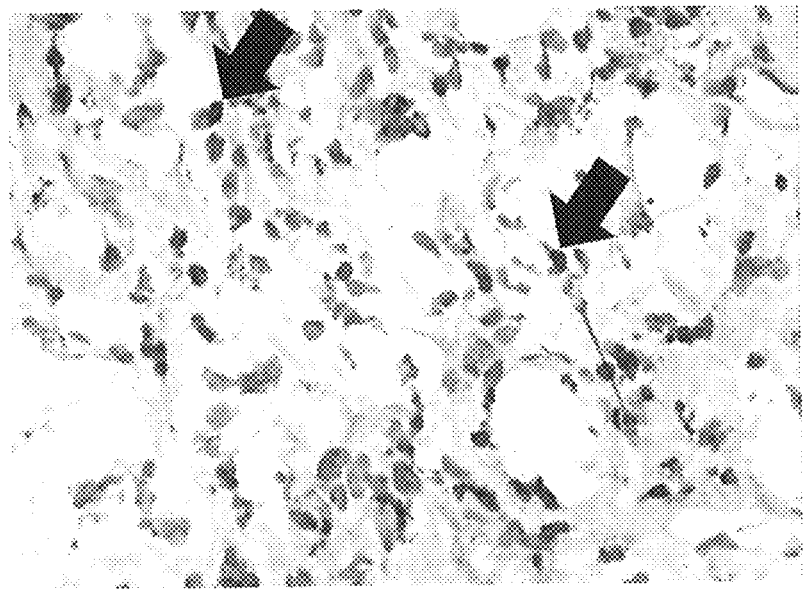
FIGS. 29A and 29B are representative 40× images of human hepatocellular carcinoma in which immunohistochemistry was performed using 28G11 (FIG. 29A) and 2C9 (FIG. 29B) antibodies.
Figure 29B:
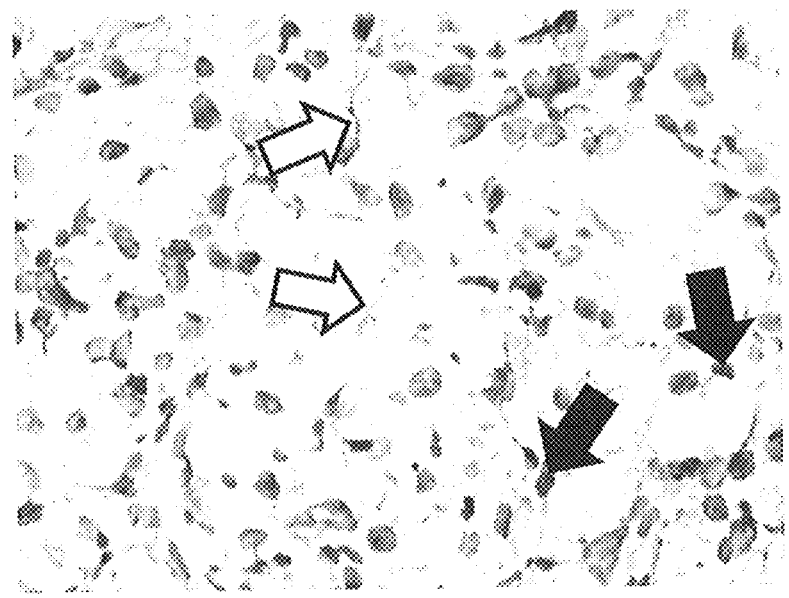

As shown in FIG. 29A, 28G11 detects LAP expression on a large number of infiltrating cells (representative cells are labeled with the filled arrows). No binding is seen to the extracellular matrix. In contrast, 2C9 detects LAP expression on infiltrating cells and also detects LAP in the extracellular matrix (FIG. 29B). These results are consistent with the results presented in Examples 4 and 8 and establish the relevance of the antibody selectivity in the context of a human tumor.

Example 10: Efficacy of Anti-LAP Antibodies in CT26 Syngeneic Model

This Example describes the efficacy of anti-LAP antibodies in combination with anti-PD-1 antibodies in the CT26 colorectal cancer tumor model, a syngeneic model of cancer. In this experiment, variants of the anti-LAP antibodies were used in which the Fc portion of the antibody was the IgG2a isotype rather than the isotype found in the parental hybridoma.

Briefly, 6-8 week-old Balb/c mice were subcutaneously implanted with $3\times10^5$ CT26 colorectal cancer cells. Tumors were grown until an average size of 48 mm$^2$ at which point tumor-bearing animals were randomized to groups of 10 animals each.

One set of animals was dosed intraperitoneally with either rat anti-PD-1 clone RMP1-14-IgG2a at 3 mg/kg or a combination of anti-PD-1 and antibody 28G11-IgG2a at 10 mg/kg on days 0, 3, 6, 9, and 12. Animal groups were also dosed with isotype control antibodies (rat-IgG2a and/or mouse IgG2a, not shown).

Another set of animals was dosed intraperitoneally with either rat anti-PD-1 clone RMP1-14-IgG2a at 3 mg/kg, antibody 16B4-IgG2a at 10 mg/kg, or a combination of anti-PD-1 and antibody 16B4-IgG2a at 10 mg/kg on days 0, 3, 6, 9, and 12. Animal groups were also dosed with isotype control antibodies (rat-IgG2a and/or mouse IgG2a, not shown).

Survival was assessed daily and tumor volumes were measured 3 times per week by caliper using the formula V=W2×L/2. Animals were followed for 53 days post dosing.

Figure 30A:
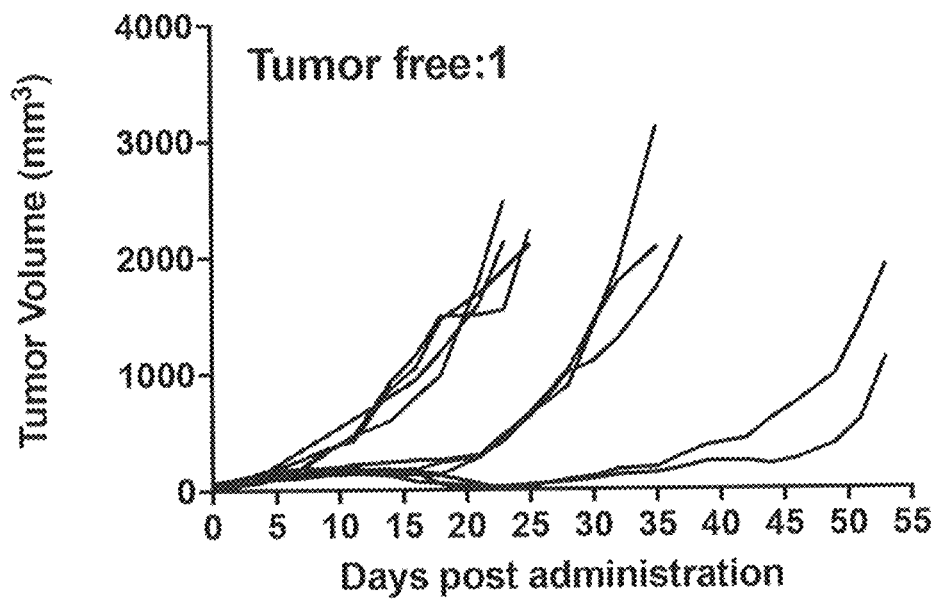
FIGS. 30A-30F show the effects of anti-LAP antibodies 28G11 and 16B4 in combination with an anti-PD-1 antibody on tumor volume in a syngeneic CT26 colorectal cancer tumor model.
Figure 30B:
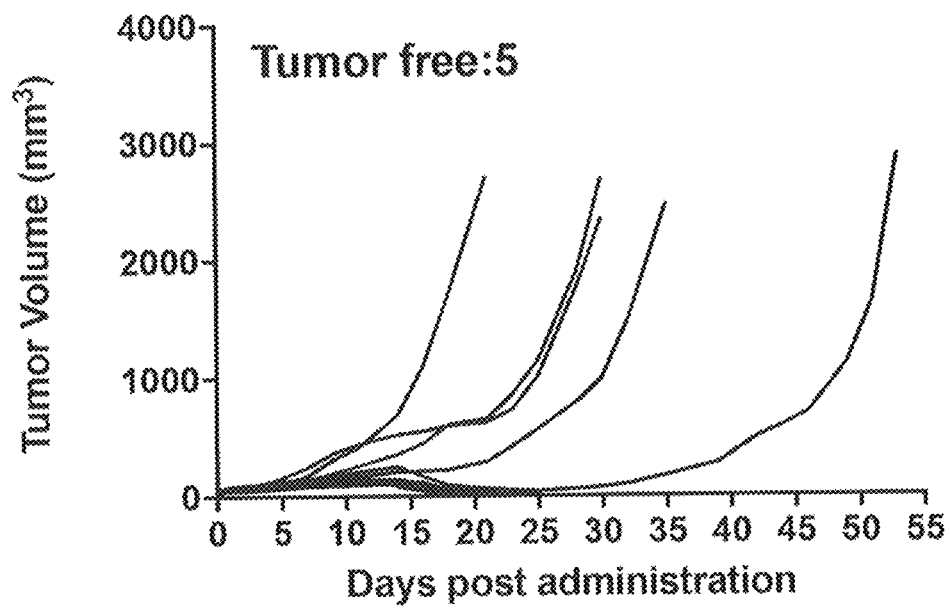
Figure 30C:
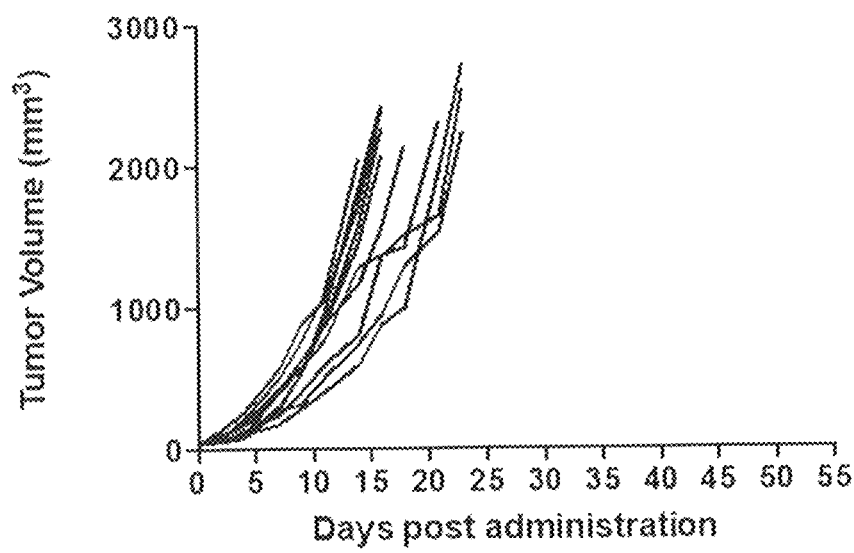
Figure 30D:
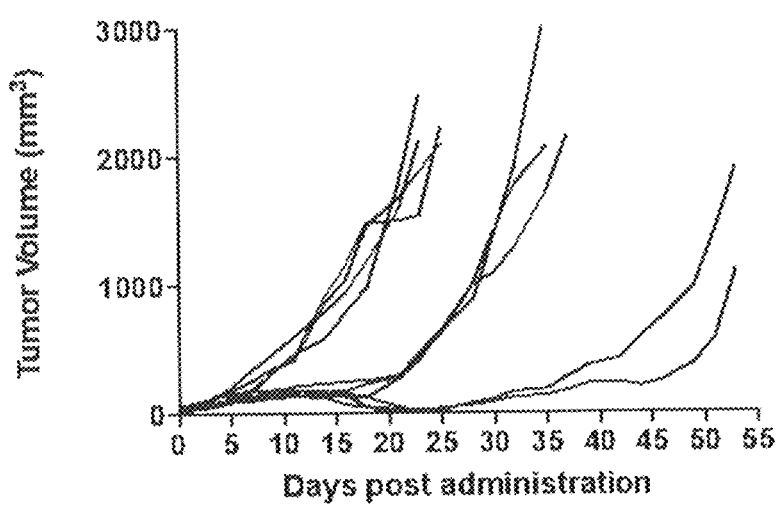
Figure 30E:
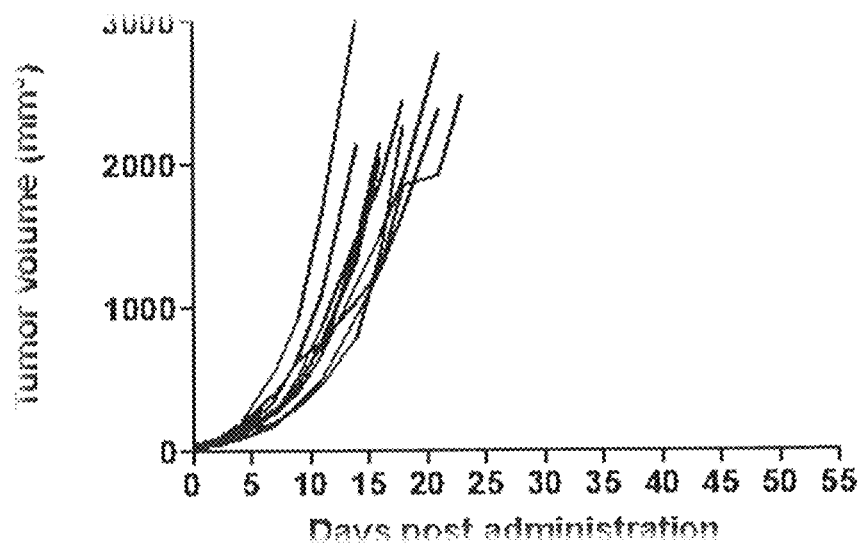
Figure 30F:
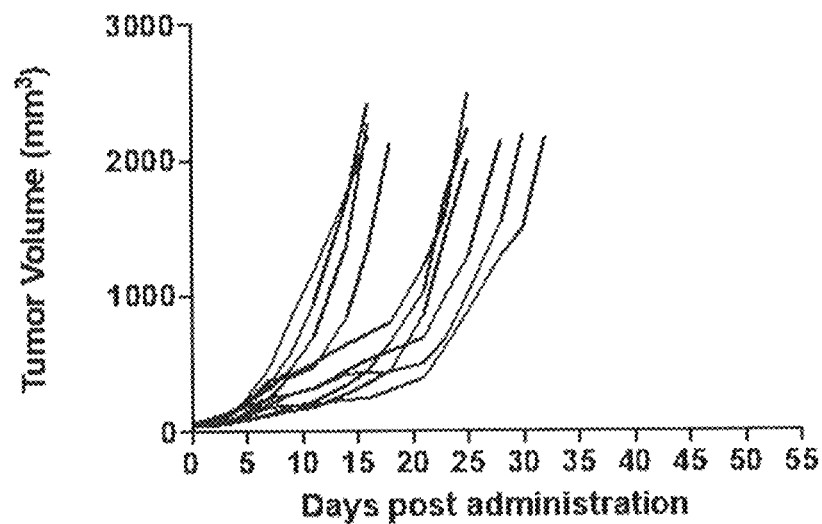

As shown in FIGS. 30A and 30B, treatment of this syngeneic model with antibody 28G11 resulted in a 5-fold increase in complete response rate over anti-PD-1 alone. In contrast, as shown in FIGS. 30C-30F, treatment of animals with antibody 16B4 had no effect on tumor growth. In fact, treatment of animals with a combination of 16B4 and anti-PD-1 resulted in a reduction of the response rate seen with anti-PD-1 antibody alone. These data establish that the two anti-LAP antibodies 28G11 and 16B4 have different functional properties in a mouse tumor model.

Example 11: Efficacy of Anti-LAP Antibodies in EMT6 Syngeneic Model

This Example describes the efficacy of anti-LAP antibodies in combination with anti-PD-1 antibodies in another syngeneic model of cancer, i.e., the EMT6 breast cancer tumor model.

Briefly, 6-8 week-old Balb/c mice were subcutaneously implanted into the right hind flank with $3\times10^5$ EMT6 breast cancer cells. Tumors were grown until an average size of 75 mm$^2$, at which point tumor-bearing animals were randomized to 10 groups of 10 animals each, and dosed intraperitoneally on days 0, 3, 6, 9, 12, 15, 18, and 21 according to the following:

TABLE 7

| Group | Description | Dose |
| --- | --- | --- |
| 1 | Rat IgG2a | 5 mg/kg |
|  | Mouse IgG2a | 15 mg/kg |
| 2 | Rat anti-PD-1 RMP1-14-IgG2a | 5 mg/kg |
|  | Mouse IgG2a | 15 mg/kg |
| 3 | 28G11_IgG2a | 10 mg/kg |
|  | Rat IgG2a | 5 mg/kg |
| 4 | Rat anti-PD-1 RMP1-14-IgG2a | 5 mg/kg |
|  | 28G11_IgG2a | 10 mg/kg |
| 5 | 22F9_IgG2a | 10 mg/kg |
|  | Rat IgG2a | 5 mg/kg |
| 6 | 22F9_IgG2a | 15 mg/kg |
| 7 | Rat anti-PD-1 RMP1-14-IgG2a | 5 mg/kg |
|  | 22F9_IgG2a | 10 mg/kg |
| 8 | Rat anti-PD-1 RMP1-14-IgG2a | 5 mg/kg |
|  | 22F9_IgG2a | 15 mg/kg |
| 9 | 20E6_IgG2a | 10 mg/kg |
|  | Rat IgG2a | 5 mg/kg |
| 10 | Rat anti-PD-1 RMP1-14-IgG2a | 5 mg/kg |
|  | 20E6_IgG2a | 10 mg/kg |

Survival was assessed daily and tumor volumes were measured 3 times per week by caliper using the formula V=W2×L/2. Animals were followed for 28 days post dosing. Data is graphed as mean tumor volume +/−SEM.

Figure 31:
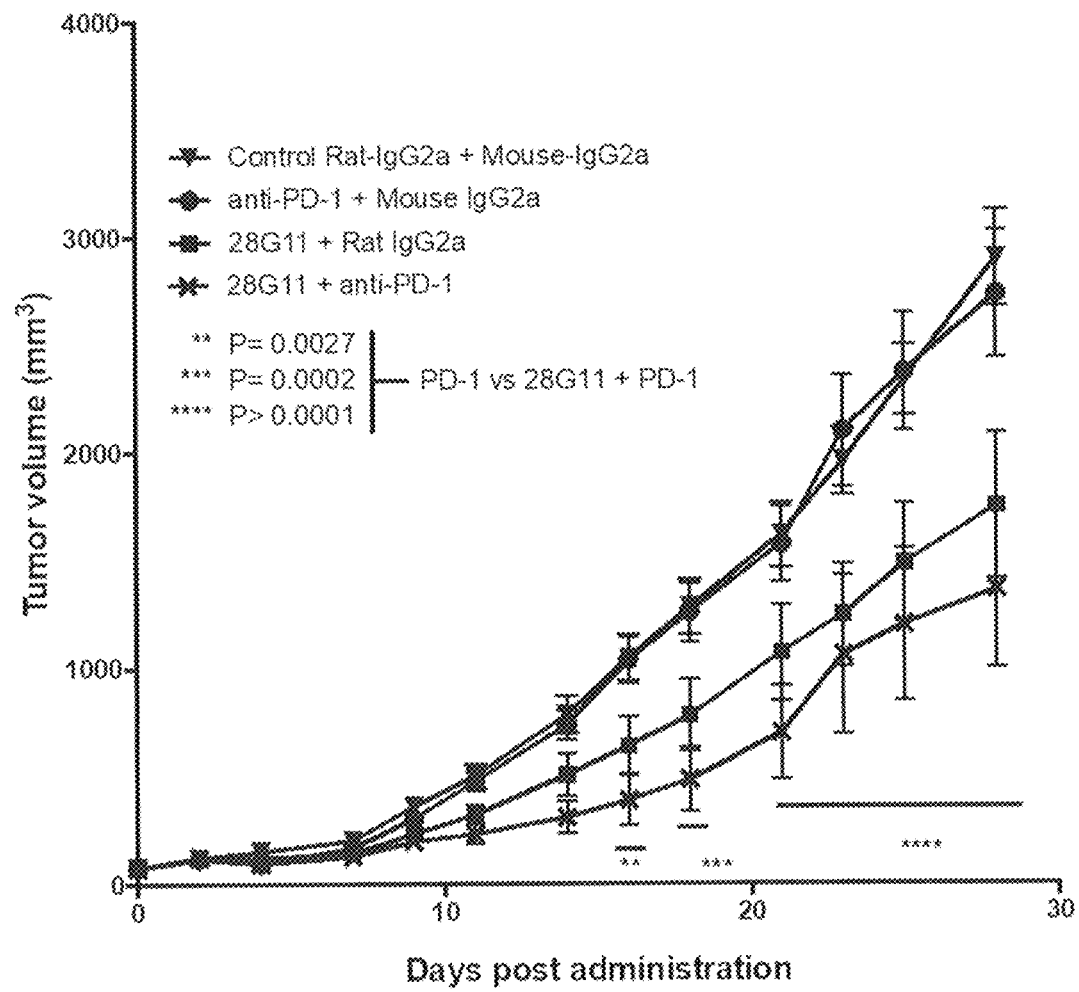
FIG. 31 shows the effects of anti-LAP antibody 28G11 in combination with an anti-PD-1 antibody on tumor volume in a syngeneic EMT6 breast cancer tumor model. The anti-PD-1 antibody was a rat anti-PD-1 RMP1-14-IgG2a antibody. The statistical test used was two-way ANOVA.
Figure 32:
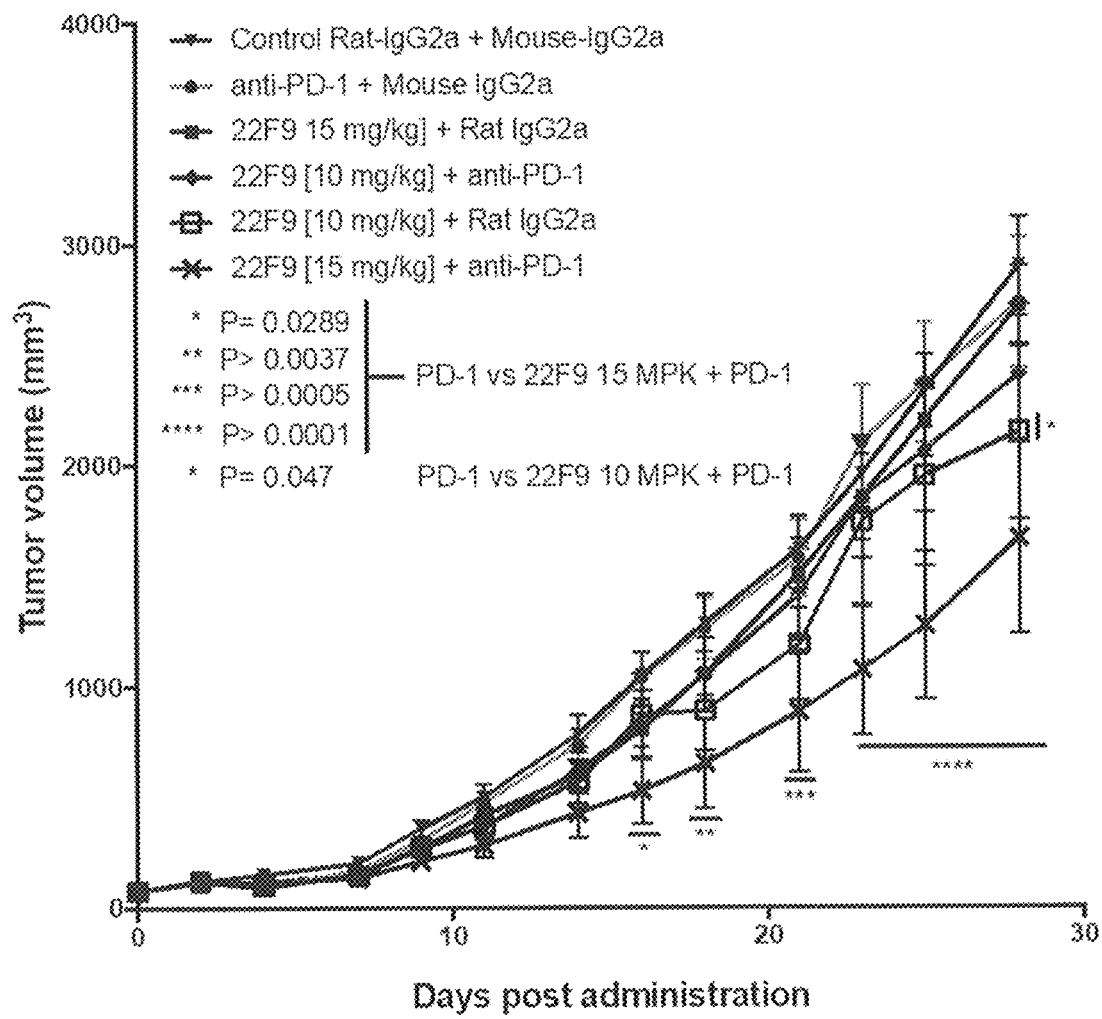
FIG. 32 shows the effects of anti-LAP antibody 22F9 in combination with an anti-PD-1 antibody on tumor volume in a syngeneic EMT6 breast cancer tumor model. The anti-PD-1 antibody was a rat anti-PD-1 RMP1-14-IgG2a antibody. The statistical test used was two-way ANOVA.
Figure 33:
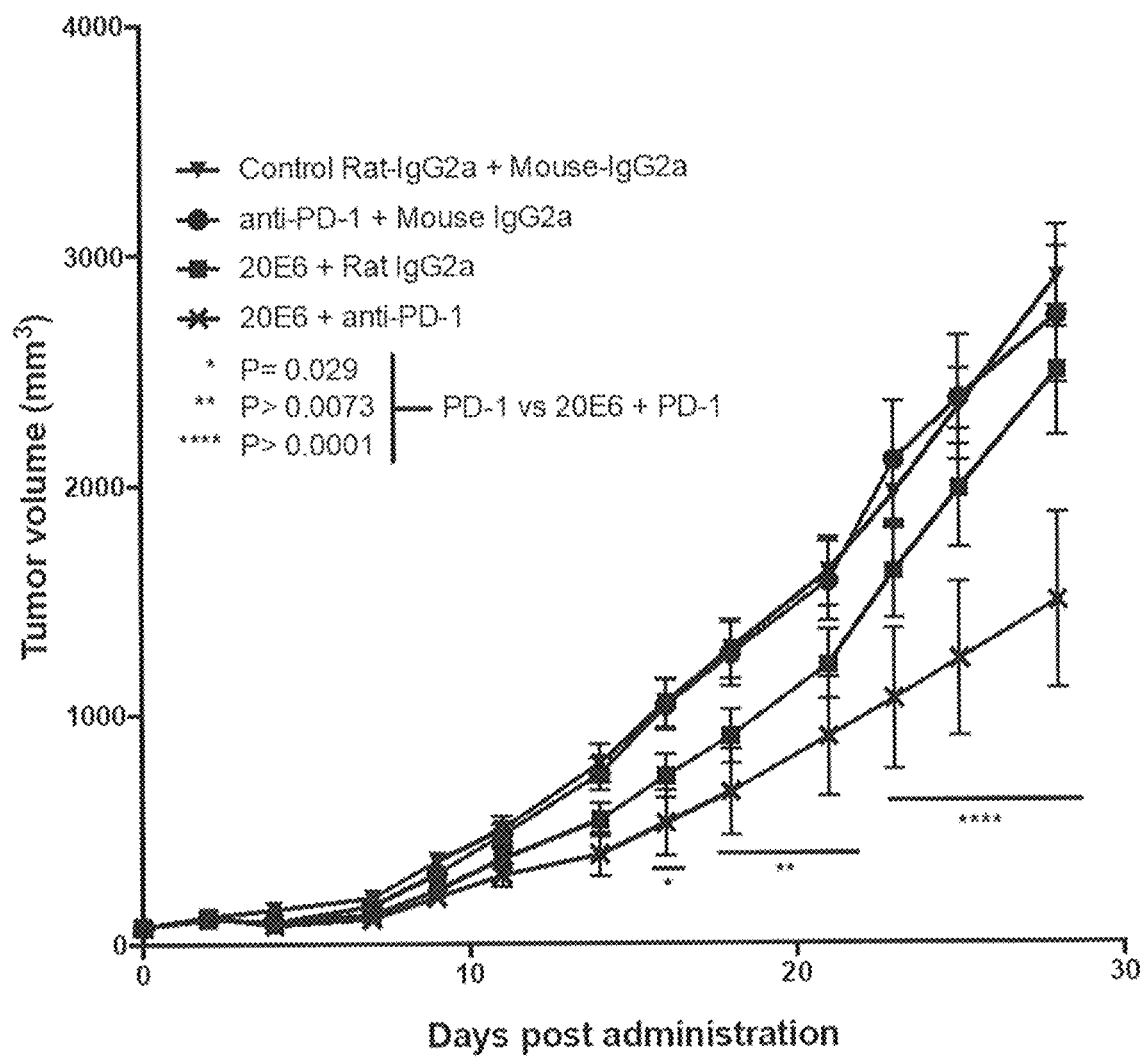
FIG. 33 shows the effects of anti-LAP antibody 20E6 in combination with an anti-PD-1 antibody on tumor volume in a syngeneic EMT6 breast cancer tumor model. The anti-PD-1 antibody was a rat anti-PD-1 RMP1-14-IgG2a antibody. The statistical test used was two-way ANOVA.

As shown in FIG. 31, treatment of animals with antibody 28G11 either alone or in combination with anti-PD-1 resulted in a statistically significant reduction in tumor growth relative to isotype control antibody or anti-PD-1 alone. Similarly, treatment of animals with antibody 22F9 (FIG. 32) and 20E6 (FIG. 33), either alone or in combination with anti-PD-1, resulted in a statistically significant reduction in tumor growth relative to isotype control antibody or anti-PD-1 alone ($p<0.05$, 2-way ANOVA). These data demonstrate that 28G11, 22F9 and 20E6 are all active in combination with anti-PD-1 antibody in the EMT6 mouse model.

Example 12: Efficacy of Anti-LAP Antibodies in 4T1 Breast Cancer Tumor Metastasis Model This Example describes the efficacy of anti-LAP antibodies as monotherapy in a model of tumor metastasis, i.e., the 4T1 breast cancer tumor metastasis model.

Briefly, $1 \times 10^5$ 4T1 breast cancer cells were implanted into the mammary fat pad of 6-8 week-old Balb/c mice. One day after implantation, animals were randomized to groups of 7 animals each. Animals were dosed with mouse IgG1 isotype control antibody, mouse-IgG2a control antibody, anti-TGFβ clone 1D11-IgG, and anti-LAP antibodies 28G11 and 16B4. All animals were dosed intraperitoneally at 10 mg/kg on days 0, 3, 6, 9, and 12. On day 29 post dosing, animals were sacrificed and metastatic lung tumor nodules were counted. Data is graphed as mean lung nodule count +/−SEM.

Figure 34:
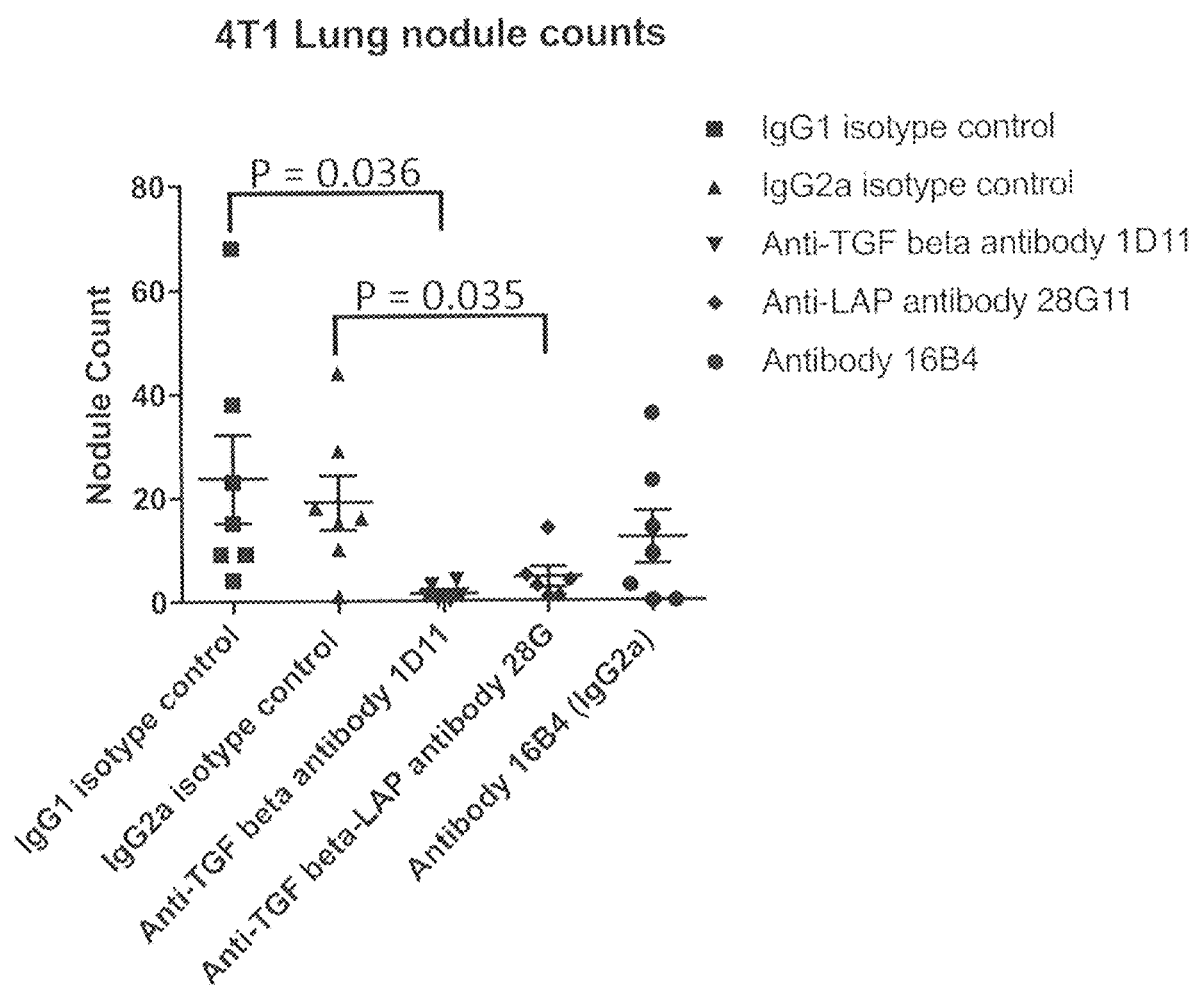
FIG. 34 shows the effects of anti-LAP antibodies 28G11_IgG2a and 16B4_IgG2a, and the anti-TGFβ antibody 1D11_IgG1, as monotherapy on lung nodule counts in the 4T1 breast cancer tumor metastasis model (p<0.05, unpaired T test following removal of outliers).

As shown in FIG. 34, treatment of animals with anti-TGFβ antibodies 1D11 and 28G11, but not 16B4, resulted in a statistically significant reduction of metastatic lung nodules relative to isotype control antibody treated animals (p<0.05, unpaired T test following removal of outliers). These data demonstrate that the two anti-LAP antibodies 28G11 and 16B4 have different functional effects in a mouse model of tumor metastasis. The finding that 28G11 has comparable efficacy to the anti-TGFβ antibody 1D11 is consistent with the effects of 28G11 being due to effects on the TGFβ pathway.

Example 13: Efficacy of Anti-LAP Antibodies in the CT26 Syngeneic Model in Combination with Radiation This Example describes the efficacy of anti-LAP antibodies in combination with radiation in a syngeneic CT26 tumor model.

Briefly, $1 \times 10^6$ CT26 colorectal cancer cells were implanted into 6-8 week-old Balb/c mice. Eight days after implantation, animals were randomized into 6 groups of 16 animals each when mean tumor volume was 300 mm² (day 0). Starting on day 0, animals were dosed with mouse IgG2a isotype control antibody (Group 1), anti-LAP antibody 28G11-IgG2a (Group 2), 12 Gy radiotherapy and mouse IgG2a isotype control antibody (Group 3), 20 Gy radiotherapy and mouse IgG2a isotype control antibody (Group 4), 12 Gy radiotherapy and anti-LAP antibody 28G11-IgG2a (Group 5), or 20 Gy radiotherapy and anti-LAP antibody 28G11-IgG2a (Group 6). All antibodies were dosed intraperitoneally at 10 mg/kg. Groups 1 and 2 received a total of 3 doses of antibody on days 0, 3, and 6 and those animals were sacrificed at day 7 due to large tumor burden. Groups 3-6 received a total of 5 doses of antibody on days 0, 3, 6, 9, and 12. Three random animals from Groups 3-6 were also sacrificed on day 7 and the remaining animals were followed to day 19. In all cases where the animals received radiation therapy, radiation was dosed only once on day 0. Survival was assessed daily and tumor volumes were measured 3 times per week by caliper using the formula V=W2×L/2. Data is presented as mean tumor volume +/−SEM of surviving animals.

Figure 35A:
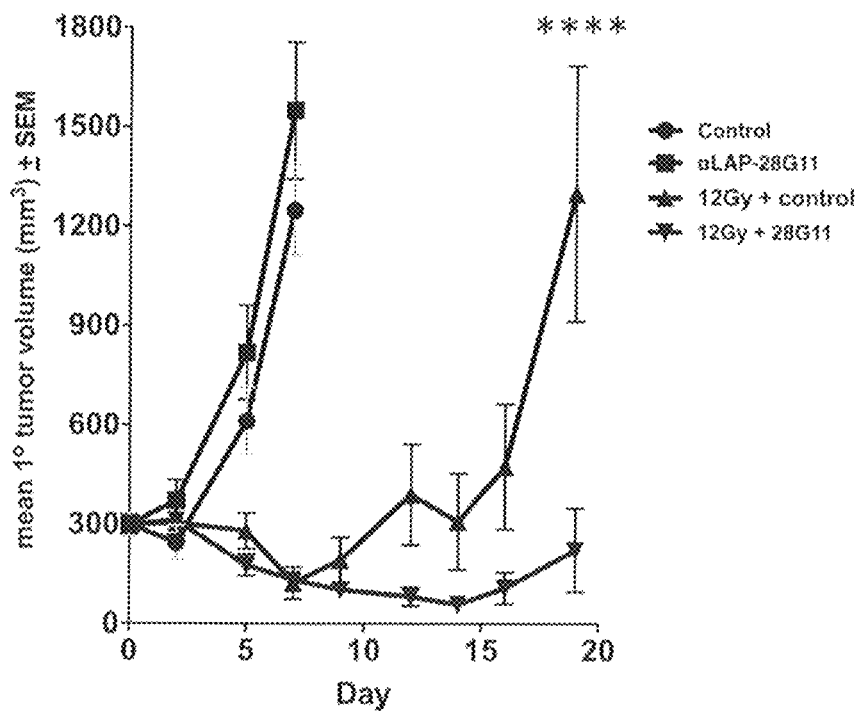
FIGS. 35A and 35B show the effects of anti-LAP antibody 28G11_IgG2a in combination with 12 Gy (FIG. 35A) and 20 Gy (FIG. 35B) radiation on tumor volume in the syngeneic CT26 tumor model. The statistical test used was 2-way ANOVA. **p<0.0001, *p=0.0004
Figure 35B:
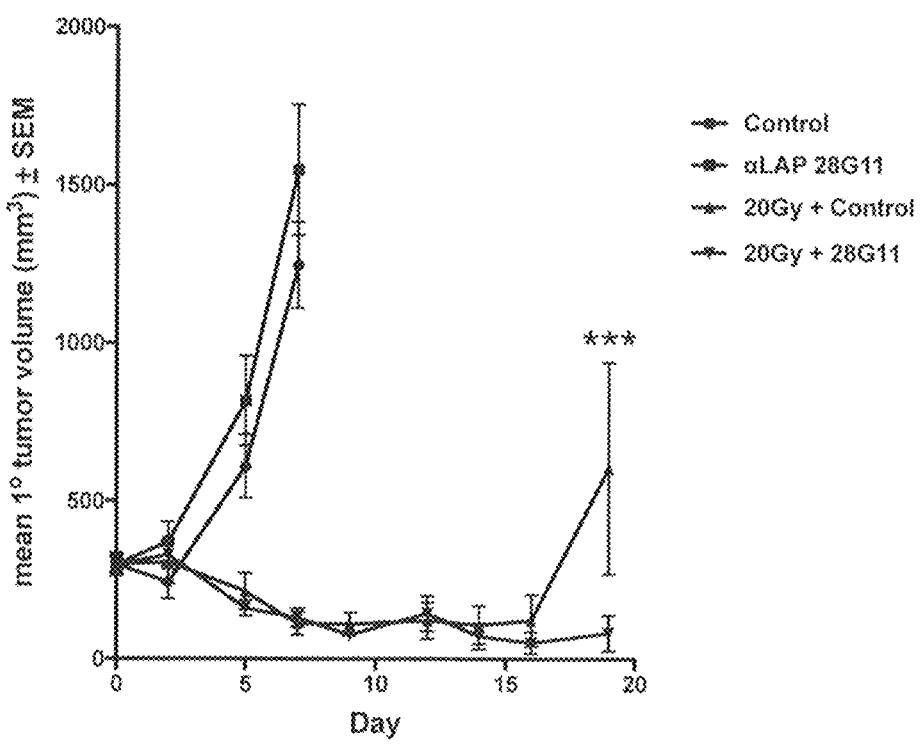

As shown in FIGS. 35A and 35B, treatment of animals with 12 or 20 Gy radiation alone resulted in a delay in tumor growth. Co-administration of 28G11 at 12 Gy radiation dose resulted in a statistically significant reduction in tumor growth relative to radiation treatment alone (**P<0.0001, *P=0.0004, 2-way ANOVA. Co-administration of 28G11 at 20 Gy radiation dose also resulted in a reduction relative to radiation treatment alone, and that effect also was statistically significant.

Example 14: Effects of Anti-LAP Antibodies on CD73 Expression

In this Example, the effect of anti-LAP antibodies on CD73 expression in the tumor microenvironment was examined. CD73 is a cell surface enzyme that processes AMP to adenosine, a molecule with known immunosuppressive effects in the tumor microenvironment.

CT26 tumors were grown in Balb/c mice to 300 mm² (designated day 0), and antibody 28G11 was dosed at 10 mg/kg on days 0, 3, and 6. Mice were treated with targeted radiation (12 Gy or 20 Gy) at a single dose on day 0. CD73 expression on monocytic myeloid-derived suppressor cells (mMDSCs), M2 macrophages, and dendritic cells was examined by flow cytometry on day 7 after radiation. Groupings were as follows:

Group 1: isotype control, no radiation (n=5)
Group 2: 28G11, no radiation (n=5)
Group 3: isotype control, 12 Gy radiation (N=3)
Group 4: isotype control, 20 Gy radiation (N=3)
Group 5: 28G11, 12 Gy radiation (N=2)
Group 6: 28G11, 20 Gy radiation (N=3)

Figure 36A:
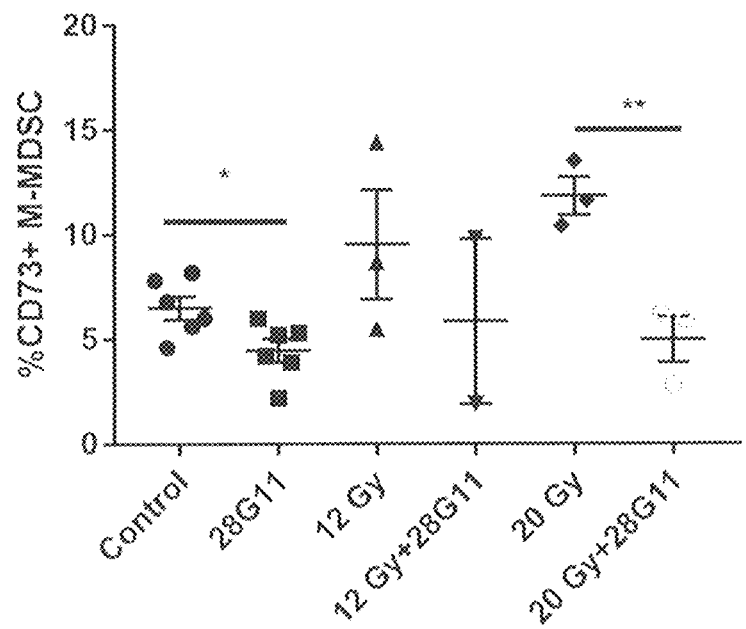
FIGS. 36A-36C show the effects of anti-LAP antibody 28G11_IgG2a on CD73 expression in M-MDSCs (FIG. 36A), M2 macrophages (FIG. 36B), and dendritic cells (FIG. 36C), with or without 12 Gy or 20 Gy radiation.
Figure 36B:
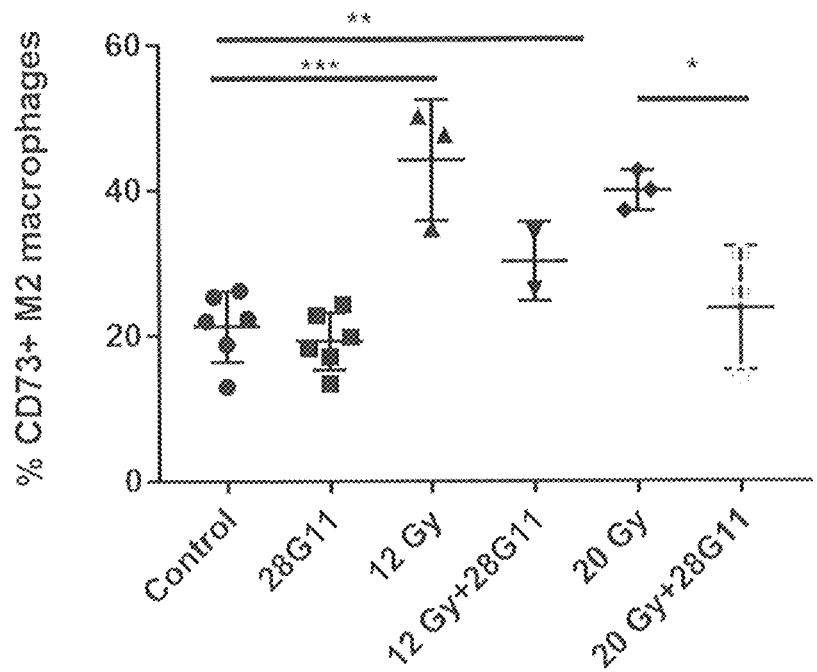
Figure 36C:
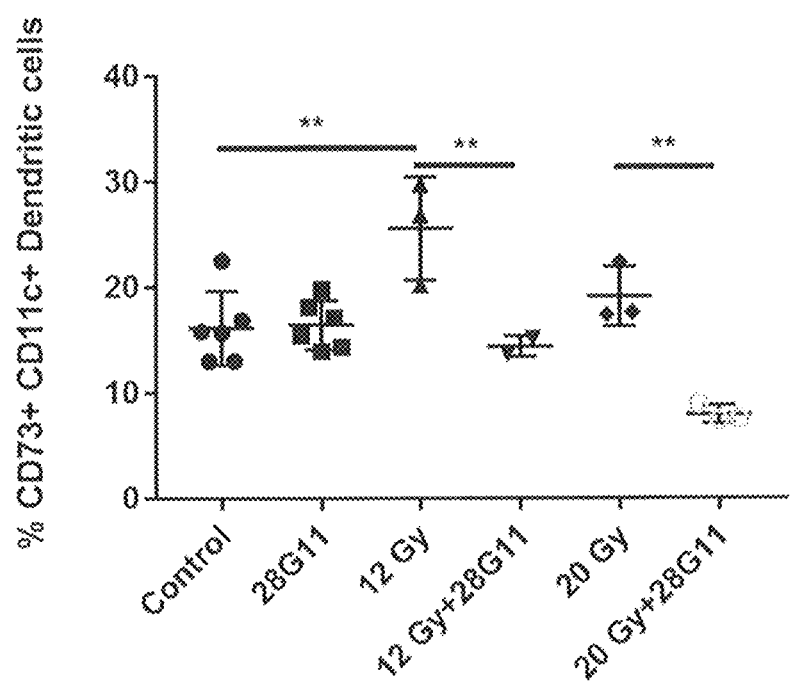

As shown in FIG. 36A-36C, radiation at both doses (12 Gy and 20 Gy) induced CD73 expression on mMDSCs, M2 macrophages, and dendritic cells. This increase in CD73 expression was attenuated by treatment with 28G11. Moreover, 28G11 reduced CD73 expression to below baseline levels in mMDSCs of mice which were not treated with radiation (FIG. 36A). These results demonstrate that anti-LAP antibody treatment reduced both the number and immunosuppressive ability of inhibitory cell populations, as reflected in the reduced proportion of CD73 positive mMDSCs, M2 macrophages, and dendritic cells.

Example 15: Summary of Antibody Properties

Characteristics of the anti-LAP antibodies described in the preceding Examples are summarized in Tables 8A and 8B.

TABLE 8A

| Ab | Binding to human TGFβ1 on transfected cells | Binding to human TGFβ1 in absence of anchor protein (ForteBio) | Binding to human TGFβ2 | Binding to human TGFβ3 | Binding to human ECM | Binding to GARP+ human cells | Binding to GARPneg human cells | Effect on human TGFβ activation |
|---|---|---|---|---|---|---|---|---|
| 28G11 | Yes | Yes | No | No | No | Yes | Yes | Inhibit |
| 7H4 | Yes | ND | ND | ND | No | Yes | ND | Inhibit |
| 22F9 | Yes | Yes | No | No | No | Yes | Yes | Inhibit |
| 20E6 | Yes | Yes | No | No | No | Yes | Yes | Inhibit |
| 17G8 | Yes | Yes | No | No | No | Yes | Yes | Inhibit |

TABLE 8A-continued

| Ab | Binding to human TGFβ1 on transfected cells | Binding to human TGFβ1 in absence of anchor protein (ForteBio) | Binding to human TGFβ2 | Binding to human TGFβ3 | Binding to human ECM | Binding to GARP+ human cells | Binding to GARPneg human cells | Effect on human TGFβ activation |
|---|---|---|---|---|---|---|---|---|
| 24E3 | Yes | Yes | No | No | Yes | Yes | Yes | Inhibit |
| 2C9 | Yes | Yes | No | No | Yes | Yes | Yes | No effect |
| 16F4 | Yes | ND | ND | ND | Yes | ND | ND | No effect |
| 3H6 | Yes | Yes | ND | ND | Yes | ND | ND | Inhibit |
| 478.E9 | Yes | ND | ND | ND | Yes | Yes | ND | Stimulate |
| 478.G3 | Yes | ND | ND | ND | Yes | ND | ND | Stimulate |
| 478.G4 | Yes | ND | ND | ND | Yes | ND | ND | Stimulate |
| 8F10 | Yes | ND | ND | ND | Yes | ND | ND | Inhibit |
| 6H10 | Yes | ND | ND | ND | Yes | ND | ND | Inhibit |
| 1E1 | Yes | Yes | ND | ND | Yes | ND | ND | Inhibit |
| 2F8 | Yes | ND | ND | ND | Yes | Yes | Yes | No effect |
| 1G12 | Yes | ND | ND | ND | Yes | ND | ND | No effect |
| 13B12 | No | ND | ND | ND | No | ND | ND | Inhibit |
| 3G5 | No | ND | ND | ND | No | ND | ND | Inhibit |
| 20B9 | No | ND | ND | ND | No | ND | ND | ND |
| 16B4 | No | ND | ND | ND | No | ND | ND | ND |

ND: not determined

TABLE 8B

| Ab | Binding to murine TGFβ1 on transfected cells | Binding to murine TGFβ1 in absence of anchor protein (ForteBio) | Binding to murine ECM | Binding to GARP+ murine cells | Binding to GARPneg murine cells | Effect on murine TGFβ activation | Inhibition of tumor growth - combo therapy with anti-PD-1 mAb (CT26 or EMT6) | Inhibition of metastasis (4T1) |
|---|---|---|---|---|---|---|---|---|
| 28G11 | Yes | Yes | No | Yes | Yes | Inhibit | Yes | Yes |
| 7H4 | Yes | ND | No | Yes | Yes | Inhibit | ND | ND |
| 22F9 | Yes | Yes | No | Yes | Yes | ND | Yes | ND |
| 20E6 | Yes | Yes | No | Yes | Yes | ND | Yes | ND |
| 17G8 | Yes | Yes | No | ND | ND | Inhibit | ND | ND |
| 24E3 | Yes | Yes | No | ND | ND | Inhibit | ND | ND |
| 2C9 | No | ND | No | ND | ND | ND | ND | ND |
| 16F4 | No | ND | No | ND | ND | ND | ND | ND |
| 3H6 | No | ND | No | ND | ND | ND | ND | ND |
| 478.E9 | ND | ND | No | ND | ND | ND | ND | ND |
| 478.G3 | Yes | ND | No | ND | ND | ND | ND | ND |
| 478.G4 | ND | ND | No | ND | ND | ND | ND | ND |
| 8F10 | No | ND | No | ND | ND | ND | ND | ND |
| 6H10 | No | ND | No | ND | ND | ND | ND | ND |
| 1E1 | No | ND | No | ND | ND | ND | ND | ND |
| 2F8 | ND | ND | No | ND | ND | ND | ND | ND |
| 1G12 | ND | ND | No | ND | ND | ND | ND | ND |
| 13B12 | ND | ND | No | ND | ND | ND | ND | ND |
| 3G5 | ND | ND | No | ND | ND | ND | ND | ND |
| 20B9 | Yes | ND | Yes | Yes | Yes | No effect | ND | ND |
| 16B4 | Yes | ND | Yes | Yes | Yes | No effect | No | No |

ND: not determined

TABLE 9

Summary of Sequences

| SEQ ID | Description | Sequence |
|---|---|---|
| 1 | LAP domain of human TGF-β1 precursor peptide | LSTCKTIDMELVKRKRIEAIRGQILSKLRLASPPSQGEVPPGPLPEAVLALYNST RDRVAGESAEPEPEPEADYYAKEVTRVLMVETHNEIYDKFKQSTHSIYMFFNTSE LREAVPEPVLLSRAELRLLRLKLKVEQHVELYQKYSNNSWRYLSNRLLAPSDSPE WLSFDVTGVVRQWLSRGGEIEGFRLSAHCSCDSRDNTLQVDINGFTTGRRGDLAT IHGMNRPFLLLMATPLERAQHLQSSRHR |
| 2 | Human LAP-TGFβ1 | LSTCKTIDMELVKRKRIEAIRGQILSKLRLASPPSQGEVPPGPLPEAVLALYNST RDRVAGESAEPEPEPEADYYAKEVTRVLMVETHNEIYDKFKQSTHSIYMFFNTSE LREAVPEPVLLSRAELRLLRLKLKVEQHVELYQKYSNNSWRYLSNRLLAPSDSPE |

TABLE 9-continued

Summary of Sequences

| SEQ ID | Description | Sequence |
|---|---|---|
| | | WLSFDVTGVVRQWLSRGGEIEGFRLSAHCSCDSRDNTLQVDINGFTTGRRGDLAT IHGMNRPFLLLMATPLERAQHLQSSRHRALDTNYCFSSTEKNCCVRQLYIDFRKD LGWKWIHEPKGYHANFCLGPCPYIWSLDTQYSKVLALYNQHNPGASAAPCCVPQA LEPLPIVYYVGRKPKVEQLSNMIVRSCKCS |
| 3 | LAP domain of human TGF-β2 precursor peptide | LSTCSTLDMDQFMRKRIEAIRGQILSKLKLTSPPEDYPEPEEVPPEVISIYNSTR DLLQEKASRRAAACERERSDEEYYAKEVYKIDMPPFFPSENAIPPTFYRPYFRIV RFDVSAMEKNASNLVKAEFRVFRLQNPKARVPEQRIELYQILKSKDLTSPTQRYI DSKVVKTRAEGEWLSFDVTDAVHEWLHHKDRNLGFKISLHCPCCTFVPSNNYIIP NKSEELEARFAGIDGTSTYTSGDQKTIKSTRKKNSGKTPHLLLMLLPSYRLESQQ TNRRKKR |
| 4 | Human LAP-TGFβ2 | LSTCSTLDMDQFMRKRIEAIRGQILSKLKLTSPPEDYPEPEEVPPEVISIYNSTR DLLQEKASRRAAACERERSDEEYYAKEVYKIDMPPFFPSENAIPPTFYRPYFRIV RFDVSAMEKNASNLVKAEFRVFRLQNPKARVPEQRIELYQILKSKDLTSPTQRYI DSKVVKTRAEGEWLSFDVTDAVHEWLHHKDRNLGFKISLHCPCCTFVPSNNYIIP NKSEELEARFAGIDGTSTYTSGDQKTIKSTRKKNSGKTPHLLLMLLPSYRLESQQ TNRRKKRALDAAYCFRNVQDNCCLRPLYIDFKRDLGWKWIHEPKGYNANFCAGAC PYLWSSDTQHSRVLSLYNTINPEASASPCCVSQDLEPLTILYYIGKTPKIEQLSN MIVKSCKCS |
| 5 | LAP domain of human TGF-β3 precursor peptide | LSTCTTLDFGHIKKKRVEAIRGQILSKLRLTSPPEPTVMTHVPYQVLALYNSTRE LLEEMHGEREEGCTQENTESEYYAKEIHKFDMIQGLAEHNELAVCPKGITSKVFR FNVSSVEKNRTNLFRAEFRVLRVPNPSSKRNEQRIELFQILRPDEHIAKQRYIGG KNLPTRGTAEWLSFDVTDTVREWLLRRESNLGLEISIHCPCHTFQPNGDILENIH EVMEIKFKGVDNEDDHGRGDLGRLKKQKDHHNPHLILMMIPPHRLDNPGQGGQRK KR |
| 6 | Human LAP-TGFβ3 | LSTCTTLDFGHIKKKRVEAIRGQILSKLRLTSPPEPTVMTHVPYQVLALYNSTRE LLEEMHGEREEGCTQENTESEYYAKEIHKFDMIQGLAEHNELAVCPKGITSKVFR FNVSSVEKNRTNLFRAEFRVLRVPNPSSKRNEQRIELFQILRPDEHIAKQRYIGG KNLPTRGTAEWLSFDVTDTVREWLLRRESNLGLEISIHCPCHTFQPNGDILENIH EVMEIKFKGVDNEDDHGRGDLGRLKKQKDHHNPHLILMMIPPHRLDNPGQGGQRK KRALDTNYCFRNLEENCCVRPLYIDFRQDLGWKWVHEPKGYYANFCSGPCPYLRS ADTTHSTVLGLYNTLNPEASASPCCVPQDLEPLTILYYVGRTPKVEQLSNMVVKS CKCS |
| 7 | LAP domain of murine TGF-β1 precursor peptide | LSTCKTIDMELVKRKRIEAIRGQILSKLRLASPPSQGEVPPGPLPEAVLALYNST RDRVAGESADPEPEPEADYYAKEVTRVLMVDRNNAIYEKTKDISHSIYMFFNTSD IREAVPEPPLLSRAELRLQRLKSSVEQHVELYQKYSNSWRYLGNRLLTPTDTPEW LSFDVTGVVRQWLNQGDGIQGFRFSAHCSCDSKDNKLHVEINGISPKRRGDLGTI HDMNRPFLLLMATPLERAQHLSSRHRR |
| 8 | Murine LAP-TGFβ1 | LSTCKTIDMELVKRKRIEAIRGQILSKLRLASPPSQGEVPPGPLPEAVLALYNST RDRVAGESADPEPEPEADYYAKEVTRVLMVDRNNAIYEKTKDISHSIYMFFNTSD IREAVPEPPLLSRAELRLQRLKSSVEQHVELYQKYSNNSWRYLGNRLLTPTDTPE WLSFDVTGVVRQWLNQGDGIQGFRFSAHCSCDSKDNKLHVEINGISPKRRGDLGT IHDMNRPFLLLMATPLERAQHLSSRHRRALDTNYCFSSTEKNCCVRQLYIDFRK DLGWKWIHEPKGYHANFCLGPCPYIWSLDTQYSKVLALYNQHNPGASASPCCVPQ ALEPLPIVYYVGRKPKVEQLSNMIVRSCKCS |
| 9 | LAP domain of murine TGF-β2 precursor peptide | LSTCSTLDMDQFMRKRIEAIRGQILSKLKLTSPPEDYPEPDEVPPEVISIYNSTR DLLQEKASRRAAACERERSDEEYYAKEVYKIDMPSHLPSENAIPPTFYRPYFRIV RFDVSTMEKNASNLVKAEFRVFRLQNPKARVAEQRIELYQILKSKDLTSPTQRYI DSKVVKTRAEGEWLSFDVTDAVQEWLHHKDRNLGFKISLHCPCCTFVPSNNYIIP NKSEELEARFAGIDGTSTYASGDQKTIKSTRKKTSGKTPHLLLMLLPSYRLESQQ SSRRKKR |
| 10 | Murine LAP-TGFβ2 | LSTCSTLDMDQFMRKRIEAIRGQILSKLKLTSPPEDYPEPDEVPPEVISIYNSTR DLLQEKASRRAAACERERSDEEYYAKEVYKIDMPSHLPSENAIPPTFYRPYFRIV RFDVSTMEKNASNLVKAEFRVFRLQNPKARVAEQRIELYQILKSKDLTSPTQRYI DSKVVKTRAEGEWLSFDVTDAVQEWLHHKDRNLGFKISLHCPCCTFVPSNNYIIP NKSEELEARFAGIDGTSTYASGDQKTIKSTRKKTSGKTPHLLLMLLPSYRLESQQ SSRRKKRALDAAYCFRNVQDNCCLRPLYIDFKRDLGWKWIHEPKGYNANFCAGAC PYLWSSDTQHTKVLSLYNTINPEASASPCCVSQDLEPLTILYYIGNTPKIEQLSN MIVKSCKCS |
| 11 | LAP domain of murine TGF-β3 precursor peptide | LSTCTTLDFGHIKKKRVEAIRGQILSKLRLTSPPEPSVMTHVPYQVLALYNSTRE LLEEMHGEREEGCTQETSESEYYAKEIHKFDMIQGLAEHNELAVCPKGITSKVFR FNVSSVEKNGTNLFRAEFRVLRVPNPSSKRTEQRIELFQILRPDEHIAKQRYIGG KNLPTRGTAEWLSFDVTDTVREWLLRRESNLGLEISIHCPCHTFQPNGDILENVH EVMEIKFKGVDNEDDHGRGDLGRLKKQKDHHNPHLILMMIPPHRLDSPGQGSQRK KR |

TABLE 9-continued

Summary of Sequences

| SEQ ID | Description | Sequence |
|---|---|---|
| 12 | Murine LAP-TGFβ3 | LSTCTTLDFGHIKKKRVEAIRGQILSKLRLTSPPEPSVMTHVPYQVLALYNSTRE LLEEMHGEREEGCTQETSESEYYAKEIHKFDMIQGLAEHNELAVCPKGITSKVFR FNVSSVEKNGTNLFRAEFRVLRVPNPSSKRTEQRIELFQILRPDEHIAKQRYIGG KNLPTRGTAEWLSFDVTDTVREWLLRRESNLGLEISIHCPCHTFQPNGDILENVH EVMEIKFKGVDNEDDHGRGDLGRLKKQKDHHNPHLILMMIPPHRLDSPGQGSQRK KRALDTNYCFRNLEENCCVRPLYIDFRQDLGWKWVHEPKGYYANFCSGPCPYLRS ADTTHSTVLGLYNTLNPEASASPCCVPQDLEPLTILYYVGRTPKVEQLSNMVVKS CKCS |
| 13 | Human LAP-TGFβ1 "open" | LSTCKTIDMELVKRKRIEAIRGQILSKLRLASPPSQGEVPPGPLPEAVLALYNST RDRVAGESAEPEPEPEADTYAKEVTRVLMVETHNEIYDKFKQSTHSIYMFFNTSE LREAVPEPVLLSRAELRLLRLKLKVEQHVELYQKYSNNSWRYLSNRLLAPSDSPE WLSFDVTGVVRQWLSRGGEIEGFRLSAHCSCDSRDNTLQVDINGFTTGRRGDLAT IHGMNRPFLLLMATPLERAQHLQSSRHRALDTNYCFSSTEKNCCVRQLYIDFRKD LGWKWIHEPKGYHANFCLGPCPYIWSLDTQYSKVLALYNQHNPGASAAPCCVPQA LEPLPIVYYVGRKPKVEQLSNMIVRSCKCS |
| 14 | Human LAP-TGFβ1 "closed" | LSTCKTIDMELVKRKRIEAIRGQILSCLRLASPPSQGEVPPGPLPEAVLALYNST RDRVAGESAEPEPEPEADYCAKEVTRVLMVETHNEIYDKFKQSTHSIYMFFNTSE LREAVPEPVLLSRAELRLLRLKLKVEQHVELYQKYSNNSWRYLSNRLLAPSDSPE WLSFDVTGVVRQWLSRGGEIEGFRLSAHCSCDSRDNTLQVDINGFTTGRRGDLAT IHGMNRPFLLLMATPLERAQHLQSSRHRALDTNYCFSSTEKNCCVRQLYIDFRKD LGWKWIHEPKGYHANFCLGPCPYIWSLDTQYSKVLALYNQHNPGASAAPCCVPQA LEPLPIVYYVGRKPKVEQLSNMIVRSCKCS |
| 15 | Human "free TGFβ1" | ALDTNYCFSSTEKNCCVRQLYIDFRKDLGWKWIHEPKGYHANFCLGPCPYIWSLD TQYSKVLALYNQHNPGASAAPCCVPQALEPLPIVYYVGRKPKVEQLSNMIVRSCK CS |
| 16 | 28G11 VHCDR1 | DYYMS |
| 17 | 28G11 VHCDR2 | FIRNKPNGYTTE |
| 18 | 28G11 VHCDR3 | YTGGGYFDY |
| 19 | 28G11 VLCDR1 | RASQDISNYLN |
| 20 | 28G11 VLCDR2 | YTSRLHS |
| 21 | 28G11 VLCDR3 | QQGDTLPWT |
| 22 | 28G11 VH | EVKLVESGGGLVQPGGSLSLSCAASGFTFTDYYMSWVRQPPGKALEWLGFIRNKP NGYTTEYSASVKGRFTISRDNSQSILYLQMNVLRAEDSATYYCARYTGGGYFDYW GQGTTLTVSS |
| 23 | 28G11 VL | DIQMTQTTSSLSASLGDRLTISCRASQDISNYLNWYQQKPDGTVKLLIYYTSRLH SGVPSRFSGSGSGTDYSLTISNLEQADIATYFCQQGDTLPWTFGGGTKLEIK |
| 24 | 3G5 VHCDR1 | SYWMN |
| 25 | 3G5 VHCDR2 | QIYPGDGDTKYNGKFKG |
| 26 | 3G5 VHCDR3 | RGYDGYYISFDV |
| 27 | 3G5 VLCDR1 | RASENIYSNLA |
| 28 | 3G5 VLCDR2 | AATNLAD |
| 29 | 3G5 VLCDR3 | QHFWVTPYT |
| 30 | 3G5 VH | QIQLQQSGAELVRPGSSVKISCKASGYAFSSYWMNWVKQRPGQGLEWIGQIYPGD GDTKYNGKFKGKATLTADKSSSTAYMQLSSLTSEDSAVYFCARRGYDGYYISFDV WGAGTTVTVSS |
| 31 | 3G5 VL | DIQMTQSPASLSVSVGETVTITCRASENIYSNLAWYQRKQGKSPQLLVYAATNLA DGVPSRFSGSGSGTQYSLKINNLQSEDFGSYYCQHFWVTPYTFGGGTKLEIK |
| 32 | 16B4 VHCDR1 | TFGMGVG |

TABLE 9-continued

Summary of Sequences

| SEQ ID | Description | Sequence |
|---|---|---|
| 33 | 16B4 VHCDR2 | HIWWDDDKYYNPALKS |
| 34 | 16B4 VHCDR3 | IYYYGSWGLYYFDY |
| 35 | 16B4 VLCDR1 | RASQDISNYLN |
| 36 | 16B4 VLCDR2 | YTSRLHS |
| 37 | 16B4 VLCDR3 | QQGNTLPPT |
| 38 | 16B4 VH | QVTLKESGPGILQPSQTLSLTCSFSGFSLNTFGMGVGWIRQPSGKGLEWLAHIWWDDDKYYNPALKSRLTISKDTSKNQVFLKIANVDTADTATYYCARIYYYGSWGLYYFDYWGQGTTLTVSS |
| 39 | 16B4 VL | DIQMTQTTSSLSASLGDRVTISCRASQDISNYLNWYQQKPDGTVKLLIYYTSRLHSGVPSRFSGSGSGTDYSLTISNLEQEDIATYFCQQGNTLPPTFGGGTKLEIK |
| 40 | 7H4 VHCDR1 | SGYYWN |
| 41 | 7H4 VHCDR2 | YISYDGTNNYNPSLKN |
| 42 | 7H4 VHCDR3 | SFYNNYFDF |
| 43 | 7H4 VLCDR1 | KASQDIDKYIA |
| 44 | 7H4 VLCDR2 | YTSTLQP |
| 45 | 7H4 VLCDR3 | LQYDNLRT |
| 46 | 7H4 VH | DVQLQESGPGLVKPSQSLSLTCSVTGYSITSGYYWNWIRQFPGNKLEWMGYISYDGTNNYNPSLKNRISITRDTSKHQFFLKLNSVTTEDTATYYCARSFYNNYFDFWGQGTTLTVSS |
| 47 | 7H4 VL | DIQMTQSPSSLSASLGGKVTITCKASQDIDKYIAWYQHKPGKGPRLLIHYTSTLQPGIPSRFSGSGSGRDYSFNISNLEPEDIATYYCLQYDNLRTFGGGTKLEIK |
| 48 | Linker | PVGVV |

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A method of selectively inhibiting TGFβ1 activation on immunosuppressive cells in a subject having cancer comprising:
   (a) contacting a plurality of anti-LAP antibodies with recombinant:
      (i) human LAP-TGFβ1 (SEQ ID NO: 2) in the absence of an anchor protein selected from the group consisting of: GARP and LRRC33;
      (ii) human LAP-TGFβ1 complexed with the anchor protein; and
      (iii) human LAP-TGFβ1 complexed with LTBP1, LTBP3 and/or LTBP4;
   (b) determining TGFβ1 inhibition of (a)(i)-a(ii) by the plurality of anti-LAP antibodies using an enzyme-linked immunosorbent assay (ELISA), respectively;
   (c) determining binding of (a)(iii) by the plurality of anti-LAP antibodies;
   (d) selecting an antibody that:
      (i) inhibits TGFβ1 in step (b) for (a)(i) and (a)(ii); and
      (ii) does not bind (a)(iii) in step (b); and
   (e) administering an amount of the antibody selected in (d) to the subject such that TGFβ1 is selectively inactivated on the immunosuppressive cells in the subject,
   wherein the plurality of anti-LAP antibodies comprises an antibody that comprises a heavy chain variable region comprising the amino acid sequence of SEQ ID NO: 22 and light chain variable region comprising the amino acid sequence of SEQ ID NO: 23, and
   wherein step (d) further comprises selecting the antibody that (i) inhibits TGFβ1 in step (b) for (a)(i) and (a)(ii) to an equal or greater degree than the antibody that comprises a heavy chain variable region comprising the amino acid sequence of SEQ ID NO: 22 and light chain variable region comprising the amino acid sequence of SEQ ID NO: 23.

2. The method of claim 1, wherein the cancer is selected from the group consisting of breast cancer, bladder cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and myelodysplastic syndromes.

3. The method of claim 1, wherein the cancer is associated with an increased number of circulating platelets or an increased platelet to lymphocyte ratio.

4. The method of claim 1, further comprising administering one or more additional therapies.

5. The method of claim 4, wherein the one or more additional therapies is selected from radiation therapy, chemotherapy, an immune checkpoint inhibitor, immunostimulatory therapy, immunosuppressive therapy, cell therapy, and a therapeutic agent.

6. The method of claim 5, wherein the immune checkpoint inhibitor is selected from the group consisting of: an anti-PD-1 antibody, an anti-PD-L1 antibody, an anti-LAG-3 antibody, an anti-CTLA-4 antibody, an anti-TIGIT antibody, and an anti-TIM3 antibody.

7. The method of claim 5, wherein the therapeutic agent is selected from the group consisting of an anti-cancer agent, a chemotherapeutic agent, an immunosuppressive agent, an immunomodulatory agent, and an anti-inflammatory agent.

8. The method of claim 1, further comprising in step (a) contacting the plurality of anti-LAP antibodies with (iv) anchor protein (v) human LAP-TGFβ2 (SEQ ID NO: 4), (vi) human LAP-TGFβ3 (SEQ ID NO: 6), and (vii) free TGFβ1 (SEQ ID NO: 15); further comprising in step (c) determining binding of (a)(iv), (a)(v), (a)(vi), and (a)(vii);
   and further comprising in step (d) selecting the antibody that does not bind to (a)(iv), (a)(v), (a)(vi) and (a)(vii), wherein the antibody does not bind to the anchor protein or to an epitope composed of residues of both LAP-TGFβ and the anchor protein.

9. The method of claim 1, wherein the immunosuppressive cells are suppressive T cells, M2 macrophages, cancer cells expressing LAP-TGFβ1, and/or monocytic myeloid-derived suppressor cells.

10. The method of claim 1, wherein the immunosuppressive cells are GARP-positive immunosuppressive cells.

11. The method of claim 1, further comprising in step (a) contacting the plurality of anti-LAP antibodies with (iv) human LAP-TGFβ1 comprising K27C and Y75C mutations (SEQ ID NO: 14); and (v) human LAP-TGFβ1 comprising the Y74T mutation (SEQ ID NO: 13); further comprising in step (c) determining binding of (a)(iv) and (a)(v) with the plurality of anti-LAP antibodies;
   and further comprising in step (d) selecting the antibody that binds to (a)(iv) and (iv) does not bind to (a)(v).

12. The method of claim 1, wherein the antibody is a human IgG1, IgG2, IgG3, IgG4, IgD, IgA, IgE, or IgM antibody, or variant thereof.

13. The method of claim 1, wherein the antibody is a chimeric, humanized, or human antibody.

14. The method of claim 1, wherein the (a)(i) and (a)(ii) comprises LAP in solution and (a)(iii) comprises LAP in solution complexed with TGFβ1 and LTBP1, LTBP3, or LTBP4.

* * * * *

SEQUENCE LISTING

<160> NUMBER OF SEQ ID NOS: 48

<210> SEQ ID NO 1
<211> LENGTH: 248
<212> TYPE: PRT
<213> ORGANISM: Homo sapiens
<220> FEATURE:
<221> NAME/KEY: misc_feature
<222> LOCATION: (1)..(248)
<223> OTHER INFORMATION: LAP domain of human TGF-beta1 precursor peptide

<400> SEQUENCE: 1

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
        130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg
                245

<210> SEQ ID NO 2
<211> LENGTH: 360
<212> TYPE: PRT
<213> ORGANISM: Homo sapiens
<220> FEATURE:
<221> NAME/KEY: misc_feature
<222> LOCATION: (1)..(360)
<223> OTHER INFORMATION: Human LAP-TGFbeta1

<400> SEQUENCE: 2

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
                100                 105                 110

```
Glu Ala Val Pro Glu Pro Val Leu Ser Arg Ala Glu Leu Arg Leu
            115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
                180                 185                 190

His Cys Ser Cys Asp Ser Arg Asp Asn Thr Leu Gln Val Asp Ile Asn
                195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Ala Leu Asp Thr Asn Tyr Cys Phe
                245                 250                 255

Ser Ser Thr Glu Lys Asn Cys Cys Val Arg Gln Leu Tyr Ile Asp Phe
                260                 265                 270

Arg Lys Asp Leu Gly Trp Lys Trp Ile His Glu Pro Lys Gly Tyr His
            275                 280                 285

Ala Asn Phe Cys Leu Gly Pro Cys Pro Tyr Ile Trp Ser Leu Asp Thr
            290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
                340                 345                 350

Ile Val Arg Ser Cys Lys Cys Ser
            355                 360

<210> SEQ ID NO 3
<211> LENGTH: 282
<212> TYPE: PRT
<213> ORGANISM: Homo sapiens
<220> FEATURE:
<221> NAME/KEY: misc_feature
<222> LOCATION: (1)..(282)
<223> OTHER INFORMATION: LAP domain of human TGF-beta2 precursor peptide

<400> SEQUENCE: 3

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Glu Glu Val Pro Pro Glu Val Ile
        35                  40                  45

Ser Ile Tyr Asn Ser Thr Arg Asp Leu Leu Gln Glu Lys Ala Ser Arg
50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Pro Phe Phe Pro Ser Glu Asn
                85                  90                  95

Ala Ile Pro Pro Thr Phe Tyr Arg Pro Tyr Phe Arg Ile Val Arg Phe
```

```
                100                 105                 110
Asp Val Ser Ala Met Glu Lys Asn Ala Ser Asn Leu Val Lys Ala Glu
            115                 120                 125

Phe Arg Val Phe Arg Leu Gln Asn Pro Lys Ala Arg Val Pro Glu Gln
        130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
        195                 200                 205

Cys Thr Phe Val Pro Ser Asn Asn Tyr Ile Ile Pro Asn Lys Ser Glu
210                 215                 220

Glu Leu Glu Ala Arg Phe Ala Gly Ile Asp Gly Thr Ser Thr Tyr Thr
225                 230                 235                 240

Ser Gly Asp Gln Lys Thr Ile Lys Ser Thr Arg Lys Lys Asn Ser Gly
                245                 250                 255

Lys Thr Pro His Leu Leu Leu Met Leu Leu Pro Ser Tyr Arg Leu Glu
            260                 265                 270

Ser Gln Gln Thr Asn Arg Arg Lys Lys Arg
        275                 280

<210> SEQ ID NO 4
<211> LENGTH: 394
<212> TYPE: PRT
<213> ORGANISM: Homo sapiens
<220> FEATURE:
<221> NAME/KEY: misc_feature
<222> LOCATION: (1)..(394)
<223> OTHER INFORMATION: Human LAP-TGFbeta2

<400> SEQUENCE: 4

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Glu Glu Val Pro Pro Glu Val Ile
        35                  40                  45

Ser Ile Tyr Asn Ser Thr Arg Asp Leu Leu Gln Glu Lys Ala Ser Arg
    50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Pro Phe Phe Pro Ser Glu Asn
                85                  90                  95

Ala Ile Pro Pro Thr Phe Tyr Arg Pro Tyr Phe Arg Ile Val Arg Phe
            100                 105                 110

Asp Val Ser Ala Met Glu Lys Asn Ala Ser Asn Leu Val Lys Ala Glu
        115                 120                 125

Phe Arg Val Phe Arg Leu Gln Asn Pro Lys Ala Arg Val Pro Glu Gln
    130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175
```

```
Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
            195                 200                 205

Cys Thr Phe Val Pro Ser Asn Asn Tyr Ile Ile Pro Asn Lys Ser Glu
210                 215                 220

Glu Leu Glu Ala Arg Phe Ala Gly Ile Asp Gly Thr Ser Thr Tyr Thr
225                 230                 235                 240

Ser Gly Asp Gln Lys Thr Ile Lys Ser Thr Arg Lys Lys Asn Ser Gly
            245                 250                 255

Lys Thr Pro His Leu Leu Leu Met Leu Leu Pro Ser Tyr Arg Leu Glu
            260                 265                 270

Ser Gln Gln Thr Asn Arg Arg Lys Lys Arg Ala Leu Asp Ala Ala Tyr
            275                 280                 285

Cys Phe Arg Asn Val Gln Asp Asn Cys Cys Leu Arg Pro Leu Tyr Ile
            290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                        325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
            355                 360                 365

Thr Ile Leu Tyr Tyr Ile Gly Lys Thr Pro Lys Ile Glu Gln Leu Ser
            370                 375                 380

Asn Met Ile Val Lys Ser Cys Lys Cys Ser
385                 390

<210> SEQ ID NO 5
<211> LENGTH: 277
<212> TYPE: PRT
<213> ORGANISM: Homo sapiens
<220> FEATURE:
<221> NAME/KEY: misc_feature
<222> LOCATION: (1)..(277)
<223> OTHER INFORMATION: LAP domain of human TGF-beta3 precursor peptide

<400> SEQUENCE: 5

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Thr Val Met Thr His Val Pro Tyr Gln Val Leu Ala
        35                  40                  45

Leu Tyr Asn Ser Thr Arg Glu Leu Leu Glu Glu Met His Gly Glu Arg
50                  55                  60

Glu Glu Gly Cys Thr Gln Glu Asn Thr Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Arg Thr Asn Leu Phe Arg Ala Glu Phe
        115                 120                 125
```

```
Arg Val Leu Arg Val Pro Asn Pro Ser Ser Lys Arg Asn Glu Gln Arg
130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
                180                 185                 190

Glu Ser Asn Leu Gly Leu Glu Ile Ser Ile His Cys Pro Cys His Thr
                195                 200                 205

Phe Gln Pro Asn Gly Asp Ile Leu Glu Asn Ile His Glu Val Met Glu
210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Asn Pro Gly Gln Gly Gly
                260                 265                 270

Gln Arg Lys Lys Arg
        275

<210> SEQ ID NO 6
<211> LENGTH: 389
<212> TYPE: PRT
<213> ORGANISM: Homo sapiens
<220> FEATURE:
<221> NAME/KEY: misc_feature
<222> LOCATION: (1)..(389)
<223> OTHER INFORMATION: Human LAP-TGFbeta3

<400> SEQUENCE: 6

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
                20                  25                  30

Pro Pro Glu Pro Thr Val Met Thr His Val Pro Tyr Gln Val Leu Ala
                35                  40                  45

Leu Tyr Asn Ser Thr Arg Glu Leu Leu Glu Glu Met His Gly Glu Arg
50                  55                  60

Glu Glu Gly Cys Thr Gln Glu Asn Thr Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
                100                 105                 110

Val Ser Ser Val Glu Lys Asn Arg Thr Asn Leu Phe Arg Ala Glu Phe
                115                 120                 125

Arg Val Leu Arg Val Pro Asn Pro Ser Ser Lys Arg Asn Glu Gln Arg
130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
                180                 185                 190

Glu Ser Asn Leu Gly Leu Glu Ile Ser Ile His Cys Pro Cys His Thr
```

```
                     195                 200                 205

Phe Gln Pro Asn Gly Asp Ile Leu Glu Asn Ile His Glu Val Met Glu
    210                 215                 220

Ile Lys Phe Lys Gly Val Asp Asn Glu Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Asn Pro Gly Gln Gly Gly
            260                 265                 270

Gln Arg Lys Lys Arg Ala Leu Asp Thr Asn Tyr Cys Phe Arg Asn Leu
        275                 280                 285

Glu Glu Asn Cys Cys Val Arg Pro Leu Tyr Ile Asp Phe Arg Gln Asp
    290                 295                 300

Leu Gly Trp Lys Trp Val His Glu Pro Lys Gly Tyr Tyr Ala Asn Phe
305                 310                 315                 320

Cys Ser Gly Pro Cys Pro Tyr Leu Arg Ser Ala Asp Thr Thr His Ser
                325                 330                 335

Thr Val Leu Gly Leu Tyr Asn Thr Leu Asn Pro Glu Ala Ser Ala Ser
            340                 345                 350

Pro Cys Cys Val Pro Gln Asp Leu Glu Pro Leu Thr Ile Leu Tyr Tyr
        355                 360                 365

Val Gly Arg Thr Pro Lys Val Glu Gln Leu Ser Asn Met Val Val Lys
    370                 375                 380

Ser Cys Lys Cys Ser
385

<210> SEQ ID NO 7
<211> LENGTH: 248
<212> TYPE: PRT
<213> ORGANISM: Mus musculus
<220> FEATURE:
<221> NAME/KEY: misc_feature
<222> LOCATION: (1)..(248)
<223> OTHER INFORMATION: LAP domain of murine TGF-beta1 precursor
      peptide

<400> SEQUENCE: 7

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
        50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Ser Trp Arg Tyr Leu Gly Asn Arg Leu Leu Thr Pro Thr
```

```
145                 150                 155                 160

Asp Thr Pro Glu Trp Leu Ser Phe Asp Val Thr Gly Val Val Arg Gln
            165                 170                 175

Trp Leu Asn Gln Gly Asp Gly Ile Gln Gly Phe Arg Phe Ser Ala His
            180                 185                 190

Cys Ser Cys Asp Ser Lys Asp Asn Lys Leu His Val Glu Ile Asn Gly
            195                 200                 205

Ile Ser Pro Lys Arg Arg Gly Asp Leu Gly Thr Ile His Asp Met Asn
            210                 215                 220

Arg Pro Phe Leu Leu Leu Met Ala Thr Pro Leu Glu Arg Ala Gln His
225                 230                 235                 240

Leu His Ser Ser Arg His Arg Arg
            245

<210> SEQ ID NO 8
<211> LENGTH: 361
<212> TYPE: PRT
<213> ORGANISM: Mus musculus
<220> FEATURE:
<221> NAME/KEY: misc_feature
<222> LOCATION: (1)..(361)
<223> OTHER INFORMATION: Murine LAP-TGFbeta1

<400> SEQUENCE: 8

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
            115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
            195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
                245                 250                 255
```

```
Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 9
<211> LENGTH: 282
<212> TYPE: PRT
<213> ORGANISM: Mus musculus
<220> FEATURE:
<221> NAME/KEY: misc_feature
<222> LOCATION: (1)..(282)
<223> OTHER INFORMATION: LAP domain of murine TGF-beta2 precursor
      peptide

<400> SEQUENCE: 9

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Asp Glu Val Pro Pro Glu Val Ile
        35                  40                  45

Ser Ile Tyr Asn Ser Thr Arg Asp Leu Leu Gln Glu Lys Ala Ser Arg
    50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Ser His Leu Pro Ser Glu Asn
                85                  90                  95

Ala Ile Pro Pro Thr Phe Tyr Arg Pro Tyr Phe Arg Ile Val Arg Phe
            100                 105                 110

Asp Val Ser Thr Met Glu Lys Asn Ala Ser Asn Leu Val Lys Ala Glu
        115                 120                 125

Phe Arg Val Phe Arg Leu Gln Asn Pro Lys Ala Arg Val Ala Glu Gln
    130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val Gln Glu Trp Leu His
            180                 185                 190

His Lys Asp Arg Asn Leu Gly Phe Lys Ile Ser Leu His Cys Pro Cys
        195                 200                 205

Cys Thr Phe Val Pro Ser Asn Asn Tyr Ile Ile Pro Asn Lys Ser Glu
    210                 215                 220

Glu Leu Glu Ala Arg Phe Ala Gly Ile Asp Gly Thr Ser Thr Tyr Ala
225                 230                 235                 240
```

```
Ser Gly Asp Gln Lys Thr Ile Lys Ser Thr Arg Lys Lys Thr Ser Gly
            245                 250                 255

Lys Thr Pro His Leu Leu Leu Met Leu Leu Pro Ser Tyr Arg Leu Glu
            260                 265                 270

Ser Gln Gln Ser Ser Arg Arg Lys Lys Arg
            275                 280

<210> SEQ ID NO 10
<211> LENGTH: 394
<212> TYPE: PRT
<213> ORGANISM: Mus musculus
<220> FEATURE:
<221> NAME/KEY: misc_feature
<222> LOCATION: (1)..(394)
<223> OTHER INFORMATION: Murine LAP-TGFbeta2

<400> SEQUENCE: 10

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
                20                  25                  30

Pro Pro Glu Asp Tyr Pro Glu Pro Asp Glu Val Pro Pro Glu Val Ile
            35                  40                  45

Ser Ile Tyr Asn Ser Thr Arg Asp Leu Leu Gln Glu Lys Ala Ser Arg
        50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Ser His Leu Pro Ser Glu Asn
                85                  90                  95

Ala Ile Pro Pro Thr Phe Tyr Arg Pro Tyr Phe Arg Ile Val Arg Phe
            100                 105                 110

Asp Val Ser Thr Met Glu Lys Asn Ala Ser Asn Leu Val Lys Ala Glu
        115                 120                 125

Phe Arg Val Phe Arg Leu Gln Asn Pro Lys Ala Arg Val Ala Glu Gln
130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val Gln Glu Trp Leu His
            180                 185                 190

His Lys Asp Arg Asn Leu Gly Phe Lys Ile Ser Leu His Cys Pro Cys
        195                 200                 205

Cys Thr Phe Val Pro Ser Asn Asn Tyr Ile Ile Pro Asn Lys Ser Glu
210                 215                 220

Glu Leu Glu Ala Arg Phe Ala Gly Ile Asp Gly Thr Ser Thr Tyr Ala
225                 230                 235                 240

Ser Gly Asp Gln Lys Thr Ile Lys Ser Thr Arg Lys Lys Thr Ser Gly
                245                 250                 255

Lys Thr Pro His Leu Leu Leu Met Leu Leu Pro Ser Tyr Arg Leu Glu
            260                 265                 270

Ser Gln Gln Ser Ser Arg Arg Lys Lys Arg Ala Leu Asp Ala Ala Tyr
        275                 280                 285

Cys Phe Arg Asn Val Gln Asp Asn Cys Cys Leu Arg Pro Leu Tyr Ile
290                 295                 300
```

```
Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Thr Lys Val Leu Ser Leu Tyr Asn Thr Ile Asn Pro
                340                 345                 350

Glu Ala Ser Ala Ser Pro Cys Cys Val Ser Gln Asp Leu Glu Pro Leu
                355                 360                 365

Thr Ile Leu Tyr Tyr Ile Gly Asn Thr Pro Lys Ile Glu Gln Leu Ser
                370                 375                 380

Asn Met Ile Val Lys Ser Cys Lys Cys Ser
385                 390
```

<210> SEQ ID NO 11
<211> LENGTH: 277
<212> TYPE: PRT
<213> ORGANISM: Mus musculus
<220> FEATURE:
<221> NAME/KEY: misc_feature
<222> LOCATION: (1)..(277)
<223> OTHER INFORMATION: LAP domain of murine TGF-beta3 precursor
      peptide

<400> SEQUENCE: 11

```
Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
                20                  25                  30

Pro Pro Glu Pro Ser Val Met Thr His Val Pro Tyr Gln Val Leu Ala
                35                  40                  45

Leu Tyr Asn Ser Thr Arg Glu Leu Leu Glu Glu Met His Gly Glu Arg
50                  55                  60

Glu Gly Cys Thr Gln Glu Thr Ser Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
                100                 105                 110

Val Ser Ser Val Glu Lys Asn Gly Thr Asn Leu Phe Arg Ala Glu Phe
                115                 120                 125

Arg Val Leu Arg Val Pro Asn Pro Ser Ser Lys Arg Thr Glu Gln Arg
                130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
                180                 185                 190

Glu Ser Asn Leu Gly Leu Glu Ile Ser Ile His Cys Pro Cys His Thr
                195                 200                 205

Phe Gln Pro Asn Gly Asp Ile Leu Glu Asn Val His Glu Val Met Glu
                210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255
```

Leu Met Met Ile Pro Pro His Arg Leu Asp Ser Pro Gly Gln Gly Ser
            260                 265                 270

Gln Arg Lys Lys Arg
        275

<210> SEQ ID NO 12
<211> LENGTH: 389
<212> TYPE: PRT
<213> ORGANISM: Mus musculus
<220> FEATURE:
<221> NAME/KEY: misc_feature
<222> LOCATION: (1)..(389)
<223> OTHER INFORMATION: Murine LAP-TGFbeta3

<400> SEQUENCE: 12

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Ser Val Met Thr His Val Pro Tyr Gln Val Leu Ala
        35                  40                  45

Leu Tyr Asn Ser Thr Arg Glu Leu Leu Glu Glu Met His Gly Glu Arg
    50                  55                  60

Glu Glu Gly Cys Thr Gln Glu Thr Ser Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Gly Thr Asn Leu Phe Arg Ala Glu Phe
        115                 120                 125

Arg Val Leu Arg Val Pro Asn Pro Ser Ser Lys Arg Thr Glu Gln Arg
    130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
        195                 200                 205

Phe Gln Pro Asn Gly Asp Ile Leu Glu Asn Val His Glu Val Met Glu
    210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Ser Pro Gly Gln Gly Ser
            260                 265                 270

Gln Arg Lys Lys Arg Ala Leu Asp Thr Asn Tyr Cys Phe Arg Asn Leu
        275                 280                 285

Glu Glu Asn Cys Cys Val Arg Pro Leu Tyr Ile Asp Phe Arg Gln Asp
    290                 295                 300

Leu Gly Trp Lys Trp Val His Glu Pro Lys Gly Tyr Tyr Ala Asn Phe
305                 310                 315                 320

Cys Ser Gly Pro Cys Pro Tyr Leu Arg Ser Ala Asp Thr Thr His Ser

```
                    325                 330                 335
Thr Val Leu Gly Leu Tyr Asn Thr Leu Asn Pro Glu Ala Ser Ala Ser
                340                 345                 350

Pro Cys Cys Val Pro Gln Asp Leu Glu Pro Leu Thr Ile Leu Tyr Tyr
            355                 360                 365

Val Gly Arg Thr Pro Lys Val Glu Gln Leu Ser Asn Met Val Val Lys
370                 375                 380

Ser Cys Lys Cys Ser
385

<210> SEQ ID NO 13
<211> LENGTH: 360
<212> TYPE: PRT
<213> ORGANISM: Homo sapiens
<220> FEATURE:
<221> NAME/KEY: misc_feature
<222> LOCATION: (1)..(360)
<223> OTHER INFORMATION: Human LAP-TGFbeta1  open

<400> SEQUENCE: 13

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Thr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285
```

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
            355                 360

<210> SEQ ID NO 14
<211> LENGTH: 360
<212> TYPE: PRT
<213> ORGANISM: Homo sapiens
<220> FEATURE:
<221> NAME/KEY: misc_feature
<222> LOCATION: (1)..(360)
<223> OTHER INFORMATION: Human LAP-TGFbeta1 closed

<400> SEQUENCE: 14

Leu Ser Thr Cys Lys Thr Ile Asp Met Glu Leu Val Lys Arg Lys Arg
1               5                   10                  15

Ile Glu Ala Ile Arg Gly Gln Ile Leu Ser Cys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Cys Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
                275                 280                 285

Ala Asn Phe Cys Leu Gly Pro Cys Pro Tyr Ile Trp Ser Leu Asp Thr
            290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
            355                 360

<210> SEQ ID NO 15
<211> LENGTH: 112
<212> TYPE: PRT
<213> ORGANISM: Homo sapiens
<220> FEATURE:
<221> NAME/KEY: misc_feature
<222> LOCATION: (1)..(112)
<223> OTHER INFORMATION: Human free TGFbeta1

<400> SEQUENCE: 15

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 16
<211> LENGTH: 5
<212> TYPE: PRT
<213> ORGANISM: Artificial Sequence
<220> FEATURE:
<223> OTHER INFORMATION: Synthetic: 28G11 VHCDR1

<400> SEQUENCE: 16

Asp Tyr Tyr Met Ser
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic: 28G11 VHCDR2

<400> SEQUENCE: 17

Phe Ile Arg Asn Lys Pro Asn Gly Tyr Thr Thr Glu
1               5                   10

<210> SEQ ID NO 18

```
<211> LENGTH: 9
<212> TYPE: PRT
<213> ORGANISM: Artificial Sequence
<220> FEATURE:
<223> OTHER INFORMATION: Synthetic: 28G11 VHCDR3

<400> SEQUENCE: 18

Tyr Thr Gly Gly Gly Tyr Phe Asp Tyr
1               5

<210> SEQ ID NO 19
<211> LENGTH: 11
<212> TYPE: PRT
<213> ORGANISM: Artificial Sequence
<220> FEATURE:
<223> OTHER INFORMATION: Synthetic: 28G11 VLCDR1

<400> SEQUENCE: 19

Arg Ala Ser Gln Asp Ile Ser Asn Tyr Leu Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic: 28G11 VLCDR2

<400> SEQUENCE: 20

Tyr Thr Ser Arg Leu His Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic: 28G11 VLCDR3

<400> SEQUENCE: 21

Gln Gln Gly Asp Thr Leu Pro Trp Thr
1               5

<210> SEQ ID NO 22
<211> LENGTH: 120
<212> TYPE: PRT
<213> ORGANISM: Artificial Sequence
<220> FEATURE:
<223> OTHER INFORMATION: Synthetic: 28G11 VH

<400> SEQUENCE: 22

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Val Leu Arg Ala Glu Asp Ser Ala Thr Tyr
                85                  90                  95

Tyr Cys Ala Arg Tyr Thr Gly Gly Gly Tyr Phe Asp Tyr Trp Gly Gln
```

```
                    100                 105                 110

Gly Thr Thr Leu Thr Val Ser Ser
        115                 120

<210> SEQ ID NO 23
<211> LENGTH: 107
<212> TYPE: PRT
<213> ORGANISM: Artificial Sequence
<220> FEATURE:
<223> OTHER INFORMATION: Synthetic: 28G11 VL

<400> SEQUENCE: 23

Asp Ile Gln Met Thr Gln Thr Thr Ser Ser Leu Ser Ala Ser Leu Gly
1               5                   10                  15

Asp Arg Leu Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Ala Asp Ile Ala Thr Tyr Phe Cys Gln Gln Gly Asp Thr Leu Pro Trp
                85                  90                  95

Thr Phe Gly Gly Gly Thr Lys Leu Glu Ile Lys
            100                 105

<210> SEQ ID NO 24
<211> LENGTH: 5
<212> TYPE: PRT
<213> ORGANISM: Artificial Sequence
<220> FEATURE:
<223> OTHER INFORMATION: Synthetic: 3G5 VHCDR1

<400> SEQUENCE: 24

Ser Tyr Trp Met Asn
1               5

<210> SEQ ID NO 25
<211> LENGTH: 17
<212> TYPE: PRT
<213> ORGANISM: Artificial Sequence
<220> FEATURE:
<223> OTHER INFORMATION: Synthetic: 3G5 VHCDR2

<400> SEQUENCE: 25

Gln Ile Tyr Pro Gly Asp Gly Asp Thr Lys Tyr Asn Gly Lys Phe Lys
1               5                   10                  15

Gly

<210> SEQ ID NO 26
<211> LENGTH: 12
<212> TYPE: PRT
<213> ORGANISM: Artificial Sequence
<220> FEATURE:
<223> OTHER INFORMATION: Synthetic: 3G5 VHCDR3

<400> SEQUENCE: 26

Arg Gly Tyr Asp Gly Tyr Tyr Ile Ser Phe Asp Val
1               5                   10

<210> SEQ ID NO 27
```

```
<211> LENGTH: 11
<212> TYPE: PRT
<213> ORGANISM: Artificial Sequence
<220> FEATURE:
<223> OTHER INFORMATION: Synthetic: 3G5 VLCDR1

<400> SEQUENCE: 27

Arg Ala Ser Glu Asn Ile Tyr Ser Asn Leu Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic: 3G5 VLCDR2

<400> SEQUENCE: 28

Ala Ala Thr Asn Leu Ala Asp
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic: 3G5 VLCDR3

<400> SEQUENCE: 29

Gln His Phe Trp Val Thr Pro Tyr Thr
1               5

<210> SEQ ID NO 30
<211> LENGTH: 121
<212> TYPE: PRT
<213> ORGANISM: Artificial Sequence
<220> FEATURE:
<223> OTHER INFORMATION: Synthetic: 3G5 VH

<400> SEQUENCE: 30

Gln Ile Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Lys Tyr Asn Gly Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Tyr Asp Gly Tyr Tyr Ile Ser Phe Asp Val Trp Gly
            100                 105                 110

Ala Gly Thr Thr Val Thr Val Ser Ser
        115                 120

<210> SEQ ID NO 31
<211> LENGTH: 107
<212> TYPE: PRT
<213> ORGANISM: Artificial Sequence
<220> FEATURE:
<223> OTHER INFORMATION: Synthetic: 3G5 VL
```

-continued

```
<400> SEQUENCE: 31

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Arg Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Asn Leu Gln Ser
65                  70                  75                  80

Glu Asp Phe Gly Ser Tyr Tyr Cys Gln His Phe Trp Val Thr Pro Tyr
                85                  90                  95

Thr Phe Gly Gly Gly Thr Lys Leu Glu Ile Lys
            100                 105

<210> SEQ ID NO 32
<211> LENGTH: 7
<212> TYPE: PRT
<213> ORGANISM: Artificial Sequence
<220> FEATURE:
<223> OTHER INFORMATION: Synthetic: 16B4 VHCDR1

<400> SEQUENCE: 32

Thr Phe Gly Met Gly Val Gly
1               5

<210> SEQ ID NO 33
<211> LENGTH: 16
<212> TYPE: PRT
<213> ORGANISM: Artificial Sequence
<220> FEATURE:
<223> OTHER INFORMATION: Synthetic: 16B4 VHCDR2

<400> SEQUENCE: 33

His Ile Trp Trp Asp Asp Lys Tyr Tyr Asn Pro Ala Leu Lys Ser
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: Synthetic: 16B4 VHCDR3

<400> SEQUENCE: 34

Ile Tyr Tyr Tyr Gly Ser Trp Gly Leu Tyr Tyr Phe Asp Tyr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic: 16B4 VLCDR1

<400> SEQUENCE: 35

Arg Ala Ser Gln Asp Ile Ser Asn Tyr Leu Asn
1               5                   10

<210> SEQ ID NO 36
<211> LENGTH: 7
<212> TYPE: PRT
```

-continued

```
<213> ORGANISM: Artificial Sequence
<220> FEATURE:
<223> OTHER INFORMATION: Synthetic: 16B4 VLCDR2

<400> SEQUENCE: 36

Tyr Thr Ser Arg Leu His Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic: 16B4 VLCDR3

<400> SEQUENCE: 37

Gln Gln Gly Asn Thr Leu Pro Pro Thr
1               5

<210> SEQ ID NO 38
<211> LENGTH: 124
<212> TYPE: PRT
<213> ORGANISM: Artificial Sequence
<220> FEATURE:
<223> OTHER INFORMATION: Synthetic: 16B4 VH

<400> SEQUENCE: 38

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Phe
                20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ile Tyr Tyr Tyr Gly Ser Trp Gly Leu Tyr Tyr Phe Asp
                100                 105                 110

Tyr Trp Gly Gln Gly Thr Thr Leu Thr Val Ser Ser
            115                 120

<210> SEQ ID NO 39
<211> LENGTH: 107
<212> TYPE: PRT
<213> ORGANISM: Artificial Sequence
<220> FEATURE:
<223> OTHER INFORMATION: Synthetic: 16B4 VL

<400> SEQUENCE: 39

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
```

```
                65                  70                  75                  80
Glu Asp Ile Ala Thr Tyr Phe Cys Gln Gln Gly Asn Thr Leu Pro Pro
                    85                  90                  95

Thr Phe Gly Gly Gly Thr Lys Leu Glu Ile Lys
            100                 105
```

<210> SEQ ID NO 40
<211> LENGTH: 6
<212> TYPE: PRT
<213> ORGANISM: Artificial Sequence
<220> FEATURE:
<223> OTHER INFORMATION: Synthetic: 7H4 VHCDR1

<400> SEQUENCE: 40

```
Ser Gly Tyr Tyr Trp Asn
1               5
```

<210> SEQ ID NO 41
<211> LENGTH: 16
<212> TYPE: PRT
<213> ORGANISM: Artificial Sequence
<220> FEATURE:
<223> OTHER INFORMATION: Synthetic: 7H4 VHCDR2

<400> SEQUENCE: 41

```
Tyr Ile Ser Tyr Asp Gly Thr Asn Asn Tyr Asn Pro Ser Leu Lys Asn
1               5                   10                  15
```

<210> SEQ ID NO 42
<211> LENGTH: 9
<212> TYPE: PRT
<213> ORGANISM: Artificial Sequence
<220> FEATURE:
<223> OTHER INFORMATION: Synthetic: 7H4 VHCDR3

<400> SEQUENCE: 42

```
Ser Phe Tyr Asn Asn Tyr Phe Asp Phe
1               5
```

<210> SEQ ID NO 43
<211> LENGTH: 11
<212> TYPE: PRT
<213> ORGANISM: Artificial Sequence
<220> FEATURE:
<223> OTHER INFORMATION: Synthetic: 7H4 VLCDR1

<400> SEQUENCE: 43

```
Lys Ala Ser Gln Asp Ile Asp Lys Tyr Ile Ala
1               5                   10
```

<210> SEQ ID NO 44
<211> LENGTH: 7
<212> TYPE: PRT
<213> ORGANISM: Artificial Sequence
<220> FEATURE:
<223> OTHER INFORMATION: Synthetic: 7H4 VLCDR2

<400> SEQUENCE: 44

```
Tyr Thr Ser Thr Leu Gln Pro
1               5
```

<210> SEQ ID NO 45
<211> LENGTH: 8
<212> TYPE: PRT
<213> ORGANISM: Artificial Sequence
<220> FEATURE:

<223> OTHER INFORMATION: Synthetic: 7H4 VLCDR3

<400> SEQUENCE: 45

Leu Gln Tyr Asp Asn Leu Arg Thr
1               5

<210> SEQ ID NO 46
<211> LENGTH: 118
<212> TYPE: PRT
<213> ORGANISM: Artificial Sequence
<220> FEATURE:
<223> OTHER INFORMATION: Synthetic: 7H4 VH

<400> SEQUENCE: 46

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Ser Tyr Asp Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser
        115

<210> SEQ ID NO 47
<211> LENGTH: 106
<212> TYPE: PRT
<213> ORGANISM: Artificial Sequence
<220> FEATURE:
<223> OTHER INFORMATION: Synthetic: 7H4 VL

<400> SEQUENCE: 47

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asp Lys Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Asn Ile Ser Asn Leu Glu Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Leu Glu Ile Lys
            100                 105

<210> SEQ ID NO 48
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 48

Pro Val Gly Val Val
1               5